(12) United States Patent
Cowsar

(10) Patent No.: US 8,324,346 B2
(45) Date of Patent: *Dec. 4, 2012

(54) BIOACTIVE KERATIN PEPTIDES

(75) Inventor: Donald R. Cowsar, Savannah, GA (US)

(73) Assignee: Keraplast Technologies, Ltd., San Antonio, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/393,694

(22) Filed: Feb. 26, 2009

(65) Prior Publication Data

US 2011/0070276 A1 Mar. 24, 2011

Related U.S. Application Data

(62) Division of application No. 10/352,786, filed on Jan. 28, 2003, now Pat. No. 7,501,485.

(60) Provisional application No. 60/352,396, filed on Jan. 28, 2002.

(51) Int. Cl.
*C07K 7/04* (2006.01)
*A61K 38/00* (2006.01)

(52) U.S. Cl. .................. 530/330; 514/21.8; 514/9.4

(58) Field of Classification Search ................ None
See application file for complete search history.

(56) References Cited

U.S. PATENT DOCUMENTS

| | | | |
|---|---|---|---|
| 922,692 A | 5/1909 | Goldsmith | |
| 926,999 A | 7/1909 | Neuberg | |
| 960,914 A | 6/1910 | Heinemann | |
| 1,214,299 A | 1/1917 | Grosvenor et al. | |
| 2,434,688 A | 11/1942 | Evans | 18/47.5 |
| 2,445,028 A | 7/1948 | Jones et al. | 106/155 |
| 2,517,572 A | 8/1950 | Jones et al. | 106/155 |
| 2,814,851 A | 12/1957 | Hervey | 28/82 |
| 3,033,755 A | 5/1962 | Jacobi et al. | 167/90 |
| 3,642,498 A | 2/1972 | Anker | 99/166 |
| 3,655,416 A | 4/1972 | Vinson et al. | 106/155 |
| 4,178,361 A | 12/1979 | Cohen et al. | 424/22 |
| 4,357,274 A | 11/1982 | Werner | 260/123.7 |
| 4,423,032 A | 12/1983 | Abe et al. | 424/70 |
| 4,495,173 A | 1/1985 | Matsunaga et al. | 424/70 |
| 4,570,629 A | 2/1986 | Widra | 128/156 |
| 4,751,074 A | 6/1988 | Matsunaga et al. | 424/70 |
| 4,816,441 A | 3/1989 | Zeuthen et al. | |
| 4,895,722 A | 1/1990 | Abe et al. | 424/71 |
| 4,959,213 A | 9/1990 | Brod et al. | 514/21 |
| 5,047,249 A | 9/1991 | Rothman et al. | 424/543 |
| 5,320,796 A | 6/1994 | Harashima et al. | 264/349 |
| 5,527,773 A * | 6/1996 | Steinert et al. | 514/1.2 |
| 5,634,945 A | 6/1997 | Pernia et al. | 623/11 |
| 5,679,819 A | 10/1997 | Jones et al. | 556/418 |
| 5,712,252 A | 1/1998 | Smith | 514/21 |
| 5,763,583 A | 6/1998 | Arai et al. | 530/353 |
| 5,942,490 A * | 8/1999 | Korsmeyer | 424/1.69 |
| 5,965,536 A | 10/1999 | Cohen et al. | |
| 6,110,889 A | 8/2000 | Miller et al. | |
| 6,290,953 B1 * | 9/2001 | Ballance et al. | 424/94.5 |
| 6,586,570 B1 | 7/2003 | Frudakis et al. | |
| 7,501,485 B2 * | 3/2009 | Cowsar | 530/324 |

FOREIGN PATENT DOCUMENTS

| | | |
|---|---|---|
| EP | 0 223 579 A2 | 5/1987 |
| EP | 0 454 600 A1 | 10/1991 |
| EP | 0468797 B1 | 12/1995 |
| GB | 531446 | 1/1941 |
| JP | S55-187190 | 12/1980 |
| JP | 54-124043 | 2/1982 |
| JP | 60-220068 | 11/1985 |
| JP | 62-1731 | 1/1987 |
| JP | 1988-202582 | 8/1988 |
| JP | 63-47470 | 9/1988 |
| JP | 2-212410 | 8/1990 |
| JP | 03011099 A | 1/1991 |
| JP | 3-223207 | 10/1991 |
| JP | 04091138 A | 3/1992 |
| JP | 04091138 A2 | 3/1992 |
| JP | 1992-174659 | 5/1992 |
| JP | HEI 4-189833 | 7/1992 |
| JP | 1993285374 A | 11/1993 |
| JP | 1993285375 A | 11/1993 |
| JP | 1994100600 A | 4/1994 |
| JP | 1994116300 A | 4/1994 |
| JP | 6-240579 | 8/1994 |
| JP | 06336499 A | 12/1994 |
| JP | 8-157342 | 6/1996 |
| JP | 1998291999 A | 11/1998 |
| JP | 1998337466 A | 12/1998 |
| JP | 11-240822 | 9/1999 |
| JP | 2001-114647 | 4/2001 |
| JP | 2001087754 | 4/2001 |
| JP | 2002-138022 | 5/2002 |
| RU | 2106154 | 3/1998 |
| RU | 2108079 | 4/1998 |
| WO | WO 91/02538 | 3/1991 |
| WO | WO 98/08550 | 3/1998 |
| WO | WO 03/011894 A1 | 2/2003 |
| WO | WO 03/018673 A1 | 3/2003 |

OTHER PUBLICATIONS

Wheeless, Clifford; Chondroitin and keratin sulfate, Wheeless' Textbook of Orthopedics. Duke Orthopedics, http://www.wheelesonline.com/ortho/chondroitin_and_keratin_sulfat, (1996).*
Scgkagebgayf et. al., Noncollagenous Proteins of Gingiva J. Dent Res. 67 (8):1109-1113, 1111, 1988.*
Lane, Birgette, Connective Tissue and Its Heritable Disorders, Ch. 6 Keratins, p. 337, Wiley-Liss, Inc. 2002.*
Buchta, et al., "Peptides Related to the Calcium Binding Domains II and III of Calmodulin," Peptide Protein Res. 28, pp. 289-297 (1986).
Bayer, et al., "Structural and Immunological Characterization of Friend Murine Leukaemia Virus Glycopolypeptide Using Synthetic Oligopeptides," EMBO Journal, vol. 3, No. 8, pp. 1925-1930 (1984).
Rogers, Michael A., et al., "Characterization of a 190-Kilobase Pair Domain of Human Type I Hair Keratin Genes," *The Journal of Biological Chemistry*, Oct. 9, 1998, pp. 26683-26691, vol. 273:41, USA.
Roop, Dennis R., et al., "Synthetic Peptides Corresponding to Keratin Subunits Elicit Highly Specific Antibodies," *The Journal of Biological Chemistry*, Jul. 10, 1984, pp. 8037-8040, vol. 259:13, USA.
EPO Search Report dated Jul. 29, 2009.

(Continued)

*Primary Examiner* — Christina Bradley
*Assistant Examiner* — Jeanette Lieb
(74) *Attorney, Agent, or Firm* — Vinson & Elkins LLP

(57) ABSTRACT

Compositions containing biologically active peptides are disclosed. Active peptides are isolated fragments derived from human hair or sheep wool keratin proteins. Compositions may be prepared for pharmaceutical or topical administration or for use in cosmetic preparations.

36 Claims, No Drawings

OTHER PUBLICATIONS

Aoki, "Isolation and characterization of mouse high-glycine/tyrosine proteins," The Journal of Biological Chemistry, Nov. 28, 1997, 30512-30518, 272:48, The American Society for Biochemistry and Molecular Biology, Inc., USA.
Thomas et al., "Isolation of microfibrillar proteins of wool in disulfide form," Melliand Textiberichte, 65(3):20809, 1984.
van de Löcht, "Reconstitution of microfibrils from wool and filaments from epidermis proteins," Melliand Textiberichte, 10:780-6, 1987.
Yoshioka et al., "Cosmetic base," unexamined Japanese Patent Application No. 3-223207, Oct. 2, 1991.
Yoshioka et al., "Water-soluble hair dressing agent," unexamined Japanese Patent Application No. 8-157342, Jun. 18, 1996.
Hyuku et al., "Novel amino acid silicone polymer, production thereof, cosmetic particles surface treated with the polymer, and cosmetic containing said particles," unexamined Japanese Patent Application No. 2001-114647, Apr. 24, 2001.
Ito et al., "Biocompatibility of denatured wool keratin," 39:4, 249-256, Apr. 1982.
Yamauchi, "The development of keratin: characteristics of polymer films," Fragrance J, 21(5), 62-7, 1993.
Sauk et al, "Reconstitution of cytokeratin filaments in vitro: further evidence for the role of nonhelical peptides in filament assembly," The Journal of Cell Biology, 99, 1590-1597, Nov. 1984.
Weber et al., "The structural relation between intermediate filament proteins in living cells and the α-keratins of sheep wool," The EMBO Journal, 1:10, 1155-1160, 1982.
Hanukoglu et al., "The cDNA sequence of a human epidermal keratin: divergence of sequence but conservation of structure among intermediate filament proteins," Cell, 31, 243-252, Nov. 1982.
Fraser at al., "Intermediate filaments in α-keratins," Proc. Natl. Acad. Sci. USA, 83, 1179-1183, Mar. 1986.
Jones, "Studies on microfibrils from a-keratin," Biochimica et Biophysica Acta, 446, 515-524, Received Apr. 5, 1976.
Zackroff, et al., "In vitro assembly of intermediate filaments from baby hamster kidney (BHK-21) cells," Proc. Natl. Acad. Sci. USA, 76:12, 6226-6230, Dec. 1979.
Mack, et al., "Solid-state NMR studies of the dynamics and structure of mouse keratin intermediate filaments," Biochemistry, 27, 5418-5426, 1988.
Skerrow, et al., "Epidermal α-keratin is neutral-buffer-soluble and forms intermediate filaments under physiological conditions in vitro," Biochimica et Biophysica Acta, 915, 125-131, 1987.
Kvedar, et al., "Cytokeratins of the bovine hoof: classification and studies on expression," Biochimica et Biophysica Acta, 884, 462-473, 1986.
Moll, et al., "The catalog of human cytokeratins: patterns of expression in normal epithelia, tumors and cultured cells," Cell, 31, 11-24, Nov. 1982.
Iwatsuki, et al., "Comparative studies on naturally occurring antikeratin antibodies in human sera," The Journal of Investigative Dermatology, 87:2, 179-184, Aug. 1986.
Lambré, et al., "An enzyme immunoassay for auto-antibodies to keratin in normal human serum and in pleural fluids from patients with various malignant or non-malignant lung diseases," J. Clin. Lab. Immunol., 20, 171-176, 1986.
Stokes, et al., "Passage of water and electrolytes through natural and artificial keratin membranes," Desalination, 42, 321-328, 1982.
Dedeurwaerder, et al., "Selective extraction of a protein fraction from wool keratin," Nature, 265, 48-49 and 274-276, Jan. 20, 1977.
Brunner, et al., "Fractionation of tyrosine-rich proteins from oxidized wool by ion-exchange chromatography and preparative electrophoresis," Eur. J. Biochem., 32, 350-355, 1973.
Mies, et al., "Chromatographic and electrophoretic investigations of the properties of unprotected low-sulphur wool kerateins," Journal of Chromatography, 405, 365-370, 1987.
Katsuumi, et al., "Two-dimensional electrophoretic analysis of human hair keratins, especially hair matrix proteins," Arch. Dermatol Res., 281, 495-501, 1989.
Horn, et al., "Relative molecular masses of reduced wool keratin polypeptides," Biochem Soc Trans, 14, 333-334, 1986.

Harrap, et al., "Species differences in the proteins of feathers," Comp. Biochem. Physiol., 20, 449-460, 1967.
Harrap, et al., "Soluble derivatives of feather keratin," Biochem. J., 92, 8-18, 1964.
Yoshimizu, et al., "$^{13}$C CP/MAS NMR. study of the conformation of stretched or heated low-sulfur keratin protein films," Macromolecules, 24, 862-866,1991.
Schaller, et al., "Membranes prepared from keratin-polyacrylonitrile graft copolymers," Journal of Applied Polymer Science, 25, 783-794, 1980.
Weiss, et al., "The use of monoclonal antibody to keratin in human epidermal disease: alterations in immunohistocheniical staining pattern," The Journal of Investigative Dermatology, 81, 224-230, 1983.
Starger, et al., "Biochemical and immunological analysis of rapidly purified 10-nm filaments from baby hamster kidney (BHK-21) cells," J. Cell Biology, 78, 93-109, 1978.
Noishiki, et al., "Application of denatured wool keratin derivatives to an antithrombogenic biomaterial-vascular graft coated with a heparinized keratin derivative—," Inst. Thermal Spring Res. Okayama Univ., 39:4, 221-227, 1982.
Valherie, "Chemical modifications of keratins. Application to the preparation of biomaterials and study of their physical, physiocochemical and biological properties," Ph.D. Thesis presented to the National Institute of Applied Sciences of Lyon, 1992.
Dale, "Keratin and other coatings for pills," Pharm. J., 129, 494-495, 1932, Abstract.
Schrooyen, et al., "Biodegradable films from selectively modified feather keratin dispersions," Polymer Preprints (American Chemical Society, Division of Polymer Chemistry), 39(2), 160, 1998, Abstract.
Schrooyen, et al., "Polymer films from chicken feather keratin," Book of Abstracts, 216th ACS National Meeting, Boston, Aug. 23-27, 1998, Abstract.
Kikkawa, et al., "Solubilization of keratin. 6. Solubilization of feather keratin by oxidation with performic acid," Hikaku Kagaku, 20(3), 151-162, 1974, Abstract.
Matsunaga, et al., "Studies on the chemical property of human hair keratin. Part 1. Fractionation and amino acid composition of human hair keratin solubilized by performic acid oxidation," Hikaku Kagaku, 27(1), 21-29, 1981, Abstract.
Noishiki, et al., "Application of denatured wool keratin derivatives to an antithrombogenic biomaterial. Vascular graft coated with a heparinized keratin derivative," Kobunshi Ronbunshu, 39(4), 221-227, 1982, Abstract.
Ito, et al., "Biocompatibility of denatured keratins from wool," Kobunshi Ronbunshu, 39(4), 249-256, 1982, Abstract.
Gillespie, et al., "Amino acid composition of a sulphur-rich protein from wool," Biochimica et Biophysica Acta, 39, 538-539, 1960.
Gough, et al., "Amino acid sequences of α-helical segments from S-carboxymethylkerateine-A. Complete sequence of a type-I segment," Biochem. J., 173, 373-385, 1978.
Elleman, et al., "Amino acid sequences of α-helical segments from S-carboxymethylkerateine-A. Statistical analysis," Biochem. J., 173, 387-391, 1978.
Hogg, et al., "Amino acid sequences of α-helical segments from S-carboxymethylkerateine-A. Tryptic and chymotryptic peptides from a type-II segment," Biochem. J., 173, 353-363, 1978.
Earland, et al., "Studies on the structure of keratin. II. The amino acid content of fractions isolated from oxidized wool," Biochimica at Biophysica Acta, 22, 405-411, 1956.
Crewther, et al., "Amino acid sequences of α-helical segments from S-carboxymethylkerateine-A. Complete sequence of a type-II segment," Biochem. J., 173, 365-371, 1978.
Fraser, et al., "Microscopic observations of the alkaline-thioglycollate extraction of wool," Biochimica at Biophysica Acta, 22, 484-485,1953.
Gillespie, et al., "Preparation of an electrophoretically homogeneous keratin derivative from wool," Biochimica et Biophysica Acta, 12, 481-483, 1953.
Blagrove, et al., "The electrophoresis of the high-tyrosine proteins of keratins on cellulose acetate strips," Comp. Biochem. Physiol., 50B, 571-572, 1975.
Frenkel, et al., "The isolation and properties of a tyrosine-rich protein from wool: component 0.62," Eur. J. Biochem., 34, 112-119, 1973.

Marshall, et al., "Successful isoelectric focusing of wool low-sulphur proteins," *Journal of Chromatography*, 172, 351-356, 1979.
Marshall, "Characterization of the proteins of human hair and nail by electrophoresis," *The Journal of Investigative Dermatology*, 80:6, 519-524, 1983.
Lindley, et al., "Occurrence of the cys-cys sequence in keratins," *J. Mol. Biol.*, 30, 63-67, 1967.
Marshall, "Genetic variation in the proteins of human nail," *The Journal of Investigative Dermatology*, 75:3, 264-269, 1980.
Goddard, et al., "A study on keratin," *J. Bio. Chem.*, 106, 605-614, 1934.
Dowling, et al., "Isolation of components from the low-sulphur proteins of wool by fractional precipitation," *Preparative Biochemistry*, 4(3), 203-226, 1974.
Crewther, et al., "Reduction of S-carboxymethylcysteine and methionine with sodium in liquid ammonia," *Biochimica et Biophysica Acta*, 194, 606-609, 1969.
Gillespie, "The isolation from wool of a readily extractable protein of low sulphur content," *Biochimica at Biophysica Acta*, 27, 225-226, 1958.
Lindley, et al., "The reactivity of the disulphide bonds of wool," *Biochem. J.*, 139, 515-523, 1974.
Mitsui, et al., "Genes for a range of growth factors and cyclin-dependent kinase inhibitors are expressed by isolated human hair follicles," *British Journal of Dermatology*, 137(5), 693-698, 1997, Abstract.
Schörnig, et al., "Synthesis of nerve growth factor mRNA in cultures of developing mouse whisker pad, a peripheral target tissue of sensory trigeminal neurons," *The Journal of Cell Biology*, 120:6, 1471-1479, 1993.
Filshie, et al., "The fine structure of α-keratin," *J. Mol. Biol.*, 3, 784-786, 1961.
Filshie; et al., "An electron microscope study of the fine structure of feather keratin," *The Journal of Cell Biology*, 13, 1-12, 1962.
Crewther, et al., "Low-sulfur proteins from α-keratins. Interrelationships between their amino acid compositions, α-helix contents, and the supercontraction of the parent keratin," *Biopolymers*, 4, 905-916, 1966.
Bhatnagar, et al., "The conformation of the high-sulphur proteins of wool. I. The preparation and properties of a water-soluble metakeratin," *Int. J. Protein Research I*, 199-212, 1969.
Crewther, et al., "The preparation and properties of a helix-rich fraction obtained by partial proteolysis of low sulfur S-carboxymethylkerateine from wool," *The Journal of Biological Chemistry*, 242:19, 4310-4319, 1967.
Parry, et al., "Structure of α-keratin: structural implication of the amino acid sequences of the type I and type II chain segments," *J. Mol. Biol.*, 113, 449-454, 1977.
Suzuki, et al, "X-ray diffraction and infrared studies of an α-helical fragment from α-keratin," *J. Mol. Biol.*, 73, 275-278, 1973.
Bhatnagar, et al., "The conformation of the high-sulphur proteins of wool. II. Difference spectra of kerateine-B," *Int. J. Protein Research I*, 213-219, 1969.
Steinert, et al., "In vitro studies on the synthesis of guinea pig hair keratin proteins," *Biochimica et Biophysica Acta*, 312, 403-412, 1973.
Rogers, "Some observations on the proteins of the inner root sheath cells of hair follicles," *Biochimica et Biophysica Acta*, 29, 33-42, 1958.
Tachibana, et al., "Fabrication of wool keratin sponge scaffolds for long-term cell cultivation," *Journal of Biotechnology*, 93, 165-170, 2002.
Gillespie, "Proteins rich in glycine and tyrosine from keratins," *Comp. Biochem. Physiol.*, 41B, 723-734, 1972.
Fraser, et al., "Tyrosine-rich proteins in keratins," *Comp. Biochem. Physiol.*, 44B, 943-947, 1973.
Bendit, et al., "Communications to the Editor. The probable role and location of high-glycine-tyrosine proteins in the structure of keratins," *Biopolymers*, 17, 2743-2745, 1978.
Lindley, et al., "The preparation and properties of a group of proteins from the high-sulphur fraction of wool," *Biochem. J.*, 128, 859-867, 1972.

Gillespie, et al., "Evidence of homology in a high-sulphur protein fraction (SCMK-B2) of wool and hair α-keratins," *Biochem. J.*, 110, 193-198, 1968.
Gillespie, et al., "A comparative study of high-sulphur proteins from α-keratins," *Comp. Biochem. Physiol.*, 15, 175-185, 1965.
Wormell, "Regenerated protein fibres from wool and casein," *The Journal of the Textile Institute*, 18, T219-T224, 1948.
Harding, et al., "Formation of the $_e$-(γ-glutamyl) lysine cross-link in hair proteins. Investigation of transamidases in hair follicles," *Biochemistry*, 11:15, 2858-2863, 1972.
Powell, et al., "Control of feather keratin synthesis by the availability of keratin mRNA," *Biochemical and Biophysical Research Communications*, 68:4, 1263-1271, 1976.
Strüssmann, et al., "Specific radiolabelling of keratin proteins by amidination," *Journal of Chromatography*, 268, 306-310, 1983.
Lindley, et al., "Disulphide interchange reactions involving cyclocystine and their relevance to problems of α-keratin structure," *Biochem. J.*, 108, 701-703, 1968.
Damoglou, et al., "The hydrolysis by thermolysin of dipeptide derivatives that contain substituted cysteine," *Biochem. J.*, 123, 379-384, 1971.
Lennox, et al., "Photochemical degradation of keratins," *Photochemistry and Photobiology*, 9, 359-367, 1969.
Crewther, et al., "Preliminary Notes. The relation between the disulphide content of wool and the two-stage supercontraction of wool fibres in solutions of LiBr," *Biochimica et Biophysica Acta*, 46, 605-606, 1961.
Gillespie, et al., "A comparison of the proteins of normal and trichothiodystrophic human hair," *The Journal of Investigative Dermatology*, 80, 195-202, 1983.
Gillespie, et al., "Changes in the proteins of wool following treatment of sheep with epidermal growth factor," *The Journal of Investigative Dermatology*, 79:3, 197-200, 1982.
Gillespie, et al., "Changes in the matrix proteins of wool and mouse hair following the administration of depilatory compounds," *Aust. J. Biol. Sei.*, 33, 125-136, 1980.
Darskus, at al., "Breed and species differences in the hair proteins of four genera of caprini," *Aust. J. Biol. Sci.*, 24, 515-524, 1971.
Kemp, et al., "Differentiation of avian keratinocytes. Characterization and relationships of the keratin proteins of adult and embryonic feathers and scales," *Biochemistry*, 11:6, 969-975, 1972.
Gillespie, et al., "The diversity of keratins," *Comp. Biochem. Physiol.*, 47B, 339-346, 1974.
Fraser, et al., "Wool structure and biosynthesis," *Nature*, 261, 650-654, 1976.
Stenn, et al., editors, "The molecular and structural biology of hair," *Annals of the New York Academy of Sciences*, vol. 642, Title p.-31, 1991.
Reis, et al., "The utilization of abomasal supplements of proteins and amino acids by sheep with special reference to wool growth," *Aust. J. Biol., Sci.*, 25, 1057-1071, 1972.
Broad, et al., "The influence of sulphur-containing amino acids on the biosynthesis of high-sulphur wool proteins," *Aust. J. Biol. Sci.*, 23, 149-164, 1970.
Reis, "The influence of dietary protein and methionine on the sulphur content and growth rate of wool in milk-fed lambs," *Aust. J. Biol. Sci.*, 23, 193-200, 1970.
Downes, et al., "Metabolic fate of parenterally administered sulphur-containing amino acids in sheep and effects on growth and composition of wool," *Aust. J. Biol. Set.*, 23, 1077-1088, 1970.
Reis, "The growth and composition of wool. IV. The differential response of growth and of sulphur content of wool to the level of sulphur-containing amino acids given per abomasum," *Aust. J. Biol. Sci.*, 20, 809-825, 1967.
Reis, et al., "Effects of phenylalanine and analogues of methionine and phenylalanine on the composition of wool and mouse hair," *Aust. J. Biol. Sci.*, 38:2, 151-163.
Frenkel, et al., "Studies on the inhibition of synthesis of the tyrosine-rich proteins of wool," *Aust. J. Biol. Sci.*, 28, 331-338, 1975.
Frenkel, et al., "Factors influencing the biosynthesis of the tyrosine-rich proteins of wool," *Aust. J. Biol. Sci.*, 27, 31-38, 1974.
Reis, "The growth and composition of wool. III. Variations in the sulphur content of wool," *Aust. J. Biol. Sci.*, 18, 671-687, 1965.

Reis, et al., "The influence of abomasal and intravenous supplements of sulphur-containing amino acids on wool growth rate," *Aust. J. Biol. Sci.*, 26, 249-258, 1973.

Gillespie, et al., "A further study on the dietary-regulated biosynthesis of high-sulphur wool proteins," *Biochem. J.*, 112, 41-49, 1969.

Gillespie, et al., "The dietary-regulated biosynthesis of high-sulphur wool proteins," *Biochem. J.*, 98, 669-677, 1966.

Powell, et al., "Characterization of a gene encoding a cysteine-rich keratin associated protein synthesized late in rabbit hair follicle differentiation," *Differentiation*, 58, 227-232, 1995.

Powell, et al., "Cyclic hair-loss and regrowth in transgenic mice overexpressing an intermediate filament gene," *The EMBO Journal*, 9:5, 1485-1493, 1990.

Raphael, et al., "Protein and amino acid composition of hair from mice carrying the naked (*N*) gene," *Genet. Res. Comb.*, 44:1, 29-38, 1984.

Frenkel, et al., "The keratin BIIIB gene family: isolation of cDNA clones and structure of a gene and a related pseudogene," *Genomics*, 4, 182-191, 1989.

Dowling, et al., "The primary structure of component 8c-1, a subunit protein of intermediate filaments in wool keratin," *Biochem. J.*, 236, 695-703, 1986.

Dowling, et al., "Secondary structure of component 8c-1 of α-keratin," *Biochem. J.*, 236, 705-712, 1986.

Kuczek, et al., "Sheep wool (glycine +tyrosine)-rich keratin genes," *Eur. J. Biochem.*, 166, 79-85, 1987.

Inagaki, et al., "Functionality of lamb wool keratin derivatives and a few characteristics of polymer materials for medical applications," *Chemical Research Institute, Kyoto University*.

Sakabe, et al., "Differential thermal analysis of component proteins from wool," *Sen-I Gakkaisbi* 39(12): T-517-T-522(1982).

"Biomaterial forefront. Keratin which can be extracted by a simple chemical technique," Kogyo Zaityo (Engineering Materials), 41:15, 106-109, 1993.

Kulkarni, "Further studies on the microfibrils from wool keratin. Part I: the isolation of microfibrils," Text. Res. J., 46:11, 833-5, 1976, Abstract.

Edwards, "Chemical studies on powdered keratins," *The Journal of Biological Chemistry*, 154, 593-596, 1944.

\* cited by examiner

BIOACTIVE KERATIN PEPTIDES

CROSS-REFERENCE TO RELATED APPLICATIONS

This application is a divisional of U.S. Ser. No. 10/352,786, filed Jan. 28, 2003, now U.S. Pat. No. 7,501,485, and claims benefit of priority of U.S. Provisional Application No. 60/352,396, filed Jan. 28, 2002, the disclosures of both of which are incorporated herein in their entirety by reference.

STATEMENT REGARDING FEDERALLY SPONSORED RESEARCH OR DEVELOPMENT

N/A

BACKGROUND OF THE INVENTION

Chronic wounds can be caused by a variety of events, including surgery, prolonged bedrest and traumatic injuries. Partial thickness wounds can include second degree burns, abrasions, and skin graft donor sites. Healing of these wounds can be problematic, especially in cases of diabetes mellitus or chronic immune disorders. Full thickness wounds have no skin remaining, and can be the result of trauma, diabetes (e.g., leg ulcers) and venous stasis disease, which can cause full thickness ulcers of the lower extremities. Full thickness wounds tend to heal very slowly or not at all. Proper wound care technique including the use of wound dressings is extremely important to successful chronic wound management. Chronic wounds affect an estimated four million people a year, resulting in health care costs in the billions of dollars. T. Phillips, O. Kehinde, and H. Green, "Treatment of Skin Ulcers with Cultivated Epidermal Allografts," J. Am. Acad. Dermatol, V. 21, pp. 191-199 (1989).

The wound-healing process involves a complex series of biological interactions at the cellular level which can be grouped into three phases: homeostasis and inflammation; granulation tissue formation and reepithelization; and remodeling. R. A. F. Clark, "Cutaneous Tissue Repair: Basic Biological Considerations," J. Am. Acad. Dermatol, Vol. 13, pp. 701-725 (1985). Keratinocytes (epidermal cells that manufacture and contain keratin) migrate from wound edges to cover the wound. Growth factors such as transforming growth factor-β (TGF-β) play a critical role in stimulating the migration process. The migration occurs optimally under the cover of a moist layer. Keratins have also been found to be necessary for reepithelization. Specifically, keratin types K5 and K14 have been found in the lower, generating, epidermal cells, and types K1 and K10 have been found in the upper, differentiated cells. I. K. Cohen, R. F. Diegleman, and W. J. Lindblad, eds., Wound Healing: Biochemical and Clinical Aspects, W.W. Saunders Company, 1992. Keratin types K6 and K10 are believed to be present in healing wounds, but not in normal skin. Keratins are major structural proteins of all epithelial cell types and appear to play a major role in wound healing.

Although not ideal for chronic wounds, several wound dressings are currently on the market, including occlusive dressings, non-adherent dressings, absorbent dressings, and dressings in the form of sheets, foams, powders and gels. S. Thomas, Wound Management and Dressing, The Pharmaceutical Press, London, 1990.

Attempts have been made to provide improved dressings that would assist in the wound-healing process using biological materials such as growth factors. These biologicals have proven very costly and, due to the lack of an appropriate delivery vehicle, have shown minimal clinical relevance in accelerating the chronic wound-healing process relative to their cost. In cases of severe full thickness wounds, autografts (skin grafts from the patient's body) are often used. Although the graft is non-antigenic, it must be harvested from a donor site on the patient's body, creating an additional wound. In addition, availability of autologous tissue may not be adequate. Allografts (skin grafts from donors other than the patient) are also used when donor sites are not an option. Allografts essentially provide a "wound dressing" that provides a moist, water-permeable layer, but are rejected by the patient, usually within two weeks, and do not become part of the new epidermis.

SUMMARY

The present disclosure arises from the surprising discovery that certain peptides derived from keratin proteins exhibit biological activity. The activity of these peptides has been demonstrated by their ability to stimulate growth of dermal fibroblasts comparable with known fibroblast growth factors. Compositions containing the peptides are thus useful in the treatment of conditions involving damaged, aged, or diseased epithelial tissue and skin. Because of the cytokine-like activity of the peptides, compositions containing these peptides are also contemplated to be useful in stimulation of tissue or cell growth in applications including, but not limited to tissue growth and repair including skin and bone tissue. The amino acid sequences of the active peptides indicate that the peptides are derived from a region of 39 amino acids that appears in various human hair and sheep wool keratin proteins. This conserved segment contains single amino acid changes in several locations in the consensus. The claimed compositions include peptides of from 4 to 39 amino acids in length that incorporate each of the sequence variations.

The present disclosure may be described therefore, in a preferred embodiment, as a composition that includes one or more biologically active peptides and in which the peptides are from about 4 to about 39 amino acids in length and occur as contiguous sequences in the peptides disclosed herein as SEQ ID NOs:1-32. The peptides may be made by any means known in the art, including isolation from natural sources, recombinant production or chemical synthesis. Natural sources would include keratin proteins that naturally occur in inter alia, human hair, animal hair, wool, fur, nails, hooves, horns, beaks, skin and feathers. Recombinantly produced peptides may also be expressed in a bacterial host cell or a eukaryotic host cell.

An alternative embodiment of the present disclosure is an isolated nucleic acid molecule that encodes any of the peptides disclosed herein and described in the previous paragraph, and more specifically, an isolated nucleic acid molecule that encodes any peptide of from about 4 to about 39 amino acids that occurs as a contiguous amino acid sequence in the peptides designated herein as SEQ ID NOs:1-32. Such peptides include all the peptides disclosed herein as SEQ ID NOS:1-4469, inclusively. The isolated nucleic acid sequences or molecules may be fragments of naturally occurring nucleic acid sequences that encode keratin proteins, for example, or they may be variations of such sequences that encode the disclosed peptides due to redundancies in the genetic code. Alternatively, the nucleic acid molecules may be chemically synthesized based on the desired amino acid sequences to be expressed. The isolated nucleic acid sequences or molecules are preferably contained in vectors, including expression vectors capable of directing expression of the peptides in an appropriate host cell. The host cell may preferably be a bacterial cell or a eukaryotic cell. Certain embodiments of the present disclosure are vectors containing the described nucleic acid segments and host cells that contain those vectors.

In certain embodiments of the disclosure, the peptides are contained in, or combined with pharmaceutically acceptable carriers. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the peptide ingredients, its use in the therapeutic or cosmetic compositions is contemplated.

The pharmaceutical compositions are preferably formulated for administration to veterinary or human subjects, and may be optionally formulated for oral, topical or optical administration. Similarly, the claimed compositions may be formulated for implantation, coated on a surface to be implanted or contained within an implant. Additionally, in certain preferred embodiments, the compositions are formulated for application to wounds. In certain embodiments, the claimed compositions are formulated for application to burned, aged, wrinkled, scarred, or damaged skin, and are also useful in the relief of pain, burning, or itching. In certain embodiments, the peptide containing compositions of the present disclosure are formulated for the treatment of gastrointestinal, anal, vaginal, ear, eye, lung, nasal, oral or urogenital epithelial tissue, including, but not limited to, for example, the treatment of Crohn's disease, skin grafts or ulcers, including diabetic ulcers.

The biological activity of the disclosed peptides may be any activity that is beneficial as a research tool for or for the benefit of a human or animal recipient of the formulations, including cell growth activation or inhibition, or cytokine-like activity. The cytokine-like activity is preferably cell differentiation, cell proliferation, cell adhesion, effect on cell morphology, cell migration, inflammatory response, angiogenesis; cell death or the like. The disclosed peptides may also be combined with other growth factors in order to enhance the healing activity of damaged skin, for example. In certain embodiments, then, a composition may contain any of the peptides derived from the peptides designated as SEQ ID NO:1-32 in combination with a growth factor such as epidermal growth factor (EGF), transforming growth factor-alpha (TGF-a), fibroblast growth factor (FGF), keratinocyte growth factor (KGF), platelet derived growth factor (PDGF) or a mixture of these in any combination.

An additional preferred embodiment of the present disclosure is compositions containing the described peptides in which the peptide or peptides are present in an amount effective to inhibit microbial growth. It has been observed by the present inventor that solutions containing the disclosed peptides may be kept "on the shelf" for extended periods of time without becoming contaminated with microbial growth. The compositions are contemplated, therefore, to be effective in inhibition of microbial contamination or growth.

In certain embodiments, the compositions of the present disclosure may be formulated as cosmetics. The cosmetic preparations may be in the form of a powder, lotion, hydrogel, oil, emulsion, paste; polish or cream. The cosmetics may optionally contain a coloring agent and/or a fragrance.

The compositions of the present disclosure may be used with benefit in virtually all categories of skin cosmetics for both women and men. These would include, but are not limited to preparations formulated as moisturizers, deodorants, anti-aging/skin repair preparations, cleansers and toners, eye care, lip care, fingernail or toenail care, scalp care, sun care, and hand and body preparations. Moreover, after-care products for such skin insults as chemical peels, sunburn, depilatory irritation, razor-shaving nicks and abrasions, scalp irritation from hair perming and straightening, and the like that include the disclosed peptides would fill a much needed void in the cosmetics arena. Many water-based make-up products may be fortified with the disclosed compositions to provide continuing skin therapy during their daily use. The disclosed peptide compositions will also find use in hair care products, such as shampoo, for example. Because of the benefits to skin, shampoos and conditioners are contemplated to be an effective way to deliver the peptides to the scalp.

Compositions including the peptides disclosed herein may also include a cell or tissue growth scaffold. The tissue growth scaffold may preferably be defined as a spinal implant, bone growth scaffold, scaffold for growth of epithelial tissue, a bandage, a non-woven sheet or a woven sheet. It may also be preferable for the non-woven or woven sheets to be keratin derived or to contain natural keratins, including, but not limited to wool pads, woven keratin, keratin bonded to polymer sheets, or cross-linked keratin. Additionally, the tissue growth scaffold may include an envelope containing the peptides or peptides coated or bonded to the surface of a metal, silicone or polymer implant.

DETAILED DESCRIPTION

The present disclosure provides a new family of biologically active peptides derived from plentiful and renewable resources. In a significant number of in vitro cell-culture studies, the present inventor has shown that the cell proliferation activity of the keratin-derived peptides mimic most all of the known growth factors, including FGF, KGF, EGF, and PDGF. In vivo studies in animals have shown that these peptides are potent anti-irritants and that they promote and/or accelerate wound healing. Moreover, these peptides, when applied topically to human volunteers, significantly restore skin barrier properties and rejuvenate aged skin. Based on these early findings, it is concluded that these keratin-derived peptides are "potent" cellular activators effecting both cell proliferation and cell differentiation in mammals, and that they have multiple uses in the medical and cosmetics arenas.

When isolated from natural sources such as human hair or wool, the biologically active peptides can yield one or several soluble peptide fractions from each raw material. These fractions appear to differ from each other mostly in their average molecular weight and their acid solubility. All fractions are readily soluble in the near-neutral pH range used for most cosmetics formulary. In cell culture studies with human fibroblasts, peptide preparations exhibited significant activation of cell proliferation at a concentration of from 100 to 0.001 µg/mL. Based on the data and the activities of known bioactive peptides, it is contemplated that the peptide compositions are active in the range of from 0.0001 to 0.00001 µg/mL. Although the specific cosmetic formulations may affect the delivery of these peptides to and/or through the skin, this in vitro cell-culture result suggests that a useful concentration of the peptides for cell activation could be less than 1%, or less than 0.4%, less than 0.1%, less than 0.01% or even less than 0.001%.

In addition to the in vitro and in vivo studies mentioned above, addition anecdotal information has been gathered regarding the disclosed peptides when opportunities for human experimentation were available. From these studies, it is contemplated that the peptide compositions are both anti-inflammatory and anti-microbial and that they mediate pain at wound-healing sites. Moreover, application of the peptide compositions to skin burns, including chemical burns and sunburn, expedites healing and minimizes discomfort.

The present disclosure arises from the surprising discovery that certain peptide fragments disclosed herein have beneficial biological activities, primarily demonstrated in in vitro studies by their effect on the growth of certain types of biological cells, and particularly dermal fibroblast cells. Because of the ability of certain of the disclosed peptide containing compositions to stimulate or to inhibit growth of fibroblast cells, the compositions find particular utility in applications that involve healing of aging, damage or pathologies of epithelial or connective tissues.

The cytokine-like properties of the peptide compositions can be used to promote healing, repair, and cell growth in keratinous tissue generally. The peptides can be used to treat damaged skin and skin wounds including, for example, rashes, including diaper rash, burns including sunburn, cuts, abrasions, punctures, sores including bed sores, ulcers including diabetic ulcers and other skin injuries or irritations. The peptide compositions can also be used to treat aging, weakened or damaged skin, including, for example, wrinkled skin. Particular applications include the treatment of damaged tissue in the external skin, or epidermal layers, in oral, pulmonary, gastro-intestinal, or spinal tissues.

The peptide containing compositions may be formulated as a powder, lotion, hydrogel, oil, emulsion, paste, cream, or gel for application to the skin or gums, or it may be formulated as an aerosol, an implant, an implant coating or a scaffolding material for tissue growth. For example, the peptide compositions may be contained in a woven or non-woven sheet material, or adsorbed in a hydrogel, or in a hydrogel contained in a biocompatible envelope material.

Preparation of Peptides

In certain embodiments the disclosed peptides may be isolated from naturally occurring sources such as human hair or sheep wool, for example. Preferred methods of preparing a small sample composition containing the claimed peptides follows. It is understood, of course, that this preparation may be made at a much larger scale in order to obtain larger, commercial quantities of the composition.

General methods of producing the peptide containing compositions from a keratin substrate include oxidizing the keratin substrate with an oxidizing agent, to substantially break the disulfide bonds that make keratins insoluble and inert. Examples of oxidizing agents that can be used include, but are not limited to, hydrogen peroxide, peracetic acid, percarbonates, persulfates, chlorine dioxide, sodium and calcium peroxides, perborates, and hypochlorite. The oxidized hair is filtered, the filtrate collected, and neutralized with base. Water soluble peptides from the neutralized filtrate may be precipitated from solution by mixing the filtrate with a water-miscible organic solvent such as methanol. Alternatively the oxidized keratin may be partially or totally dissolved in dilute aqueous alkali, filtered to remove solids, and the filtrate may be precipitated by acidification or by adding a miscible non-solvent such as ethanol or methanol, to obtain a greater fraction of the keratin material. The precipitate is collected with filtration and the collected filtrate is dried.

A more specific protocol follows:

Hot Method

Weigh 100 g of washed cut-up keratin substrate (hair, scoured unbleached, or un-dyed wool, ~0.25-0.5 inches in length) into a 3 L RB flask containing a stirring assembly and gas adaptor Add 1565 mL of distilled, de-ionized (DI) $H_2O$
Add 110 mL of 30% $H_2O_2$
Heat to reflux with stirring
Stir at reflux for ~2 hours
Remove heating mantle
Continue to stir and cool to <50° C. allow to settle and filter using Buchner funnel and fast filter paper.
Rinse filtrate twice with 250 mL hot (~50° C.) DI $H_2O$
Save oxidized keratin filtrant (Intermediate A) for further processing later
Allow filtrate to cool to ~room temperature
Neutralize filtrate to pH=7.0±0.2 with ~3N $NH_4OH$
Concentrate with aspirator vacuum to ~165 mL.
Cool to about freezing
Precipitate into 1 L of freezer-cold MeOH
Filter immediately in Buchner funnel with medium-fast filter paper, washing filtrant with 2-250 mL portions of freezer cold MeOH
Alternatively:
Store entire mixture overnight in freezer allowing precipitate to settle
Decant excess MeOH
Filter remaining mixture in Buchner funnel with medium-fast filter paper, washing filtrant with 2-250 mL portions of freezer cold MeOH
Dry filtrant on filter paper overnight in a vacuum oven
Carefully scrape dried material from filter paper into mortar and grind if necessary with a pestle
Weigh product into a labeled glass jar with a Teflon-lined cap, record % SKP (soluble keratin peptide) yield based on keratin substrate, and store product at room temperature.

Enhanced Peptide Yields

Put oxidized keratin filtrant (Intermediate A from Hot Process above) in a 5-L beaker, add 4 L of 0.1 N ammonium hydroxide and stir for 24 hr at room temperature.
Filter solution and discard filtrant.
To filtrate, add glacial acetic acid dropwise with constant stirring to pH 4 causing acid-insoluble peptides to precipitate. Filter with Buchner funnel and save filtrate (acid soluble gamma fraction).
Wash filtrant (acid-insoluble alpha fraction) with 1 L of water and reject washings. Redissolve filtrant in 2 L of 0.01 N ammonium hydroxide and add this solution with constant stirring to 4 L of ethanol containing 10 mL of acetic acid. Filter with Buchner funnel and discard filtrate.
Wash filtrant with 1 L of ethanol and dry filtrant (alpha peptides) in a warm vacuum oven.
Carefully scrape dried material from filter paper and store in a glass jar labeled "alpha peptide".
Take acid-soluble gamma filtrate from the first step, and concentrate it in vacuo to about 200 mL. Pour concentrate into 2 L of ethanol with constant stirring to precipitate gamma peptides.
Recover gamma peptides by filtration with a Buchner funnel and discard filtrate.
Suspend filtrant in 1 L of ethanol and stir for 2 hr to dissolve residual ammonium acetate. Filter with Buchner funnel, discard filtrant, and dry filtrant in a warm vacuum oven.
Carefully scrape dried material from filter paper and store in a glass jar labeled "gamma peptide".

In certain embodiments, the peptides in the disclosed compositions may be chemically synthesized by methods well known in the art. Solid phase peptide synthesis involves a stepwise assembly of a peptide chain while anchored to a support or solid phase peptide resin. There are two generally well-known methods of the solid phase synthesis of peptides.

The first, known as the Merrifield method, utilizes a solid support or resin which holds the C-terminal amino acid by the carboxyl group as the peptide is being synthesized through the attachment of amino acid or peptide residues as building blocks. The N-terminus of the resin-bound peptide is deblocked and N-protected amino acids are added, usually with a coupling agent. Activating agents may be used to improve rate and selectivity. After the peptide bond is formed, the protected group is removed and the cycle is repeated, if desired, until all the amino acids have been added to the peptide in the desired order.

The second method of chemical synthesis is the "polymeric reagent synthesis", also known as the "inverse Merrifield" method. This technique involves reagents bound to solid supports in a series of columns and passing the amino acid or peptide residues through the columns to form the peptide or amino acid sequence.

In certain embodiments, the peptides may be produced recombinantly from isolated nucleic acid molecules that encode the disclosed peptides. For example, the present disclosure provides recombinant cloning and expression vectors containing DNA, as well as host cells containing the recombinant vectors. Expression vectors comprising DNA may be used to prepare the disclosed peptides encoded by the DNA. A method for producing peptides comprises culturing host cells transformed with a recombinant expression vector encoding the peptide, under conditions that promote expression of the peptide, then recovering the expressed peptides from the culture. The skilled artisan will recognize that the procedure for purifying the expressed peptides will vary according to such factors as the type of host cells employed, and the level of purity required for the particular preparation. It is understood that the peptide compositions of the present invention can be of any useful purity, including crude extracts of cell or tissue culture.

Any suitable expression system may be employed. The vectors include a DNA encoding a peptide of the invention, operably linked to suitable transcriptional or translational regulatory nucleotide sequences, such as those derived from a mammalian, microbial, viral, or insect gene. Examples of regulatory sequences include transcriptional promoters, operators, or enhancers, an mRNA ribosomal binding site, and appropriate sequences which control transcription and translation initiation and termination. Nucleotide sequences are operably linked when the regulatory sequence functionally relates to the DNA sequence. Thus, a promoter nucleotide sequence is operably linked to a DNA sequence if the promoter nucleotide sequence controls the transcription of the DNA sequence. An origin of replication that confers the ability to replicate in the desired host cells, and a selection gene by which transformants are identified, are generally incorporated into the expression vector.

In addition, a sequence encoding an appropriate signal peptide (native or heterologous) can be incorporated into expression vectors. A DNA sequence for a signal peptide (secretory leader) may be fused in frame to the nucleic acid sequence of the invention so that the DNA is initially transcribed, and the mRNA translated, into a fusion protein comprising the signal peptide. A signal peptide that is functional in the intended host cells promotes extracellular secretion of the peptide. The signal peptide is cleaved from the peptide upon secretion of peptide from the cell.

Suitable host cells for expression of peptides include prokaryotes, yeast or higher eukaryotic cells. Prokaryotic host cells, such as bacterial cells are generally preferred for use as host cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce peptides using RNAs derived from DNA constructs disclosed herein.

Prokaryotes include gram-negative or gram-positive organisms. Suitable prokaryotic host cells for transformation include, for example, *E. coli, Bacillus subtilis, Salmonella typhimurium*, and various other species within the genera *Pseudomonas, Streptomyces*, and *Staphylococcus*. In a prokaryotic host cell, such as *E. coli*, a peptide may include an N-terminal methionine residue to facilitate expression of the recombinant peptide in the prokaryotic host cell. The N-terminal Met may be cleaved from the expressed recombinant peptide.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. An appropriate promoter and a DNA sequence are inserted into the pBR322 vector. Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., *Nature* 275:615, 1978; and Goeddel et al., *Nature* 281:544, 1979), tryptophan (trp) promoter system (Goeddel et al., *Nucl. Acids Res.* 8:4057, 1980; and EP-A-36776) and tac promoter (Maniatis, *Molecular Cloning: A Laboratory Manual*, Cold Spring Harbor Laboratory, p. 412, 1982). A particularly useful prokaryotic host cell expression system employs a phage $\lambda P_L$ promoter and a cI857ts thermolabile repressor sequence. Plasmid vectors available from the American Type Culture Collection which incorporate derivatives of the $\lambda P_L$ promoter include plasmid pHUB2 (resident in *E. coli* strain JMB9, ATCC 37092) and pPLc28 (resident in *E. coli* RR1, ATCC 53082).

Alternatively, the peptides may be expressed in yeast host cells, preferably from the *Saccharomyces* genus (e.g., *S. cerevisiae*). Other genera of yeast, such as *Pichia* or *Kluyveromyces*, may also be employed. Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255:2073, 1980) or other glycolytic enzymes (Hess et al., *J. Adv. Enzyme Reg.* 7:149, 1968; and Holland et al., *Biochem.* 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phospho-glucose isomerase, and glucokinase. Other suitable vectors and promoters for use in yeast expression are further described in Hitzeman, EPA-73,657. Another alternative is the glucoserepressible ADH2 promoter described by Russell et al. (*J. Biol. Chem.* 258:2674, 1982) and Beier et al. (*Nature* 300: 724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the peptide. The α-factor leader sequence is often inserted between the promoter sequence and the structural gene sequence. See, e.g., Kurjan et al., *Cell* 30:933, 1982 and Bitter et al., *Proc. Natl. Acad. Sci. USA* 81:5330, 1984. Other leader sequences suitable for facilitating secretion of recombinant peptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 mg/ml adenine and 20 mg/ml uracil.

Yeast host cells transformed by vectors containing an ADH2 promoter sequence may be grown for inducing expression in a "rich" medium. An example of a rich medium is one consisting of 1% yeast extract, 2% peptone, and 1% glucose supplemented with 80 mg/ml adenine and 80 mg/ml uracil. Derepression of the ADH2 promoter occurs when glucose is exhausted from the medium.

Mammalian or insect host cell culture systems also may be employed to express recombinant peptides. Bacculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV1/EBNA cell line derived from the African green monkey kidney cell line CV1 (ATCC CCL 70) as described by McMahan et al. (*EMBO J.* 10: 2821, 1991).

Established methods for introducing DNA into mammalian cells have been described (Kaufman, R. J., *Large Scale Mammalian Cell Culture,* 1990, pp. 15-69). Additional protocols using commercially available reagents, such as Lipofectamine lipid reagent (Gibco/BRL) or Lipofectamine-Phis lipid reagent, can be used to transfect cells (Felgner et al., *Proc. Natl. Acad. Sci. USA* 84:7413-7417, 1987). In addition, electroporation can be used to transfect mammalian cells using conventional procedures, such as those in Sambrook et al. (*Molecular Cloning: A Laboratory Manual,* 2 ed. Vol. 1-3, Cold Spring Harbor Laboratory Press, 1989). Selection of stable transformants can be performed using methods known in the art, such as, for example, resistance to cytotoxic drugs. Kaufman et al., *Meth. in Enzymology* 185:487-511, 1990, describes several selection schemes, such as dihydrofolate reductase (DHFR) resistance. A suitable host strain for DHFR selection can be CHO strain DX-B11, which is deficient in DHFR (Urlaub and Chasin, *Proc. Natl. Acad. Sci. USA* 77:4216-4220, 1980). A plasmid expressing the DHFR cDNA can be introduced into strain DX-B11, and only cells that contain the plasmid can grow in the appropriate selective media. Other examples of selectable markers that can be incorporated into an expression vector include cDNAs conferring resistance to antibiotics, such as G418 and hygromycin B. Cells harboring the vector can be selected on the basis of resistance to these compounds.

Transcriptional and translational control sequences for mammalian host cell expression vectors can be excised from viral genomes. Commonly used promoter sequences and enhancer sequences are derived from polyoma virus, adenovirus 2, simian virus 40 (SV40), and human cytomegalovirus. DNA sequences derived from the SV40 viral genome, for example, SV40 origin, early and late promoter, enhancer, splice, and polyadenylation sites can be used to provide other genetic elements for expression of a structural gene sequence in a mammalian host cell. Viral early and late promoters are particularly useful because both are easily obtained from a viral genome as a fragment, which can also contain a viral origin of replication (Fiers et al., *Nature* 273:113, 1978; Kaufman, *Meth. in Enzymology,* 1990). Smaller or larger SV40 fragments can also be used, provided the approximately 250 by sequence extending from the Hind III site toward the Bgl I site located in the SV40 viral origin of replication site is included.

Additional control sequences shown to improve expression of heterologous genes from mammalian expression vectors include such elements as the expression augmenting sequence element (EASE) derived from CHO cells (Morris et al., *Animal Cell Technology,* 1997, pp. 529-534 and PCT Application WO 97/25420) and the tripartite leader (TPL) and VA gene RNAs from Adenovirus 2 (Gingeras et al., *J. Biol. Chem.* 257:13475-13491, 1982). The internal ribosome entry site (IRES) sequences of viral origin allows dicistronic mRNAs to be translated efficiently (Oh and Sarnow, *Current Opinion in Genetics and Development* 3:295-300, 1993; Ramesh et al., *Nucleic Acids Research* 24:2697-2700, 1996). Expression of a heterologous cDNA as part of a dicistronic mRNA followed by the gene for a selectable marker (e.g. DHFR) has been shown to improve transfectability of the host and expression of the heterologous cDNA (Kaufman, *Meth. in Enzymology,* 1990). Exemplary expression vectors that employ dicistronic mRNAs are pTR-DC/GFP described by Mosser et al., *Biotechniques* 22:150-161, 1997, and p2A5I described by Morris et al., *Animal Cell Technology,* 1997, pp. 529-534.

A useful high expression vector, pCAVNOT, has been described by Mosley et al., *Cell* 59:335-348, 1989. Other expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1/N4, described by Cosman et al., *Nature* 312:768, 1984, has been deposited as ATCC 39890. Additional useful mammalian expression vectors are described in EP-A-0367566, and in WO 91/18982, incorporated by reference herein. In yet another alternative, the vectors can be derived from retroviruses.

The disclosure also includes methods of isolating and purifying the peptides. The "isolated" peptides encompassed by this invention are peptides that are not in an environment identical to an environment in which they can be found in nature. The "purified" peptides or fragments thereof encompassed by this invention are essentially free of association with other proteins or polypeptides, for example, as a purification product of recombinant expression systems such as those described above or as a purified product from a nonrecombinant source such as naturally occurring cells and/or tissues, or as peptides isolated from the native keratin proteins in which they occur.

In one preferred embodiment, the purification of recombinant peptides or fragments can be accomplished using fusions of peptides or fragments of the invention to another polypeptide to aid in the purification of peptides or fragments of the invention. Such fusion partners can include the poly-His or other antigenic identification peptides described above as well as the Fe moieties.

Pharmaceutical Compositions

Compositions comprising an effective amount of a peptide or combination of peptides of the present invention, in combination with other components such as a physiologically acceptable diluent, carrier, or excipient, are provided herein. The peptides can be formulated according to known methods used to prepare pharmaceutically useful compositions. They can be combined in admixture, either as the sole active material or with other known active materials suitable for a given indication, with pharmaceutically acceptable diluents (e.g., saline, Tris-HCl, acetate, and phosphate buffered solutions), preservatives (e.g., thimerosal, benzyl alcohol, parabens), emulsifiers, solubilizers, adjuvants and/or carriers. A peptide may be formulated into a composition in a neutral or salt form. Pharmaceutically acceptable salts, include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. The compositions disclosed herein may be formulated in any appropriate delivery vehicle, including, but not limited to hydrogels, lotions, aqueous solutions, non-aqueous solutions, non-woven mediums, woven mediums, tissue or cell growth scaffolds and powders. Suitable formulations for pharmaceutical compositions include those described in *Remington's Pharmaceutical Sciences*, 16th ed. 1980, Mack Publishing Company, Easton, Pa.

In addition, such compositions can be complexed with polyethylene glycol (PEG), metal ions, or incorporated into polymeric compounds such as polylactic acid, polyglycolic acid, hydrogels, dextran, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance, and are thus chosen according to the intended application.

The compositions of the invention can be administered in any suitable manner, e.g., topically, parenterally, or by inhalation. The term "parenteral" includes injection, e.g., by subcutaneous, intravenous, or intramuscular routes, also including localized administration, e.g., at a site of disease or injury. Sustained release from implants is also contemplated. One skilled in the pertinent art will recognize that suitable dosages will vary, depending upon such factors as the nature of the disorder to be treated, the patient's body weight, age, and general condition, and the route of administration. Preliminary doses can be determined according to animal tests, and the scaling of dosages for human administration is performed according to art-accepted practices.

In certain preferred embodiments of use, the peptide containing compositions may be formulated as a powder to be placed over a wound, for example. The peptide powder can also be formulated into any water-based solution, cream, gel, or other vehicle for convenient application to a wound. In addition, a peptide solution could be incorporated into or cast onto a polymer wound dressing or a keratin wound dressing sheet for application to a wound. In in vitro trials, compositions containing the disclosed peptides were shown to enhance proliferation of human skin keratinocytes, human dermal fibroblasts, and microvascular endothelial cells, thus demonstrating the efficacy of the peptides in wound-healing applications.

The peptides can also be added as a cell growth stimulant to a tissue engineering scaffold such as the sheet described in U.S. Pat. No. 6,110,487, incorporated herein by reference. The peptides are contemplated to speed repair of sun or weather damaged skin. The peptides may be mixed with a carrier lotion such as lanolin and applied to the skin. The peptides may also be added to cosmetics to impart a skin healing property to the cosmetic. Cosmetic bases are believed suitable for inclusion of peptides made according to the present invention.

In certain embodiments, the peptides compositions disclosed herein may be included in, attached to, or adhered to other products, including wound dressings, woven or non-woven sheets or films, hydrogel preparations, tissue engineering scaffolds, implants, or metal or polymer materials. Such materials are described in commonly owned U.S. Pat. Nos. 5,358,935, 5,932,552, 6,274,163, 6,124,265, 6,432,435, 6,316,598, 6,371,984, 6274,155, 6,270,793, 6,461,628, and U.S. patent application Ser. No. 09/815,387, all of which are incorporated herein by reference.

Peptide Containing Compositions

In previous studies, crude compositions containing the disclosed peptides have been used to investigate the mitogenic effects on keratinocytes after 3 days of exposure. Peptide concentrations of 0.5 to 10 ug/ml produced increases in optical densities (OD) at 530 nanometer (nm) of greater than 20% compared to negative controls. One exception was the 5 ug/ml concentration that produced over a 15% greater response. The positive control in these studies, epidermal growth factor (EGF25), produced greater than 20% increase in cell proliferation. In a similar study, after 5 days of exposure the keratinocyte proliferation was 25% or greater for peptide concentrations of 0.5 to 10 ug/ml. The positive control, EGF25, also produced a greater than 25% increase.

A second set of studies was performed that tested the biological effect of the peptide compositions on human dermal fibroblasts after three and five days of exposure. After three days of exposure, the peptide composition produced a greater than 25% increase in cell proliferation at concentrations between 0.5 and 10 ug/ml. The positive control, bovine-derived fibroblast growth factor (bFGF25), produced a greater than 30% increase in cell proliferation. After five days of exposure, peptide compositions at a concentration of 0.5 to 10 ug/ml produced increases in cell proliferation of between 9% and 12%. The positive control produced a greater than 13% increase.

Related in vitro tests confirmed that the mitogenic effect of the peptide compositions on dermal fibroblasts increased with concentration up to nearly 150% of the negative control at 1000 ug/ml concentration. Compositions with greater purity increased the mitogenic effect to over 1000% of the negative control. The positive control in these studies, platelet derived growth factor (PDGF), increased the mitogenic effect to nearly 700% of the negative control.

The present disclosure includes further refined preparations that can be separated into two distinct components, the first, alpha-keratose comprises about 60% of the total peptides and is water soluble and acid insoluble. The gamma keratose is both acid and water soluble. Compositions containing mixtures of the disclosed peptides at various concentrations from the alpha and gamma fractions from hair and wool were added to dermal fibroblast cell cultures for three and five days. The cellular response was measured using optical density techniques (OD490) to quantify the cell proliferation. In all cases the highest concentrations produced a greater cell proliferation response than the lower concentrations after three days of exposure. The 100 ug/ml concentration of the peptides from hair and wool produced approximately a 35% and 30% increase in cell proliferation respectively compared to the negative control.

Human dermal fibroblasts were also exposed to alpha and gamma fractions of the peptide compositions products from hair and wool for five days. The negative control was saline, and FGF was used as a positive control. The compositions containing the alpha and gamma fractions of the peptides from hair and wool at 1 and 10 ug/ml concentrations produced an increase in cell proliferation of between 30% and 60% compared to the control.

The peptide compositions reported above were fractionated and amino acid sequences obtained using tandem mass spectrometry (MS/MS). Based on the amino acid sequence data and comparison to known hair and wool keratin proteins, the peptides were localized to a conserved region of human hair and sheep wool keratin proteins. By these sequence comparisons the bioactive peptides are shown to be derived from the following conserved consensus sequence:

EVNTLR(C/S)(Q/P)LGDRLNVEVD(A/T)APTVDLN(Q/R)VLNETR(S/N)QYEAL

The peptide compositions of the present disclosure may contain, therefore, any of the following peptides in any combination.

```
                                              SEQ ID NO: 1
EVNTLRCQLGDRLNVEVDAAPTVDLNQVLNETRSQYEAL,

SEQ ID NO: 2
EVNTLRSQLGDRLNVEVDAAPTVDLNQVLNETRSQYEAL,

SEQ ID NO: 3
EVNTLRCPLGDRLNVEVDAAPTVDLNQVLNETRSQYEAL,

SEQ ID NO: 4
EVNTLRSPLGDRLNVEVDAAPTVDLNQVLNETRSQYEAL,

SEQ ID NO: 5
EVNTLRCQLGDRLNVEVDTAPTVDLNQVLNETRSQYEAL,

SEQ ID NO: 6
EVNTLRSQLGDRLNVEVDTAPTVDLNQVLNETRSQYEAL,

SEQ ID NO: 7
EVNTLRCPLGDRLNVEVDTAPTVDLNQVLNETRSQYEAL,

SEQ ID NO: 8
EVNTLRSPLGDRLNVEVDTAPTVDLNQVLNETRSQYEAL,

SEQ ID NO: 9
EVNTLRCQLGDRLNVEVDAAPTVDLNRVLNETRSQYEAL,

SEQ ID NO: 10
EVNTLRSQLGDRLNVEVDAAPTVDLNRVLNETRSQYEAL,

SEQ ID NO: 11
EVNTLRCPLGDRLNVEVDAAPTVDLNRVLNETRSQYEAL,

SEQ ID NO: 12
EVNTLRSPLGDRLNVEVDAAPTVDLNRVLNETRSQYEAL,

SEQ ID NO: 13
EVNTLRCQLGDRLNVEVDTAPTVDLNRVLNETRSQYEAL,

SEQ ID NO: 14
EVNTLRSQLGDRLNVEVDTAPTVDLNRVLNETRSQYEAL,

SEQ ID NO: 15
EVNTLRCPLGDRLNVEVDTAPTVDLNRVLNETRSQYEAL,

SEQ ID NO: 16
EVNTLRSPLGDRLNVEVDTAPTVDLNRVLNETRSQYEAL,

SEQ ID NO: 17
EVNTLRCQLGDRLNVEVDAAPTVDLNQVLNETRNQYEAL,

SEQ ID NO: 18
EVNTLRSQLGDRLNVEVDAAPTVDLNQVLNETRNQYEAL,

SEQ ID NO: 19
EVNTLRCPLGDRLNVEVDAAPTVDLNQVLNETRNQYEAL,

SEQ ID NO: 20
EVNTLRSPLGDRLNVEVDAAPTVDLNQVLNETRNQYEAL,

SEQ ID NO: 21
EVNTLRCQLGDRLNVEVDTAPTVDLNQVLNETRNQYEAL,

SEQ ID NO: 22
EVNTLRSQLGDRLNVEVDTAPTVDLNQVLNETRNQYEAL,

SEQ ID NO: 23
EVNTLRCPLGDRLNVEVDTAPTVDLNQVLNETRNQYEAL,

SEQ ID NO: 24
EVNTLRSPLGDRLNVEVDTAPTVDLNQVLNETRNQYEAL,

SEQ ID NO: 25
EVNTLRCQLGDRLNVEVDAAPTVDLNRVLNETRNQYEAL,

SEQ ID NO: 26
EVNTLRSQLGDRLNVEVDAAPTVDLNRVLNETRNQYEAL,

SEQ ID NO: 27
EVNTLRCPLGDRLNVEVDAAPTVDLNRVLNETRNQYEAL,

SEQ ID NO: 28
EVNTLRSPLGDRLNVEVDAAPTVDLNRVLNETRNQYEAL,

SEQ ID NO: 29
EVNTLRCQLGDRLNVEVDTAPTVDLNRVLNETRNQYEAL,

SEQ ID NO: 30
EVNTLRSQLGDRLNVEVDTAPTVDLNRVLNETRNQYEAL,

SEQ ID NO: 31
EVNTLRCPLGDRLNVEVDTAPTVDLNRVLNETRNQYEAL,

SEQ ID NO: 32
EVNTLRSPLGDRLNVEVDTAPTVDLNRVLNETRNQYEAL,

SEQ ID NO: 33
EVNT,

SEQ ID NO: 34
VNTL,

SEQ ID NO: 35
NTLR,

SEQ ID NO: 36
TLRC,

SEQ ID NO: 37
TLRS,

SEQ ID NO: 38
LRCQ,

SEQ ID NO: 39
LRCP,
```

-continued

LRSQ, SEQ ID NO: 40

LRSP, SEQ ID NO: 41

RCQL, SEQ ID NO: 42

RSQL, SEQ ID NO: 43

RCPL, SEQ ID NO: 44

RSPL, SEQ ID NO: 45

CQLG, SEQ ID NO: 46

CPLG, SEQ ID NO: 47

SQLG, SEQ ID NO: 48

SPLG, SEQ ID NO: 49

QLGD, SEQ ID NO: 50

PLGD, SEQ ID NO: 51

LGDR, SEQ ID NO: 52

GDRL, SEQ ID NO: 53

DRLN, SEQ ID NO: 54

RLNV, SEQ ID NO: 55

LNVE, SEQ ID NO: 56

NVEV, SEQ ID NO: 57

VEVD, SEQ ID NO: 58

EVDA, SEQ ID NO: 59

EVDT, SEQ ID NO: 60

VDAA, SEQ ID NO: 61

VDTA, SEQ ID NO: 62

DAAP, SEQ ID NO: 63

DTAP, SEQ ID NO: 64

AAPT, SEQ ID NO: 65

TATP, SEQ ID NO: 66

-continued

APTV, SEQ ID NO: 67

PTVD, SEQ ID NO: 68

TVDL, SEQ ID NO: 69

VDLN, SEQ ID NO: 70

DLNQ, SEQ ID NO: 71

DLNR, SEQ ID NO: 72

LNQV, SEQ ID NO: 73

LNRV, SEQ ID NO: 74

NQVL, SEQ ID NO: 75

NRVL, SEQ ID NO: 76

QVLN, SEQ ID NO: 77

RVLN, SEQ ID NO: 78

VLNE, SEQ ID NO: 79

LNET, SEQ ID NO: 80

NETR, SEQ ID NO: 81

ETRS, SEQ ID NO: 82

ETRN, SEQ ID NO: 83

TRSQ, SEQ ID NO: 84

TRNQ, SEQ ID NO: 85

RSQY, SEQ ID NO: 86

RNQY, SEQ ID NO: 87

SQYE, SEQ ID NO: 88

NQYE, SEQ ID NO: 89

QYEA, SEQ ID NO: 90

YEAL, SEQ ID NO: 91

EVNTL, SEQ ID NO: 92

VNTLR, SEQ ID NO: 93

NTLRC, SEQ ID NO: 94

NTLRS, SEQ ID NO: 95

TLRCQ, SEQ ID NO: 96

TLRSQ, SEQ ID NO: 97

TLRCP, SEQ ID NO: 98

TLRSP, SEQ ID NO: 99

LRCPL, SEQ ID NO: 100

LRCPL, SEQ ID NO: 101

LRSQL, SEQ ID NO: 102

LRSPL, SEQ ID NO: 103

RCQLG, SEQ ID NO: 104

RCPLG, SEQ ID NO: 105

RSQLG, SEQ ID NO: 106

RSPLG, SEQ ID NO: 107

CQLGD, SEQ ID NO: 108

CPLGD, SEQ ID NO: 109

SQLGD, SEQ ID NO: 110

SPLGD, SEQ ID NO: 111

QLGDR, SEQ ID NO: 112

PLGDR, SEQ ID NO: 113

LGDRL, SEQ ID NO: 114

GDRLN, SEQ ID NO: 115

DRLNV, SEQ ID NO: 116

RLNVE, SEQ ID NO: 117

LNVEV, SEQ ID NO: 118

NVEVD, SEQ ID NO: 119

VEVDA, SEQ ID NO: 120

VEVDT, SEQ ID NO: 121

EVDAA, SEQ ID NO: 122

EVDTA, SEQ ID NO: 123

VDAAP, SEQ ID NO: 124

VDTAP, SEQ ID NO: 125

DAAPT, SEQ ID NO: 126

DTAPT, SEQ ID NO: 127

AAPTV, SEQ ID NO: 128

TAPTV, SEQ ID NO: 129

APTVD, SEQ ID NO: 130

PTVDL, SEQ ID NO: 131

TVDLN, SEQ ID NO: 132

VDLNQ, SEQ ID NO: 133

VDLNR, SEQ ID NO: 134

DLNQV, SEQ ID NO: 135

DLNRV, SEQ ID NO: 136

LNQVL, SEQ ID NO: 137

LNRVL, SEQ ID NO: 138

NQVLN, SEQ ID NO: 139

NRVLN, SEQ ID NO: 140

QVLNE, SEQ ID NO: 141

RVLNE, SEQ ID NO: 142

VLNET, SEQ ID NO: 143

LNETR, SEQ ID NO: 144

NETRS, SEQ ID NO: 145

NETRN, SEQ ID NO: 146

ETRSQ, SEQ ID NO: 147

| | |
|---|---|
| ETRNQ, | SEQ ID NO: 148 |
| TRSQY, | SEQ ID NO: 149 |
| TRNQY, | SEQ ID NO: 150 |
| RSQYE, | SEQ ID NO: 151 |
| RNQYE, | SEQ ID NO: 152 |
| SQYEA, | SEQ ID NO: 153 |
| NQYEA, | SEQ ID NO: 154 |
| QYEAL, | SEQ ID NO: 155 |
| EVNTLR, | SEQ ID NO: 156 |
| VNTLRC, | SEQ ID NO: 157 |
| VNTLRS, | SEQ ID NO: 158 |
| NTLRCQ, | SEQ ID NO: 159 |
| NTLRCP, | SEQ ID NO: 160 |
| NTLRSQ, | SEQ ID NO: 161 |
| NTLRSP, | SEQ ID NO: 162 |
| TLRCQL, | SEQ ID NO: 163 |
| TLRCPL, | SEQ ID NO: 164 |
| TLRSQL, | SEQ ID NO: 165 |
| TLRSPL, | SEQ ID NO: 166 |
| LRCQLG, | SEQ ID NO: 167 |
| LRCPLG, | SEQ ID NO: 168 |
| LRSQLG, | SEQ ID NO: 169 |
| LRSPLG, | SEQ ID NO: 170 |
| RCQLGD, | SEQ ID NO: 171 |
| RCPLGD, | SEQ ID NO: 172 |
| RSQLGD, | SEQ ID NO: 173 |
| RSPLGD, | SEQ ID NO: 174 |
| CQLGDR, | SEQ ID NO: 175 |
| CPLGDR, | SEQ ID NO: 176 |
| SQLGDR, | SEQ ID NO: 177 |
| SPLGDR, | SEQ ID NO: 178 |
| QLGDRL, | SEQ ID NO: 179 |
| PLGDRL, | SEQ ID NO: 180 |
| LGDRLN, | SEQ ID NO: 181 |
| GDRLNV, | SEQ ID NO: 182 |
| DRLNVE, | SEQ ID NO: 183 |
| RLNVEV, | SEQ ID NO: 184 |
| LNVEVD, | SEQ ID NO: 185 |
| NVEVDA, | SEQ ID NO: 186 |
| NVEVDT, | SEQ ID NO: 187 |
| VEVDAA, | SEQ ID NO: 188 |
| VEVDTA, | SEQ ID NO: 189 |
| EVDAAP, | SEQ ID NO: 190 |
| EVDTAP, | SEQ ID NO: 191 |
| VDAAPT, | SEQ ID NO: 192 |
| VDTAPT, | SEQ ID NO: 193 |
| DAAPTV, | SEQ ID NO: 194 |
| DTAPTV, | SEQ ID NO: 195 |
| AAPTVD, | SEQ ID NO: 196 |
| TAPTVD, | SEQ ID NO: 197 |
| APTVDL, | SEQ ID NO: 198 |
| PTVDLN, | SEQ ID NO: 199 |
| TVDLNQ, | SEQ ID NO: 200 |
| TVDLNR, | SEQ ID NO: 201 |

| | |
|---|---|
| VDLNQV, | SEQ ID NO: 202 |
| VDLNRV, | SEQ ID NO: 203 |
| DLNQVL, | SEQ ID NO: 204 |
| DLNRVL, | SEQ ID NO: 205 |
| LNQVLN, | SEQ ID NO: 206 |
| LNRVLN, | SEQ ID NO: 207 |
| NQVLNE, | SEQ ID NO: 208 |
| NRVLNE, | SEQ ID NO: 209 |
| QVLNET, | SEQ ID NO: 210 |
| RVLNET, | SEQ ID NO: 211 |
| VLNETR, | SEQ ID NO: 212 |
| LNETRS, | SEQ ID NO: 213 |
| LNETRN, | SEQ ID NO: 214 |
| NETRSQ, | SEQ ID NO: 215 |
| NETRNQ, | SEQ ID NO: 216 |
| ETRSQY, | SEQ ID NO: 217 |
| ETRNQY, | SEQ ID NO: 218 |
| TRSQYE, | SEQ ID NO: 219 |
| TRNQYE, | SEQ ID NO: 220 |
| RSQYEA, | SEQ ID NO: 221 |
| RNQYEA, | SEQ ID NO: 222 |
| SQYEAL, | SEQ ID NO: 223 |
| NQYEAL, | SEQ ID NO: 224 |
| EVNTLRC, | SEQ ID NO: 225 |
| EVNTLRS, | SEQ ID NO: 226 |
| VNTLRCQ, | SEQ ID NO: 227 |
| VNTLRCP, | SEQ ID NO: 228 |
| VNTLRSQ, | SEQ ID NO: 229 |
| VNTLRSP, | SEQ ID NO: 230 |
| NTLRCQL, | SEQ ID NO: 231 |
| NTLRCPL, | SEQ ID NO: 232 |
| NTLRSQL, | SEQ ID NO: 233 |
| NTLRSPL, | SEQ ID NO: 234 |
| TLRCQLG, | SEQ ID NO: 235 |
| TLRCPLG, | SEQ ID NO: 236 |
| TLRSQLG, | SEQ ID NO: 237 |
| TLRSPLG, | SEQ ID NO: 238 |
| LRCQLGD, | SEQ ID NO: 239 |
| LRCPLGD, | SEQ ID NO: 240 |
| LRSQLGD, | SEQ ID NO: 241 |
| LRSPLGD, | SEQ ID NO: 242 |
| RCQLGDR, | SEQ ID NO: 243 |
| RCPLGDR, | SEQ ID NO: 244 |
| RSQLGDR, | SEQ ID NO: 245 |
| RSPLGDR, | SEQ ID NO: 246 |
| CQLGDRL, | SEQ ID NO: 247 |
| CPLGDRL, | SEQ ID NO: 248 |
| SQLGDRL, | SEQ ID NO: 249 |
| SPLGDRL, | SEQ ID NO: 250 |
| QLGDRLN, | SEQ ID NO: 251 |
| PLGDRLN, | SEQ ID NO: 252 |
| LGDRLNV, | SEQ ID NO: 253 |
| GDRLNVE, | SEQ ID NO: 254 |
| DRLNVEV, | SEQ ID NO: 255 |

| | |
|---|---|
| RLNVEVD, | SEQ ID NO: 256 |
| LNVEVDA, | SEQ ID NO: 257 |
| LNVEVDT, | SEQ ID NO: 258 |
| NVEVDAA, | SEQ ID NO: 259 |
| NVEVDTA, | SEQ ID NO: 260 |
| VEVDAAP, | SEQ ID NO: 261 |
| VEVDTAP, | SEQ ID NO: 262 |
| EVDAAPT, | SEQ ID NO: 263 |
| EVDTAPT, | SEQ ID NO: 264 |
| VDAAPTV, | SEQ ID NO: 265 |
| VDTAPTV, | SEQ ID NO: 266 |
| DAAPTVD, | SEQ ID NO: 267 |
| DTAPTVD, | SEQ ID NO: 268 |
| AAPTVDL, | SEQ ID NO: 269 |
| TAPTVDL, | SEQ ID NO: 270 |
| APTVDLN, | SEQ ID NO: 271 |
| PTVDLNQ, | SEQ ID NO: 272 |
| PTVDLNR, | SEQ ID NO: 273 |
| TVDLNQV, | SEQ ID NO: 274 |
| TVDLNRV, | SEQ ID NO: 275 |
| VDLNQVL, | SEQ ID NO: 276 |
| VDLNRVL, | SEQ ID NO: 277 |
| DLNQVLN, | SEQ ID NO: 278 |
| DLNRVLN, | SEQ ID NO: 279 |
| LNQVLNE, | SEQ ID NO: 280 |
| LNRVLNE, | SEQ ID NO: 281 |
| NQVLNET, | SEQ ID NO: 282 |
| NRVLNET, | SEQ ID NO: 283 |
| QVLNETR, | SEQ ID NO: 284 |
| RVLNETR, | SEQ ID NO: 285 |
| VLNETRS, | SEQ ID NO: 286 |
| VLNETRN, | SEQ ID NO: 287 |
| LNETRSQ, | SEQ ID NO: 288 |
| LNETRNQ, | SEQ ID NO: 289 |
| NETRSQY, | SEQ ID NO: 290 |
| NETRNQY, | SEQ ID NO: 291 |
| ETRSQYE, | SEQ ID NO: 292 |
| ETRNQYE, | SEQ ID NO: 293 |
| TRSQYEA, | SEQ ID NO: 294 |
| TRNQYEA, | SEQ ID NO: 295 |
| RSQYEAL, | SEQ ID NO: 296 |
| RNQYEAL, | SEQ ID NO: 297 |
| EVNTLRCQ, | SEQ ID NO: 298 |
| EVNTLRCP, | SEQ ID NO: 299 |
| EVNTLRSQ, | SEQ ID NO: 300 |
| EVNTLRSP, | SEQ ID NO: 301 |
| VNTLRCQL, | SEQ ID NO: 302 |
| VNTLRCPL, | SEQ ID NO: 303 |
| VNTLRSQL, | SEQ ID NO: 304 |
| VNTLRSPL, | SEQ ID NO: 305 |
| NTLRCQLG, | SEQ ID NO: 306 |
| NTLRCPLG, | SEQ ID NO: 307 |
| NTLRSQLG, | SEQ ID NO: 308 |
| NTLRSPLG, | SEQ ID NO: 309 |

| | |
|---|---|
| TLRCQLGD, | SEQ ID NO: 310 |
| TLRCPLGD, | SEQ ID NO: 311 |
| TLRSQLGD, | SEQ ID NO: 312 |
| TLRSPLGD, | SEQ ID NO: 313 |
| LRCQLGDR, | SEQ ID NO: 314 |
| LRCPLGDR, | SEQ ID NO: 315 |
| LRSQLGDR, | SEQ ID NO: 316 |
| LRSPLGDR, | SEQ ID NO: 317 |
| RCQLGDRL, | SEQ ID NO: 318 |
| RCPLGDRL, | SEQ ID NO: 319 |
| RSQLGDRL, | SEQ ID NO: 320 |
| RSPLGDRL, | SEQ ID NO: 321 |
| CQLGDRLN, | SEQ ID NO: 322 |
| CPLGDRLN, | SEQ ID NO: 323 |
| SQLGDRLN, | SEQ ID NO: 324 |
| SPLGDRLN, | SEQ ID NO: 325 |
| QLGDRLNV, | SEQ ID NO: 326 |
| PLGDRLNV, | SEQ ID NO: 327 |
| LGDRLNVE, | SEQ ID NO: 328 |
| GDRLNVEV, | SEQ ID NO: 329 |
| DRLNVEVD, | SEQ ID NO: 330 |
| RLNVEVDA, | SEQ ID NO: 331 |
| RLNVEVDT, | SEQ ID NO: 332 |
| LNVEVDAA, | SEQ ID NO: 333 |
| LNVEVDTA, | SEQ ID NO: 334 |
| NVEVDAAP, | SEQ ID NO: 335 |
| NVEVDTAP, | SEQ ID NO: 336 |
| VEVDAAPT, | SEQ ID NO: 337 |
| VEVDTAPT, | SEQ ID NO: 338 |
| EVDAAPTV, | SEQ ID NO: 339 |
| EVDTAPTV, | SEQ ID NO: 340 |
| VDAAPTVD, | SEQ ID NO: 341 |
| VDTAPTVD, | SEQ ID NO: 342 |
| DAAPTVDL, | SEQ ID NO: 343 |
| DTAPTVDL, | SEQ ID NO: 344 |
| AAPTVDLN, | SEQ ID NO: 345 |
| TAPTVDLN, | SEQ ID NO: 346 |
| APTVDLNQ, | SEQ ID NO: 347 |
| APTVDLNR, | SEQ ID NO: 348 |
| PTVDLNQV, | SEQ ID NO: 349 |
| PTVDLNRV, | SEQ ID NO: 350 |
| TVDLNQVL, | SEQ ID NO: 351 |
| TVDLNRVL, | SEQ ID NO: 352 |
| VDLNQVLN, | SEQ ID NO: 353 |
| VDLNRVLN, | SEQ ID NO: 354 |
| DLNQVLNE, | SEQ ID NO: 355 |
| DLNRVLNE, | SEQ ID NO: 356 |
| LNQVLNET, | SEQ ID NO: 357 |
| LNRVLNET, | SEQ ID NO: 358 |
| NQVLNETR, | SEQ ID NO: 359 |
| NRVLNETR, | SEQ ID NO: 360 |
| QVLNETRS, | SEQ ID NO: 361 |
| QVLNETRN, | SEQ ID NO: 362 |
| RVLNETRS, | SEQ ID NO: 363 |

| | |
|---|---|
| RVLNETRN, | SEQ ID NO: 364 |
| VLNETRSQ, | SEQ ID NO: 365 |
| VLNETRNQ, | SEQ ID NO: 366 |
| LNETRSQY, | SEQ ID NO: 367 |
| LNETRNQY, | SEQ ID NO: 368 |
| NETRSQYE, | SEQ ID NO: 369 |
| NETRNQYE, | SEQ ID NO: 370 |
| ETRSQYEA, | SEQ ID NO: 371 |
| ETRNQYEA, | SEQ ID NO: 372 |
| TRSQYEAL, | SEQ ID NO: 373 |
| TRNQYEAL, | SEQ ID NO: 374 |
| EVNTLRCQL, | SEQ ID NO: 375 |
| EVNTLRCPL, | SEQ ID NO: 376 |
| EVNTLRSQL, | SEQ ID NO: 377 |
| EVNTLRSPL, | SEQ ID NO: 378 |
| VNTLRCQLG, | SEQ ID NO: 379 |
| VNTLRCPLG, | SEQ ID NO: 380 |
| VNTLRSQLG, | SEQ ID NO: 381 |
| VNTLRSPLG, | SEQ ID NO: 382 |
| NTLRCQLGD, | SEQ ID NO: 383 |
| NTLRCPLGD, | SEQ ID NO: 384 |
| NTLRSQLGD, | SEQ ID NO: 385 |
| NTLRSPLGD, | SEQ ID NO: 386 |
| TLRCQLGDR, | SEQ ID NO: 387 |
| TLRCPLGDR, | SEQ ID NO: 388 |
| TLRSQLGDR, | SEQ ID NO: 389 |
| TLRSPLGDR, | SEQ ID NO: 390 |
| LRCQLGDRL, | SEQ ID NO: 391 |
| LRCPLGDRL, | SEQ ID NO: 392 |
| LRSQLGDRL, | SEQ ID NO: 393 |
| LRSPLGDRL, | SEQ ID NO: 394 |
| RCQLGDRLN, | SEQ ID NO: 395 |
| RCPLGDRLN, | SEQ ID NO: 396 |
| RSQLGDRLN, | SEQ ID NO: 397 |
| RSPLGDRLN, | SEQ ID NO: 398 |
| CQLGDRLNV, | SEQ ID NO: 399 |
| CPLGDRLNV, | SEQ ID NO: 400 |
| SQLGDRLNV, | SEQ ID NO: 401 |
| SPLGDRLNV, | SEQ ID NO: 402 |
| QLGDRLNVE, | SEQ ID NO: 403 |
| PLGDRLNVE, | SEQ ID NO: 404 |
| LGDRLNVEV, | SEQ ID NO: 405 |
| GDRLNVEVD, | SEQ ID NO: 406 |
| DRLNVEVDA, | SEQ ID NO: 407 |
| DRLNVEVDT, | SEQ ID NO: 408 |
| RLNVEVDAA, | SEQ ID NO: 409 |
| RLNVEVDTA, | SEQ ID NO: 410 |
| LNVEVDAAP, | SEQ ID NO: 411 |
| LNVEVDTAP, | SEQ ID NO: 412 |
| NVEVDTAPT, | SEQ ID NO: 413 |
| NVEVDAAPT, | SEQ ID NO: 414 |
| VEVDAAPTV, | SEQ ID NO: 415 |
| VEVDTAPTV, | SEQ ID NO: 416 |
| EVDAAPTVD, | SEQ ID NO: 417 |

| | |
|---|---|
| EVDTAPTVD, | SEQ ID NO: 418 |
| VDAAPTVDL, | SEQ ID NO: 419 |
| VDTAPTVDL, | SEQ ID NO: 420 |
| DAAPTVDLN, | SEQ ID NO: 421 |
| DTAPTVDLN, | SEQ ID NO: 422 |
| AAPTVDLNQ, | SEQ ID NO: 423 |
| AAPTVDLNR, | SEQ ID NO: 424 |
| TAPTVDLNQ, | SEQ ID NO: 425 |
| TAPTVDLNR, | SEQ ID NO: 426 |
| APTVDLNQV, | SEQ ID NO: 427 |
| APTVDLNRV, | SEQ ID NO: 428 |
| PTVDLNQVL, | SEQ ID NO: 429 |
| PTVDLNRVL, | SEQ ID NO: 430 |
| TVDLNQVLN, | SEQ ID NO: 431 |
| TVDLNRVLN, | SEQ ID NO: 432 |
| VDLNQVLNE, | SEQ ID NO: 433 |
| VDLNRVLNE, | SEQ ID NO: 434 |
| DLNQVLNET, | SEQ ID NO: 435 |
| DLNRVLNET, | SEQ ID NO: 436 |
| LNQVLNETR, | SEQ ID NO: 437 |
| LNRVLNETR, | SEQ ID NO: 438 |
| NQVLNETRS, | SEQ ID NO: 439 |
| NQVLNETRN, | SEQ ID NO: 440 |
| NRVLNETRS, | SEQ ID NO: 441 |
| NRVLNETRN, | SEQ ID NO: 442 |
| QVLNETRSQ, | SEQ ID NO: 443 |
| QVLNETRNQ, | SEQ ID NO: 444 |
| RVLNETRSQ, | SEQ ID NO: 445 |
| RVLNETRNQ, | SEQ ID NO: 446 |
| VLNETRSQY, | SEQ ID NO: 447 |
| VLNETRNQY, | SEQ ID NO: 448 |
| LNETRSQYE, | SEQ ID NO: 449 |
| LNETRNQYE, | SEQ ID NO: 450 |
| NETRSQYEA, | SEQ ID NO: 451 |
| NETRNQYEA, | SEQ ID NO: 452 |
| ETRSQYEAL, | SEQ ID NO: 453 |
| ETRNQYEAL, | SEQ ID NO: 454 |
| EVNTLRCQLG, | SEQ ID NO: 455 |
| EVNTLRCPLG, | SEQ ID NO: 456 |
| EVNTLRSQLG, | SEQ ID NO: 457 |
| EVNTLRSPLG, | SEQ ID NO: 458 |
| VNTLRCQLGD, | SEQ ID NO: 459 |
| VNTLRCPLGD, | SEQ ID NO: 460 |
| VNTLRSQLGD, | SEQ ID NO: 461 |
| VNTLRSPLGD, | SEQ ID NO: 462 |
| NTLRCQLGDR, | SEQ ID NO: 463 |
| NTLRCPLGDR, | SEQ ID NO: 464 |
| NTLRSQLGDR, | SEQ ID NO: 465 |
| NTLRSPLGDR, | SEQ ID NO: 466 |
| TLRCQLGDRL, | SEQ ID NO: 467 |
| TLRCPLGDRL, | SEQ ID NO: 468 |
| TLRSQLGDRL, | SEQ ID NO: 469 |
| TLRSPLGDRL, | SEQ ID NO: 470 |
| LRCQLGDRLN, | SEQ ID NO: 471 |

| Sequence | SEQ ID NO |
|---|---|
| LRCPLGDRLN, | SEQ ID NO: 472 |
| LRSQLGDRLN, | SEQ ID NO: 473 |
| LRSPLGDRLN, | SEQ ID NO: 474 |
| RCQLGDRLNV, | SEQ ID NO: 475 |
| RCPLGDRLNV, | SEQ ID NO: 476 |
| RSQLGDRLNV, | SEQ ID NO: 477 |
| RSPLGDRLNV, | SEQ ID NO: 478 |
| CQLGDRLNVE, | SEQ ID NO: 479 |
| CPLGDRLNVE, | SEQ ID NO: 480 |
| SQLGDRLNVE, | SEQ ID NO: 481 |
| SPLGDRLNVE, | SEQ ID NO: 482 |
| QLGDRLNVEV, | SEQ ID NO: 483 |
| PLGDRLNVEV, | SEQ ID NO: 484 |
| LGDRLNVEVD, | SEQ ID NO: 485 |
| GDRLNVEVDA, | SEQ ID NO: 486 |
| GDRLNVEVDT, | SEQ ID NO: 487 |
| DRLNVEVDAA, | SEQ ID NO: 488 |
| DRLNVEVDTA, | SEQ ID NO: 489 |
| RLNVEVDAAP, | SEQ ID NO: 490 |
| RLNVEVDTAP, | SEQ ID NO: 491 |
| LNVEVDAAPT, | SEQ ID NO: 492 |
| LNVEVDTAPT, | SEQ ID NO: 493 |
| NVEVDAAPTV, | SEQ ID NO: 494 |
| NVEVDTAPTV, | SEQ ID NO: 495 |
| VEVDAAPTVD, | SEQ ID NO: 496 |
| VEVDTAPTVD, | SEQ ID NO: 497 |
| EVDAAPTVDL, | SEQ ID NO: 498 |
| EVDTAPTVDL, | SEQ ID NO: 499 |
| VDAAPTVDLN, | SEQ ID NO: 500 |
| VDTAPTVDLN, | SEQ ID NO: 501 |
| DAAPTVDLNR, | SEQ ID NO: 502 |
| DAAPTVDLNQ, | SEQ ID NO: 503 |
| DTAPTVDLNR, | SEQ ID NO: 504 |
| DTAPTVDLNQ, | SEQ ID NO: 505 |
| AAPTVDLNQV, | SEQ ID NO: 506 |
| AAPTVDLNRV, | SEQ ID NO: 507 |
| TAPTVDLNQV, | SEQ ID NO: 508 |
| TAPTVDLNRV, | SEQ ID NO: 509 |
| APTVDLNQVL, | SEQ ID NO: 510 |
| APTVDLNRVL, | SEQ ID NO: 511 |
| PTVDLNQVLN, | SEQ ID NO: 512 |
| PTVDLNRVLN, | SEQ ID NO: 513 |
| TVDLNQVLNE, | SEQ ID NO: 514 |
| TVDLNRVLNE, | SEQ ID NO: 515 |
| VDLNQVLNET, | SEQ ID NO: 516 |
| VDLNRVLNET, | SEQ ID NO: 517 |
| DLNQVLNETR, | SEQ ID NO: 518 |
| DLNRVLNETR, | SEQ ID NO: 519 |
| LNQVLNETRS, | SEQ ID NO: 520 |
| LNQVLNETRN, | SEQ ID NO: 521 |
| LNRVLNETRS, | SEQ ID NO: 522 |
| LNRVLNETRN, | SEQ ID NO: 523 |
| NQVLNETRSQ, | SEQ ID NO: 524 |
| NQVLNETRNQ, | SEQ ID NO: 525 |

| | |
|---|---|
| NRVLNETRSQ, | SEQ ID NO: 526 |
| NRVLNETRNQ, | SEQ ID NO: 527 |
| QVLNETRSQY, | SEQ ID NO: 528 |
| QVLNETRNQY, | SEQ ID NO: 529 |
| RVLNETRSQY, | SEQ ID NO: 530 |
| RVLNETRNQY, | SEQ ID NO: 531 |
| QVLNETRSQY, | SEQ ID NO: 532 |
| QVLNETRNQY, | SEQ ID NO: 533 |
| RVLNETRSQY, | SEQ ID NO: 534 |
| RVLNETRNQY, | SEQ ID NO: 535 |
| VLNETRSQYE, | SEQ ID NO: 536 |
| VLNETRNQYE, | SEQ ID NO: 537 |
| LNETRSQYEA, | SEQ ID NO: 538 |
| LNETRNQYEA, | SEQ ID NO: 539 |
| NETRSQYEAL, | SEQ ID NO: 540 |
| NETRNQYEAL, | SEQ ID NO: 541 |
| EVNTLRCQLGD, | SEQ ID NO: 542 |
| EVNTLRCPLGD, | SEQ ID NO: 543 |
| EVNTLRSQLGD, | SEQ ID NO: 544 |
| EVNTLRSPLGD, | SEQ ID NO: 545 |
| VNTLRCQLGDR, | SEQ ID NO: 546 |
| VNTLRCPLGDR, | SEQ ID NO: 547 |
| VNTLRSQLGDR, | SEQ ID NO: 548 |
| VNTLRSPLGDR, | SEQ ID NO: 549 |
| NTLRCQLGDRL, | SEQ ID NO: 550 |
| NTLRCPLGDRL, | SEQ ID NO: 551 |
| NTLRSQLGDRL, | SEQ ID NO: 552 |
| NTLRSPLGDRL, | SEQ ID NO: 553 |
| TLRCQLGDRLN, | SEQ ID NO: 554 |
| TLRCPLGDRLN, | SEQ ID NO: 555 |
| TLRSQLGDRLN, | SEQ ID NO: 556 |
| TLRSPLGDRLN, | SEQ ID NO: 557 |
| LRCQLGDRLNV, | SEQ ID NO: 558 |
| LRCPLGDRLNV, | SEQ ID NO: 559 |
| LRSQLGDRLNV, | SEQ ID NO: 560 |
| LRSPLGDRLNV, | SEQ ID NO: 561 |
| RCQLGDRLNVE, | SEQ ID NO: 562 |
| RCPLGDRLNVE, | SEQ ID NO: 563 |
| RSQLGDRLNVE, | SEQ ID NO: 564 |
| RSPLGDRLNVE, | SEQ ID NO: 565 |
| CQLGDRLNVEV, | SEQ ID NO: 566 |
| CPLGDRLNVEV, | SEQ ID NO: 567 |
| SQLGDRLNVEV, | SEQ ID NO: 568 |
| SPLGDRLNVEV, | SEQ ID NO: 569 |
| QLGDRLNVEVD, | SEQ ID NO: 570 |
| PLGDRLNVEVD, | SEQ ID NO: 571 |
| LGDRLNVEVDA, | SEQ ID NO: 572 |
| LGDRLNVEVDT, | SEQ ID NO: 573 |
| GDRLNVEVDAA, | SEQ ID NO: 574 |
| GDRLNVEVDTA, | SEQ ID NO: 575 |
| DRLNVEVDAAP, | SEQ ID NO: 576 |
| DRLNVEVDTAP, | SEQ ID NO: 577 |
| RLNVEVDAAPT, | SEQ ID NO: 578 |
| RLNVEVDTAPT, | SEQ ID NO: 579 |

-continued

| | |
|---|---|
| LNVEVDAAPTV, | SEQ ID NO: 580 |
| LNVEVDTAPTV, | SEQ ID NO: 581 |
| NVEVDAAPTVD, | SEQ ID NO: 582 |
| NVEVDTAPTVD, | SEQ ID NO: 583 |
| VEVDAAPTVDL, | SEQ ID NO: 584 |
| VEVDTAPTVDL, | SEQ ID NO: 585 |
| EVDAAPTVDLN, | SEQ ID NO: 586 |
| EVDTAPTVDLN, | SEQ ID NO: 587 |
| VDAAPTVDLNQ, | SEQ ID NO: 588 |
| VDAAPTVDLNR, | SEQ ID NO: 589 |
| VDTAPTVDLNQ, | SEQ ID NO: 590 |
| VDTAPTVDLNR, | SEQ ID NO: 591 |
| DAAPTVDLNQV, | SEQ ID NO: 592 |
| DAAPTVDLNRV, | SEQ ID NO: 593 |
| DTAPTVDLNQV, | SEQ ID NO: 594 |
| DTAPTVDLNRV, | SEQ ID NO: 595 |
| AAPTVDLNQVL, | SEQ ID NO: 596 |
| AAPTVDLNRVL, | SEQ ID NO: 597 |
| TAPTVDLNQVL, | SEQ ID NO: 598 |
| TAPTVDLNRVL, | SEQ ID NO: 599 |
| APTVDLNQVLN, | SEQ ID NO: 600 |
| APTVDLNRVLN, | SEQ ID NO: 601 |
| PTVDLNQVLNE, | SEQ ID NO: 602 |
| PTVDLNRVLNE, | SEQ ID NO: 603 |
| TVDLNQVLNET, | SEQ ID NO: 604 |
| TVDLNRVLNET, | SEQ ID NO: 605 |
| VDLNQVLNETR, | SEQ ID NO: 606 |

-continued

| | |
|---|---|
| VDLNRVLNETR, | SEQ ID NO: 607 |
| DLNQVLNETRS, | SEQ ID NO: 608 |
| DLNQVLNETRN, | SEQ ID NO: 609 |
| DLNRVLNETRS, | SEQ ID NO: 610 |
| DLNRVLNETRN, | SEQ ID NO: 611 |
| LNQVLNETRSQ, | SEQ ID NO: 612 |
| LNQVLNETRNQ, | SEQ ID NO: 613 |
| LNRVLNETRSQ, | SEQ ID NO: 614 |
| LNRVLNETRNQ, | SEQ ID NO: 615 |
| NQVLNETRSQY, | SEQ ID NO: 616 |
| NQVLNETRNQY, | SEQ ID NO: 617 |
| NRVLNETRSQY, | SEQ ID NO: 618 |
| NRVLNETRNQY, | SEQ ID NO: 619 |
| QVLNETRSQYE, | SEQ ID NO: 620 |
| QVLNETRNQYE, | SEQ ID NO: 621 |
| RVLNETRSQYE, | SEQ ID NO: 622 |
| RVLNETRNQYE, | SEQ ID NO: 623 |
| VLNETRSQYEA, | SEQ ID NO: 624 |
| VLNETRNQYEA, | SEQ ID NO: 625 |
| LNETRSQYEAL, | SEQ ID NO: 626 |
| LNETRNQYEAL, | SEQ ID NO: 627 |
| EVNTLRCQLGDR, | SEQ ID NO: 628 |
| EVNTLRCPLGDR, | SEQ ID NO: 629 |
| EVNTLRSQLGDR, | SEQ ID NO: 630 |
| EVNTLRSPLGDR, | SEQ ID NO: 631 |
| VNTLRCQLGDRL, | SEQ ID NO: 632 |
| VNTLRCPLGDRL, | SEQ ID NO: 633 |

| | |
|---|---|
| VNTLRSQLGDRL, | SEQ ID NO: 634 |
| VNTLRSPLGDRL, | SEQ ID NO: 635 |
| NTLRCQLGDRLN, | SEQ ID NO: 636 |
| NTLRCPLGDRLN, | SEQ ID NO: 637 |
| NTLRSQLGDRLN, | SEQ ID NO: 638 |
| NTLRSPLGDRLN, | SEQ ID NO: 639 |
| TLRCQLGDRLNV, | SEQ ID NO: 640 |
| TLRCPLGDRLNV, | SEQ ID NO: 641 |
| TLRSQLGDRLNV, | SEQ ID NO: 642 |
| TLRSPLGDRLNV, | SEQ ID NO: 643 |
| LRCQLGDRLNVE, | SEQ ID NO: 644 |
| LRCPLGDRLNVE, | SEQ ID NO: 645 |
| LRSQLGDRLNVE, | SEQ ID NO: 646 |
| LRSPLGDRLNVE, | SEQ ID NO: 647 |
| RCQLGDRLNVEV, | SEQ ID NO: 648 |
| RCPLGDRLNVEV, | SEQ ID NO: 649 |
| RSQLGDRLNVEV, | SEQ ID NO: 650 |
| RSPLGDRLNVEV, | SEQ ID NO: 651 |
| CQLGDRLNVEVD, | SEQ ID NO: 652 |
| CPLGDRLNVEVD, | SEQ ID NO: 653 |
| SQLGDRLNVEVD, | SEQ ID NO: 654 |
| SPLGDRLNVEVD, | SEQ ID NO: 655 |
| QLGDRLNVEVDA, | SEQ ID NO: 656 |
| QLGDRLNVEVDT, | SEQ ID NO: 657 |
| PLGDRLNVEVDA, | SEQ ID NO: 658 |
| PLGDRLNVEVDT, | SEQ ID NO: 659 |
| LGDRLNVEVDAA, | SEQ ID NO: 660 |
| LGDRLNVEVDTA, | SEQ ID NO: 661 |
| GDRLNVEVDAAP, | SEQ ID NO: 662 |
| GDRLNVEVDTAP, | SEQ ID NO: 663 |
| DRLNVEVDAAPT, | SEQ ID NO: 664 |
| DRLNVEVDTAPT, | SEQ ID NO: 665 |
| RLNVEVDAAPTV, | SEQ ID NO: 666 |
| RLNVEVDTAPTV, | SEQ ID NO: 667 |
| LNVEVDAAPTVD, | SEQ ID NO: 668 |
| LNVEVDTAPTVD, | SEQ ID NO: 669 |
| NVEVDAAPTVDL, | SEQ ID NO: 670 |
| NVEVDTAPTVDL, | SEQ ID NO: 671 |
| VEVDAAPTVDLN, | SEQ ID NO: 672 |
| VEVDTAPTVDLN, | SEQ ID NO: 673 |
| EVDAAPTVDLNQ, | SEQ ID NO: 674 |
| EVDAAPTVDLNR, | SEQ ID NO: 675 |
| EVDTAPTVDLNQ, | SEQ ID NO: 676 |
| EVDTAPTVDLNR, | SEQ ID NO: 677 |
| VDAAPTVDLNQV, | SEQ ID NO: 678 |
| VDAAPTVDLNRV, | SEQ ID NO: 679 |
| VDTAPTVDLNQV, | SEQ ID NO: 680 |
| VDTAPTVDLNRV, | SEQ ID NO: 681 |
| DAAPTVDLNQVL, | SEQ ID NO: 682 |
| DAAPTVDLNRVL, | SEQ ID NO: 683 |
| DTAPTVDLNQVL, | SEQ ID NO: 684 |
| DTAPTVDLNRVL, | SEQ ID NO: 685 |
| AAPTVDLNQVLN, | SEQ ID NO: 686 |
| AAPTVDLNRVLN, | SEQ ID NO: 687 |

| | |
|---|---|
| TAPTVDLNQVLN, | SEQ ID NO: 688 |
| TAPTVDLNRVLN, | SEQ ID NO: 689 |
| APTVDLNQVLNE, | SEQ ID NO: 690 |
| APTVDLNRVLNE, | SEQ ID NO: 691 |
| PTVDLNQVLNET, | SEQ ID NO: 692 |
| PTVDLNRVLNET, | SEQ ID NO: 693 |
| TVDLNQVLNETR, | SEQ ID NO: 694 |
| TVDLNRVLNETR, | SEQ ID NO: 695 |
| VDLNQVLNETRS, | SEQ ID NO: 696 |
| VDLNQVLNETRN, | SEQ ID NO: 697 |
| VDLNRVLNETRS, | SEQ ID NO: 698 |
| VDLNRVLNETRN, | SEQ ID NO: 699 |
| DLNQVLNETRSQ, | SEQ ID NO: 700 |
| DLNQVLNETRNQ, | SEQ ID NO: 701 |
| DLNRVLNETRSQ, | SEQ ID NO: 702 |
| DLNRVLNETRNQ, | SEQ ID NO: 703 |
| LNQVLNETRSQY, | SEQ ID NO: 704 |
| LNQVLNETRNQY, | SEQ ID NO: 705 |
| LNRVLNETRSQY, | SEQ ID NO: 706 |
| LNRVLNETRNQY, | SEQ ID NO: 707 |
| NQVLNETRSQYE, | SEQ ID NO: 708 |
| LNQVLNETRNQY, | SEQ ID NO: 709 |
| LNRVLNETRSQY, | SEQ ID NO: 710 |
| LNRVLNETRNQY, | SEQ ID NO: 711 |
| QVLNETRSQYEA, | SEQ ID NO: 712 |
| QVLNETRNQYEA, | SEQ ID NO: 713 |
| RVLNETRSQYEA, | SEQ ID NO: 714 |
| RVLNETRNQYEA, | SEQ ID NO: 715 |
| VLNETRSQYEAL, | SEQ ID NO: 716 |
| VLNETRNQYEAL, | SEQ ID NO: 717 |
| EVNTLRCQLGDRL, | SEQ ID NO: 718 |
| EVNTLRCPLGDRL, | SEQ ID NO: 719 |
| EVNTLRSQLGDRL, | SEQ ID NO: 720 |
| EVNTLRSPLGDRL, | SEQ ID NO: 721 |
| VNTLRCQLGDRLN, | SEQ ID NO: 722 |
| VNTLRCPLGDRLN, | SEQ ID NO: 723 |
| VNTLRSQLGDRLN, | SEQ ID NO: 724 |
| VNTLRSPLGDRLN, | SEQ ID NO: 725 |
| NTLRCQLGDRLNV, | SEQ ID NO: 726 |
| NTLRCPLGDRLNV, | SEQ ID NO: 727 |
| NTLRSQLGDRLNV, | SEQ ID NO: 728 |
| NTLRSPLGDRLNV, | SEQ ID NO: 729 |
| TLRCQLGDRLNVE, | SEQ ID NO: 730 |
| TLRCPLGDRLNVE, | SEQ ID NO: 731 |
| TLRSQLGDRLNVE, | SEQ ID NO: 732 |
| TLRSPLGDRLNVE, | SEQ ID NO: 733 |
| LRCQLGDRLNVEV, | SEQ ID NO: 734 |
| LRCPLGDRLNVEV, | SEQ ID NO: 735 |
| LRSQLGDRLNVEV, | SEQ ID NO: 736 |
| LRSPLGDRLNVEV, | SEQ ID NO: 737 |
| RCQLGDRLNVEVD, | SEQ ID NO: 738 |
| RCPLGDRLNVEVD, | SEQ ID NO: 739 |
| RSQLGDRLNVEVD, | SEQ ID NO: 740 |
| RSPLGDRLNVEVD, | SEQ ID NO: 741 |

| Sequence | SEQ ID NO |
|---|---|
| CQLGDRLNVEVDA, | SEQ ID NO: 742 |
| CQLGDRLNVEVDT, | SEQ ID NO: 743 |
| CPLGDRLNVEVDA, | SEQ ID NO: 744 |
| CPLGDRLNVEVDT, | SEQ ID NO: 745 |
| SQLGDRLNVEVDA, | SEQ ID NO: 746 |
| SQLGDRLNVEVDT, | SEQ ID NO: 747 |
| SPLGDRLNVEVDA, | SEQ ID NO: 748 |
| SPLGDRLNVEVDT, | SEQ ID NO: 749 |
| QLGDRLNVEVDAA, | SEQ ID NO: 750 |
| QLGDRLNVEVDTA, | SEQ ID NO: 751 |
| PLGDRLNVEVDAA, | SEQ ID NO: 752 |
| PLGDRLNVEVDTA, | SEQ ID NO: 753 |
| LGDRLNVEVDAAP, | SEQ ID NO: 754 |
| LGDRLNVEVDTAP, | SEQ ID NO: 755 |
| GDRLNVEVDAAPT, | SEQ ID NO: 756 |
| GDRLNVEVDTAPT, | SEQ ID NO: 757 |
| DRLNVEVDAAPTV, | SEQ ID NO: 758 |
| DRLNVEVDTAPTV, | SEQ ID NO: 759 |
| RLNVEVDAAPTVD, | SEQ ID NO: 760 |
| RLNVEVDTAPTVD, | SEQ ID NO: 761 |
| LNVEVDAAPTVDL, | SEQ ID NO: 762 |
| LNVEVDTAPTVDL, | SEQ ID NO: 763 |
| NVEVDAAPTVDLN, | SEQ ID NO: 764 |
| NVEVDTAPTVDLN, | SEQ ID NO: 765 |
| VEVDAAPTVDLNQ, | SEQ ID NO: 766 |
| VEVDAAPTVDLNR, | SEQ ID NO: 767 |
| VEVDTAPTVDLNQ, | SEQ ID NO: 768 |
| VEVDTAPTVDLNR, | SEQ ID NO: 769 |
| EVDAAPTVDLNQV, | SEQ ID NO: 770 |
| EVDAAPTVDLNRV, | SEQ ID NO: 771 |
| EVDTAPTVDLNQV, | SEQ ID NO: 772 |
| EVDTAPTVDLNRV, | SEQ ID NO: 773 |
| VDAAPTVDLNQVL, | SEQ ID NO: 774 |
| VDAAPTVDLNRVL, | SEQ ID NO: 775 |
| VDTAPTVDLNQVL, | SEQ ID NO: 776 |
| VDTAPTVDLNRVL, | SEQ ID NO: 777 |
| DAAPTVDLNQVLN, | SEQ ID NO: 778 |
| DAAPTVDLNRVLN, | SEQ ID NO: 779 |
| DTAPTVDLNQVLN, | SEQ ID NO: 780 |
| DTAPTVDLNRVLN, | SEQ ID NO: 781 |
| AAPTVDLNQVLNE, | SEQ ID NO: 782 |
| AAPTVDLNRVLNE, | SEQ ID NO: 783 |
| TAPTVDLNQVLNE, | SEQ ID NO: 784 |
| TAPTVDLNRVLNE, | SEQ ID NO: 785 |
| APTVDLNQVLNET, | SEQ ID NO: 786 |
| APTVDLNRVLNET, | SEQ ID NO: 787 |
| PTVDLNQVLNETR, | SEQ ID NO: 788 |
| PTVDLNRVLNETR, | SEQ ID NO: 789 |
| TVDLNQVLNETRS, | SEQ ID NO: 790 |
| TVDLNQVLNETRN, | SEQ ID NO: 791 |
| TVDLNRVLNETRS, | SEQ ID NO: 792 |
| TVDLNRVLNETRN, | SEQ ID NO: 793 |
| VDLNQVLNETRSQ, | SEQ ID NO: 794 |
| VDLNQVLNETRNQ, | SEQ ID NO: 795 |

| | |
|---|---|
| VDLNRVLNETRSQ, | SEQ ID NO: 796 |
| VDLNRVLNETRNQ, | SEQ ID NO: 797 |
| DLNQVLNETRSQY, | SEQ ID NO: 798 |
| DLNQVLNETRNQY, | SEQ ID NO: 799 |
| DLNRVLNETRSQY, | SEQ ID NO: 800 |
| DLNRVLNETRNQY, | SEQ ID NO: 801 |
| LNQVLNETRSQYE, | SEQ ID NO: 802 |
| LNQVLNETRNQYE, | SEQ ID NO: 803 |
| LNRVLNETRSQYE, | SEQ ID NO: 804 |
| LNRVLNETRNQYE, | SEQ ID NO: 805 |
| NQVLNETRSQYEA, | SEQ ID NO: 806 |
| NQVLNETRNQYEA, | SEQ ID NO: 807 |
| NRVLNETRSQYEA, | SEQ ID NO: 808 |
| NRVLNETRNQYEA, | SEQ ID NO: 809 |
| QVLNETRSQYEAL, | SEQ ID NO: 810 |
| QVLNETRNQYEAL, | SEQ ID NO: 811 |
| RVLNETRSQYEAL, | SEQ ID NO: 812 |
| RVLNETRNQYEAL, | SEQ ID NO: 813 |
| EVNTLRCQLGDRLN, | SEQ ID NO: 814 |
| EVNTLRCPLGDRLN, | SEQ ID NO: 815 |
| EVNTLRSQLGDRLN, | SEQ ID NO: 816 |
| EVNTLRSPLGDRLN, | SEQ ID NO: 817 |
| VNTLRCQLGDRLNV, | SEQ ID NO: 818 |
| VNTLRCPLGDRLNV, | SEQ ID NO: 819 |
| VNTLRSQLGDRLNV, | SEQ ID NO: 820 |
| VNTLRSPLGDRLNV, | SEQ ID NO: 821 |
| NTLRCQLGDRLNVE, | SEQ ID NO: 822 |
| NTLRCPLGDRLNVE, | SEQ ID NO: 823 |
| NTLRSQLGDRLNVE, | SEQ ID NO: 824 |
| NTLRSPLGDRLNVE, | SEQ ID NO: 825 |
| TLRCQLGDRLNVEV, | SEQ ID NO: 826 |
| TLRCPLGDRLNVEV, | SEQ ID NO: 827 |
| TLRSQLGDRLNVEV, | SEQ ID NO: 828 |
| TLRSPLGDRLNVEV, | SEQ ID NO: 829 |
| LRCQLGDRLNVEVD, | SEQ ID NO: 830 |
| LRCPLGDRLNVEVD, | SEQ ID NO: 831 |
| LRSQLGDRLNVEVD, | SEQ ID NO: 832 |
| LRSPLGDRLNVEVD, | SEQ ID NO: 833 |
| RCQLGDRLNVEVDA, | SEQ ID NO: 834 |
| RCQLGDRLNVEVDT, | SEQ ID NO: 835 |
| RCPLGDRLNVEVDA, | SEQ ID NO: 836 |
| RCPLGDRLNVEVDT, | SEQ ID NO: 837 |
| RSQLGDRLNVEVDA, | SEQ ID NO: 838 |
| RSQLGDRLNVEVDT, | SEQ ID NO: 839 |
| RSPLGDRLNVEVDA, | SEQ ID NO: 840 |
| RSPLGDRLNVEVDT, | SEQ ID NO: 841 |
| CQLGDRLNVEVDAA, | SEQ ID NO: 842 |
| CQLGDRLNVEVDTA, | SEQ ID NO: 843 |
| CPLGDRLNVEVDAA, | SEQ ID NO: 844 |
| CPLGDRLNVEVDTA, | SEQ ID NO: 845 |
| SQLGDRLNVEVDAA, | SEQ ID NO: 846 |
| SQLGDRLNVEVDTA, | SEQ ID NO: 847 |
| SPLGDRLNVEVDAA, | SEQ ID NO: 848 |
| SPLGDRLNVEVDTA, | SEQ ID NO: 849 |

| Sequence | SEQ ID NO |
|---|---|
| QLGDRLNVEVDAAP, | SEQ ID NO: 850 |
| QLGDRLNVEVDTAP, | SEQ ID NO: 851 |
| PLGDRLNVEVDAAP, | SEQ ID NO: 852 |
| PLGDRLNVEVDTAP, | SEQ ID NO: 853 |
| LGDRLNVEVDAAPT, | SEQ ID NO: 854 |
| LGDRLNVEVDTAPT, | SEQ ID NO: 855 |
| GDRLNVEVDAAPTV, | SEQ ID NO: 856 |
| GDRLNVEVDTAPTV, | SEQ ID NO: 857 |
| DRLNVEVDAAPTVD, | SEQ ID NO: 858 |
| DRLNVEVDTAPTVD, | SEQ ID NO: 859 |
| RLNVEVDAAPTVDL, | SEQ ID NO: 860 |
| RLNVEVDTAPTVDL, | SEQ ID NO: 861 |
| LNVEVDAAPTVDLN, | SEQ ID NO: 862 |
| LNVEVDTAPTVDLN, | SEQ ID NO: 863 |
| NVEVDAAPTVDLNQ, | SEQ ID NO: 864 |
| NVEVDAAPTVDLNR, | SEQ ID NO: 865 |
| NVEVDTAPTVDLNQ, | SEQ ID NO: 866 |
| NVEVDTAPTVDLNR, | SEQ ID NO: 867 |
| VEVDAAPTVDLNQV, | SEQ ID NO: 868 |
| VEVDAAPTVDLNRV, | SEQ ID NO: 869 |
| VEVDTAPTVDLNQV, | SEQ ID NO: 870 |
| VEVDTAPTVDLNRV, | SEQ ID NO: 871 |
| EVDAAPTVDLNQVL, | SEQ ID NO: 872 |
| EVDAAPTVDLNRVL, | SEQ ID NO: 873 |
| EVDTAPTVDLNQVL, | SEQ ID NO: 874 |
| EVDTAPTVDLNRVL, | SEQ ID NO: 875 |
| VDAAPTVDLNQVLN, | SEQ ID NO: 876 |
| VDAAPTVDLNRVLN, | SEQ ID NO: 877 |
| VDTAPTVDLNQVLN, | SEQ ID NO: 878 |
| VDTAPTVDLNRVLN, | SEQ ID NO: 879 |
| DAAPTVDLNQVLNE, | SEQ ID NO: 880 |
| DAAPTVDLNRVLNE, | SEQ ID NO: 881 |
| DTAPTVDLNQVLNE, | SEQ ID NO: 882 |
| DTAPTVDLNRVLNE, | SEQ ID NO: 883 |
| AAPTVDLNQVLNET, | SEQ ID NO: 884 |
| AAPTVDLNRVLNET, | SEQ ID NO: 885 |
| TAPTVDLNQVLNET, | SEQ ID NO: 886 |
| TAPTVDLNRVLNET, | SEQ ID NO: 887 |
| APTVDLNQVLNETR, | SEQ ID NO: 888 |
| APTVDLNRVLNETR, | SEQ ID NO: 889 |
| PTVDLNQVLNETRS, | SEQ ID NO: 890 |
| PTVDLNQVLNETRN, | SEQ ID NO: 891 |
| PTVDLNRVLNETRS, | SEQ ID NO: 892 |
| PTVDLNRVLNETRN, | SEQ ID NO: 893 |
| TVDLNQVLNETRSQ, | SEQ ID NO: 894 |
| TVDLNQVLNETRNQ, | SEQ ID NO: 895 |
| TVDLNRVLNETRSQ, | SEQ ID NO: 896 |
| TVDLNRVLNETRNQ, | SEQ ID NO: 897 |
| VDLNQVLNETRSQY, | SEQ ID NO: 898 |
| VDLNQVLNETRNQY, | SEQ ID NO: 899 |
| VDLNRVLNETRSQY, | SEQ ID NO: 900 |
| VDLNRVLNETRNQY, | SEQ ID NO: 901 |
| DLNQVLNETRSQYE, | SEQ ID NO: 902 |
| DLNQVLNETRNQYE, | SEQ ID NO: 903 |

-continued

DLNRVLNETRSQYE, SEQ ID NO: 904

DLNRVLNETRNQYE, SEQ ID NO: 905

LNQVLNETRSQYEA, SEQ ID NO: 906

LNQVLNETRNQYEA, SEQ ID NO: 907

LNRVLNETRSQYEA, SEQ ID NO: 908

LNRVLNETRNQYEA, SEQ ID NO: 909

NQVLNETRSQYEAL, SEQ ID NO: 910

NQVLNETRNQYEAL, SEQ ID NO: 911

NRVLNETRSQYEAL, SEQ ID NO: 912

NRVLNETRNQYEAL, SEQ ID NO: 913

EVNTLRCQLGDRLNV, SEQ ID NO: 914

EVNTLRCPLGDRLNV, SEQ ID NO: 915

EVNTLRSQLGDRLNV, SEQ ID NO: 916

EVNTLRSPLGDRLNV, SEQ ID NO: 917

VNTLRCQLGDRLNVE, SEQ ID NO: 918

VNTLRCPLGDRLNVE, SEQ ID NO: 919

VNTLRSQLGDRLNVE, SEQ ID NO: 920

VNTLRSPLGDRLNVE, SEQ ID NO: 921

NTLRCQLGDRLNVEV, SEQ ID NO: 922

NTLRCPLGDRLNVEV, SEQ ID NO: 923

NTLRSQLGDRLNVEV, SEQ ID NO: 924

NTLRSPLGDRLNVEV, SEQ ID NO: 925

TLRCQLGDRLNVEVD, SEQ ID NO: 926

TLRCPLGDRLNVEVD, SEQ ID NO: 927

TLRSQLGDRLNVEVD, SEQ ID NO: 928

TLRSPLGDRLNVEVD, SEQ ID NO: 929

LRCQLGDRLNVEVDA, SEQ ID NO: 930

-continued

LRCQLGDRLNVEVDT, SEQ ID NO: 931

LRCPLGDRLNVEVDA, SEQ ID NO: 932

LRCPLGDRLNVEVDT, SEQ ID NO: 933

LRSQLGDRLNVEVDA, SEQ ID NO: 934

LRSQLGDRLNVEVDT, SEQ ID NO: 935

LRSPLGDRLNVEVDA, SEQ ID NO: 936

LRSPLGDRLNVEVDT, SEQ ID NO: 937

RCQLGDRLNVEVDAA, SEQ ID NO: 938

RCQLGDRLNVEVDTA, SEQ ID NO: 939

RCPLGDRLNVEVDAA, SEQ ID NO: 940

RCPLGDRLNVEVDTA, SEQ ID NO: 941

RSQLGDRLNVEVDAA, SEQ ID NO: 942

RSQLGDRLNVEVDTA, SEQ ID NO: 943

RSPLGDRLNVEVDAA, SEQ ID NO: 944

RSPLGDRLNVEVDTA, SEQ ID NO: 945

CQLGDRLNVEVDAAP, SEQ ID NO: 946

CQLGDRLNVEVDTAP, SEQ ID NO: 947

CPLGDRLNVEVDAAP, SEQ ID NO: 948

CPLGDRLNVEVDTAP, SEQ ID NO: 949

SQLGDRLNVEVDAAP, SEQ ID NO: 950

SQLGDRLNVEVDTAP, SEQ ID NO: 951

SPLGDRLNVEVDAAP, SEQ ID NO: 952

SPLGDRLNVEVDTAP, SEQ ID NO: 953

QLGDRLNVEVDAAPT, SEQ ID NO: 954

QLGDRLNVEVDTAPT, SEQ ID NO: 955

PLGDRLNVEVDAAPT, SEQ ID NO: 956

PLGDRLNVEVDTAPT, SEQ ID NO: 957

| | |
|---|---|
| LGDRLNVEVDAAPTV, | SEQ ID NO: 958 |
| LGDRLNVEVDTAPTV, | SEQ ID NO: 959 |
| GDRLNVEVDAAPTVD, | SEQ ID NO: 960 |
| GDRLNVEVDTAPTVD, | SEQ ID NO: 961 |
| DRLNVEVDAAPTVDL, | SEQ ID NO: 962 |
| DRLNVEVDTAPTVDL, | SEQ ID NO: 963 |
| RLNVEVDAAPTVDLN, | SEQ ID NO: 964 |
| RLNVEVDTAPTVDLN, | SEQ ID NO: 965 |
| LNVEVDAAPTVDLNQ, | SEQ ID NO: 966 |
| LNVEVDAAPTVDLNR, | SEQ ID NO: 967 |
| LNVEVDTAPTVDLNQ, | SEQ ID NO: 968 |
| LNVEVDTAPTVDLNR, | SEQ ID NO: 969 |
| NVEVDAAPTVDLNQV, | SEQ ID NO: 970 |
| NVEVDAAPTVDLNRV, | SEQ ID NO: 971 |
| NVEVDTAPTVDLNQV, | SEQ ID NO: 972 |
| NVEVDTAPTVDLNRV, | SEQ ID NO: 973 |
| VEVDAAPTVDLNQVL, | SEQ ID NO: 974 |
| VEVDAAPTVDLNRVL, | SEQ ID NO: 975 |
| VEVDTAPTVDLNQVL, | SEQ ID NO: 976 |
| VEVDTAPTVDLNRVL, | SEQ ID NO: 977 |
| EVDAAPTVDLNQVLN, | SEQ ID NO: 978 |
| EVDAAPTVDLNRVLN, | SEQ ID NO: 979 |
| EVDTAPTVDLNQVLN, | SEQ ID NO: 980 |
| EVDTAPTVDLNRVLN, | SEQ ID NO: 981 |
| VDAAPTVDLNQVLNE, | SEQ ID NO: 982 |
| VDAAPTVDLNRVLNE, | SEQ ID NO: 983 |
| VDTAPTVDLNQVLNE, | SEQ ID NO: 984 |
| VDTAPTVDLNRVLNE, | SEQ ID NO: 985 |
| DAAPTVDLNQVLNET, | SEQ ID NO: 986 |
| DAAPTVDLNRVLNET, | SEQ ID NO: 987 |
| DTAPTVDLNQVLNET, | SEQ ID NO: 988 |
| DTAPTVDLNRVLNET, | SEQ ID NO: 989 |
| AAPTVDLNQVLNETR, | SEQ ID NO: 990 |
| AAPTVDLNRVLNETR, | SEQ ID NO: 991 |
| TAPTVDLNQVLNETR, | SEQ ID NO: 992 |
| TAPTVDLNRVLNETR, | SEQ ID NO: 993 |
| APTVDLNQVLNETRS, | SEQ ID NO: 994 |
| APTVDLNQVLNETRN, | SEQ ID NO: 995 |
| APTVDLNRVLNETRS, | SEQ ID NO: 996 |
| APTVDLNRVLNETRN, | SEQ ID NO: 997 |
| PTVDLNQVLNETRSQ, | SEQ ID NO: 998 |
| PTVDLNQVLNETRNQ, | SEQ ID NO: 999 |
| PTVDLNRVLNETRSQ, | SEQ ID NO: 1000 |
| PTVDLNRVLNETRNQ, | SEQ ID NO: 1001 |
| TVDLNQVLNETRSQY, | SEQ ID NO: 1002 |
| TVDLNQVLNETRNQY, | SEQ ID NO: 1003 |
| TVDLNRVLNETRSQY, | SEQ ID NO: 1004 |
| TVDLNRVLNETRNQY, | SEQ ID NO: 1005 |
| VDLNQVLNETRSQYE, | SEQ ID NO: 1006 |
| VDLNQVLNETRNQYE, | SEQ ID NO: 1007 |
| VDLNRVLNETRSQYE, | SEQ ID NO: 1008 |
| VDLNRVLNETRNQYE, | SEQ ID NO: 1009 |
| DLNQVLNETRSQYEA, | SEQ ID NO: 1010 |
| DLNQVLNETRNQYEA, | SEQ ID NO: 1011 |

-continued

| | |
|---|---|
| DLNRVLNETRSQYEA, | SEQ ID NO: 1012 |
| DLNRVLNETRNQYEA, | SEQ ID NO: 1013 |
| LNQVLNETRSQYEAL, | SEQ ID NO: 1014 |
| LNQVLNETRNQYEAL, | SEQ ID NO: 1015 |
| LNRVLNETRSQYEAL, | SEQ ID NO: 1016 |
| LNRVLNETRNQYEAL, | SEQ ID NO: 1017 |
| EVNTLRCQLGDRLNVE, | SEQ ID NO: 1018 |
| EVNTLRCPLGDRLNVE, | SEQ ID NO: 1019 |
| EVNTLRSQLGDRLNVE, | SEQ ID NO: 1020 |
| EVNTLRSPLGDRLNVE, | SEQ ID NO: 1021 |
| VNTLRCQLGDRLNVEV, | SEQ ID NO: 1022 |
| VNTLRCPLGDRLNVEV, | SEQ ID NO: 1023 |
| VNTLRSQLGDRLNVEV, | SEQ ID NO: 1024 |
| VNTLRSPLGDRLNVEV, | SEQ ID NO: 1025 |
| NTLRCQLGDRLNVEVD, | SEQ ID NO: 1026 |
| NTLRCPLGDRLNVEVD, | SEQ ID NO: 1027 |
| NTLRSQLGDRLNVEVD, | SEQ ID NO: 1028 |
| NTLRSPLGDRLNVEVD, | SEQ ID NO: 1029 |
| TLRCQLGDRLNVEVDA, | SEQ ID NO: 1030 |
| TLRCQLGDRLNVEVDT, | SEQ ID NO: 1031 |
| TLRCPLGDRLNVEVDA, | SEQ ID NO: 1032 |
| TLRCPLGDRLNVEVDT, | SEQ ID NO: 1033 |
| TLRSQLGDRLNVEVDA, | SEQ ID NO: 1034 |
| TLRSQLGDRLNVEVDT, | SEQ ID NO: 1035 |
| TLRSPLGDRLNVEVDA, | SEQ ID NO: 1036 |
| TLRSPLGDRLNVEVDT, | SEQ ID NO: 1037 |
| LRCQLGDRLNVEVDAA, | SEQ ID NO: 1038 |
| LRCQLGDRLNVEVDTA, | SEQ ID NO: 1039 |
| LRCPLGDRLNVEVDAA, | SEQ ID NO: 1040 |
| LRCPLGDRLNVEVDTA, | SEQ ID NO: 1041 |
| LRSQLGDRLNVEVDAA, | SEQ ID NO: 1042 |
| LRSQLGDRLNVEVDTA, | SEQ ID NO: 1043 |
| LRSPLGDRLNVEVDAA, | SEQ ID NO: 1044 |
| LRSPLGDRLNVEVDTA, | SEQ ID NO: 1045 |
| RCQLGDRLNVEVDAAP, | SEQ ID NO: 1046 |
| RCQLGDRLNVEVDTAP, | SEQ ID NO: 1047 |
| RCPLGDRLNVEVDAAP, | SEQ ID NO: 1048 |
| RCPLGDRLNVEVDTAP, | SEQ ID NO: 1049 |
| RSQLGDRLNVEVDAAP, | SEQ ID NO: 1050 |
| RSQLGDRLNVEVDTAP, | SEQ ID NO: 1051 |
| RSPLGDRLNVEVDAAP, | SEQ ID NO: 1052 |
| RSPLGDRLNVEVDTAP, | SEQ ID NO: 1053 |
| CQLGDRLNVEVDAAPT, | SEQ ID NO: 1054 |
| CQLGDRLNVEVDTAPT, | SEQ ID NO: 1055 |
| CPLGDRLNVEVDAAPT, | SEQ ID NO: 1056 |
| CPLGDRLNVEVDTAPT, | SEQ ID NO: 1057 |
| SQLGDRLNVEVDAAPT, | SEQ ID NO: 1058 |
| SQLGDRLNVEVDTAPT, | SEQ ID NO: 1059 |
| SPLGDRLNVEVDAAPT, | SEQ ID NO: 1060 |
| SPLGDRLNVEVDTAPT, | SEQ ID NO: 1061 |
| QLGDRLNVEVDAAPTV, | SEQ ID NO: 1062 |
| QLGDRLNVEVDTAPTV, | SEQ ID NO: 1063 |
| PLGDRLNVEVDAAPTV, | SEQ ID NO: 1064 |
| PLGDRLNVEVDTAPTV, | SEQ ID NO: 1065 |

| Sequence | SEQ ID NO |
|---|---|
| LGDRLNVEVDAAPTVD, | SEQ ID NO: 1066 |
| LGDRLNVEVDTAPTVD, | SEQ ID NO: 1067 |
| GDRLNVEVDAAPTVDL, | SEQ ID NO: 1068 |
| GDRLNVEVDTAPTVDL, | SEQ ID NO: 1069 |
| DRLNVEVDAAPTVDLN, | SEQ ID NO: 1070 |
| DRLNVEVDTAPTVDLN, | SEQ ID NO: 1071 |
| RLNVEVDAAPTVDLNQ, | SEQ ID NO: 1072 |
| RLNVEVDAAPTVDLNR, | SEQ ID NO: 1073 |
| RLNVEVDTAPTVDLNQ, | SEQ ID NO: 1074 |
| RLNVEVDTAPTVDLNR, | SEQ ID NO: 1075 |
| LNVEVDAAPTVDLNQV, | SEQ ID NO: 1076 |
| LNVEVDAAPTVDLNRV, | SEQ ID NO: 1077 |
| LNVEVDTAPTVDLNQV, | SEQ ID NO: 1078 |
| LNVEVDTAPTVDLNRV, | SEQ ID NO: 1079 |
| NVEVDAAPTVDLNQVL, | SEQ ID NO: 1080 |
| NVEVDAAPTVDLNQVL, | SEQ ID NO: 1081 |
| NVEVDTAPTVDLNQVL, | SEQ ID NO: 1082 |
| NVEVDTAPTVDLNRVL, | SEQ ID NO: 1083 |
| VEVDAAPTVDLNQVLN, | SEQ ID NO: 1084 |
| VEVDAAPTVDLNRVLN, | SEQ ID NO: 1085 |
| VEVDTAPTVDLNQVLN, | SEQ ID NO: 1086 |
| VEVDTAPTVDLNRVLN, | SEQ ID NO: 1087 |
| EVDAAPTVDLNQVLNE, | SEQ ID NO: 1088 |
| EVDAAPTVDLNRVLNE, | SEQ ID NO: 1089 |
| EVDTAPTVDLNQVLNE, | SEQ ID NO: 1090 |
| EVDTAPTVDLNRVLNE, | SEQ ID NO: 1091 |
| VDAAPTVDLNQVLNET, | SEQ ID NO: 1092 |
| VDAAPTVDLNRVLNET, | SEQ ID NO: 1093 |
| VDTAPTVDLNQVLNET, | SEQ ID NO: 1094 |
| VDTAPTVDLNRVLNET, | SEQ ID NO: 1095 |
| DAAPTVDLNQVLNETR, | SEQ ID NO: 1096 |
| DAAPTVDLNRVLNETR, | SEQ ID NO: 1097 |
| DTAPTVDLNQVLNETR, | SEQ ID NO: 1098 |
| DTAPTVDLNRVLNETR, | SEQ ID NO: 1099 |
| AAPTVDLNQVLNETRS, | SEQ ID NO: 1100 |
| AAPTVDLNQVLNETRN, | SEQ ID NO: 1101 |
| AAPTVDLNRVLNETRS, | SEQ ID NO: 1102 |
| AAPTVDLNRVLNETRN, | SEQ ID NO: 1103 |
| TAPTVDLNQVLNETRS, | SEQ ID NO: 1104 |
| TAPTVDLNQVLNETRN, | SEQ ID NO: 1105 |
| TAPTVDLNRVLNETRS, | SEQ ID NO: 1106 |
| TAPTVDLNRVLNETRN, | SEQ ID NO: 1107 |
| APTVDLNQVLNETRSQ, | SEQ ID NO: 1108 |
| APTVDLNQVLNETRNQ, | SEQ ID NO: 1109 |
| APTVDLNRVLNETRSQ, | SEQ ID NO: 1110 |
| APTVDLNRVLNETRNQ, | SEQ ID NO: 1111 |
| PTVDLNQVLNETRSQY, | SEQ ID NO: 1112 |
| PTVDLNQVLNETRNQY, | SEQ ID NO: 1113 |
| PTVDLNRVLNETRSQY, | SEQ ID NO: 1114 |
| PTVDLNRVLNETRNQY, | SEQ ID NO: 1115 |
| TVDLNQVLNETRSQYE, | SEQ ID NO: 1116 |
| TVDLNQVLNETRNQYE, | SEQ ID NO: 1117 |
| TVDLNRVLNETRSQYE, | SEQ ID NO: 1118 |
| TVDLNRVLNETRNQYE, | SEQ ID NO: 1119 |

-continued

| | |
|---|---|
| VDLNQVLNETRSQYEA, | SEQ ID NO: 1120 |
| VDLNQVLNETRNQYEA, | SEQ ID NO: 1121 |
| VDLNRVLNETRSQYEA, | SEQ ID NO: 1122 |
| VDLNRVLNETRNQYEA, | SEQ ID NO: 1123 |
| DLNQVLNETRSQYEAL, | SEQ ID NO: 1124 |
| DLNQVLNETRNQYEAL, | SEQ ID NO: 1125 |
| DLNRVLNETRSQYEAL, | SEQ ID NO: 1126 |
| DLNRVLNETRNQYEAL, | SEQ ID NO: 1127 |
| EVNTLRCQLGDRLNVEV, | SEQ ID NO: 1128 |
| EVNTLRCPLGDRLNVEV, | SEQ ID NO: 1129 |
| EVNTLRSQLGDRLNVEV, | SEQ ID NO: 1130 |
| EVNTLRSPLGDRLNVEV, | SEQ ID NO: 1131 |
| VNTLRCQLGDRLNVEVD, | SEQ ID NO: 1132 |
| VNTLRCPLGDRLNVEVD, | SEQ ID NO: 1133 |
| VNTLRSQLGDRLNVEVD, | SEQ ID NO: 1134 |
| VNTLRSPLGDRLNVEVD, | SEQ ID NO: 1135 |
| NTLRCQLGDRLNVEVDA, | SEQ ID NO: 1136 |
| NTLRCQLGDRLNVEVDT, | SEQ ID NO: 1137 |
| NTLRCPLGDRLNVEVDA, | SEQ ID NO: 1138 |
| NTLRCPLGDRLNVEVDT, | SEQ ID NO: 1139 |
| NTLRSQLGDRLNVEVDA, | SEQ ID NO: 1140 |
| NTLRSQLGDRLNVEVDT, | SEQ ID NO: 1141 |
| NTLRSPLGDRLNVEVDA, | SEQ ID NO: 1142 |
| NTLRSPLGDRLNVEVDT, | SEQ ID NO: 1143 |
| TLRCQLGDRLNVEVDAA, | SEQ ID NO: 1144 |
| TLRCQLGDRLNVEVDTA, | SEQ ID NO: 1145 |
| TLRCPLGDRLNVEVDAA, | SEQ ID NO: 1146 |
| TLRCPLGDRLNVEVDTA, | SEQ ID NO: 1147 |
| TLRSQLGDRLNVEVDAA, | SEQ ID NO: 1148 |
| TLRSQLGDRLNVEVDTA, | SEQ ID NO: 1149 |
| TLRSPLGDRLNVEVDAA, | SEQ ID NO: 1150 |
| TLRSPLGDRLNVEVDTA, | SEQ ID NO: 1151 |
| LRCQLGDRLNVEVDAAP, | SEQ ID NO: 1152 |
| LRCQLGDRLNVEVDTAP, | SEQ ID NO: 1153 |
| LRCPLGDRLNVEVDAAP, | SEQ ID NO: 1154 |
| LRCPLGDRLNVEVDTAP, | SEQ ID NO: 1155 |
| LRSQLGDRLNVEVDAAP, | SEQ ID NO: 1156 |
| LRSQLGDRLNVEVDTAP, | SEQ ID NO: 1157 |
| LRSPLGDRLNVEVDAAP, | SEQ ID NO: 1158 |
| LRSPLGDRLNVEVDTAP, | SEQ ID NO: 1159 |
| RCQLGDRLNVEVDAAPT, | SEQ ID NO: 1160 |
| RCQLGDRLNVEVDTAPT, | SEQ ID NO: 1161 |
| RCPLGDRLNVEVDAAPT, | SEQ ID NO: 1162 |
| RCPLGDRLNVEVDTAPT, | SEQ ID NO: 1163 |
| RSQLGDRLNVEVDAAPT, | SEQ ID NO: 1164 |
| RSQLGDRLNVEVDTAPT, | SEQ ID NO: 1165 |
| RSPLGDRLNVEVDAAPT, | SEQ ID NO: 1166 |
| RSPLGDRLNVEVDTAPT, | SEQ ID NO: 1167 |
| CQLGDRLNVEVDAAPTV, | SEQ ID NO: 1168 |
| CQLGDRLNVEVDTAPTV, | SEQ ID NO: 1169 |
| CPLGDRLNVEVDAAPTV, | SEQ ID NO: 1170 |
| CPLGDRLNVEVDTAPTV, | SEQ ID NO: 1171 |
| SQLGDRLNVEVDAAPTV, | SEQ ID NO: 1172 |
| SQLGDRLNVEVDTAPTV, | SEQ ID NO: 1173 |

| | |
|---|---|
| SPLGDRLNVEVDAAPTV, | SEQ ID NO: 1174 |
| SPLGDRLNVEVDTAPTV, | SEQ ID NO: 1175 |
| QLGDRLNVEVDAAPTVD, | SEQ ID NO: 1176 |
| QLGDRLNVEVDTAPTVD, | SEQ ID NO: 1177 |
| PLGDRLNVEVDAAPTVD, | SEQ ID NO: 1178 |
| PLGDRLNVEVDTAPTVD, | SEQ ID NO: 1179 |
| LGDRLNVEVDAAPTVDL, | SEQ ID NO: 1180 |
| LGDRLNVEVDTAPTVDL, | SEQ ID NO: 1181 |
| GDRLNVEVDAAPTVDLN, | SEQ ID NO: 1182 |
| GDRLNVEVDTAPTVDLN, | SEQ ID NO: 1183 |
| DRLNVEVDAAPTVDLNQ, | SEQ ID NO: 1184 |
| DRLNVEVDAAPTVDLNR, | SEQ ID NO: 1185 |
| DRLNVEVDTAPTVDLNQ, | SEQ ID NO: 1186 |
| DRLNVEVDTAPTVDLNR, | SEQ ID NO: 1187 |
| RLNVEVDAAPTVDLNQV, | SEQ ID NO: 1188 |
| RLNVEVDAAPTVDLNQV, | SEQ ID NO: 1189 |
| RLNVEVDTAPTVDLNQV, | SEQ ID NO: 1190 |
| RLNVEVDTAPTVDLNRV, | SEQ ID NO: 1191 |
| LNVEVDAAPTVDLNQVL, | SEQ ID NO: 1192 |
| LNVEVDAAPTVDLNRVL, | SEQ ID NO: 1193 |
| LNVEVDTAPTVDLNQVL, | SEQ ID NO: 1194 |
| LNVEVDTAPTVDLNRVL, | SEQ ID NO: 1195 |
| NVEVDAAPTVDLNQVLN, | SEQ ID NO: 1196 |
| NVEVDAAPTVDLNRVLN, | SEQ ID NO: 1197 |
| NVEVDTAPTVDLNQVLN, | SEQ ID NO: 1198 |
| NVEVDTAPTVDLNRVLN, | SEQ ID NO: 1199 |
| VEVDAAPTVDLNQVLNE, | SEQ ID NO: 1200 |
| VEVDAAPTVDLNRVLNE, | SEQ ID NO: 1201 |
| VEVDTAPTVDLNQVLNE, | SEQ ID NO: 1202 |
| VEVDTAPTVDLNRVLNE, | SEQ ID NO: 1203 |
| EVDAAPTVDLNQVLNET, | SEQ ID NO: 1204 |
| EVDAAPTVDLNRVLNET, | SEQ ID NO: 1205 |
| EVDTAPTVDLNQVLNET, | SEQ ID NO: 1206 |
| EVDTAPTVDLNRVLNET, | SEQ ID NO: 1207 |
| VDAAPTVDLNQVLNETR, | SEQ ID NO: 1208 |
| VDAAPTVDLNRVLNETR, | SEQ ID NO: 1209 |
| VDTAPTVDLNQVLNETR, | SEQ ID NO: 1210 |
| VDTAPTVDLNRVLNETR, | SEQ ID NO: 1211 |
| DAAPTVDLNQVLNETRS, | SEQ ID NO: 1212 |
| DAAPTVDLNQVLNETRN, | SEQ ID NO: 1213 |
| DAAPTVDLNRVLNETRS, | SEQ ID NO: 1214 |
| DTAPTVDLNRVLNETRN, | SEQ ID NO: 1215 |
| DTAPTVDLNQVLNETRS, | SEQ ID NO: 1216 |
| DTAPTVDLNQVLNETRN, | SEQ ID NO: 1217 |
| DTAPTVDLNRVLNETRS, | SEQ ID NO: 1218 |
| DTAPTVDLNRVLNETRN, | SEQ ID NO: 1219 |
| AAPTVDLNQVLNETRSQ, | SEQ ID NO: 1220 |
| AAPTVDLNQVLNETRNQ, | SEQ ID NO: 1221 |
| AAPTVDLNRVLNETRSQ, | SEQ ID NO: 1222 |
| AAPTVDLNRVLNETRNQ, | SEQ ID NO: 1223 |
| TAPTVDLNQVLNETRSQ, | SEQ ID NO: 1224 |
| TAPTVDLNQVLNETRNQ, | SEQ ID NO: 1225 |
| TAPTVDLNRVLNETRSQ, | SEQ ID NO: 1226 |
| TAPTVDLNRVLNETRNQ, | SEQ ID NO: 1227 |

-continued

| | |
|---|---|
| APTVDLNQVLNETRSQY, | SEQ ID NO: 1228 |
| APTVDLNQVLNETRNQY, | SEQ ID NO: 1229 |
| APTVDLNRVLNETRSQY, | SEQ ID NO: 1230 |
| APTVDLNRVLNETRNQY, | SEQ ID NO: 1231 |
| PTVDLNQVLNETRSQYE, | SEQ ID NO: 1232 |
| PTVDLNQVLNETRNQYE, | SEQ ID NO: 1233 |
| PTVDLNRVLNETRSQYE, | SEQ ID NO: 1234 |
| PTVDLNRVLNETRNQYE, | SEQ ID NO: 1235 |
| TVDLNQVLNETRSQYEA, | SEQ ID NO: 1236 |
| TVDLNQVLNETRNQYEA, | SEQ ID NO: 1237 |
| TVDLNRVLNETRSQYEA, | SEQ ID NO: 1238 |
| TVDLNRVLNETRNQYEA, | SEQ ID NO: 1239 |
| VDLNQVLNETRSQYEAL, | SEQ ID NO: 1240 |
| VDLNQVLNETRNQYEAL, | SEQ ID NO: 1241 |
| VDLNRVLNETRSQYEAL, | SEQ ID NO: 1242 |
| VDLNRVLNETRNQYEAL, | SEQ ID NO: 1243 |
| EVNTLRCQLGDRLNVEVD, | SEQ ID NO: 1244 |
| EVNTLRCPLGDRLNVEVD, | SEQ ID NO: 1245 |
| EVNTLRSQLGDRLNVEVD, | SEQ ID NO: 1246 |
| EVNTLRSPLGDRLNVEVD, | SEQ ID NO: 1247 |
| VNTLRCQLGDRLNVEVDA, | SEQ ID NO: 1248 |
| VNTLRCQLGDRLNVEVDT, | SEQ ID NO: 1249 |
| VNTLRCPLGDRLNVEVDA, | SEQ ID NO: 1250 |
| VNTLRCPLGDRLNVEVDT, | SEQ ID NO: 1251 |
| VNTLRSQLGDRLNVEVDA, | SEQ ID NO: 1252 |
| VNTLRSQLGDRLNVEVDT, | SEQ ID NO: 1253 |
| VNTLRSPLGDRLNVEVDA, | SEQ ID NO: 1254 |
| VNTLRSPLGDRLNVEVDT, | SEQ ID NO: 1255 |
| NTLRCQLGDRLNVEVDAA, | SEQ ID NO: 1256 |
| NTLRCQLGDRLNVEVDTA, | SEQ ID NO: 1257 |
| NTLRCPLGDRLNVEVDAA, | SEQ ID NO: 1258 |
| NTLRCPLGDRLNVEVDTA, | SEQ ID NO: 1259 |
| NTLRSQLGDRLNVEVDAA, | SEQ ID NO: 1260 |
| NTLRSQLGDRLNVEVDTA, | SEQ ID NO: 1261 |
| NTLRSPLGDRLNVEVDAA, | SEQ ID NO: 1262 |
| NTLRSPLGDRLNVEVDTA, | SEQ ID NO: 1263 |
| TLRCQLGDRLNVEVDAAP, | SEQ ID NO: 1264 |
| TLRCQLGDRLNVEVDTAP, | SEQ ID NO: 1265 |
| TLRCPLGDRLNVEVDAAP, | SEQ ID NO: 1266 |
| TLRCPLGDRLNVEVDTAP, | SEQ ID NO: 1267 |
| TLRSQLGDRLNVEVDAAP, | SEQ ID NO: 1268 |
| TLRSQLGDRLNVEVDTAP, | SEQ ID NO: 1269 |
| TLRSPLGDRLNVEVDAAP, | SEQ ID NO: 1270 |
| TLRSPLGDRLNVEVDTAP, | SEQ ID NO: 1271 |
| LRCQLGDRLNVEVDAAPT, | SEQ ID NO: 1272 |
| LRCQLGDRLNVEVDTAPT, | SEQ ID NO: 1273 |
| LRCPLGDRLNVEVDAAPT, | SEQ ID NO: 1274 |
| LRCPLGDRLNVEVDTAPT, | SEQ ID NO: 1275 |
| LRSQLGDRLNVEVDAAPT, | SEQ ID NO: 1276 |
| LRSQLGDRLNVEVDTAPT, | SEQ ID NO: 1277 |
| LRSPLGDRLNVEVDAAPT, | SEQ ID NO: 1278 |
| LRSPLGDRLNVEVDTAPT, | SEQ ID NO: 1279 |
| RCQLGDRLNVEVDAAPTV, | SEQ ID NO: 1280 |
| RCQLGDRLNVEVDTAPTV, | SEQ ID NO: 1281 |

| Sequence | SEQ ID NO |
|---|---|
| RCPLGDRLNVEVDAAPTV, | SEQ ID NO: 1282 |
| RCPLGDRLNVEVDTAPTV, | SEQ ID NO: 1283 |
| RSQLGDRLNVEVDAAPTV, | SEQ ID NO: 1284 |
| RSQLGDRLNVEVDTAPTV, | SEQ ID NO: 1285 |
| RSPLGDRLNVEVDAAPTV, | SEQ ID NO: 1286 |
| RSPLGDRLNVEVDTAPTV, | SEQ ID NO: 1287 |
| CQLGDRLNVEVDAAPTVD, | SEQ ID NO: 1288 |
| CQLGDRLNVEVDTAPTVD, | SEQ ID NO: 1289 |
| CPLGDRLNVEVDAAPTVD, | SEQ ID NO: 1290 |
| CPLGDRLNVEVDTAPTVD, | SEQ ID NO: 1291 |
| SQLGDRLNVEVDAAPTVD, | SEQ ID NO: 1292 |
| SQLGDRLNVEVDTAPTVD, | SEQ ID NO: 1293 |
| SPLGDRLNVEVDAAPTVD, | SEQ ID NO: 1294 |
| SPLGDRLNVEVDTAPTVD, | SEQ ID NO: 1295 |
| QLGDRLNVEVDAAPTVDL, | SEQ ID NO: 1296 |
| QLGDRLNVEVDTAPTVDL, | SEQ ID NO: 1297 |
| PLGDRLNVEVDAAPTVDL, | SEQ ID NO: 1298 |
| PLGDRLNVEVDTAPTVDL, | SEQ ID NO: 1299 |
| LGDRLNVEVDAAPTVDLN, | SEQ ID NO: 1300 |
| LGDRLNVEVDTAPTVDLN, | SEQ ID NO: 1301 |
| GDRLNVEVDAAPTVDLNQ, | SEQ ID NO: 1302 |
| GDRLNVEVDAAPTVDLNR, | SEQ ID NO: 1303 |
| GDRLNVEVDTAPTVDLNQ, | SEQ ID NO: 1304 |
| GDRLNVEVDTAPTVDLNR, | SEQ ID NO: 1305 |
| DRLNVEVDAAPTVDLNQV, | SEQ ID NO: 1306 |
| DRLNVEVDAAPTVDLNRV, | SEQ ID NO: 1307 |
| DRLNVEVDTAPTVDLNQV, | SEQ ID NO: 1308 |
| DRLNVEVDTAPTVDLNRV, | SEQ ID NO: 1309 |
| RLNVEVDAAPTVDLNQVL, | SEQ ID NO: 1310 |
| RLNVEVDAAPTVDLNRVL, | SEQ ID NO: 1311 |
| RLNVEVDTAPTVDLNQVL, | SEQ ID NO: 1312 |
| RLNVEVDTAPTVDLNRVL, | SEQ ID NO: 1313 |
| LNVEVDAAPTVDLNQVLN, | SEQ ID NO: 1314 |
| LNVEVDAAPTVDLNRVLN, | SEQ ID NO: 1315 |
| LNVEVDTAPTVDLNQVLN, | SEQ ID NO: 1316 |
| LNVEVDTAPTVDLNRVLN, | SEQ ID NO: 1317 |
| NVEVDAAPTVDLNQVLNE, | SEQ ID NO: 1318 |
| NVEVDAAPTVDLNRVLNE, | SEQ ID NO: 1319 |
| NVEVDTAPTVDLNQVLNE, | SEQ ID NO: 1320 |
| NVEVDTAPTVDLNRVLNE, | SEQ ID NO: 1321 |
| VEVDAAPTVDLNQVLNET, | SEQ ID NO: 1322 |
| VEVDAAPTVDLNRVLNET, | SEQ ID NO: 1323 |
| VEVDTAPTVDLNQVLNET, | SEQ ID NO: 1324 |
| VEVDTAPTVDLNRVLNET, | SEQ ID NO: 1325 |
| EVDAAPTVDLNQVLNETR, | SEQ ID NO: 1326 |
| EVDAAPTVDLNRVLNETR, | SEQ ID NO: 1327 |
| EVDTAPTVDLNQVLNETR, | SEQ ID NO: 1328 |
| EVDTAPTVDLNRVLNETR, | SEQ ID NO: 1329 |
| VDAAPTVDLNQVLNETRS, | SEQ ID NO: 1330 |
| VDAAPTVDLNQVLNETRN, | SEQ ID NO: 1331 |
| VDAAPTVDLNRVLNETRS, | SEQ ID NO: 1332 |
| VDAAPTVDLNRVLNETRN, | SEQ ID NO: 1333 |
| VDTAPTVDLNQVLNETRS, | SEQ ID NO: 1334 |
| VDTAPTVDLNQVLNETRN, | SEQ ID NO: 1335 |

| Sequence | SEQ ID NO |
|---|---|
| VDTAPTVDLNRVLNETRS, | 1336 |
| VDTAPTVDLNRVLNETRN, | 1337 |
| DAAPTVDLNQVLNETRSQ, | 1338 |
| DAAPTVDLNQVLNETRNQ, | 1339 |
| DAAPTVDLNRVLNETRSQ, | 1340 |
| DAAPTVDLNRVLNETRNQ, | 1341 |
| DTAPTVDLNQVLNETRSQ, | 1342 |
| DTAPTVDLNQVLNETRNQ, | 1343 |
| DTAPTVDLNRVLNETRSQ, | 1344 |
| DTAPTVDLNRVLNETRNQ, | 1345 |
| AAPTVDLNQVLNETRNQY, | 1346 |
| AAPTVDLNQVLNETRNQY, | 1347 |
| AAPTVDLNRVLNETRSQY, | 1348 |
| AAPTVDLNRVLNETRNQY, | 1349 |
| TAPTVDLNQVLNETRSQY, | 1350 |
| TAPTVDLNQVLNETRNQY, | 1351 |
| TAPTVDLNRVLNETRSQY, | 1352 |
| TAPTVDLNRVLNETRNQY, | 1353 |
| APTVDLNQVLNETRSQYE, | 1354 |
| APTVDLNQVLNETRNQYE, | 1355 |
| APTVDLNRVLNETRSQYE, | 1356 |
| APTVDLNRVLNETRNQYE, | 1357 |
| PTVDLNQVLNETRSQYEA, | 1358 |
| PTVDLNQVLNETRSQYEA, | 1359 |
| PTVDLNRVLNETRSQYEA, | 1360 |
| PTVDLNRVLNETRNQYEA, | 1361 |
| TVDLNQVLNETRSQYEAL, | 1362 |
| TVDLNQVLNETRNQYEAL, | 1363 |
| TVDLNRVLNETRSQYEAL, | 1364 |
| TVDLNRVLNETRNQYEAL, | 1365 |
| EVNTLRCQLGDRLNVEVDA, | 1366 |
| EVNTLRCQLGDRLNVEVDT, | 1367 |
| EVNTLRCPLGDRLNVEVDA, | 1368 |
| EVNTLRCPLGDRLNVEVDT, | 1369 |
| EVNTLRSQLGDRLNVEVDA, | 1370 |
| EVNTLRSQLGDRLNVEVDT, | 1371 |
| EVNTLRSPLGDRLNVEVDA, | 1372 |
| EVNTLRSPLGDRLNVEVDT, | 1373 |
| VNTLRCQLGDRLNVEVDAA, | 1374 |
| VNTLRCQLGDRLNVEVDTA, | 1375 |
| VNTLRCPLGDRLNVEVDAA, | 1376 |
| VNTLRCPLGDRLNVEVDTA, | 1377 |
| VNTLRSQLGDRLNVEVDAA, | 1378 |
| VNTLRSQLGDRLNVEVDTA, | 1379 |
| VNTLRSPLGDRLNVEVDAA, | 1380 |
| VNTLRSPLGDRLNVEVDTA, | 1381 |
| VNTLRCQLGDRLNVEVDAA, | 1382 |
| VNTLRCQLGDRLNVEVDTA, | 1383 |
| VNTLRCPLGDRLNVEVDAA, | 1384 |
| VNTLRCPLGDRLNVEVDTA, | 1385 |
| VNTLRSQLGDRLNVEVDAA, | 1386 |
| VNTLRSQLGDRLNVEVDTA, | 1387 |
| VNTLRSPLGDRLNVEVDAA, | 1388 |
| VNTLRSPLGDRLNVEVDTA, | 1389 |

| | |
|---|---|
| TLRCQLGDRLNVEVDAAPT, | SEQ ID NO: 1390 |
| TLRCQLGDRLNVEVDTAPT, | SEQ ID NO: 1391 |
| TLRCPLGDRLNVEVDAAPT, | SEQ ID NO: 1392 |
| TLRCPLGDRLNVEVDTAPT, | SEQ ID NO: 1393 |
| TLRSQLGDRLNVEVDAAPT, | SEQ ID NO: 1394 |
| TLRSQLGDRLNVEVDTAPT, | SEQ ID NO: 1395 |
| TLRSPLGDRLNVEVDAAPT, | SEQ ID NO: 1396 |
| TLRSPLGDRLNVEVDTAPT, | SEQ ID NO: 1397 |
| LRCQLGDRLNVEVDAAPTV, | SEQ ID NO: 1398 |
| LRCQLGDRLNVEVDTAPTV, | SEQ ID NO: 1399 |
| LRCPLGDRLNVEVDAAPTV, | SEQ ID NO: 1400 |
| LRCPLGDRLNVEVDTAPTV, | SEQ ID NO: 1401 |
| LRSQLGDRLNVEVDAAPTV, | SEQ ID NO: 1402 |
| LRSQLGDRLNVEVDTAPTV, | SEQ ID NO: 1403 |
| LRSPLGDRLNVEVDAAPTV, | SEQ ID NO: 1404 |
| LRSPLGDRLNVEVDTAPTV, | SEQ ID NO: 1405 |
| LRCQLGDRLNVEVDAAPTV, | SEQ ID NO: 1406 |
| LRCQLGDRLNVEVDTAPTV, | SEQ ID NO: 1407 |
| LRCPLGDRLNVEVDAAPTV, | SEQ ID NO: 1408 |
| LRCPLGDRLNVEVDTAPTV, | SEQ ID NO: 1409 |
| LRSQLGDRLNVEVDAAPTV, | SEQ ID NO: 1410 |
| LRSQLGDRLNVEVDTAPTV, | SEQ ID NO: 1411 |
| LRSPLGDRLNVEVDAAPTV, | SEQ ID NO: 1412 |
| LRSPLGDRLNVEVDTAPTV, | SEQ ID NO: 1413 |
| LRCQLGDRLNVEVDAAPTV, | SEQ ID NO: 1414 |
| LRCQLGDRLNVEVDTAPTV, | SEQ ID NO: 1415 |
| LRCPLGDRLNVEVDAAPTV, | SEQ ID NO: 1416 |
| LRCPLGDRLNVEVDTAPTV, | SEQ ID NO: 1417 |
| LRSQLGDRLNVEVDAAPTV, | SEQ ID NO: 1418 |
| LRSQLGDRLNVEVDTAPTV, | SEQ ID NO: 1419 |
| LRSPLGDRLNVEVDAAPTV, | SEQ ID NO: 1420 |
| LRSPLGDRLNVEVDTAPTV, | SEQ ID NO: 1421 |
| QLGDRLNVEVDAAPTVDLN, | SEQ ID NO: 1422 |
| QLGDRLNVEVDTAPTVDLN, | SEQ ID NO: 1423 |
| PLGDRLNVEVDAAPTVDLN, | SEQ ID NO: 1424 |
| PLGDRLNVEVDTAPTVDLN, | SEQ ID NO: 1425 |
| LGDRLNVEVDAAPTVDLNQ, | SEQ ID NO: 1426 |
| LGDRLNVEVDAAPTVDLNR, | SEQ ID NO: 1427 |
| LGDRLNVEVDTAPTVDLNQ, | SEQ ID NO: 1428 |
| LGDRLNVEVDTAPTVDLNR, | SEQ ID NO: 1429 |
| GDRLNVEVDAAPTVDLNQV, | SEQ ID NO: 1430 |
| GDRLNVEVDAAPTVDLNRV, | SEQ ID NO: 1431 |
| GDRLNVEVDTAPTVDLNQV, | SEQ ID NO: 1432 |
| GDRLNVEVDTAPTVDLNRV, | SEQ ID NO: 1433 |
| DRLNVEVDAAPTVDLNQVL, | SEQ ID NO: 1434 |
| DRLNVEVDAAPTVDLNRVL, | SEQ ID NO: 1435 |
| DRLNVEVDTAPTVDLNQVL, | SEQ ID NO: 1436 |
| DRLNVEVDTAPTVDLNRVL, | SEQ ID NO: 1437 |
| RLNVEVDAAPTVDLNQVLN, | SEQ ID NO: 1438 |
| RLNVEVDAAPTVDLNRVLN, | SEQ ID NO: 1439 |
| RLNVEVDTAPTVDLNQVLN, | SEQ ID NO: 1440 |
| RLNVEVDTAPTVDLNRVLN, | SEQ ID NO: 1441 |
| LNVEVDAAPTVDLNQVLNE, | SEQ ID NO: 1442 |
| LNVEVDAAPTVDLNRVLNE, | SEQ ID NO: 1443 |

LNVEVDTAPTVDLNQVLNE, SEQ ID NO: 1444

LNVEVDTAPTVDLNRVLNE, SEQ ID NO: 1445

NVEVDAAPTVDLNQVLNET, SEQ ID NO: 1446

NVEVDAAPTVDLNRVLNET, SEQ ID NO: 1447

NVEVDTAPTVDLNQVLNET, SEQ ID NO: 1448

NVEVDTAPTVDLNRVLNET, SEQ ID NO: 1449

VEVDAAPTVDLNQVLNETR, SEQ ID NO: 1450

VEVDAAPTVDLNRVLNETR, SEQ ID NO: 1451

VEVDTAPTVDLNQVLNETR, SEQ ID NO: 1452

VEVDTAPTVDLNRVLNETR, SEQ ID NO: 1453

EVDAAPTVDLNQVLNETRS, SEQ ID NO: 1454

EVDAAPTVDLNQVLNETRN, SEQ ID NO: 1455

EVDAAPTVDLNRVLNETRS, SEQ ID NO: 1456

EVDAAPTVDLNRVLNETRN, SEQ ID NO: 1457

EVDTAPTVDLNQVLNETRS, SEQ ID NO: 1458

EVDTAPTVDLNQVLNETRN, SEQ ID NO: 1459

EVDTAPTVDLNRVLNETRS, SEQ ID NO: 1460

EVDTAPTVDLNRVLNETRN, SEQ ID NO: 1461

VDAAPTVDLNQVLNETRSQ, SEQ ID NO: 1462

VDAAPTVDLNQVLNETRNQ, SEQ ID NO: 1463

VDAAPTVDLNRVLNETRSQ, SEQ ID NO: 1464

VDAAPTVDLNRVLNETRNQ, SEQ ID NO: 1465

VDTAPTVDLNQVLNETRSQ, SEQ ID NO: 1466

VDTAPTVDLNQVLNETRNQ, SEQ ID NO: 1467

VDTAPTVDLNRVLNETRSQ, SEQ ID NO: 1468

VDTAPTVDLNRVLNETRNQ, SEQ ID NO: 1469

DAAPTVDLNQVLNETRSQY, SEQ ID NO: 1470

DAAPTVDLNQVLNETRNQY, SEQ ID NO: 1471

DAAPTVDLNRVLNETRSQY, SEQ ID NO: 1472

DAAPTVDLNRVLNETRNQY, SEQ ID NO: 1473

DTAPTVDLNQVLNETRSQY, SEQ ID NO: 1474

DTAPTVDLNQVLNETRNQY, SEQ ID NO: 1475

DTAPTVDLNRVLNETRSQY, SEQ ID NO: 1476

DTAPTVDLNRVLNETRNQY, SEQ ID NO: 1477

AAPTVDLNQVLNETRSQYE, SEQ ID NO: 1478

AAPTVDLNQVLNETRNQYE, SEQ ID NO: 1479

AAPTVDLNRVLNETRSQYE, SEQ ID NO: 1480

AAPTVDLNRVLNETRNQYE, SEQ ID NO: 1481

TAPTVDLNQVLNETRSQYE, SEQ ID NO: 1482

TAPTVDLNQVLNETRNQYE, SEQ ID NO: 1483

TAPTVDLNRVLNETRSQYE, SEQ ID NO: 1484

TAPTVDLNRVLNETRNQYE, SEQ ID NO: 1485

APTVDLNQVLNETRSQYEA, SEQ ID NO: 1486

APTVDLNQVLNETRNQYEA, SEQ ID NO: 1487

APTVDLNRVLNETRSQYEA, SEQ ID NO: 1488

APTVDLNRVLNETRNQYEA, SEQ ID NO: 1489

PTVDLNQVLNETRNQYEAL, SEQ ID NO: 1490

PTVDLNQVLNETRNQYEAL, SEQ ID NO: 1491

PTVDLNRVLNETRSQYEAL, SEQ ID NO: 1492

PTVDLNRVLNETRNQYEAL, SEQ ID NO: 1493

EVNTLRCQLGDRLNVEVDAA, SEQ ID NO: 1494

EVNTLRCQLGDRLNVEVDTA, SEQ ID NO: 1495

EVNTLRCPLGDRLNVEVDAA, SEQ ID NO: 1496

EVNTLRCPLGDRLNVEVDTA, SEQ ID NO: 1497

| | |
|---|---|
| EVNTLRSQLGDRLNVEVDAA, | SEQ ID NO: 1498 |
| EVNTLRSQLGDRLNVEVDTA, | SEQ ID NO: 1499 |
| EVNTLRSPLGDRLNVEVDAA, | SEQ ID NO: 1500 |
| EVNTLRSPLGDRLNVEVDTA, | SEQ ID NO: 1501 |
| VNTLRCQLGDRLNVEVDAAP, | SEQ ID NO: 1502 |
| VNTLRCQLGDRLNVEVDTAP, | SEQ ID NO: 1503 |
| VNTLRCPLGDRLNVEVDAAP, | SEQ ID NO: 1504 |
| VNTLRCPLGDRLNVEVDTAP, | SEQ ID NO: 1505 |
| VNTLRSQLGDRLNVEVDAAP, | SEQ ID NO: 1506 |
| VNTLRSQLGDRLNVEVDTAP, | SEQ ID NO: 1507 |
| VNTLRSPLGDRLNVEVDAAP, | SEQ ID NO: 1508 |
| VNTLRSPLGDRLNVEVDTAP, | SEQ ID NO: 1509 |
| NTLRCQLGDRLNVEVDAAPT, | SEQ ID NO: 1510 |
| NTLRCQLGDRLNVEVDTAPT, | SEQ ID NO: 1511 |
| NTLRCPLGDRLNVEVDAAPT, | SEQ ID NO: 1512 |
| NTLRCPLGDRLNVEVDTAPT, | SEQ ID NO: 1513 |
| NTLRSQLGDRLNVEVDAAPT, | SEQ ID NO: 1514 |
| NTLRSQLGDRLNVEVDTAPT, | SEQ ID NO: 1515 |
| NTLRSPLGDRLNVEVDAAPT, | SEQ ID NO: 1516 |
| NTLRSPLGDRLNVEVDTAPT, | SEQ ID NO: 1517 |
| TLRCQLGDRLNVEVDAAPTV, | SEQ ID NO: 1518 |
| TLRCQLGDRLNVEVDTAPTV, | SEQ ID NO: 1519 |
| TLRCPLGDRLNVEVDAAPTV, | SEQ ID NO: 1520 |
| TLRCPLGDRLNVEVDTAPTV, | SEQ ID NO: 1521 |
| TLRSQLGDRLNVEVDAAPTV, | SEQ ID NO: 1522 |
| TLRSQLGDRLNVEVDTAPTV, | SEQ ID NO: 1523 |
| TLRSPLGDRLNVEVDAAPTV, | SEQ ID NO: 1524 |
| TLRSPLGDRLNVEVDTAPTV, | SEQ ID NO: 1525 |
| LRCQLGDRLNVEVDAAPTVD, | SEQ ID NO: 1526 |
| LRCQLGDRLNVEVDTAPTVD, | SEQ ID NO: 1527 |
| LRCPLGDRLNVEVDAAPTVD, | SEQ ID NO: 1528 |
| LRCPLGDRLNVEVDTAPTVD, | SEQ ID NO: 1529 |
| LRSQLGDRLNVEVDAAPTVD, | SEQ ID NO: 1530 |
| LRSQLGDRLNVEVDTAPTVD, | SEQ ID NO: 1531 |
| LRSPLGDRLNVEVDAAPTVD, | SEQ ID NO: 1532 |
| LRSPLGDRLNVEVDTAPTVD, | SEQ ID NO: 1533 |
| RCQLGDRLNVEVDAAPTVDL, | SEQ ID NO: 1534 |
| RCQLGDRLNVEVDTAPTVDL, | SEQ ID NO: 1535 |
| RCPLGDRLNVEVDAAPTVDL, | SEQ ID NO: 1536 |
| RCPLGDRLNVEVDTAPTVDL, | SEQ ID NO: 1537 |
| RSQLGDRLNVEVDAAPTVDL, | SEQ ID NO: 1538 |
| RSQLGDRLNVEVDTAPTVDL, | SEQ ID NO: 1539 |
| RSPLGDRLNVEVDAAPTVDL, | SEQ ID NO: 1540 |
| RSPLGDRLNVEVDTAPTVDL, | SEQ ID NO: 1541 |
| CQLGDRLNVEVDAAPTVDLN, | SEQ ID NO: 1542 |
| CQLGDRLNVEVDTAPTVDLN, | SEQ ID NO: 1543 |
| CPLGDRLNVEVDAAPTVDLN, | SEQ ID NO: 1544 |
| CPLGDRLNVEVDTAPTVDLN, | SEQ ID NO: 1545 |
| SQLGDRLNVEVDAAPTVDLN, | SEQ ID NO: 1546 |
| SQLGDRLNVEVDTAPTVDLN, | SEQ ID NO: 1547 |
| SPLGDRLNVEVDAAPTVDLN, | SEQ ID NO: 1548 |
| SPLGDRLNVEVDTAPTVDLN, | SEQ ID NO: 1549 |
| QLGDRLNVEVDAAPTVDLNQ, | SEQ ID NO: 1550 |
| QLGDRLNVEVDAAPTVDLNR, | SEQ ID NO: 1551 |

QLGDRLNVEVDTAPTVDLNQ, SEQ ID NO: 1552

QLGDRLNVEVDTAPTVDLNR, SEQ ID NO: 1553

PLGDRLNVEVDAAPTVDLNQ, SEQ ID NO: 1554

PLGDRLNVEVDAAPTVDLNR, SEQ ID NO: 1555

PLGDRLNVEVDTAPTVDLNQ, SEQ ID NO: 1556

PLGDRLNVEVDTAPTVDLNR, SEQ ID NO: 1557

LGDRLNVEVDAAPTVDLNQV, SEQ ID NO: 1558

LGDRLNVEVDAAPTVDLNRV, SEQ ID NO: 1559

LGDRLNVEVDTAPTVDLNQV, SEQ ID NO: 1560

LGDRLNVEVDTAPTVDLNRV, SEQ ID NO: 1561

GDRLNVEVDAAPTVDLNQVL, SEQ ID NO: 1562

GDRLNVEVDAAPTVDLNRVL, SEQ ID NO: 1563

GDRLNVEVDTAPTVDLNQVL, SEQ ID NO: 1564

GDRLNVEVDTAPTVDLNRVL, SEQ ID NO: 1565

DRLNVEVDAAPTVDLNQVLN, SEQ ID NO: 1566

DRLNVEVDAAPTVDLNRVLN, SEQ ID NO: 1567

DRLNVEVDTAPTVDLNQVLN, SEQ ID NO: 1568

DRLNVEVDTAPTVDLNRVLN, SEQ ID NO: 1569

RLNVEVDAAPTVDLNQVLNE, SEQ ID NO: 1570

RLNVEVDAAPTVDLNRVLNE, SEQ ID NO: 1571

RLNVEVDTAPTVDLNQVLNE, SEQ ID NO: 1572

RLNVEVDTAPTVDLNRVLNE, SEQ ID NO: 1573

LNVEVDAAPTVDLNQVLNET, SEQ ID NO: 1574

LNVEVDAAPTVDLNRVLNET, SEQ ID NO: 1575

LNVEVDTAPTVDLNQVLNET, SEQ ID NO: 1576

LNVEVDTAPTVDLNRVLNET, SEQ ID NO: 1577

NVEVDAAPTVDLNQVLNETR, SEQ ID NO: 1578

NVEVDAAPTVDLNRVLNETR, SEQ ID NO: 1579

NVEVDTAPTVDLNQVLNETR, SEQ ID NO: 1580

NVEVDTAPTVDLNRVLNETR, SEQ ID NO: 1581

VEVDAAPTVDLNQVLNETRS, SEQ ID NO: 1582

VEVDAAPTVDLNQVLNETRN, SEQ ID NO: 1583

VEVDAAPTVDLNRVLNETRS, SEQ ID NO: 1584

VEVDAAPTVDLNRVLNETRN, SEQ ID NO: 1585

VEVDTAPTVDLNQVLNETRS, SEQ ID NO: 1586

VEVDTAPTVDLNQVLNETRN, SEQ ID NO: 1587

VEVDTAPTVDLNRVLNETRS, SEQ ID NO: 1588

VEVDTAPTVDLNRVLNETRN, SEQ ID NO: 1589

EVDAAPTVDLNQVLNETRSQ, SEQ ID NO: 1590

EVDAAPTVDLNQVLNETRNQ, SEQ ID NO: 1591

EVDAAPTVDLNRVLNETRSQ, SEQ ID NO: 1592

EVDAAPTVDLNRVLNETRNQ, SEQ ID NO: 1593

EVDTAPTVDLNQVLNETRSQ, SEQ ID NO: 1594

EVDTAPTVDLNQVLNETRNQ, SEQ ID NO: 1595

EVDTAPTVDLNRVLNETRSQ, SEQ ID NO: 1596

EVDTAPTVDLNRVLNETRNQ, SEQ ID NO: 1597

VDAAPTVDLNQVLNETRSQY, SEQ ID NO: 1598

VDAAPTVDLNQVLNETRNQY, SEQ ID NO: 1599

VDAAPTVDLNRVLNETRSQY, SEQ ID NO: 1600

VDAAPTVDLNRVLNETRNQY, SEQ ID NO: 1601

VDTAPTVDLNQVLNETRSQY, SEQ ID NO: 1602

VDTAPTVDLNQVLNETRNQY, SEQ ID NO: 1603

VDTAPTVDLNRVLNETRSQY, SEQ ID NO: 1604

VDTAPTVDLNRVLNETRSQY, SEQ ID NO: 1605

| Sequence | SEQ ID NO |
|---|---|
| DAAPTVDLNQVLNETRSQYE, | SEQ ID NO: 1606 |
| DAAPTVDLNQVLNETRNQYE, | SEQ ID NO: 1607 |
| DAAPTVDLNRVLNETRSQYE, | SEQ ID NO: 1608 |
| DAAPTVDLNRVLNETRNQYE, | SEQ ID NO: 1609 |
| DTAPTVDLNQVLNETRSQYE, | SEQ ID NO: 1610 |
| DTAPTVDLNQVLNETRNQYE, | SEQ ID NO: 1611 |
| DTAPTVDLNRVLNETRSQYE, | SEQ ID NO: 1612 |
| DTAPTVDLNRVLNETRNQYE, | SEQ ID NO: 1613 |
| AAPTVDLNQVLNETRSQYEA, | SEQ ID NO: 1614 |
| AAPTVDLNQVLNETRNQYEA, | SEQ ID NO: 1615 |
| AAPTVDLNRVLNETRSQYEA, | SEQ ID NO: 1616 |
| AAPTVDLNRVLNETRNQYEA, | SEQ ID NO: 1617 |
| TAPTVDLNQVLNETRSQYEA, | SEQ ID NO: 1618 |
| TAPTVDLNQVLNETRNQYEA, | SEQ ID NO: 1619 |
| TAPTVDLNRVLNETRSQYEA, | SEQ ID NO: 1620 |
| TAPTVDLNRVLNETRNQYEA, | SEQ ID NO: 1621 |
| APTVDLNQVLNETRSQYEAL, | SEQ ID NO: 1622 |
| APTVDLNQVLNETRNQYEAL, | SEQ ID NO: 1623 |
| APTVDLNRVLNETRSQYEAL, | SEQ ID NO: 1624 |
| APTVDLNRVLNETRNQYEAL, | SEQ ID NO: 1625 |
| EVNTLRCQLGDRLNVEVDAAP, | SEQ ID NO: 1626 |
| EVNTLRCQLGDRLNVEVDTAP, | SEQ ID NO: 1627 |
| EVNTLRCPLGDRLNVEVDAAP, | SEQ ID NO: 1628 |
| EVNTLRCPLGDRLNVEVDTAP, | SEQ ID NO: 1629 |
| EVNTLRSQLGDRLNVEVDAAP, | SEQ ID NO: 1630 |
| EVNTLRSQLGDRLNVEVDTAP, | SEQ ID NO: 1631 |
| EVNTLRSPLGDRLNVEVDAAP, | SEQ ID NO: 1632 |
| EVNTLRSPLGDRLNVEVDTAP, | SEQ ID NO: 1633 |
| VNTLRCQLGDRLNVEVDAAPT, | SEQ ID NO: 1634 |
| VNTLRCQLGDRLNVEVDTAPT, | SEQ ID NO: 1635 |
| VNTLRCPLGDRLNVEVDAAPT, | SEQ ID NO: 1636 |
| VNTLRCPLGDRLNVEVDTAPT, | SEQ ID NO: 1637 |
| VNTLRSQLGDRLNVEVDAAPT, | SEQ ID NO: 1638 |
| VNTLRSQLGDRLNVEVDTAPT, | SEQ ID NO: 1639 |
| VNTLRSPLGDRLNVEVDAAPT, | SEQ ID NO: 1640 |
| VNTLRSPLGDRLNVEVDTAPT, | SEQ ID NO: 1641 |
| NTLRCQLGDRLNVEVDAAPTV, | SEQ ID NO: 1642 |
| NTLRCQLGDRLNVEVDTAPTV, | SEQ ID NO: 1643 |
| NTLRCPLGDRLNVEVDAAPTV, | SEQ ID NO: 1644 |
| NTLRCPLGDRLNVEVDTAPTV, | SEQ ID NO: 1645 |
| NTLRSQLGDRLNVEVDAAPTV, | SEQ ID NO: 1646 |
| NTLRSQLGDRLNVEVDTAPTV, | SEQ ID NO: 1647 |
| NTLRSPLGDRLNVEVDAAPTV, | SEQ ID NO: 1648 |
| NTLRSPLGDRLNVEVDTAPTV, | SEQ ID NO: 1649 |
| TLRCQLGDRLNVEVDAAPTVD, | SEQ ID NO: 1650 |
| TLRCQLGDRLNVEVDTAPTVD, | SEQ ID NO: 1651 |
| TLRCPLGDRLNVEVDAAPTVD, | SEQ ID NO: 1652 |
| TLRCPLGDRLNVEVDTAPTVD, | SEQ ID NO: 1653 |
| TLRSQLGDRLNVEVDAAPTVD, | SEQ ID NO: 1654 |
| TLRSQLGDRLNVEVDTAPTVD, | SEQ ID NO: 1655 |
| TLRSPLGDRLNVEVDAAPTVD, | SEQ ID NO: 1656 |
| TLRSPLGDRLNVEVDTAPTVD, | SEQ ID NO: 1657 |
| LRCQLGDRLNVEVDAAPTVDL, | SEQ ID NO: 1658 |
| LRCQLGDRLNVEVDTAPTVDL, | SEQ ID NO: 1659 |

LRCPLGDRLNVEVDAAPTVDL, SEQ ID NO: 1660

LRCPLGDRLNVEVDTAPTVDL, SEQ ID NO: 1661

LRSQLGDRLNVEVDAAPTVDL, SEQ ID NO: 1662

LRSQLGDRLNVEVDTAPTVDL, SEQ ID NO: 1663

LRCPLGDRLNVEVDAAPTVDL, SEQ ID NO: 1664

LRSPLGDRLNVEVDTAPTVDL, SEQ ID NO: 1665

RCQLGDRLNVEVDAAPTVDLN, SEQ ID NO: 1666

RCQLGDRLNVEVDTAPTVDLN, SEQ ID NO: 1667

RCPLGDRLNVEVDAAPTVDLN, SEQ ID NO: 1668

RCPLGDRLNVEVDTAPTVDLN, SEQ ID NO: 1669

RSQLGDRLNVEVDAAPTVDLN, SEQ ID NO: 1670

RSQLGDRLNVEVDTAPTVDLN, SEQ ID NO: 1671

RSPLGDRLNVEVDAAPTVDLN, SEQ ID NO: 1672

RSPLGDRLNVEVDTAPTVDLN, SEQ ID NO: 1673

CQLGDRLNVEVDAAPTVDLNQ, SEQ ID NO: 1674

SQLGDRLNVEVDAAPTVDLNQ, SEQ ID NO: 1675

CPLGDRLNVEVDAAPTVDLNQ, SEQ ID NO: 1676

SPLGDRLNVEVDAAPTVDLNQ, SEQ ID NO: 1677

CQLGDRLNVEVDTAPTVDLNQ, SEQ ID NO: 1678

SQLGDRLNVEVDTAPTVDLNQ, SEQ ID NO: 1679

CPLGDRLNVEVDTAPTVDLNQ, SEQ ID NO: 1680

SPLGDRLNVEVDTAPTVDLNQ, SEQ ID NO: 1681

CQLGDRLNVEVDAAPTVDLNR, SEQ ID NO: 1682

SQLGDRLNVEVDAAPTVDLNR, SEQ ID NO: 1683

CPLGDRLNVEVDAAPTVDLNR, SEQ ID NO: 1684

SPLGDRLNVEVDAAPTVDLNR, SEQ ID NO: 1685

CQLGDRLNVEVDTAPTVDLNR, SEQ ID NO: 1686

SQLGDRLNVEVDTAPTVDLNR, SEQ ID NO: 1687

CPLGDRLNVEVDTAPTVDLNR, SEQ ID NO: 1688

SPLGDRLNVEVDTAPTVDLNR, SEQ ID NO: 1689

QLGDRLNVEVDAAPTVDLNQV, SEQ ID NO: 1690

QLGDRLNVEVDAAPTVDLNRV, SEQ ID NO: 1691

QLGDRLNVEVDTAPTVDLNQV, SEQ ID NO: 1692

QLGDRLNVEVDTAPTVDLNRV, SEQ ID NO: 1693

PLGDRLNVEVDAAPTVDLNQV, SEQ ID NO: 1694

PLGDRLNVEVDAAPTVDLNRV, SEQ ID NO: 1695

PLGDRLNVEVDTAPTVDLNQV, SEQ ID NO: 1696

PLGDRLNVEVDTAPTVDLNRV, SEQ ID NO: 1697

LGDRLNVEVDAAPTVDLNQVL, SEQ ID NO: 1698

LGDRLNVEVDAAPTVDLNRVL, SEQ ID NO: 1699

LGDRLNVEVDTAPTVDLNQVL, SEQ ID NO: 1700

LGDRLNVEVDTAPTVDLNRVL, SEQ ID NO: 1701

GDRLNVEVDAAPTVDLNQVLN, SEQ ID NO: 1702

GDRLNVEVDAAPTVDLNRVLN, SEQ ID NO: 1703

GDRLNVEVDTAPTVDLNQVLN, SEQ ID NO: 1704

GDRLNVEVDTAPTVDLNRVLN, SEQ ID NO: 1705

DRLNVEVDAAPTVDLNQVLNE, SEQ ID NO: 1706

DRLNVEVDAAPTVDLNRVLNE, SEQ ID NO: 1707

DRLNVEVDTAPTVDLNQVLNE, SEQ ID NO: 1708

DRLNVEVDTAPTVDLNRVLNE, SEQ ID NO: 1709

RLNVEVDAAPTVDLNQVLNET, SEQ ID NO: 1710

RLNVEVDAAPTVDLNRVLNET, SEQ ID NO: 1711

RLNVEVDTAPTVDLNQVLNET, SEQ ID NO: 1712

RLNVEVDTAPTVDLNRVLNET, SEQ ID NO: 1713

| Sequence | SEQ ID NO |
|---|---|
| LNVEVDAAPTVDLNQVLNETR, | SEQ ID NO: 1714 |
| LNVEVDAAPTVDLNRVLNETR, | SEQ ID NO: 1715 |
| LNVEVDTAPTVDLNQVLNETR, | SEQ ID NO: 1716 |
| LNVEVDTAPTVDLNRVLNETR, | SEQ ID NO: 1717 |
| NVEVDAAPTVDLNQVLNETRS, | SEQ ID NO: 1718 |
| NVEVDAAPTVDLNQVLNETRN, | SEQ ID NO: 1719 |
| NVEVDAAPTVDLNRVLNETRS, | SEQ ID NO: 1720 |
| NVEVDAAPTVDLNRVLNETRN, | SEQ ID NO: 1721 |
| NVEVDTAPTVDLNQVLNETRS, | SEQ ID NO: 1722 |
| NVEVDTAPTVDLNQVLNETRN, | SEQ ID NO: 1723 |
| NVEVDTAPTVDLNRVLNETRS, | SEQ ID NO: 1724 |
| NVEVDTAPTVDLNRVLNETRN, | SEQ ID NO: 1725 |
| VEVDAAPTVDLNQVLNETRSQ, | SEQ ID NO: 1726 |
| VEVDAAPTVDLNQVLNETRNQ, | SEQ ID NO: 1727 |
| VEVDAAPTVDLNRVLNETRSQ, | SEQ ID NO: 1728 |
| VEVDAAPTVDLNRVLNETRNQ, | SEQ ID NO: 1729 |
| VEVDTAPTVDLNQVLNETRSQ, | SEQ ID NO: 1730 |
| VEVDTAPTVDLNQVLNETRNQ, | SEQ ID NO: 1731 |
| VEVDTAPTVDLNRVLNETRSQ, | SEQ ID NO: 1732 |
| VEVDTAPTVDLNRVLNETRNQ, | SEQ ID NO: 1733 |
| EVDAAPTVDLNQVLNETRSQY, | SEQ ID NO: 1734 |
| EVDAAPTVDLNQVLNETRNQY, | SEQ ID NO: 1735 |
| EVDAAPTVDLNRVLNETRSQY, | SEQ ID NO: 1736 |
| EVDAAPTVDLNRVLNETRNQY, | SEQ ID NO: 1737 |
| EVDTAPTVDLNQVLNETRSQY, | SEQ ID NO: 1738 |
| EVDTAPTVDLNQVLNETRNQY, | SEQ ID NO: 1739 |
| EVDTAPTVDLNRVLNETRSQY, | SEQ ID NO: 1740 |
| EVDTAPTVDLNRVLNETRNQY, | SEQ ID NO: 1741 |
| VDAAPTVDLNQVLNETRSQYE, | SEQ ID NO: 1742 |
| VDAAPTVDLNQVLNETRNQYE, | SEQ ID NO: 1743 |
| VDAAPTVDLNRVLNETRSQYE, | SEQ ID NO: 1744 |
| VDAAPTVDLNRVLNETRNQYE, | SEQ ID NO: 1745 |
| VDTAPTVDLNQVLNETRSQYE, | SEQ ID NO: 1746 |
| VDTAPTVDLNQVLNETRNQYE, | SEQ ID NO: 1747 |
| VDTAPTVDLNRVLNETRSQYE, | SEQ ID NO: 1748 |
| VDTAPTVDLNRVLNETRNQYE, | SEQ ID NO: 1749 |
| DAAPTVDLNQVLNETRSQYEA, | SEQ ID NO: 1750 |
| DAAPTVDLNQVLNETRNQYEA, | SEQ ID NO: 1751 |
| DAAPTVDLNRVLNETRSQYEA, | SEQ ID NO: 1752 |
| DAAPTVDLNRVLNETRNQYEA, | SEQ ID NO: 1753 |
| DTAPTVDLNQVLNETRSQYEA, | SEQ ID NO: 1754 |
| DTAPTVDLNQVLNETRNQYEA, | SEQ ID NO: 1755 |
| DTAPTVDLNRVLNETRSQYEA, | SEQ ID NO: 1756 |
| DTAPTVDLNRVLNETRNQYEA, | SEQ ID NO: 1757 |
| AAPTVDLNQVLNETRSQYEAL, | SEQ ID NO: 1758 |
| AAPTVDLNQVLNETRNQYEAL, | SEQ ID NO: 1759 |
| AAPTVDLNRVLNETRSQYEAL, | SEQ ID NO: 1760 |
| AAPTVDLNRVLNETRNQYEAL, | SEQ ID NO: 1761 |
| TAPTVDLNQVLNETRSQYEAL, | SEQ ID NO: 1762 |
| TAPTVDLNQVLNETRNQYEAL, | SEQ ID NO: 1763 |
| TAPTVDLNRVLNETRSQYEAL, | SEQ ID NO: 1764 |
| TAPTVDLNRVLNETRNQYEAL, | SEQ ID NO: 1765 |
| EVNTLRCQLGDRLNVEVDAAPT, | SEQ ID NO: 1766 |
| EVNTLRCQLGDRLNVEVDTAPT, | SEQ ID NO: 1767 |

-continued

| Sequence | SEQ ID NO |
|---|---|
| EVNTLRCPLGDRLNVEVDAAPT, | SEQ ID NO: 1768 |
| EVNTLRCPLGDRLNVEVDTAPT, | SEQ ID NO: 1769 |
| EVNTLRSQLGDRLNVEVDAAPT, | SEQ ID NO: 1770 |
| EVNTLRSQLGDRLNVEVDTAPT, | SEQ ID NO: 1771 |
| EVNTLRSPLGDRLNVEVDAAPT, | SEQ ID NO: 1772 |
| EVNTLRSPLGDRLNVEVDTAPT, | SEQ ID NO: 1773 |
| VNTLRCQLGDRLNVEVDAAPTV, | SEQ ID NO: 1774 |
| VNTLRCQLGDRLNVEVDTAPTV, | SEQ ID NO: 1775 |
| VNTLRCPLGDRLNVEVDAAPTV, | SEQ ID NO: 1776 |
| VNTLRCPLGDRLNVEVDTAPTV, | SEQ ID NO: 1777 |
| VNTLRSQLGDRLNVEVDAAPTV, | SEQ ID NO: 1778 |
| VNTLRSQLGDRLNVEVDTAPTV, | SEQ ID NO: 1779 |
| VNTLRSPLGDRLNVEVDAAPTV, | SEQ ID NO: 1780 |
| VNTLRSPLGDRLNVEVDTAPTV, | SEQ ID NO: 1781 |
| NTLRCQLGDRLNVEVDAAPTVD, | SEQ ID NO: 1782 |
| NTLRCQLGDRLNVEVDTAPTVD, | SEQ ID NO: 1783 |
| NTLRCPLGDRLNVEVDAAPTVD, | SEQ ID NO: 1784 |
| NTLRCPLGDRLNVEVDTAPTVD, | SEQ ID NO: 1785 |
| NTLRSQLGDRLNVEVDAAPTVD, | SEQ ID NO: 1786 |
| NTLRSQLGDRLNVEVDTAPTVD, | SEQ ID NO: 1787 |
| NTLRSPLGDRLNVEVDAAPTVD, | SEQ ID NO: 1788 |
| NTLRSPLGDRLNVEVDTAPTVD, | SEQ ID NO: 1789 |
| TLRCQLGDRLNVEVDAAPTVDL, | SEQ ID NO: 1790 |
| TLRCQLGDRLNVEVDTAPTVDL, | SEQ ID NO: 1791 |
| TLRCPLGDRLNVEVDAAPTVDL, | SEQ ID NO: 1792 |
| TLRCPLGDRLNVEVDTAPTVDL, | SEQ ID NO: 1793 |
| TLRSQLGDRLNVEVDAAPTVDL, | SEQ ID NO: 1794 |
| TLRSQLGDRLNVEVDTAPTVDL, | SEQ ID NO: 1795 |
| TLRSPLGDRLNVEVDAAPTVDL, | SEQ ID NO: 1796 |
| TLRSPLGDRLNVEVDTAPTVDL, | SEQ ID NO: 1797 |
| LRCQLGDRLNVEVDAAPTVDLN, | SEQ ID NO: 1798 |
| LRCQLGDRLNVEVDTAPTVDLN, | SEQ ID NO: 1799 |
| LRCPLGDRLNVEVDAAPTVDLN, | SEQ ID NO: 1800 |
| LRCPLGDRLNVEVDTAPTVDLN, | SEQ ID NO: 1801 |
| LRSQLGDRLNVEVDAAPTVDLN, | SEQ ID NO: 1802 |
| LRSQLGDRLNVEVDTAPTVDLN, | SEQ ID NO: 1803 |
| LRSPLGDRLNVEVDAAPTVDLN, | SEQ ID NO: 1804 |
| LRSPLGDRLNVEVDTAPTVDLN, | SEQ ID NO: 11805 |
| RCQLGDRLNVEVDAAPTVDLNQ, | SEQ ID NO: 1806 |
| RSQLGDRLNVEVDAAPTVDLNQ, | SEQ ID NO: 1807 |
| RCPLGDRLNVEVDAAPTVDLNQ, | SEQ ID NO: 1808 |
| RSPLGDRLNVEVDAAPTVDLNQ, | SEQ ID NO: 1809 |
| RCQLGDRLNVEVDTAPTVDLNQ, | SEQ ID NO: 1810 |
| RSQLGDRLNVEVDTAPTVDLNQ, | SEQ ID NO: 1811 |
| RCPLGDRLNVEVDTAPTVDLNQ, | SEQ ID NO: 1812 |
| RSPLGDRLNVEVDTAPTVDLNQ, | SEQ ID NO: 1813 |
| RCQLGDRLNVEVDAAPTVDLNR, | SEQ ID NO: 1814 |
| RSQLGDRLNVEVDAAPTVDLNR, | SEQ ID NO: 1815 |
| RCPLGDRLNVEVDAAPTVDLNR, | SEQ ID NO: 1816 |
| RSPLGDRLNVEVDAAPTVDLNR, | SEQ ID NO: 1817 |
| RCQLGDRLNVEVDTAPTVDLNR, | SEQ ID NO: 1818 |
| RSQLGDRLNVEVDTAPTVDLNR, | SEQ ID NO: 1819 |
| RCPLGDRLNVEVDTAPTVDLNR, | SEQ ID NO: 1820 |
| RSPLGDRLNVEVDTAPTVDLNR, | SEQ ID NO: 1821 |

CQLGDRLNVEVDAAPTVDLNQV, SEQ ID NO: 1822

SQLGDRLNVEVDAAPTVDLNQV, SEQ ID NO: 1823

CPLGDRLNVEVDAAPTVDLNQV, SEQ ID NO: 1824

SPLGDRLNVEVDAAPTVDLNQV, SEQ ID NO: 1825

CQLGDRLNVEVDTAPTVDLNQV, SEQ ID NO: 1826

SQLGDRLNVEVDTAPTVDLNQV, SEQ ID NO: 1827

CPLGDRLNVEVDTAPTVDLNQV, SEQ ID NO: 1828

SPLGDRLNVEVDTAPTVDLNQV, SEQ ID NO: 1829

CQLGDRLNVEVDAAPTVDLNRV, SEQ ID NO: 1830

SQLGDRLNVEVDAAPTVDLNRV, SEQ ID NO: 1831

CPLGDRLNVEVDAAPTVDLNRVL, SEQ ID NO: 1832

SPLGDRLNVEVDAAPTVDLNRV, SEQ ID NO: 1833

CQLGDRLNVEVDTAPTVDLNRV, SEQ ID NO: 1834

SQLGDRLNVEVDTAPTVDLNRV, SEQ ID NO: 1835

CPLGDRLNVEVDTAPTVDLNRV, SEQ ID NO: 1836

SPLGDRLNVEVDTAPTVDLNRV, SEQ ID NO: 1837

QLGDRLNVEVDAAPTVDLNQVL, SEQ ID NO: 1838

QLGDRLNVEVDAAPTVDLNRVL, SEQ ID NO: 1839

QLGDRLNVEVDTAPTVDLNQVL, SEQ ID NO: 1840

QLGDRLNVEVDTAPTVDLNRVL, SEQ ID NO: 1841

PLGDRLNVEVDAAPTVDLNQVL, SEQ ID NO: 1842

PLGDRLNVEVDAAPTVDLNRVL, SEQ ID NO: 1843

PLGDRLNVEVDTAPTVDLNQVL, SEQ ID NO: 1844

PLGDRLNVEVDTAPTVDLNRVL, SEQ ID NO: 1845

LGDRLNVEVDAAPTVDLNQVLN, SEQ ID NO: 1846

LGDRLNVEVDAAPTVDLNRVLN, SEQ ID NO: 1847

LGDRLNVEVDTAPTVDLNQVLN, SEQ ID NO: 1848

LGDRLNVEVDTAPTVDLNRVLN, SEQ ID NO: 1849

GDRLNVEVDAAPTVDLNQVLNE, SEQ ID NO: 1850

GDRLNVEVDAAPTVDLNRVLNE, SEQ ID NO: 1851

GDRLNVEVDTAPTVDLNQVLNE, SEQ ID NO: 1852

GDRLNVEVDTAPTVDLNRVLNE, SEQ ID NO: 1853

DRLNVEVDAAPTVDLNQVLNET, SEQ ID NO: 1854

DRLNVEVDAAPTVDLNRVLNET, SEQ ID NO: 1855

DRLNVEVDTAPTVDLNQVLNET, SEQ ID NO: 1856

DRLNVEVDTAPTVDLNRVLNET, SEQ ID NO: 1857

RLNVEVDAAPTVDLNQVLNETR, SEQ ID NO: 1858

RLNVEVDAAPTVDLNRVLNETR, SEQ ID NO: 1859

RLNVEVDTAPTVDLNQVLNETR, SEQ ID NO: 1860

RLNVEVDTAPTVDLNRVLNETR, SEQ ID NO: 1861

LNVEVDAAPTVDLNQVLNETRS, SEQ ID NO: 1862

LNVEVDAAPTVDLNQVLNETRN, SEQ ID NO: 1863

LNVEVDAAPTVDLNRVLNETRS, SEQ ID NO: 1864

LNVEVDAAPTVDLNRVLNETRN, SEQ ID NO: 1865

LNVEVDTAPTVDLNQVLNETRS, SEQ ID NO: 1866

LNVEVDTAPTVDLNQVLNETRN, SEQ ID NO: 1867

LNVEVDTAPTVDLNRVLNETRS, SEQ ID NO: 1868

LNVEVDTAPTVDLNRVLNETRN, SEQ ID NO: 1869

NVEVDAAPTVDLNQVLNETRSQ, SEQ ID NO: 1870

NVEVDAAPTVDLNQVLNETRNQ, SEQ ID NO: 1871

NVEVDAAPTVDLNRVLNETRSQ, SEQ ID NO: 1872

NVEVDAAPTVDLNRVLNETRNQ, SEQ ID NO: 1873

NVEVDTAPTVDLNQVLNETRSQ, SEQ ID NO: 1874

NVEVDTAPTVDLNQVLNETRNQ, SEQ ID NO: 1875

-continued

NVEVDTAPTVDLNRVLNETRSQ, SEQ ID NO: 1876

NVEVDTAPTVDLNRVLNETRNQ, SEQ ID NO: 1877

EVNTLRCQLGDRLNVEVDAAPTV, SEQ ID NO: 1878

EVNTLRCQLGDRLNVEVDTAPTV, SEQ ID NO: 1879

EVNTLRCPLGDRLNVEVDAAPTV, SEQ ID NO: 1880

EVNTLRCPLGDRLNVEVDTAPTV, SEQ ID NO: 1881

EVNTLRSQLGDRLNVEVDAAPTV, SEQ ID NO: 1882

EVNTLRSQLGDRLNVEVDTAPTV, SEQ ID NO: 1883

EVNTLRSPLGDRLNVEVDAAPTV, SEQ ID NO: 1884

EVNTLRSPLGDRLNVEVDTAPTV, SEQ ID NO: 11885

VNTLRCQLGDRLNVEVDAAPTVD, SEQ ID NO: 1886

VNTLRSQLGDRLNVEVDAAPTVD, SEQ ID NO: 1887

VNTLRCPLGDRLNVEVDAAPTVD, SEQ ID NO: 1888

VNTLRSPLGDRLNVEVDAAPTVD, SEQ ID NO: 1889

VNTLRCQLGDRLNVEVDTAPTVD, SEQ ID NO: 1890

VNTLRSQLGDRLNVEVDTAPTVD, SEQ ID NO: 1891

VNTLRCPLGDRLNVEVDTAPTVD, SEQ ID NO: 1892

VNTLRSPLGDRLNVEVDTAPTVD, SEQ ID NO: 1893

NTLRCQLGDRLNVEVDAAPTVDL, SEQ ID NO: 1894

NTLRSQLGDRLNVEVDAAPTVDL, SEQ ID NO: 1895

NTLRCPLGDRLNVEVDAAPTVDL, SEQ ID NO: 1896

NTLRSPLGDRLNVEVDAAPTVDL, SEQ ID NO: 1897

NTLRCQLGDRLNVEVDTAPTVDL, SEQ ID NO: 1898

NTLRSQLGDRLNVEVDTAPTVDL, SEQ ID NO: 1899

NTLRCPLGDRLNVEVDTAPTVDL, SEQ ID NO: 1900

NTLRSPLGDRLNVEVDTAPTVDL, SEQ ID NO: 1901

TLRCQLGDRLNVEVDAAPTVDLN, SEQ ID NO: 1902

TLRSQLGDRLNVEVDAAPTVDLN, SEQ ID NO: 1903

TLRCPLGDRLNVEVDAAPTVDLN, SEQ ID NO: 1904

TLRSPLGDRLNVEVDAAPTVDLN, SEQ ID NO: 1905

TLRCQLGDRLNVEVDTAPTVDLN, SEQ ID NO: 1906

TLRSQLGDRLNVEVDTAPTVDLN, SEQ ID NO: 1907

TLRCPLGDRLNVEVDTAPTVDLN, SEQ ID NO: 1908

TLRSPLGDRLNVEVDTAPTVDLN, SEQ ID NO: 1909

LRCQLGDRLNVEVDAAPTVDLNQ, SEQ ID NO: 1910

LRSQLGDRLNVEVDAAPTVDLNQ, SEQ ID NO: 1911

LRCPLGDRLNVEVDAAPTVDLNQ, SEQ ID NO: 1912

LRSPLGDRLNVEVDAAPTVDLNQ, SEQ ID NO: 1913

LRCQLGDRLNVEVDTAPTVDLNQ, SEQ ID NO: 1914

LRSQLGDRLNVEVDTAPTVDLNQ, SEQ ID NO: 1915

LRCPLGDRLNVEVDTAPTVDLNQ, SEQ ID NO: 1916

LRSPLGDRLNVEVDTAPTVDLNQ, SEQ ID NO: 1917

LRCQLGDRLNVEVDAAPTVDLNR, SEQ ID NO: 1918

LRSQLGDRLNVEVDAAPTVDLNR, SEQ ID NO: 1919

LRCPLGDRLNVEVDAAPTVDLNR, SEQ ID NO: 1920

LRSPLGDRLNVEVDAAPTVDLNR, SEQ ID NO: 1921

LRCQLGDRLNVEVDTAPTVDLNR, SEQ ID NO: 1922

LRSQLGDRLNVEVDTAPTVDLNR, SEQ ID NO: 1923

LRCPLGDRLNVEVDTAPTVDLNR, SEQ ID NO: 1924

LRSPLGDRLNVEVDTAPTVDLNR, SEQ ID NO: 1925

RCQLGDRLNVEVDAAPTVDLNQV, SEQ ID NO: 1926

RSQLGDRLNVEVDAAPTVDLNQV, SEQ ID NO: 1927

RCPLGDRLNVEVDAAPTVDLNQV, SEQ ID NO: 1928

RSPLGDRLNVEVDAAPTVDLNQV, SEQ ID NO: 1929

| | |
|---|---|
| RCQLGDRLNVEVDTAPTVDLNQV, | SEQ ID NO: 1930 |
| RSQLGDRLNVEVDTAPTVDLNQV, | SEQ ID NO: 1931 |
| RCPLGDRLNVEVDTAPTVDLNQV, | SEQ ID NO: 1932 |
| RSPLGDRLNVEVDTAPTVDLNQV, | SEQ ID NO: 1933 |
| RCQLGDRLNVEVDAAPTVDLNRV, | SEQ ID NO: 1934 |
| RSQLGDRLNVEVDAAPTVDLNRV, | SEQ ID NO: 1935 |
| RCPLGDRLNVEVDAAPTVDLNRV, | SEQ ID NO: 1936 |
| RSPLGDRLNVEVDAAPTVDLNRV, | SEQ ID NO: 1937 |
| RCQLGDRLNVEVDTAPTVDLNRV, | SEQ ID NO: 1938 |
| RSQLGDRLNVEVDTAPTVDLNRV, | SEQ ID NO: 1939 |
| RCPLGDRLNVEVDTAPTVDLNRV, | SEQ ID NO: 1940 |
| RSPLGDRLNVEVDTAPTVDLNRV, | SEQ ID NO: 1941 |
| CQLGDRLNVEVDAAPTVDLNQVL, | SEQ ID NO: 1942 |
| SQLGDRLNVEVDAAPTVDLNQVL, | SEQ ID NO: 1943 |
| CPLGDRLNVEVDAAPTVDLNQVL, | SEQ ID NO: 1944 |
| SPLGDRLNVEVDAAPTVDLNQVL, | SEQ ID NO: 1945 |
| CQLGDRLNVEVDTAPTVDLNQVL, | SEQ ID NO: 1946 |
| SQLGDRLNVEVDTAPTVDLNQVL, | SEQ ID NO: 1947 |
| CPLGDRLNVEVDTAPTVDLNQVL, | SEQ ID NO: 1948 |
| SPLGDRLNVEVDTAPTVDLNQVL, | SEQ ID NO: 1949 |
| CQLGDRLNVEVDAAPTVDLNRVL, | SEQ ID NO: 1950 |
| SQLGDRLNVEVDAAPTVDLNRVL, | SEQ ID NO: 1951 |
| CPLGDRLNVEVDAAPTVDLNRVL, | SEQ ID NO: 1952 |
| SPLGDRLNVEVDAAPTVDLNRVL, | SEQ ID NO: 1953 |
| CQLGDRLNVEVDTAPTVDLNRVL, | SEQ ID NO: 1954 |
| SQLGDRLNVEVDTAPTVDLNRVL, | SEQ ID NO: 1955 |
| CPLGDRLNVEVDTAPTVDLNRVL, | SEQ ID NO: 1956 |
| SPLGDRLNVEVDTAPTVDLNRVL, | SEQ ID NO: 1957 |
| QLGDRLNVEVDAAPTVDLNQVLN, | SEQ ID NO: 1958 |
| PLGDRLNVEVDAAPTVDLNQVLN, | SEQ ID NO: 1959 |
| QLGDRLNVEVDTAPTVDLNQVLN, | SEQ ID NO: 1960 |
| PLGDRLNVEVDTAPTVDLNQVLN, | SEQ ID NO: 1961 |
| QLGDRLNVEVDAAPTVDLNRVLN, | SEQ ID NO: 1962 |
| PLGDRLNVEVDAAPTVDLNRVLN, | SEQ ID NO: 1963 |
| QLGDRLNVEVDTAPTVDLNRVLN, | SEQ ID NO: 1964 |
| PLGDRLNVEVDTAPTVDLNRVLN, | SEQ ID NO: 1965 |
| LGDRLNVEVDAAPTVDLNQVLNE, | SEQ ID NO: 1966 |
| LGDRLNVEVDAAPTVDLNRVLNE, | SEQ ID NO: 1967 |
| LGDRLNVEVDTAPTVDLNQVLNE, | SEQ ID NO: 1968 |
| LGDRLNVEVDTAPTVDLNQVLNE, | SEQ ID NO: 1969 |
| GDRLNVEVDAAPTVDLNQVLNET, | SEQ ID NO: 1970 |
| GDRLNVEVDAAPTVDLNRVLNET, | SEQ ID NO: 1971 |
| GDRLNVEVDTAPTVDLNQVLNET, | SEQ ID NO: 1972 |
| GDRLNVEVDTAPTVDLNRVLNET, | SEQ ID NO: 1973 |
| DRLNVEVDAAPTVDLNQVLNETR, | SEQ ID NO: 1974 |
| DRLNVEVDAAPTVDLNRVLNETR, | SEQ ID NO: 1975 |
| DRLNVEVDTAPTVDLNQVLNETR, | SEQ ID NO: 1976 |
| DRLNVEVDTAPTVDLNRVLNETR, | SEQ ID NO: 21977 |
| RLNVEVDAAPTVDLNQVLNETRS, | SEQ ID NO: 1978 |
| RLNVEVDTAPTVDLNQVLNETRS, | SEQ ID NO: 1979 |
| RLNVEVDAAPTVDLNRVLNETRS, | SEQ ID NO: 1980 |
| RLNVEVDTAPTVDLNRVLNETRS, | SEQ ID NO: 1981 |
| RLNVEVDAAPTVDLNQVLNETRN, | SEQ ID NO: 1982 |
| RLNVEVDTAPTVDLNQVLNETRN, | SEQ ID NO: 1983 |

| Sequence | SEQ ID NO |
|---|---|
| RLNVEVDAAPTVDLNRVLNETRN, | SEQ ID NO: 1984 |
| RLNVEVDTAPTVDLNRVLNETRN, | SEQ ID NO: 1985 |
| LNVEVDAAPTVDLNQVLNETRSQ, | SEQ ID NO: 1986 |
| LNVEVDTAPTVDLNQVLNETRSQ, | SEQ ID NO: 1987 |
| LNVEVDAAPTVDLNRVLNETRSQ, | SEQ ID NO: 1988 |
| LNVEVDTAPTVDLNRVLNETRSQ, | SEQ ID NO: 1989 |
| LNVEVDAAPTVDLNQVLNETRNQ, | SEQ ID NO: 1990 |
| LNVEVDTAPTVDLNQVLNETRNQ, | SEQ ID NO: 1991 |
| LNVEVDAAPTVDLNRVLNETRNQ, | SEQ ID NO: 1992 |
| LNVEVDTAPTVDLNRVLNETRNQ, | SEQ ID NO: 1993 |
| NVEVDAAPTVDLNQVLNETRSQY, | SEQ ID NO: 1994 |
| NVEVDTAPTVDLNQVLNETRSQY, | SEQ ID NO: 1995 |
| NVEVDAAPTVDLNRVLNETRSQY, | SEQ ID NO: 1996 |
| NVEVDTAPTVDLNRVLNETRSQY, | SEQ ID NO: 1997 |
| NVEVDAAPTVDLNQVLNETRNQY, | SEQ ID NO: 1998 |
| NVEVDTAPTVDLNQVLNETRNQY, | SEQ ID NO: 1999 |
| NVEVDAAPTVDLNRVLNETRNQY, | SEQ ID NO: 2000 |
| NVEVDTAPTVDLNRVLNETRNQY, | SEQ ID NO: 2001 |
| VEVDAAPTVDLNQVLNETRSQYE, | SEQ ID NO: 2002 |
| VEVDTAPTVDLNQVLNETRSQYE, | SEQ ID NO: 2003 |
| VEVDAAPTVDLNRVLNETRSQYE, | SEQ ID NO: 2004 |
| VEVDTAPTVDLNRVLNETRSQYE, | SEQ ID NO: 2005 |
| EVDAAPTVDLNQVLNETRNQYE, | SEQ ID NO: 2006 |
| VEVDTAPTVDLNQVLNETRNQYE, | SEQ ID NO: 2007 |
| VEVDAAPTVDLNRVLNETRNQYE, | SEQ ID NO: 2008 |
| VEVDTAPTVDLNRVLNETRNQYE, | SEQ ID NO: 2009 |
| EVDAAPTVDLNQVLNETRSQYEA, | SEQ ID NO: 2010 |
| EVDTAPTVDLNQVLNETRSQYEA, | SEQ ID NO: 2011 |
| EVDAAPTVDLNRVLNETRSQYEA, | SEQ ID NO: 2012 |
| EVDTAPTVDLNRVLNETRSQYEA, | SEQ ID NO: 2013 |
| EVDAAPTVDLNQVLNETRNQYEA, | SEQ ID NO: 2014 |
| EVDTAPTVDLNQVLNETRNQYEA, | SEQ ID NO: 2015 |
| EVDAAPTVDLNRVLNETRNQYEA, | SEQ ID NO: 2016 |
| EVDTAPTVDLNRVLNETRNQYEA, | SEQ ID NO: 2017 |
| VDAAPTVDLNQVLNETRSQYEAL, | SEQ ID NO: 2018 |
| VDTAPTVDLNQVLNETRSQYEAL, | SEQ ID NO: 2019 |
| VDAAPTVDLNRVLNETRSQYEAL, | SEQ ID NO: 2020 |
| VDTAPTVDLNRVLNETRSQYEAL, | SEQ ID NO: 2021 |
| VDAAPTVDLNQVLNETRNQYEAL, | SEQ ID NO: 2022 |
| VDTAPTVDLNQVLNETRNQYEAL, | SEQ ID NO: 2023 |
| VDAAPTVDLNRVLNETRNQYEAL, | SEQ ID NO: 2024 |
| VDTAPTVDLNRVLNETRNQYEAL, | SEQ ID NO: 2025 |
| EVNTLRCQLGDRLNVEVDAAPTVD, | SEQ ID NO: 2026 |
| EVNTLRSQLGDRLNVEVDAAPTVD, | SEQ ID NO: 2027 |
| EVNTLRCPLGDRLNVEVDAAPTVD, | SEQ ID NO: 2028 |
| EVNTLRSPLGDRLNVEVDAAPTVD, | SEQ ID NO: 2029 |
| EVNTLRCQLGDRLNVEVDTAPTVD, | SEQ ID NO: 2030 |
| EVNTLRSQLGDRLNVEVDTAPTVD, | SEQ ID NO: 2031 |
| EVNTLRCPLGDRLNVEVDTAPTVD, | SEQ ID NO: 2032 |
| EVNTLRSPLGDRLNVEVDTAPTVD, | SEQ ID NO: 2033 |
| VNTLRCQLGDRLNVEVDAAPTVDL, | SEQ ID NO: 2034 |
| VNTLRSQLGDRLNVEVDAAPTVDL, | SEQ ID NO: 2035 |
| VNTLRCPLGDRLNVEVDAAPTVDL, | SEQ ID NO: 2036 |
| VNTLRSPLGDRLNVEVDAAPTVDL, | SEQ ID NO: 2037 |

VNTLRCQLGDRLNVEVDTAPTVDL, SEQ ID NO: 2038

VNTLRSQLGDRLNVEVDTAPTVDL, SEQ ID NO: 2039

VNTLRCPLGDRLNVEVDTAPTVDL, SEQ ID NO: 2040

VNTLRSPLGDRLNVEVDTAPTVDL, SEQ ID NO: 2041

NTLRCQLGDRLNVEVDAAPTVDLN, SEQ ID NO: 2042

NTLRSQLGDRLNVEVDAAPTVDLN, SEQ ID NO: 2043

NTLRCPLGDRLNVEVDAAPTVDLN, SEQ ID NO: 2044

NTLRSPLGDRLNVEVDAAPTVDLN, SEQ ID NO: 2045

NTLRCQLGDRLNVEVDTAPTVDLN, SEQ ID NO: 2046

NTLRSQLGDRLNVEVDTAPTVDLN, SEQ ID NO: 2047

NTLRCPLGDRLNVEVDTAPTVDLN, SEQ ID NO: 2048

NTLRSPLGDRLNVEVDTAPTVDLN, SEQ ID NO: 2049

TLRCQLGDRLNVEVDAAPTVDLNQ, SEQ ID NO: 2050

TLRSQLGDRLNVEVDAAPTVDLNQ, SEQ ID NO: 2051

TLRCPLGDRLNVEVDAAPTVDLNQ, SEQ ID NO: 2052

TLRSPLGDRLNVEVDAAPTVDLNQ, SEQ ID NO: 2053

TLRCQLGDRLNVEVDTAPTVDLNQ, SEQ ID NO: 2054

TLRSQLGDRLNVEVDTAPTVDLNQ, SEQ ID NO: 2055

TLRCPLGDRLNVEVDTAPTVDLNQ, SEQ ID NO: 2056

TLRSPLGDRLNVEVDTAPTVDLNQ, SEQ ID NO: 2057

TLRCQLGDRLNVEVDAAPTVDLNR, SEQ ID NO: 2058

TLRSQLGDRLNVEVDAAPTVDLNR, SEQ ID NO: 2059

TLRCPLGDRLNVEVDAAPTVDLNR, SEQ ID NO: 2060

TLRSPLGDRLNVEVDAAPTVDLNR, SEQ ID NO: 2061

TLRCQLGDRLNVEVDTAPTVDLNR, SEQ ID NO: 2062

TLRSQLGDRLNVEVDTAPTVDLNR, SEQ ID NO: 2063

TLRCPLGDRLNVEVDTAPTVDLNR, SEQ ID NO: 2064

TLRSPLGDRLNVEVDTAPTVDLNR, SEQ ID NO: 2065

LRCQLGDRLNVEVDAAPTVDLNQV, SEQ ID NO: 2066

LRSQLGDRLNVEVDAAPTVDLNQV, SEQ ID NO: 2067

LRCPLGDRLNVEVDAAPTVDLNQV, SEQ ID NO: 2068

LRSPLGDRLNVEVDAAPTVDLNQV, SEQ ID NO: 2069

LRCQLGDRLNVEVDTAPTVDLNQV, SEQ ID NO: 2070

LRSQLGDRLNVEVDTAPTVDLNQV, SEQ ID NO: 2071

LRCPLGDRLNVEVDTAPTVDLNQV, SEQ ID NO: 2072

LRSPLGDRLNVEVDTAPTVDLNQV, SEQ ID NO: 2073

LRCQLGDRLNVEVDAAPTVDLNRV, SEQ ID NO: 2074

LRSQLGDRLNVEVDAAPTVDLNRV, SEQ ID NO: 2075

LRCPLGDRLNVEVDAAPTVDLNRV, SEQ ID NO: 2076

LRSPLGDRLNVEVDAAPTVDLNRV, SEQ ID NO: 2077

LRCQLGDRLNVEVDTAPTVDLNRV, SEQ ID NO: 2078

LRSQLGDRLNVEVDTAPTVDLNRV, SEQ ID NO: 2079

LRCPLGDRLNVEVDTAPTVDLNRV, SEQ ID NO: 2080

LRSPLGDRLNVEVDTAPTVDLNRV, SEQ ID NO: 2081

RCQLGDRLNVEVDAAPTVDLNQVL, SEQ ID NO: 2082

RSQLGDRLNVEVDAAPTVDLNQVL, SEQ ID NO: 2083

RCPLGDRLNVEVDAAPTVDLNQVL, SEQ ID NO: 2084

RSPLGDRLNVEVDAAPTVDLNQVL, SEQ ID NO: 2085

RCQLGDRLNVEVDTAPTVDLNQVL, SEQ ID NO: 2086

RSQLGDRLNVEVDTAPTVDLNQVL, SEQ ID NO: 2087

RCPLGDRLNVEVDTAPTVDLNQVL, SEQ ID NO: 2088

RSPLGDRLNVEVDTAPTVDLNQVL, SEQ ID NO: 2089

RCQLGDRLNVEVDAAPTVDLNRVL, SEQ ID NO: 2090

RSQLGDRLNVEVDAAPTVDLNRVL, SEQ ID NO: 2091

| | |
|---|---|
| RCPLGDRLNVEVDAAPTVDLNRVL, | SEQ ID NO: 2092 |
| RSPLGDRLNVEVDAAPTVDLNRVL, | SEQ ID NO: 2093 |
| RCQLGDRLNVEVDTAPTVDLNRVL, | SEQ ID NO: 2094 |
| RSQLGDRLNVEVDTAPTVDLNRVL, | SEQ ID NO: 2095 |
| RCPLGDRLNVEVDTAPTVDLNRVL, | SEQ ID NO: 2096 |
| RSPLGDRLNVEVDTAPTVDLNRVL, | SEQ ID NO: 2097 |
| CQLGDRLNVEVDAAPTVDLNQVLN, | SEQ ID NO: 2098 |
| SQLGDRLNVEVDAAPTVDLNQVLN, | SEQ ID NO: 2099 |
| CPLGDRLNVEVDAAPTVDLNQVLN, | SEQ ID NO: 2100 |
| SPLGDRLNVEVDAAPTVDLNQVLN, | SEQ ID NO: 2101 |
| CQLGDRLNVEVDTAPTVDLNQVLN, | SEQ ID NO: 2102 |
| SQLGDRLNVEVDTAPTVDLNQVLN, | SEQ ID NO: 2103 |
| CPLGDRLNVEVDTAPTVDLNQVLN, | SEQ ID NO: 2104 |
| SPLGDRLNVEVDTAPTVDLNQVLN, | SEQ ID NO: 2105 |
| CQLGDRLNVEVDAAPTVDLNRVLN, | SEQ ID NO: 2106 |
| SQLGDRLNVEVDAAPTVDLNRVLN, | SEQ ID NO: 2107 |
| CPLGDRLNVEVDAAPTVDLNRVLN, | SEQ ID NO: 2108 |
| SPLGDRLNVEVDAAPTVDLNRVLN, | SEQ ID NO: 2109 |
| CQLGDRLNVEVDTAPTVDLNRVLN, | SEQ ID NO: 2110 |
| SQLGDRLNVEVDTAPTVDLNRVLN, | SEQ ID NO: 2111 |
| CPLGDRLNVEVDTAPTVDLNRVLN, | SEQ ID NO: 2112 |
| SPLGDRLNVEVDTAPTVDLNRVLN, | SEQ ID NO: 2113 |
| QLGDRLNVEVDAAPTVDLNQVLNE, | SEQ ID NO: 2114 |
| PLGDRLNVEVDAAPTVDLNQVLNE, | SEQ ID NO: 2115 |
| QLGDRLNVEVDTAPTVDLNQVLNE, | SEQ ID NO: 2116 |
| PLGDRLNVEVDTAPTVDLNQVLNE, | SEQ ID NO: 2117 |
| QLGDRLNVEVDAAPTVDLNRVLNE, | SEQ ID NO: 2118 |
| PLGDRLNVEVDAAPTVDLNRVLNE, | SEQ ID NO: 2119 |
| QLGDRLNVEVDTAPTVDLNRVLNE, | SEQ ID NO: 2120 |
| PLGDRLNVEVDTAPTVDLNRVLNE, | SEQ ID NO: 2121 |
| LGDRLNVEVDAAPTVDLNQVLNET, | SEQ ID NO: 2122 |
| LGDRLNVEVDAAPTVDLNRVLNET, | SEQ ID NO: 2123 |
| LGDRLNVEVDTAPTVDLNQVLNET, | SEQ ID NO: 2124 |
| LGDRLNVEVDTAPTVDLNRVLNET, | SEQ ID NO: 2125 |
| GDRLNVEVDAAPTVDLNQVLNETR, | SEQ ID NO: 2126 |
| GDRLNVEVDAAPTVDLNRVLNETR, | SEQ ID NO: 2127 |
| GDRLNVEVDTAPTVDLNQVLNETR, | SEQ ID NO: 2128 |
| GDRLNVEVDTAPTVDLNRVLNETR, | SEQ ID NO: 2129 |
| DRLNVEVDAAPTVDLNQVLNETRS, | SEQ ID NO: 2130 |
| DRLNVEVDTAPTVDLNQVLNETRS, | SEQ ID NO: 2131 |
| DRLNVEVDAAPTVDLNRVLNETRS, | SEQ ID NO: 2132 |
| DRLNVEVDTAPTVDLNRVLNETRS, | SEQ ID NO: 2133 |
| DRLNVEVDAAPTVDLNQVLNETRN, | SEQ ID NO: 2134 |
| DRLNVEVDTAPTVDLNQVLNETRN, | SEQ ID NO: 2135 |
| DRLNVEVDAAPTVDLNRVLNETRN, | SEQ ID NO: 2136 |
| DRLNVEVDTAPTVDLNRVLNETRN, | SEQ ID NO: 2137 |
| RLNVEVDAAPTVDLNQVLNETRSQ, | SEQ ID NO: 2138 |
| RLNVEVDTAPTVDLNQVLNETRSQ, | SEQ ID NO: 2139 |
| RLNVEVDAAPTVDLNRVLNETRSQ, | SEQ ID NO: 2140 |
| RLNVEVDTAPTVDLNRVLNETRSQ, | SEQ ID NO: 2141 |
| RLNVEVDAAPTVDLNQVLNETRNQ, | SEQ ID NO: 2142 |
| RLNVEVDTAPTVDLNQVLNETRNQ, | SEQ ID NO: 2143 |
| RLNVEVDAAPTVDLNRVLNETRNQ, | SEQ ID NO: 2144 |
| RLNVEVDTAPTVDLNRVLNETRNQ, | SEQ ID NO: 2145 |

| Sequence | SEQ ID NO |
|---|---|
| LNVEVDAAPTVDLNQVLNETRSQY, | 2146 |
| LNVEVDTAPTVDLNQVLNETRSQY, | 2147 |
| LNVEVDAAPTVDLNRVLNETRSQY, | 2148 |
| LNVEVDTAPTVDLNRVLNETRSQY, | 2149 |
| LNVEVDAAPTVDLNQVLNETRNQY, | 2150 |
| LNVEVDTAPTVDLNQVLNETRNQY, | 2151 |
| LNVEVDAAPTVDLNRVLNETRNQY, | 2152 |
| LNVEVDTAPTVDLNRVLNETRNQY, | 2153 |
| NVEVDAAPTVDLNQVLNETRSQYE, | 2154 |
| NVEVDTAPTVDLNQVLNETRSQYE, | 2155 |
| NVEVDAAPTVDLNRVLNETRSQYE, | 2156 |
| NVEVDTAPTVDLNRVLNETRSQYE, | 2157 |
| NVEVDAAPTVDLNQVLNETRNQYE, | 2158 |
| NVEVDTAPTVDLNQVLNETRNQYE, | 2159 |
| NVEVDAAPTVDLNRVLNETRNQYE, | 2160 |
| NVEVDTAPTVDLNRVLNETRNQYE, | 2161 |
| VEVDAAPTVDLNQVLNETRSQYEA, | 2162 |
| VEVDTAPTVDLNQVLNETRSQYEA, | 2163 |
| VEVDAAPTVDLNRVLNETRSQYEA, | 2164 |
| VEVDTAPTVDLNRVLNETRSQYEA, | 2165 |
| VEVDAAPTVDLNQVLNETRNQYEA, | 2166 |
| VEVDTAPTVDLNQVLNETRNQYEA, | 2167 |
| VEVDAAPTVDLNRVLNETRNQYEA, | 2168 |
| VEVDTAPTVDLNRVLNETRNQYEA, | 2169 |
| EVDAAPTVDLNQVLNETRSQYEAL, | 2170 |
| EVDTAPTVDLNQVLNETRSQYEAL, | 2171 |
| EVDAAPTVDLNRVLNETRSQYEAL, | 2172 |
| EVDTAPTVDLNRVLNETRSQYEAL, | 2173 |
| EVDAAPTVDLNQVLNETRNQYEAL, | 2174 |
| EVDTAPTVDLNQVLNETRNQYEAL, | 2175 |
| EVDAAPTVDLNRVLNETRNQYEAL, | 2176 |
| EVDTAPTVDLNRVLNETRNQYEAL, | 2177 |
| EVNTLRCQLGDRLNVEVDAAPTVDL, | 2178 |
| EVNTLRSQLGDRLNVEVDAAPTVDL, | 2179 |
| EVNTLRCPLGDRLNVEVDAAPTVDL, | 2180 |
| EVNTLRSPLGDRLNVEVDAAPTVDL, | 2181 |
| EVNTLRCQLGDRLNVEVDTAPTVDL, | 2182 |
| EVNTLRSQLGDRLNVEVDTAPTVDL, | 2183 |
| EVNTLRCPLGDRLNVEVDTAPTVDL, | 2184 |
| EVNTLRSPLGDRLNVEVDTAPTVDL, | 2185 |
| VNTLRCQLGDRLNVEVDAAPTVDLN, | 2186 |
| VNTLRSQLGDRLNVEVDAAPTVDLN, | 2187 |
| VNTLRCPLGDRLNVEVDAAPTVDLN, | 2188 |
| VNTLRSPLGDRLNVEVDAAPTVDLN, | 2189 |
| VNTLRCQLGDRLNVEVDTAPTVDLN, | 2190 |
| VNTLRSQLGDRLNVEVDTAPTVDLN, | 2191 |
| VNTLRCPLGDRLNVEVDTAPTVDLN, | 2192 |
| VNTLRSPLGDRLNVEVDTAPTVDLN, | 2193 |
| NTLRCQLGDRLNVEVDAAPTVDLNQ, | 2194 |
| NTLRSQLGDRLNVEVDAAPTVDLNQ, | 2195 |
| NTLRCPLGDRLNVEVDAAPTVDLNQ, | 2196 |
| NTLRSPLGDRLNVEVDAAPTVDLNQ, | 2197 |
| NTLRCQLGDRLNVEVDTAPTVDLNQ, | 2198 |
| NTLRSQLGDRLNVEVDTAPTVDLNQ, | 2199 |

NTLRCPLGDRLNVEVDTAPTVDLNQ, SEQ ID NO: 2200

NTLRSPLGDRLNVEVDTAPTVDLNQ, SEQ ID NO: 2201

NTLRCQLGDRLNVEVDAAPTVDLNR, SEQ ID NO: 2202

NTLRSQLGDRLNVEVDAAPTVDLNR, SEQ ID NO: 2203

NTLRCPLGDRLNVEVDAAPTVDLNR, SEQ ID NO: 2204

NTLRSPLGDRLNVEVDAAPTVDLNR, SEQ ID NO: 2205

NTLRCQLGDRLNVEVDTAPTVDLNR, SEQ ID NO: 2206

NTLRSQLGDRLNVEVDTAPTVDLNR, SEQ ID NO: 2207

NTLRCPLGDRLNVEVDTAPTVDLNR, SEQ ID NO: 2208

NTLRSPLGDRLNVEVDTAPTVDLNR, SEQ ID NO: 2209

TLRCQLGDRLNVEVDAAPTVDLNQV, SEQ ID NO: 2210

TLRSQLGDRLNVEVDAAPTVDLNQV, SEQ ID NO: 2211

TLRCPLGDRLNVEVDAAPTVDLNQV, SEQ ID NO: 2212

TLRSPLGDRLNVEVDAAPTVDLNQV, SEQ ID NO: 2213

TLRCQLGDRLNVEVDTAPTVDLNQV, SEQ ID NO: 2214

TLRSQLGDRLNVEVDTAPTVDLNQV, SEQ ID NO: 2215

TLRCPLGDRLNVEVDTAPTVDLNQV, SEQ ID NO: 2216

TLRSPLGDRLNVEVDTAPTVDLNQV, SEQ ID NO: 2217

TLRCQLGDRLNVEVDAAPTVDLNRV, SEQ ID NO: 2218

TLRSQLGDRLNVEVDAAPTVDLNRV, SEQ ID NO: 2219

TLRCPLGDRLNVEVDAAPTVDLNRV, SEQ ID NO: 2220

TLRSPLGDRLNVEVDAAPTVDLNRV, SEQ ID NO: 2221

TLRCQLGDRLNVEVDTAPTVDLNRV, SEQ ID NO: 2222

TLRSQLGDRLNVEVDTAPTVDLNRV, SEQ ID NO: 2223

TLRCPLGDRLNVEVDTAPTVDLNRV, SEQ ID NO: 2224

TLRSPLGDRLNVEVDTAPTVDLNRV, SEQ ID NO: 2225

LRCQLGDRLNVEVDAAPTVDLNQVL, SEQ ID NO: 2226

LRSQLGDRLNVEVDAAPTVDLNQVL, SEQ ID NO: 2227

LRCPLGDRLNVEVDAAPTVDLNQVL, SEQ ID NO: 2228

LRSPLGDRLNVEVDAAPTVDLNQVL, SEQ ID NO: 2229

LRCQLGDRLNVEVDTAPTVDLNQVL, SEQ ID NO: 2230

LRSQLGDRLNVEVDTAPTVDLNQVL, SEQ ID NO: 2231

LRCPLGDRLNVEVDTAPTVDLNQVL, SEQ ID NO: 2232

LRSPLGDRLNVEVDTAPTVDLNQVL, SEQ ID NO: 2233

LRCQLGDRLNVEVDAAPTVDLNRVL, SEQ ID NO: 2234

LRSQLGDRLNVEVDAAPTVDLNRVL, SEQ ID NO: 2235

LRCPLGDRLNVEVDAAPTVDLNRVL, SEQ ID NO: 2236

LRSPLGDRLNVEVDAAPTVDLNRVL, SEQ ID NO: 2237

LRCQLGDRLNVEVDTAPTVDLNRVL, SEQ ID NO: 2238

LRSQLGDRLNVEVDTAPTVDLNRVL, SEQ ID NO: 2239

LRCPLGDRLNVEVDTAPTVDLNRVL, SEQ ID NO: 2240

LRSPLGDRLNVEVDTAPTVDLNRV, SEQ ID NO: 2241

RCQLGDRLNVEVDAAPTVDLNQVLN, SEQ ID NO: 2242

RSQLGDRLNVEVDAAPTVDLNQVLN, SEQ ID NO: 2243

RCPLGDRLNVEVDAAPTVDLNQVLN, SEQ ID NO: 2244

RSPLGDRLNVEVDAAPTVDLNQVLN, SEQ ID NO: 2245

RCQLGDRLNVEVDTAPTVDLNQVLN, SEQ ID NO: 2246

RSQLGDRLNVEVDTAPTVDLNQVLN, SEQ ID NO: 2247

RCPLGDRLNVEVDTAPTVDLNQVLN, SEQ ID NO: 2248

RSPLGDRLNVEVDTAPTVDLNQVLN, SEQ ID NO: 2249

RCQLGDRLNVEVDAAPTVDLNRVLN, SEQ ID NO: 2250

RSQLGDRLNVEVDAAPTVDLNRVLN, SEQ ID NO: 2251

RCPLGDRLNVEVDAAPTVDLNRVLN, SEQ ID NO: 2252

RSPLGDRLNVEVDAAPTVDLNRVLN, SEQ ID NO: 2253

RCQLGDRLNVEVDTAPTVDLNRVLN, SEQ ID NO: 2254

RSQLGDRLNVEVDTAPTVDLNRVLN, SEQ ID NO: 2255

RCPLGDRLNVEVDTAPTVDLNRVLN, SEQ ID NO: 2256

RSPLGDRLNVEVDTAPTVDLNRVLN, SEQ ID NO: 2257

CQLGDRLNVEVDAAPTVDLNQVLNE, SEQ ID NO: 2258

SQLGDRLNVEVDAAPTVDLNQVLNE, SEQ ID NO: 2259

CPLGDRLNVEVDAAPTVDLNQVLNE, SEQ ID NO: 2260

SPLGDRLNVEVDAAPTVDLNQVLNE, SEQ ID NO: 2261

CQLGDRLNVEVDTAPTVDLNQVLNE, SEQ ID NO: 2262

SQLGDRLNVEVDTAPTVDLNQVLNE, SEQ ID NO: 2263

CPLGDRLNVEVDTAPTVDLNQVLNE, SEQ ID NO: 2264

SPLGDRLNVEVDTAPTVDLNQVLNE, SEQ ID NO: 2265

CQLGDRLNVEVDAAPTVDLNRVLNE, SEQ ID NO: 2266

SQLGDRLNVEVDAAPTVDLNRVLNE, SEQ ID NO: 2267

CPLGDRLNVEVDAAPTVDLNRVLNE, SEQ ID NO: 2268

SPLGDRLNVEVDAAPTVDLNRVLNE, SEQ ID NO: 2269

CQLGDRLNVEVDTAPTVDLNRVLNE, SEQ ID NO: 2274

SQLGDRLNVEVDTAPTVDLNRVLNE, SEQ ID NO: 2271

CPLGDRLNVEVDTAPTVDLNRVLNE, SEQ ID NO: 2272

SPLGDRLNVEVDTAPTVDLNRVLNE, SEQ ID NO: 2273

QLGDRLNVEVDAAPTVDLNQVLNET, SEQ ID NO: 2274

PLGDRLNVEVDAAPTVDLNQVLNET, SEQ ID NO: 2275

QLGDRLNVEVDTAPTVDLNQVLNET, SEQ ID NO: 2276

PLGDRLNVEVDTAPTVDLNQVLNET, SEQ ID NO: 2277

QLGDRLNVEVDAAPTVDLNRVLNET, SEQ ID NO: 2278

PLGDRLNVEVDAAPTVDLNRVLNET, SEQ ID NO: 2279

QLGDRLNVEVDTAPTVDLNRVLNET, SEQ ID NO: 2280

PLGDRLNVEVDTAPTVDLNRVLNET, SEQ ID NO: 2281

LGDRLNVEVDAAPTVDLNQVLNETR, SEQ ID NO: 2282

LGDRLNVEVDAAPTVDLNRVLNETR, SEQ ID NO: 2283

LGDRLNVEVDTAPTVDLNQVLNETR, SEQ ID NO: 2284

LGDRLNVEVDTAPTVDLNRVLNETR, SEQ ID NO: 42285

GDRLNVEVDAAPTVDLNQVLNETRS, SEQ ID NO: 2286

GDRLNVEVDTAPTVDLNQVLNETRS, SEQ ID NO: 2287

GDRLNVEVDAAPTVDLNRVLNETRS, SEQ ID NO: 2288

GDRLNVEVDTAPTVDLNRVLNETRS, SEQ ID NO: 2289

GDRLNVEVDAAPTVDLNQVLNETRN, SEQ ID NO: 2290

GDRLNVEVDTAPTVDLNQVLNETRN, SEQ ID NO: 2291

GDRLNVEVDAAPTVDLNRVLNETRN, SEQ ID NO: 2292

GDRLNVEVDTAPTVDLNRVLNETRN, SEQ ID NO: 2293

DRLNVEVDAAPTVDLNQVLNETRSQ, SEQ ID NO: 2294

DRLNVEVDTAPTVDLNQVLNETRSQ, SEQ ID NO: 2295

DRLNVEVDAAPTVDLNRVLNETRSQ, SEQ ID NO: 2296

DRLNVEVDTAPTVDLNRVLNETRSQ, SEQ ID NO: 2297

DRLNVEVDAAPTVDLNQVLNETRNQ, SEQ ID NO: 2298

DRLNVEVDTAPTVDLNQVLNETRNQ, SEQ ID NO: 2299

DRLNVEVDAAPTVDLNRVLNETRNQ, SEQ ID NO: 2300

DRLNVEVDTAPTVDLNRVLNETRNQ, SEQ ID NO: 2301

RLNVEVDAAPTVDLNQVLNETRSQY, SEQ ID NO: 2302

RLNVEVDTAPTVDLNQVLNETRSQY, SEQ ID NO: 2303

RLNVEVDAAPTVDLNRVLNETRSQY, SEQ ID NO: 2304

RLNVEVDTAPTVDLNRVLNETRSQY, SEQ ID NO: 2305

RLNVEVDAAPTVDLNQVLNETRNQY, SEQ ID NO: 2306

RLNVEVDTAPTVDLNQVLNETRNQY, SEQ ID NO: 2307

| Sequence | SEQ ID NO: |
|---|---|
| RLNVEVDAAPTVDLNRVLNETRNQY, | 2308 |
| RLNVEVDTAPTVDLNRVLNETRNQY, | 2309 |
| LNVEVDAAPTVDLNQVLNETRSQYE, | 2310 |
| LNVEVDTAPTVDLNQVLNETRSQYE, | 2311 |
| LNVEVDAAPTVDLNRVLNETRSQYE, | 2312 |
| LNVEVDTAPTVDLNRVLNETRSQYE, | 2313 |
| LNVEVDAAPTVDLNQVLNETRNQYE, | 2314 |
| LNVEVDTAPTVDLNQVLNETRNQYE, | 2315 |
| LNVEVDAAPTVDLNRVLNETRNQYE, | 2316 |
| LNVEVDTAPTVDLNRVLNETRNQYE, | 2317 |
| NVEVDAAPTVDLNQVLNETRSQYEA, | 2318 |
| NVEVDTAPTVDLNQVLNETRSQYEA, | 2319 |
| NVEVDAAPTVDLNRVLNETRSQYEA, | 2320 |
| NVEVDTAPTVDLNRVLNETRSQYEA, | 2321 |
| NVEVDAAPTVDLNQVLNETRNQYEA, | 2322 |
| NVEVDTAPTVDLNQVLNETRNQYEA, | 2323 |
| NVEVDAAPTVDLNRVLNETRNQYEA, | 2324 |
| NVEVDTAPTVDLNRVLNETRNQYEA, | 2325 |
| VEVDAAPTVDLNQVLNETRSQYEAL, | 2326 |
| VEVDTAPTVDLNQVLNETRSQYEAL, | 2327 |
| VEVDAAPTVDLNRVLNETRSQYEAL, | 2328 |
| VEVDTAPTVDLNRVLNETRSQYEAL, | 2329 |
| VEVDAAPTVDLNQVLNETRNQYEAL, | 2330 |
| VEVDTAPTVDLNQVLNETRNQYEAL, | 2331 |
| VEVDAAPTVDLNRVLNETRNQYEAL, | 2332 |
| VEVDTAPTVDLNRVLNETRNQYEAL, | 2333 |
| EVNTLRCQLGDRLNVEVDAAPTVDLN, | 2334 |
| EVNTLRSQLGDRLNVEVDAAPTVDLN, | 2335 |
| EVNTLRCPLGDRLNVEVDAAPTVDLN, | 2336 |
| EVNTLRSPLGDRLNVEVDAAPTVDLN, | 2337 |
| EVNTLRCQLGDRLNVEVDTAPTVDLN, | 2338 |
| EVNTLRSQLGDRLNVEVDTAPTVDLN, | 2339 |
| EVNTLRCPLGDRLNVEVDTAPTVDLN, | 2340 |
| EVNTLRSPLGDRLNVEVDTAPTVDLN, | 2341 |
| VNTLRCQLGDRLNVEVDAAPTVDLNQ, | 2342 |
| VNTLRSQLGDRLNVEVDAAPTVDLNQ, | 2343 |
| VNTLRCPLGDRLNVEVDAAPTVDLNQ, | 2344 |
| VNTLRSPLGDRLNVEVDAAPTVDLNQ, | 2345 |
| VNTLRCQLGDRLNVEVDTAPTVDLNQ, | 2346 |
| VNTLRSQLGDRLNVEVDTAPTVDLNQ, | 2347 |
| VNTLRCPLGDRLNVEVDTAPTVDLNQ, | 2348 |
| VNTLRSPLGDRLNVEVDTAPTVDLNQ, | 2349 |
| VNTLRCQLGDRLNVEVDAAPTVDLNR, | 2350 |
| VNTLRSQLGDRLNVEVDAAPTVDLNR, | 2351 |
| VNTLRCPLGDRLNVEVDAAPTVDLNR, | 2352 |
| VNTLRSPLGDRLNVEVDAAPTVDLNR, | 2353 |
| VNTLRCQLGDRLNVEVDTAPTVDLNR, | 2354 |
| VNTLRSQLGDRLNVEVDTAPTVDLNR, | 2355 |
| VNTLRCPLGDRLNVEVDTAPTVDLNR, | 2356 |
| VNTLRSPLGDRLNVEVDTAPTVDLNR, | 2357 |
| NTLRCQLGDRLNVEVDAAPTVDLNQV, | 2358 |
| NTLRSQLGDRLNVEVDAAPTVDLNQV, | 2359 |
| NTLRCPLGDRLNVEVDAAPTVDLNQV, | 2360 |
| NTLRSPLGDRLNVEVDAAPTVDLNQV, | 2361 |

| | |
|---|---|
| NTLRCQLGDRLNVEVDTAPTVDLNQV, | SEQ ID NO: 2362 |
| NTLRSQLGDRLNVEVDTAPTVDLNQV, | SEQ ID NO: 2363 |
| NTLRCPLGDRLNVEVDTAPTVDLNQV, | SEQ ID NO: 2364 |
| NTLRSPLGDRLNVEVDTAPTVDLNQV, | SEQ ID NO: 2365 |
| NTLRCQLGDRLNVEVDAAPTVDLNRV, | SEQ ID NO: 2366 |
| NTLRSQLGDRLNVEVDAAPTVDLNRV, | SEQ ID NO: 2367 |
| NTLRCPLGDRLNVEVDAAPTVDLNRV, | SEQ ID NO: 2368 |
| NTLRSPLGDRLNVEVDAAPTVDLNRV, | SEQ ID NO: 2369 |
| NTLRCQLGDRLNVEVDTAPTVDLNRV, | SEQ ID NO: 2370 |
| NTLRSQLGDRLNVEVDTAPTVDLNRV, | SEQ ID NO: 2371 |
| NTLRCPLGDRLNVEVDTAPTVDLNRV, | SEQ ID NO: 2372 |
| NTLRSPLGDRLNVEVDTAPTVDLNRV, | SEQ ID NO: 2373 |
| TLRCQLGDRLNVEVDAAPTVDLNQVL, | SEQ ID NO: 2374 |
| TLRSQLGDRLNVEVDAAPTVDLNQVL, | SEQ ID NO: 2375 |
| TLRCPLGDRLNVEVDAAPTVDLNQVL, | SEQ ID NO: 2376 |
| TLRSPLGDRLNVEVDAAPTVDLNQVL, | SEQ ID NO: 2377 |
| TLRCQLGDRLNVEVDTAPTVDLNQVL, | SEQ ID NO: 2378 |
| TLRSQLGDRLNVEVDTAPTVDLNQVL, | SEQ ID NO: 2379 |
| TLRCPLGDRLNVEVDTAPTVDLNQVL, | SEQ ID NO: 2380 |
| TLRSPLGDRLNVEVDTAPTVDLNQVL, | SEQ ID NO: 2381 |
| TLRCQLGDRLNVEVDAAPTVDLNRVL, | SEQ ID NO: 2382 |
| TLRSQLGDRLNVEVDAAPTVDLNRVL, | SEQ ID NO: 2383 |
| TLRCPLGDRLNVEVDAAPTVDLNRVL, | SEQ ID NO: 2384 |
| TLRSPLGDRLNVEVDAAPTVDLNRVL, | SEQ ID NO: 2385 |
| TLRCQLGDRLNVEVDTAPTVDLNRVL, | SEQ ID NO: 2386 |
| TLRSQLGDRLNVEVDTAPTVDLNRVL, | SEQ ID NO: 2387 |
| TLRCPLGDRLNVEVDTAPTVDLNRVL, | SEQ ID NO: 2388 |
| TLRSPLGDRLNVEVDTAPTVDLNRVL, | SEQ ID NO: 2389 |
| LRCQLGDRLNVEVDAAPTVDLNQVLN, | SEQ ID NO: 2390 |
| LRSQLGDRLNVEVDAAPTVDLNQVLN, | SEQ ID NO: 2391 |
| LRCPLGDRLNVEVDAAPTVDLNQVLN, | SEQ ID NO: 2392 |
| LRSPLGDRLNVEVDAAPTVDLNQVLN, | SEQ ID NO: 2393 |
| LRCQLGDRLNVEVDTAPTVDLNQVLN, | SEQ ID NO: 2394 |
| LRSQLGDRLNVEVDTAPTVDLNQVLN, | SEQ ID NO: 2395 |
| LRCPLGDRLNVEVDTAPTVDLNQVLN, | SEQ ID NO: 2396 |
| LRSPLGDRLNVEVDTAPTVDLNQVLN, | SEQ ID NO: 2397 |
| LRCQLGDRLNVEVDAAPTVDLNRVLN, | SEQ ID NO: 2398 |
| LRSQLGDRLNVEVDAAPTVDLNRVLN, | SEQ ID NO: 2399 |
| LRCPLGDRLNVEVDAAPTVDLNRVLN, | SEQ ID NO: 2400 |
| LRSPLGDRLNVEVDAAPTVDLNRVLN, | SEQ ID NO: 2401 |
| LRCQLGDRLNVEVDTAPTVDLNRVLN, | SEQ ID NO: 2402 |
| LRSQLGDRLNVEVDTAPTVDLNRVLN, | SEQ ID NO: 2403 |
| LRCPLGDRLNVEVDTAPTVDLNRVLN, | SEQ ID NO: 2404 |
| LRSPLGDRLNVEVDTAPTVDLNRVLN, | SEQ ID NO: 2405 |
| RCQLGDRLNVEVDAAPTVDLNQVLNE, | SEQ ID NO: 2406 |
| RSQLGDRLNVEVDAAPTVDLNQVLNE, | SEQ ID NO: 2407 |
| RCPLGDRLNVEVDAAPTVDLNQVLNE, | SEQ ID NO: 2408 |
| RSQLGDRLNVEVDAAPTVDLNQVLNE, | SEQ ID NO: 2409 |
| RCQLGDRLNVEVDTAPTVDLNQVLNE, | SEQ ID NO: 2410 |
| RSQLGDRLNVEVDTAPTVDLNQVLNE, | SEQ ID NO: 2411 |
| RCPLGDRLNVEVDTAPTVDLNQVLNE, | SEQ ID NO: 2412 |
| RSPLGDRLNVEVDTAPTVDLNQVLNE, | SEQ ID NO: 2413 |
| RCQLGDRLNVEVDAAPTVDLNRVLNE, | SEQ ID NO: 2414 |
| RSQLGDRLNVEVDAAPTVDLNRVLNE, | SEQ ID NO: 2415 |

| | |
|---|---|
| RCPLGDRLNVEVDAAPTVDLNRVLNE, | SEQ ID NO: 2416 |
| RSPLGDRLNVEVDAAPTVDLNRVLNE, | SEQ ID NO: 2417 |
| RCQLGDRLNVEVDTAPTVDLNRVLNE, | SEQ ID NO: 2418 |
| RSQLGDRLNVEVDTAPTVDLNRVLNE, | SEQ ID NO: 2419 |
| RCPLGDRLNVEVDTAPTVDLNRVLNE, | SEQ ID NO: 2420 |
| RSPLGDRLNVEVDTAPTVDLNRVLNE, | SEQ ID NO: 2421 |
| CQLGDRLNVEVDAAPTVDLNQVLNET, | SEQ ID NO: 2422 |
| SQLGDRLNVEVDAAPTVDLNQVLNET, | SEQ ID NO: 2423 |
| CPLGDRLNVEVDAAPTVDLNQVLNET, | SEQ ID NO: 2424 |
| SPLGDRLNVEVDAAPTVDLNQVLNET, | SEQ ID NO: 2425 |
| CQLGDRLNVEVDTAPTVDLNQVLNET, | SEQ ID NO: 2426 |
| SQLGDRLNVEVDTAPTVDLNQVLNET, | SEQ ID NO: 2427 |
| CPLGDRLNVEVDTAPTVDLNQVLNET, | SEQ ID NO: 2428 |
| SPLGDRLNVEVDTAPTVDLNQVLNET, | SEQ ID NO: 2429 |
| CQLGDRLNVEVDAAPTVDLNRVLNET, | SEQ ID NO: 2430 |
| SQLGDRLNVEVDAAPTVDLNRVLNET, | SEQ ID NO: 2431 |
| CPLGDRLNVEVDAAPTVDLNRVLNET, | SEQ ID NO: 2432 |
| SPLGDRLNVEVDAAPTVDLNRVLNET, | SEQ ID NO: 2433 |
| CQLGDRLNVEVDTAPTVDLNRVLNET, | SEQ ID NO: 2434 |
| SQLGDRLNVEVDTAPTVDLNRVLNET, | SEQ ID NO: 2435 |
| CPLGDRLNVEVDTAPTVDLNRVLNET, | SEQ ID NO: 2436 |
| SPLGDRLNVEVDTAPTVDLNRVLNET, | SEQ ID NO: 2437 |
| QLGDRLNVEVDAAPTVDLNQVLNETR, | SEQ ID NO: 2438 |
| PLGDRLNVEVDAAPTVDLNQVLNETR, | SEQ ID NO: 2439 |
| QLGDRLNVEVDTAPTVDLNQVLNETR, | SEQ ID NO: 2440 |
| PLGDRLNVEVDTAPTVDLNQVLNETR, | SEQ ID NO: 2441 |
| QLGDRLNVEVDAAPTVDLNRVLNETR, | SEQ ID NO: 2442 |
| PLGDRLNVEVDAAPTVDLNRVLNETR, | SEQ ID NO: 2443 |
| QLGDRLNVEVDTAPTVDLNRVLNETR, | SEQ ID NO: 2444 |
| PLGDRLNVEVDTAPTVDLNRVLNETR, | SEQ ID NO: 2445 |
| LGDRLNVEVDAAPTVDLNQVLNETRS, | SEQ ID NO: 2446 |
| LGDRLNVEVDTAPTVDLNQVLNETRS, | SEQ ID NO: 2447 |
| LGDRLNVEVDAAPTVDLNRVLNETRS, | SEQ ID NO: 2448 |
| LGDRLNVEVDTAPTVDLNRVLNETRS, | SEQ ID NO: 2449 |
| LGDRLNVEVDAAPTVDLNQVLNETRN, | SEQ ID NO: 2450 |
| LGDRLNVEVDTAPTVDLNQVLNETRN, | SEQ ID NO: 2451 |
| LGDRLNVEVDAAPTVDLNRVLNETRN, | SEQ ID NO: 2452 |
| LGDRLNVEVDTAPTVDLNRVLNETRN, | SEQ ID NO: 2453 |
| GDRLNVEVDAAPTVDLNQVLNETRSQ, | SEQ ID NO: 2454 |
| GDRLNVEVDTAPTVDLNQVLNETRSQ, | SEQ ID NO: 2455 |
| GDRLNVEVDAAPTVDLNRVLNETRSQ, | SEQ ID NO: 2456 |
| GDRLNVEVDTAPTVDLNRVLNETRSQ, | SEQ ID NO: 2457 |
| GDRLNVEVDAAPTVDLNQVLNETRNQ, | SEQ ID NO: 2458 |
| GDRLNVEVDTAPTVDLNQVLNETRNQ, | SEQ ID NO: 2459 |
| GDRLNVEVDAAPTVDLNRVLNETRNQ, | SEQ ID NO: 2460 |
| GDRLNVEVDTAPTVDLNRVLNETRNQ, | SEQ ID NO: 2461 |
| DRLNVEVDAAPTVDLNQVLNETRSQY, | SEQ ID NO: 2462 |
| DRLNVEVDTAPTVDLNQVLNETRSQY, | SEQ ID NO: 2463 |
| DRLNVEVDAAPTVDLNRVLNETRSQY, | SEQ ID NO: 2464 |
| DRLNVEVDTAPTVDLNRVLNETRSQY, | SEQ ID NO: 2465 |
| DRLNVEVDAAPTVDLNQVLNETRNQY, | SEQ ID NO: 2466 |
| DRLNVEVDTAPTVDLNQVLNETRNQY, | SEQ ID NO: 2467 |
| DRLNVEVDAAPTVDLNRVLNETRNQY, | SEQ ID NO: 2468 |
| DRLNVEVDTAPTVDLNRVLNETRNQY, | SEQ ID NO: 2469 |

| | |
|---|---|
| RLNVEVDAAPTVDLNQVLNETRSQYE, | SEQ ID NO: 2470 |
| RLNVEVDTAPTVDLNQVLNETRSQYE, | SEQ ID NO: 2471 |
| RLNVEVDAAPTVDLNRVLNETRSQYE, | SEQ ID NO: 2472 |
| RLNVEVDTAPTVDLNRVLNETRSQYE, | SEQ ID NO: 2473 |
| RLNVEVDAAPTVDLNQVLNETRNQYE, | SEQ ID NO: 2474 |
| RLNVEVDTAPTVDLNQVLNETRNQYE, | SEQ ID NO: 2475 |
| RLNVEVDAAPTVDLNRVLNETRNQYE, | SEQ ID NO: 2476 |
| RLNVEVDTAPTVDLNRVLNETRNQYE, | SEQ ID NO: 2477 |
| LNVEVDAAPTVDLNQVLNETRSQYEA, | SEQ ID NO: 2478 |
| LNVEVDTAPTVDLNQVLNETRSQYEA, | SEQ ID NO: 2479 |
| LNVEVDAAPTVDLNRVLNETRSQYEA, | SEQ ID NO: 2480 |
| LNVEVDTAPTVDLNRVLNETRSQYEA, | SEQ ID NO: 2481 |
| LNVEVDAAPTVDLNQVLNETRNQYEA, | SEQ ID NO: 2482 |
| LNVEVDTAPTVDLNQVLNETRNQYEA, | SEQ ID NO: 2483 |
| LNVEVDAAPTVDLNRVLNETRNQYEA, | SEQ ID NO: 2484 |
| LNVEVDTAPTVDLNRVLNETRNQYEA, | SEQ ID NO: 2485 |
| NVEVDAAPTVDLNQVLNETRSQYEAL, | SEQ ID NO: 2486 |
| NVEVDTAPTVDLNQVLNETRSQYEAL, | SEQ ID NO: 2487 |
| NVEVDAAPTVDLNRVLNETRSQYEAL, | SEQ ID NO: 2488 |
| NVEVDTAPTVDLNRVLNETRSQYEAL, | SEQ ID NO: 2489 |
| NVEVDAAPTVDLNQVLNETRNQYEAL, | SEQ ID NO: 2490 |
| NVEVDTAPTVDLNQVLNETRNQYEAL, | SEQ ID NO: 2491 |
| NVEVDAAPTVDLNRVLNETRNQYEAL, | SEQ ID NO: 2492 |
| NVEVDTAPTVDLNRVLNETRNQYEAL, | SEQ ID NO: 2493 |
| EVNTLRCQLGDRLNVEVDAAPTVDLNQ, | SEQ ID NO: 2494 |
| EVNTLRSQLGDRLNVEVDAAPTVDLNQ, | SEQ ID NO: 2495 |
| EVNTLRCPLGDRLNVEVDAAPTVDLNQ, | SEQ ID NO: 2496 |
| EVNTLRSPLGDRLNVEVDAAPTVDLNQ, | SEQ ID NO: 2497 |
| EVNTLRCQLGDRLNVEVDTAPTVDLNQ, | SEQ ID NO: 2498 |
| EVNTLRSQLGDRLNVEVDTAPTVDLNQ, | SEQ ID NO: 2499 |
| EVNTLRCPLGDRLNVEVDTAPTVDLNQ, | SEQ ID NO: 2500 |
| EVNTLRSPLGDRLNVEVDTAPTVDLNQ, | SEQ ID NO: 2501 |
| EVNTLRCQLGDRLNVEVDAAPTVDLNR, | SEQ ID NO: 2502 |
| EVNTLRSQLGDRLNVEVDAAPTVDLNR, | SEQ ID NO: 2503 |
| EVNTLRCPLGDRLNVEVDAAPTVDLNR, | SEQ ID NO: 2504 |
| EVNTLRSPLGDRLNVEVDAAPTVDLNR, | SEQ ID NO: 2505 |
| EVNTLRCQLGDRLNVEVDTAPTVDLNR, | SEQ ID NO: 2506 |
| EVNTLRSQLGDRLNVEVDTAPTVDLNR, | SEQ ID NO: 2507 |
| EVNTLRCPLGDRLNVEVDTAPTVDLNR, | SEQ ID NO: 2508 |
| EVNTLRSPLGDRLNVEVDTAPTVDLNR, | SEQ ID NO: 2509 |
| VNTLRCQLGDRLNVEVDAAPTVDLNQV, | SEQ ID NO: 2510 |
| VNTLRSQLGDRLNVEVDAAPTVDLNQV, | SEQ ID NO: 2511 |
| VNTLRCPLGDRLNVEVDAAPTVDLNQV, | SEQ ID NO: 2512 |
| VNTLRSPLGDRLNVEVDAAPTVDLNQV, | SEQ ID NO: 2513 |
| VNTLRCQLGDRLNVEVDTAPTVDLNQV, | SEQ ID NO: 2514 |
| VNTLRSQLGDRLNVEVDTAPTVDLNQV, | SEQ ID NO: 2515 |
| VNTLRCPLGDRLNVEVDTAPTVDLNQV, | SEQ ID NO: 2516 |
| VNTLRSPLGDRLNVEVDTAPTVDLNQV, | SEQ ID NO: 2517 |
| VNTLRCQLGDRLNVEVDAAPTVDLNRV, | SEQ ID NO: 2518 |
| VNTLRSQLGDRLNVEVDAAPTVDLNRV, | SEQ ID NO: 2519 |
| VNTLRCPLGDRLNVEVDAAPTVDLNRV, | SEQ ID NO: 2520 |
| VNTLRSPLGDRLNVEVDAAPTVDLNRV, | SEQ ID NO: 2521 |
| VNTLRCQLGDRLNVEVDTAPTVDLNRV, | SEQ ID NO: 2522 |
| VNTLRSQLGDRLNVEVDTAPTVDLNRV, | SEQ ID NO: 2523 |

VNTLRCPLGDRLNVEVDTAPTVDLNRV, SEQ ID NO: 2524

VNTLRSPLGDRLNVEVDTAPTVDLNRV, SEQ ID NO: 2525

NTLRCQLGDRLNVEVDAAPTVDLNQVL, SEQ ID NO: 2526

NTLRSQLGDRLNVEVDAAPTVDLNQVL, SEQ ID NO: 2527

NTLRCPLGDRLNVEVDAAPTVDLNQVL, SEQ ID NO: 2528

NTLRSPLGDRLNVEVDAAPTVDLNQVL, SEQ ID NO: 2529

NTLRCQLGDRLNVEVDTAPTVDLNQVL, SEQ ID NO: 2530

NTLRSQLGDRLNVEVDTAPTVDLNQVL, SEQ ID NO: 2531

NTLRCPLGDRLNVEVDTAPTVDLNQVL, SEQ ID NO: 2532

NTLRSPLGDRLNVEVDTAPTVDLNQVL, SEQ ID NO: 2533

NTLRCQLGDRLNVEVDAAPTVDLNRVL, SEQ ID NO: 2534

NTLRSQLGDRLNVEVDAAPTVDLNRVL, SEQ ID NO: 2535

NTLRCPLGDRLNVEVDAAPTVDLNRVL, SEQ ID NO: 2536

NTLRSPLGDRLNVEVDAAPTVDLNRVL, SEQ ID NO: 2537

NTLRCQLGDRLNVEVDTAPTVDLNRVL, SEQ ID NO: 2538

NTLRSQLGDRLNVEVDTAPTVDLNRVL, SEQ ID NO: 2539

NTLRCPLGDRLNVEVDTAPTVDLNRVL, SEQ ID NO: 2540

NTLRSPLGDRLNVEVDTAPTVDLNRVL, SEQ ID NO: 2541

TLRCQLGDRLNVEVDAAPTVDLNQVLN, SEQ ID NO: 2542

TLRSQLGDRLNVEVDAAPTVDLNQVLN, SEQ ID NO: 2543

TLRCPLGDRLNVEVDAAPTVDLNQVLN, SEQ ID NO: 2544

TLRSPLGDRLNVEVDAAPTVDLNQVLN, SEQ ID NO: 2545

TLRCQLGDRLNVEVDTAPTVDLNQVLN, SEQ ID NO: 2546

TLRSQLGDRLNVEVDTAPTVDLNQVLN, SEQ ID NO: 2547

TLRCPLGDRLNVEVDTAPTVDLNQVLN, SEQ ID NO: 2548

TLRSPLGDRLNVEVDTAPTVDLNQVLN, SEQ ID NO: 2549

TLRCQLGDRLNVEVDAAPTVDLNRVLN, SEQ ID NO: 2550

TLRSQLGDRLNVEVDAAPTVDLNRVLN, SEQ ID NO: 2551

TLRCPLGDRLNVEVDAAPTVDLNRVLN, SEQ ID NO: 2552

TLRSPLGDRLNVEVDAAPTVDLNRVLN, SEQ ID NO: 2553

TLRCQLGDRLNVEVDTAPTVDLNRVLN, SEQ ID NO: 2554

TLRSQLGDRLNVEVDTAPTVDLNRVLN, SEQ ID NO: 2555

TLRCPLGDRLNVEVDTAPTVDLNRVLN, SEQ ID NO: 2556

TLRSPLGDRLNVEVDTAPTVDLNRVLN, SEQ ID NO: 2557

LRCQLGDRLNVEVDAAPTVDLNQVLNE, SEQ ID NO: 2558

LRSQLGDRLNVEVDAAPTVDLNQVLNE, SEQ ID NO: 2559

LRCPLGDRLNVEVDAAPTVDLNQVLNE, SEQ ID NO: 2560

LRSPLGDRLNVEVDAAPTVDLNQVLNE, SEQ ID NO: 2561

LRCQLGDRLNVEVDTAPTVDLNQVLNE, SEQ ID NO: 2562

LRSQLGDRLNVEVDTAPTVDLNQVLNE, SEQ ID NO: 2563

LRCPLGDRLNVEVDTAPTVDLNQVLNE, SEQ ID NO: 2564

LRSPLGDRLNVEVDTAPTVDLNQVLNE, SEQ ID NO: 2565

LRCQLGDRLNVEVDAAPTVDLNRVLNE, SEQ ID NO: 2566

LRSQLGDRLNVEVDAAPTVDLNRVLNE, SEQ ID NO: 2567

LRCPLGDRLNVEVDAAPTVDLNRVLNE, SEQ ID NO: 2568

LRSPLGDRLNVEVDAAPTVDLNRVLNE, SEQ ID NO: 2569

LRCQLGDRLNVEVDTAPTVDLNRVLNE, SEQ ID NO: 2570

LRSQLGDRLNVEVDTAPTVDLNRVLNE, SEQ ID NO: 2571

LRCPLGDRLNVEVDTAPTVDLNRVLNE, SEQ ID NO: 2572

LRSPLGDRLNVEVDTAPTVDLNRVLNE, SEQ ID NO: 2573

RCQLGDRLNVEVDAAPTVDLNQVLNET, SEQ ID NO: 2574

RSQLGDRLNVEVDAAPTVDLNQVLNET, SEQ ID NO: 2575

RCPLGDRLNVEVDAAPTVDLNQVLNET, SEQ ID NO: 2576

RSPLGDRLNVEVDAAPTVDLNQVLNET, SEQ ID NO: 2577

RCQLGDRLNVEVDTAPTVDLNQVLNET, SEQ ID NO: 2578

RSQLGDRLNVEVDTAPTVDLNQVLNET, SEQ ID NO: 2579

RCPLGDRLNVEVDTAPTVDLNQVLNET, SEQ ID NO: 2580

RSPLGDRLNVEVDTAPTVDLNQVLNET, SEQ ID NO: 2581

RCQLGDRLNVEVDAAPTVDLNRVLNET, SEQ ID NO: 2582

RSQLGDRLNVEVDAAPTVDLNRVLNET, SEQ ID NO: 2583

RCPLGDRLNVEVDAAPTVDLNRVLNET, SEQ ID NO: 2584

RSPLGDRLNVEVDAAPTVDLNRVLNET, SEQ ID NO: 2585

RCQLGDRLNVEVDTAPTVDLNRVLNET, SEQ ID NO: 2586

RSQLGDRLNVEVDTAPTVDLNRVLNET, SEQ ID NO: 2587

RCPLGDRLNVEVDTAPTVDLNRVLNET, SEQ ID NO: 2588

RSPLGDRLNVEVDTAPTVDLNRVLNET, SEQ ID NO: 2589

CQLGDRLNVEVDAAPTVDLNQVLNETR, SEQ ID NO: 2590

SQLGDRLNVEVDAAPTVDLNQVLNETR, SEQ ID NO: 2591

CPLGDRLNVEVDAAPTVDLNQVLNETR, SEQ ID NO: 2592

SPLGDRLNVEVDAAPTVDLNQVLNETR, SEQ ID NO: 2593

CQLGDRLNVEVDTAPTVDLNQVLNETR, SEQ ID NO: 2594

SQLGDRLNVEVDTAPTVDLNQVLNETR, SEQ ID NO: 2595

CPLGDRLNVEVDTAPTVDLNQVLNETR, SEQ ID NO: 2596

SPLGDRLNVEVDTAPTVDLNQVLNETR, SEQ ID NO: 2597

CQLGDRLNVEVDAAPTVDLNRVLNETR, SEQ ID NO: 2598

SQLGDRLNVEVDAAPTVDLNRVLNETR, SEQ ID NO: 2599

CPLGDRLNVEVDAAPTVDLNRVLNETR, SEQ ID NO: 2600

SPLGDRLNVEVDAAPTVDLNRVLNETR, SEQ ID NO: 2601

CQLGDRLNVEVDTAPTVDLNRVLNETR, SEQ ID NO: 2602

SQLGDRLNVEVDTAPTVDLNRVLNETR, SEQ ID NO: 2603

CPLGDRLNVEVDTAPTVDLNRVLNETR, SEQ ID NO: 2604

SPLGDRLNVEVDTAPTVDLNRVLNETR, SEQ ID NO: 2605

QLGDRLNVEVDAAPTVDLNQVLNETRS, SEQ ID NO: 2606

PLGDRLNVEVDAAPTVDLNQVLNETRS, SEQ ID NO: 2607

QLGDRLNVEVDTAPTVDLNQVLNETRS, SEQ ID NO: 2608

PLGDRLNVEVDTAPTVDLNQVLNETRS, SEQ ID NO: 2609

QLGDRLNVEVDAAPTVDLNQVLNETRS, SEQ ID NO: 2610

PLGDRLNVEVDAAPTVDLNRVLNETRS, SEQ ID NO: 2611

QLGDRLNVEVDTAPTVDLNRVLNETRS, SEQ ID NO: 2612

PLGDRLNVEVDTAPTVDLNRVLNETRS, SEQ ID NO: 2613

QLGDRLNVEVDAAPTVDLNQVLNETRN, SEQ ID NO: 2614

PLGDRLNVEVDAAPTVDLNQVLNETRN, SEQ ID NO: 2615

QLGDRLNVEVDTAPTVDLNQVLNETRN, SEQ ID NO: 2616

PLGDRLNVEVDTAPTVDLNQVLNETRN, SEQ ID NO: 2617

QLGDRLNVEVDAAPTVDLNRVLNETRN, SEQ ID NO: 2618

PLGDRLNVEVDAAPTVDLNRVLNETRN, SEQ ID NO: 2619

QLGDRLNVEVDTAPTVDLNRVLNETRN, SEQ ID NO: 2620

PLGDRLNVEVDTAPTVDLNRVLNETRN, SEQ ID NO: 2621

LGDRLNVEVDAAPTVDLNQVLNETRSQ, SEQ ID NO: 2622

LGDRLNVEVDTAPTVDLNQVLNETRSQ, SEQ ID NO: 2623

LGDRLNVEVDAAPTVDLNRVLNETRSQ, SEQ ID NO: 2624

LGDRLNVEVDTAPTVDLNRVLNETRSQ, SEQ ID NO: 2625

LGDRLNVEVDAAPTVDLNQVLNETRNQ, SEQ ID NO: 2626

LGDRLNVEVDTAPTVDLNQVLNETRNQ, SEQ ID NO: 2627

LGDRLNVEVDAAPTVDLNRVLNETRNQ, SEQ ID NO: 2628

LGDRLNVEVDTAPTVDLNRVLNETRNQ, SEQ ID NO: 2629

GDRLNVEVDAAPTVDLNQVLNETRSQY, SEQ ID NO: 2630

GDRLNVEVDTAPTVDLNQVLNETRSQY, SEQ ID NO: 2631

-continued

GDRLNVEVDAAPTVDLNRVLNETRSQY, SEQ ID NO: 2632

GDRLNVEVDTAPTVDLNRVLNETRSQY, SEQ ID NO: 2633

GDRLNVEVDAAPTVDLNQVLNETRNQY, SEQ ID NO: 2634

GDRLNVEVDTAPTVDLNQVLNETRNQY, SEQ ID NO: 2635

GDRLNVEVDAAPTVDLNRVLNETRNQY, SEQ ID NO: 2636

GDRLNVEVDTAPTVDLNRVLNETRNQY, SEQ ID NO: 2637

DRLNVEVDAAPTVDLNQVLNETRSQYE, SEQ ID NO: 2638

DRLNVEVDTAPTVDLNQVLNETRSQYE, SEQ ID NO: 2639

DRLNVEVDAAPTVDLNRVLNETRSQYE, SEQ ID NO: 2640

DRLNVEVDTAPTVDLNRVLNETRSQYE, SEQ ID NO: 2641

DRLNVEVDAAPTVDLNQVLNETRNQYE, SEQ ID NO: 2642

DRLNVEVDTAPTVDLNQVLNETRNQYE, SEQ ID NO: 2643

DRLNVEVDAAPTVDLNRVLNETRNQYE, SEQ ID NO: 2644

DRLNVEVDTAPTVDLNRVLNETRNQYE, SEQ ID NO: 2645

RLNVEVDAAPTVDLNQVLNETRSQYEA, SEQ ID NO: 2646

RLNVEVDTAPTVDLNQVLNETRSQYEA, SEQ ID NO: 2647

RLNVEVDAAPTVDLNRVLNETRSQYEA, SEQ ID NO: 2648

RLNVEVDTAPTVDLNRVLNETRSQYEA, SEQ ID NO: 2649

RLNVEVDAAPTVDLNQVLNETRNQYEA, SEQ ID NO: 2650

RLNVEVDTAPTVDLNQVLNETRNQYEA, SEQ ID NO: 2651

RLNVEVDAAPTVDLNRVLNETRNQYEA, SEQ ID NO: 2652

RLNVEVDTAPTVDLNRVLNETRNQYEA, SEQ ID NO: 2653

LNVEVDAAPTVDLNQVLNETRSQYEAL, SEQ ID NO: 2654

LNVEVDTAPTVDLNQVLNETRSQYEAL, SEQ ID NO: 2655

LNVEVDAAPTVDLNRVLNETRSQYEAL, SEQ ID NO: 2656

LNVEVDTAPTVDLNRVLNETRSQYEAL, SEQ ID NO: 2657

LNVEVDAAPTVDLNQVLNETRNQYEAL, SEQ ID NO: 2658

LNVEVDTAPTVDLNQVLNETRNQYEAL, SEQ ID NO: 2659

LNVEVDAAPTVDLNRVLNETRNQYEAL, SEQ ID NO: 2660

LNVEVDTAPTVDLNRVLNETRNQYEAL, SEQ ID NO: 2661

EVNTLRCQLGDRLNVEVDAAPTVDLNQV, SEQ ID NO: 2662

EVNTLRSQLGDRLNVEVDAAPTVDLNQV, SEQ ID NO: 2663

EVNTLRCPLGDRLNVEVDAAPTVDLNQV, SEQ ID NO: 2664

EVNTLRSPLGDRLNVEVDAAPTVDLNQV, SEQ ID NO: 2665

EVNTLRCQLGDRLNVEVDTAPTVDLNQV, SEQ ID NO: 2666

EVNTLRSQLGDRLNVEVDTAPTVDLNQV, SEQ ID NO: 2667

EVNTLRCPLGDRLNVEVDTAPTVDLNQV, SEQ ID NO: 2668

EVNTLRSPLGDRLNVEVDTAPTVDLNQV, SEQ ID NO: 2669

EVNTLRCQLGDRLNVEVDAAPTVDLNRV, SEQ ID NO: 2670

EVNTLRSQLGDRLNVEVDAAPTVDLNRV, SEQ ID NO: 2671

EVNTLRCPLGDRLNVEVDAAPTVDLNRV, SEQ ID NO: 2672

EVNTLRSPLGDRLNVEVDAAPTVDLNRV, SEQ ID NO: 2673

EVNTLRCQLGDRLNVEVDTAPTVDLNRV, SEQ ID NO: 2674

EVNTLRSQLGDRLNVEVDTAPTVDLNRV, SEQ ID NO: 2675

EVNTLRCPLGDRLNVEVDTAPTVDLNRV, SEQ ID NO: 2676

EVNTLRSPLGDRLNVEVDTAPTVDLNRV, SEQ ID NO: 2677

VNTLRCQLGDRLNVEVDAAPTVDLNQVL, SEQ ID NO: 2678

VNTLRSQLGDRLNVEVDAAPTVDLNQVL, SEQ ID NO: 2679

VNTLRCPLGDRLNVEVDAAPTVDLNQVL, SEQ ID NO: 2680

VNTLRSPLGDRLNVEVDAAPTVDLNQVL, SEQ ID NO: 2681

VNTLRCQLGDRLNVEVDTAPTVDLNQVL, SEQ ID NO: 2682

VNTLRSQLGDRLNVEVDTAPTVDLNQVL, SEQ ID NO: 2683

VNTLRCPLGDRLNVEVDTAPTVDLNQVL, SEQ ID NO: 2684

VNTLRSPLGDRLNVEVDTAPTVDLNQVL, SEQ ID NO: 2685

VNTLRCQLGDRLNVEVDAAPTVDLNRVL, SEQ ID NO: 2686

VNTLRSQLGDRLNVEVDAAPTVDLNRVL, SEQ ID NO: 2687

VNTLRCPLGDRLNVEVDAAPTVDLNRVL, SEQ ID NO: 2688

VNTLRSPLGDRLNVEVDAAPTVDLNRVL, SEQ ID NO: 2689

VNTLRCQLGDRLNVEVDTAPTVDLNRVL, SEQ ID NO: 2690

VNTLRSQLGDRLNVEVDTAPTVDLNRVL, SEQ ID NO: 2691

VNTLRCPLGDRLNVEVDTAPTVDLNRVL, SEQ ID NO: 2692

VNTLRSPLGDRLNVEVDTAPTVDLNRVL, SEQ ID NO: 2693

NTLRCQLGDRLNVEVDAAPTVDLNQVLN, SEQ ID NO: 2694

NTLRSQLGDRLNVEVDAAPTVDLNQVLN, SEQ ID NO: 2695

NTLRCPLGDRLNVEVDAAPTVDLNQVLN, SEQ ID NO: 2696

NTLRSPLGDRLNVEVDAAPTVDLNQVLN, SEQ ID NO: 2697

NTLRCQLGDRLNVEVDTAPTVDLNQVLN, SEQ ID NO: 2698

NTLRSQLGDRLNVEVDTAPTVDLNQVLN, SEQ ID NO: 2699

NTLRCPLGDRLNVEVDTAPTVDLNQVLN, SEQ ID NO: 2700

NTLRSPLGDRLNVEVDTAPTVDLNQVLN, SEQ ID NO: 2701

NTLRCQLGDRLNVEVDAAPTVDLNRVLN, SEQ ID NO: 2702

NTLRSQLGDRLNVEVDAAPTVDLNRVLN, SEQ ID NO: 2703

NTLRCPLGDRLNVEVDAAPTVDLNRVLN, SEQ ID NO: 2704

NTLRSPLGDRLNVEVDAAPTVDLNRVLN, SEQ ID NO: 2705

NTLRCQLGDRLNVEVDTAPTVDLNRVLN, SEQ ID NO: 2706

NTLRSQLGDRLNVEVDTAPTVDLNRVLN, SEQ ID NO: 2707

NTLRCPLGDRLNVEVDTAPTVDLNRVLN, SEQ ID NO: 2708

NTLRSPLGDRLNVEVDTAPTVDLNRVLN, SEQ ID NO: 2709

TLRCQLGDRLNVEVDAAPTVDLNQVLNE, SEQ ID NO: 2710

TLRSQLGDRLNVEVDAAPTVDLNQVLNE, SEQ ID NO: 2711

TLRCPLGDRLNVEVDAAPTVDLNQVLNE, SEQ ID NO: 2712

TLRSPLGDRLNVEVDAAPTVDLNQVLNE, SEQ ID NO: 2713

TLRCQLGDRLNVEVDTAPTVDLNQVLNE, SEQ ID NO: 2714

TLRSQLGDRLNVEVDTAPTVDLNQVLNE, SEQ ID NO: 2715

TLRCPLGDRLNVEVDTAPTVDLNQVLNE, SEQ ID NO: 2716

TLRSPLGDRLNVEVDTAPTVDLNQVLNE, SEQ ID NO: 2717

TLRCQLGDRLNVEVDAAPTVDLNRVLNE, SEQ ID NO: 2718

TLRSQLGDRLNVEVDAAPTVDLNRVLNE, SEQ ID NO: 2719

TLRCPLGDRLNVEVDAAPTVDLNRVLNE, SEQ ID NO: 2720

TLRSPLGDRLNVEVDAAPTVDLNRVLNE, SEQ ID NO: 2721

TLRCQLGDRLNVEVDTAPTVDLNRVLNE, SEQ ID NO: 2722

TLRSQLGDRLNVEVDTAPTVDLNRVLNE, SEQ ID NO: 2723

TLRCPLGDRLNVEVDTAPTVDLNRVLNE, SEQ ID NO: 2724

TLRSPLGDRLNVEVDTAPTVDLNRVLNE, SEQ ID NO: 2725

LRCQLGDRLNVEVDAAPTVDLNQVLNET, SEQ ID NO: 2726

LRSQLGDRLNVEVDAAPTVDLNQVLNET, SEQ ID NO: 2727

LRCPLGDRLNVEVDAAPTVDLNQVLNET, SEQ ID NO: 2728

LRSPLGDRLNVEVDAAPTVDLNQVLNET, SEQ ID NO: 2729

LRCQLGDRLNVEVDTAPTVDLNQVLNET, SEQ ID NO: 2730

LRSQLGDRLNVEVDTAPTVDLNQVLNET, SEQ ID NO: 2731

LRCPLGDRLNVEVDTAPTVDLNQVLNET, SEQ ID NO: 2732

LRSPLGDRLNVEVDTAPTVDLNQVLNET, SEQ ID NO: 2733

LRCQLGDRLNVEVDAAPTVDLNRVLNET, SEQ ID NO: 2734

LRSQLGDRLNVEVDAAPTVDLNRVLNET, SEQ ID NO: 2735

LRCPLGDRLNVEVDAAPTVDLNRVLNET, SEQ ID NO: 2736

LRSPLGDRLNVEVDAAPTVDLNRVLNET, SEQ ID NO: 2737

LRCQLGDRLNVEVDTAPTVDLNRVLNET, SEQ ID NO: 2738

LRSQLGDRLNVEVDTAPTVDLNRVLNET, SEQ ID NO: 2739

-continued

LRCPLGDRLNVEVDTAPTVDLNRVLNET, SEQ ID NO: 2740

LRSPLGDRLNVEVDTAPTVDLNRVLNET, SEQ ID NO: 2741

RCQLGDRLNVEVDAAPTVDLNQVLNETR, SEQ ID NO: 2742

RSQLGDRLNVEVDAAPTVDLNQVLNETR, SEQ ID NO: 2743

RCPLGDRLNVEVDAAPTVDLNQVLNETR, SEQ ID NO: 2744

RSPLGDRLNVEVDAAPTVDLNQVLNETR, SEQ ID NO: 2745

RCQLGDRLNVEVDTAPTVDLNQVLNETR, SEQ ID NO: 2746

RSQLGDRLNVEVDTAPTVDLNQVLNETR, SEQ ID NO: 2747

RCPLGDRLNVEVDTAPTVDLNQVLNETR, SEQ ID NO: 2748

RSPLGDRLNVEVDTAPTVDLNQVLNETR, SEQ ID NO: 2749

RCQLGDRLNVEVDAAPTVDLNRVLNETR, SEQ ID NO: 2750

RSQLGDRLNVEVDAAPTVDLNRVLNETR, SEQ ID NO: 2751

RCPLGDRLNVEVDAAPTVDLNRVLNETR, SEQ ID NO: 2752

RSPLGDRLNVEVDAAPTVDLNRVLNETR, SEQ ID NO: 2753

RCQLGDRLNVEVDTAPTVDLNRVLNETR, SEQ ID NO: 2754

RSQLGDRLNVEVDTAPTVDLNRVLNETR, SEQ ID NO: 2755

RCPLGDRLNVEVDTAPTVDLNRVLNETR, SEQ ID NO: 2756

RSPLGDRLNVEVDTAPTVDLNRVLNETR, SEQ ID NO: 2757

CQLGDRLNVEVDAAPTVDLNQVLNETRS, SEQ ID NO: 2758

SQLGDRLNVEVDAAPTVDLNQVLNETRS, SEQ ID NO: 2759

CPLGDRLNVEVDAAPTVDLNQVLNETRS, SEQ ID NO: 2760

SPLGDRLNVEVDAAPTVDLNQVLNETRS, SEQ ID NO: 2761

CQLGDRLNVEVDTAPTVDLNQVLNETRS, SEQ ID NO: 2762

SQLGDRLNVEVDTAPTVDLNQVLNETRS, SEQ ID NO: 2763

CPLGDRLNVEVDTAPTVDLNQVLNETRS, SEQ ID NO: 2764

SPLGDRLNVEVDTAPTVDLNQVLNETRS, SEQ ID NO: 2765

CQLGDRLNVEVDAAPTVDLNRVLNETRS, SEQ ID NO: 2766

SQLGDRLNVEVDAAPTVDLNRVLNETRS, SEQ ID NO: 2767

CPLGDRLNVEVDAAPTVDLNRVLNETRS, SEQ ID NO: 2768

SPLGDRLNVEVDAAPTVDLNRVLNETRS, SEQ ID NO: 2769

CQLGDRLNVEVDTAPTVDLNRVLNETRS, SEQ ID NO: 2770

SQLGDRLNVEVDTAPTVDLNRVLNETRS, SEQ ID NO: 2771

CPLGDRLNVEVDTAPTVDLNRVLNETRS, SEQ ID NO: 2772

SPLGDRLNVEVDTAPTVDLNRVLNETRS, SEQ ID NO: 2773

CQLGDRLNVEVDAAPTVDLNQVLNETRN, SEQ ID NO: 2774

SQLGDRLNVEVDAAPTVDLNQVLNETRN, SEQ ID NO: 2775

CPLGDRLNVEVDAAPTVDLNQVLNETRN, SEQ ID NO: 2776

SPLGDRLNVEVDAAPTVDLNQVLNETRN, SEQ ID NO: 2777

CQLGDRLNVEVDTAPTVDLNQVLNETRN, SEQ ID NO: 2778

SQLGDRLNVEVDTAPTVDLNQVLNETRN, SEQ ID NO: 2779

CPLGDRLNVEVDTAPTVDLNQVLNETRN, SEQ ID NO: 2780

SPLGDRLNVEVDTAPTVDLNQVLNETRN, SEQ ID NO: 2781

CQLGDRLNVEVDAAPTVDLNRVLNETRN, SEQ ID NO: 2782

SQLGDRLNVEVDAAPTVDLNRVLNETRN, SEQ ID NO: 2783

CPLGDRLNVEVDAAPTVDLNRVLNETRN, SEQ ID NO: 2784

SPLGDRLNVEVDAAPTVDLNRVLNETRN, SEQ ID NO: 2785

CQLGDRLNVEVDTAPTVDLNRVLNETRN, SEQ ID NO: 2786

SQLGDRLNVEVDTAPTVDLNRVLNETRN, SEQ ID NO: 2787

CPLGDRLNVEVDTAPTVDLNRVLNETRN, SEQ ID NO: 2788

SPLGDRLNVEVDTAPTVDLNRVLNETRN, SEQ ID NO: 2789

QLGDRLNVEVDAAPTVDLNQVLNETRSQ, SEQ ID NO: 2790

PLGDRLNVEVDAAPTVDLNQVLNETRSQ, SEQ ID NO: 2791

QLGDRLNVEVDTAPTVDLNQVLNETRSQ, SEQ ID NO: 2792

PLGDRLNVEVDTAPTVDLNQVLNETRSQ, SEQ ID NO: 2793

QLGDRLNVEVDAAPTVDLNRVLNETRSQ, SEQ ID NO: 2794

PLGDRLNVEVDAAPTVDLNRVLNETRSQ, SEQ ID NO: 2795

QLGDRLNVEVDTAPTVDLNRVLNETRSQ, SEQ ID NO: 2796

PLGDRLNVEVDTAPTVDLNRVLNETRSQ, SEQ ID NO: 2797

QLGDRLNVEVDAAPTVDLNQVLNETRNQ, SEQ ID NO: 2798

PLGDRLNVEVDAAPTVDLNQVLNETRNQ, SEQ ID NO: 2799

QLGDRLNVEVDTAPTVDLNQVLNETRNQ, SEQ ID NO: 2800

PLGDRLNVEVDTAPTVDLNQVLNETRNQ, SEQ ID NO: 2801

QLGDRLNVEVDAAPTVDLNRVLNETRNQ, SEQ ID NO: 2802

PLGDRLNVEVDAAPTVDLNRVLNETRNQ, SEQ ID NO: 2803

QLGDRLNVEVDTAPTVDLNRVLNETRNQ, SEQ ID NO: 2804

PLGDRLNVEVDTAPTVDLNRVLNETRNQ, SEQ ID NO: 2805

LGDRLNVEVDAAPTVDLNQVLNETRSQY, SEQ ID NO: 2806

LGDRLNVEVDTAPTVDLNQVLNETRSQY, SEQ ID NO: 2807

LGDRLNVEVDAAPTVDLNRVLNETRSQY, SEQ ID NO: 2808

LGDRLNVEVDTAPTVDLNRVLNETRSQY, SEQ ID NO: 2809

LGDRLNVEVDAAPTVDLNQVLNETRNQY, SEQ ID NO: 2810

LGDRLNVEVDTAPTVDLNQVLNETRNQY, SEQ ID NO: 2811

LGDRLNVEVDAAPTVDLNRVLNETRNQY, SEQ ID NO: 2812

LGDRLNVEVDTAPTVDLNRVLNETRNQY, SEQ ID NO: 2813

GDRLNVEVDAAPTVDLNQVLNETRSQYE, SEQ ID NO: 2814

GDRLNVEVDTAPTVDLNQVLNETRSQYE, SEQ ID NO: 2815

GDRLNVEVDAAPTVDLNRVLNETRSQYE, SEQ ID NO: 2816

GDRLNVEVDTAPTVDLNRVLNETRSQYE, SEQ ID NO: 2817

GDRLNVEVDAAPTVDLNQVLNETRNQYE, SEQ ID NO: 2818

GDRLNVEVDTAPTVDLNQVLNETRNQYE, SEQ ID NO: 2819

GDRLNVEVDAAPTVDLNRVLNETRNQYE, SEQ ID NO: 2820

GDRLNVEVDTAPTVDLNRVLNETRNQYE, SEQ ID NO: 2821

DRLNVEVDAAPTVDLNQVLNETRSQYEA, SEQ ID NO: 2822

DRLNVEVDTAPTVDLNQVLNETRSQYEA, SEQ ID NO: 2823

DRLNVEVDAAPTVDLNRVLNETRSQYEA, SEQ ID NO: 2824

DRLNVEVDTAPTVDLNRVLNETRSQYEA, SEQ ID NO: 2825

DRLNVEVDAAPTVDLNQVLNETRNQYEA, SEQ ID NO: 2826

DRLNVEVDTAPTVDLNQVLNETRNQYEA, SEQ ID NO: 2827

DRLNVEVDAAPTVDLNRVLNETRNQYEA, SEQ ID NO: 2828

DRLNVEVDTAPTVDLNRVLNETRNQYEA, SEQ ID NO: 2829

RLNVEVDAAPTVDLNQVLNETRSQYEAL, SEQ ID NO: 2830

RLNVEVDTAPTVDLNQVLNETRSQYEAL, SEQ ID NO: 2831

RLNVEVDAAPTVDLNRVLNETRSQYEAL, SEQ ID NO: 2832

RLNVEVDTAPTVDLNRVLNETRSQYEAL, SEQ ID NO: 2833

RLNVEVDAAPTVDLNQVLNETRNQYEAL, SEQ ID NO: 2834

RLNVEVDTAPTVDLNQVLNETRNQYEAL, SEQ ID NO: 2835

RLNVEVDAAPTVDLNRVLNETRNQYEAL, SEQ ID NO: 2836

RLNVEVDTAPTVDLNRVLNETRNQYEAL, SEQ ID NO: 2837

EVNTLRCQLGDRLNVEVDAAPTVDLNQVL, SEQ ID NO: 2838

EVNTLRSQLGDRLNVEVDAAPTVDLNQVL, SEQ ID NO: 2839

EVNTLRCPLGDRLNVEVDAAPTVDLNQVL, SEQ ID NO: 2840

EVNTLRSPLGDRLNVEVDAAPTVDLNQVL, SEQ ID NO: 2841

EVNTLRCQLGDRLNVEVDTAPTVDLNQVL, SEQ ID NO: 2842

EVNTLRSQLGDRLNVEVDTAPTVDLNQVL, SEQ ID NO: 2843

EVNTLRCPLGDRLNVEVDTAPTVDLNQVL, SEQ ID NO: 2844

EVNTLRSPLGDRLNVEVDTAPTVDLNQVL, SEQ ID NO: 2845

EVNTLRCQLGDRLNVEVDAAPTVDLNRVL, SEQ ID NO: 2846

EVNTLRSQLGDRLNVEVDAAPTVDLNRVL, SEQ ID NO: 2847

-continued

EVNTLRCPLGDRLNVEVDAAPTVDLNRVL, SEQ ID NO: 2848

EVNTLRSPLGDRLNVEVDAAPTVDLNRVL, SEQ ID NO: 2849

EVNTLRCQLGDRLNVEVDTAPTVDLNRVL, SEQ ID NO: 2850

EVNTLRSQLGDRLNVEVDTAPTVDLNRVL, SEQ ID NO: 2851

EVNTLRCPLGDRLNVEVDTAPTVDLNRVL, SEQ ID NO: 2852

EVNTLRSPLGDRLNVEVDTAPTVDLNRVL, SEQ ID NO: 2853

VNTLRCQLGDRLNVEVDAAPTVDLNQVLN, SEQ ID NO: 2854

VNTLRSQLGDRLNVEVDAAPTVDLNQVLN, SEQ ID NO: 2855

VNTLRCPLGDRLNVEVDAAPTVDLNQVLN, SEQ ID NO: 2856

VNTLRSPLGDRLNVEVDAAPTVDLNQVLN, SEQ ID NO: 2857

VNTLRCQLGDRLNVEVDTAPTVDLNQVLN, SEQ ID NO: 2858

VNTLRSQLGDRLNVEVDTAPTVDLNQVLN, SEQ ID NO: 2859

VNTLRCPLGDRLNVEVDTAPTVDLNQVLN, SEQ ID NO: 2860

VNTLRSPLGDRLNVEVDTAPTVDLNQVLN, SEQ ID NO: 2861

VNTLRCQLGDRLNVEVDAAPTVDLNRVLN, SEQ ID NO: 2862

VNTLRSQLGDRLNVEVDAAPTVDLNRVLN, SEQ ID NO: 2863

VNTLRCPLGDRLNVEVDAAPTVDLNRVLN, SEQ ID NO: 2864

VNTLRSPLGDRLNVEVDAAPTVDLNRVLN, SEQ ID NO: 2865

VNTLRCQLGDRLNVEVDTAPTVDLNRVLN, SEQ ID NO: 2866

VNTLRSQLGDRLNVEVDTAPTVDLNRVLN, SEQ ID NO: 2867

VNTLRCPLGDRLNVEVDTAPTVDLNRVLN, SEQ ID NO: 2868

VNTLRSPLGDRLNVEVDTAPTVDLNRVLN, SEQ ID NO: 2869

NTLRCQLGDRLNVEVDAAPTVDLNQVLNE, SEQ ID NO: 2870

NTLRSQLGDRLNVEVDAAPTVDLNQVLNE, SEQ ID NO: 2871

NTLRCPLGDRLNVEVDAAPTVDLNQVLNE, SEQ ID NO: 2872

NTLRSPLGDRLNVEVDAAPTVDLNQVLNE, SEQ ID NO: 2873

NTLRCQLGDRLNVEVDTAPTVDLNQVLNE, SEQ ID NO: 2874

NTLRSQLGDRLNVEVDTAPTVDLNQVLNE, SEQ ID NO: 2875

NTLRCPLGDRLNVEVDTAPTVDLNQVLNE, SEQ ID NO: 2876

NTLRSPLGDRLNVEVDTAPTVDLNQVLNE, SEQ ID NO: 2877

NTLRCQLGDRLNVEVDAAPTVDLNRVLNE, SEQ ID NO: 2878

NTLRSQLGDRLNVEVDAAPTVDLNRVLNE, SEQ ID NO: 2879

NTLRCPLGDRLNVEVDAAPTVDLNRVLNE, SEQ ID NO: 2880

NTLRSPLGDRLNVEVDAAPTVDLNRVLNE, SEQ ID NO: 2881

NTLRCQLGDRLNVEVDTAPTVDLNRVLNE, SEQ ID NO: 2882

NTLRSQLGDRLNVEVDTAPTVDLNRVLNE, SEQ ID NO: 2883

NTLRCPLGDRLNVEVDTAPTVDLNRVLNE, SEQ ID NO: 2884

NTLRSPLGDRLNVEVDTAPTVDLNRVLNE, SEQ ID NO: 2885

TLRCQLGDRLNVEVDAAPTVDLNQVLNET, SEQ ID NO: 2886

TLRSQLGDRLNVEVDAAPTVDLNQVLNET, SEQ ID NO: 2887

TLRCPLGDRLNVEVDAAPTVDLNQVLNET, SEQ ID NO: 2888

TLRSPLGDRLNVEVDAAPTVDLNQVLNET, SEQ ID NO: 2889

TLRCQLGDRLNVEVDTAPTVDLNQVLNET, SEQ ID NO: 2890

TLRSQLGDRLNVEVDTAPTVDLNQVLNET, SEQ ID NO: 2891

TLRCPLGDRLNVEVDTAPTVDLNQVLNET, SEQ ID NO: 2892

TLRSPLGDRLNVEVDTAPTVDLNQVLNET, SEQ ID NO: 2893

TLRCQLGDRLNVEVDAAPTVDLNRVLNET, SEQ ID NO: 2894

TLRCQLGDRLNVEVDAAPTVDLNRVLNET, SEQ ID NO: 2895

TLRCPLGDRLNVEVDAAPTVDLNRVLNET, SEQ ID NO: 2896

TLRSPLGDRLNVEVDAAPTVDLNRVLNET, SEQ ID NO: 2897

TLRCQLGDRLNVEVDTAPTVDLNRVLNET, SEQ ID NO: 2898

TLRSQLGDRLNVEVDTAPTVDLNRVLNET, SEQ ID NO: 2899

TLRCPLGDRLNVEVDTAPTVDLNRVLNET, SEQ ID NO: 2900

TLRSPLGDRLNVEVDTAPTVDLNRVLNET, SEQ ID NO: 2901

LRCQLGDRLNVEVDAAPTVDLNQVLNETR, SEQ ID NO: 2902

LRSQLGDRLNVEVDAAPTVDLNQVLNETR, SEQ ID NO: 2903

LRCPLGDRLNVEVDAAPTVDLNQVLNETR, SEQ ID NO: 2904

LRSPLGDRLNVEVDAAPTVDLNQVLNETR, SEQ ID NO: 2905

LRCQLGDRLNVEVDTAPTVDLNQVLNETR, SEQ ID NO: 2906

LRSQLGDRLNVEVDTAPTVDLNQVLNETR, SEQ ID NO: 2907

LRCPLGDRLNVEVDTAPTVDLNQVLNETR, SEQ ID NO: 2908

LRSPLGDRLNVEVDTAPTVDLNQVLNETR, SEQ ID NO: 2909

LRCQLGDRLNVEVDAAPTVDLNRVLNETR, SEQ ID NO: 2910

LRSQLGDRLNVEVDAAPTVDLNRVLNETR, SEQ ID NO: 2911

LRCPLGDRLNVEVDAAPTVDLNRVLNETR, SEQ ID NO: 2912

LRSPLGDRLNVEVDAAPTVDLNRVLNETR, SEQ ID NO: 2913

LRCQLGDRLNVEVDTAPTVDLNRVLNETR, SEQ ID NO: 2914

LRSQLGDRLNVEVDTAPTVDLNRVLNETR, SEQ ID NO: 2915

LRCPLGDRLNVEVDTAPTVDLNRVLNETR, SEQ ID NO: 2916

LRSPLGDRLNVEVDTAPTVDLNRVLNETR, SEQ ID NO: 2917

RCQLGDRLNVEVDAAPTVDLNQVLNETRS, SEQ ID NO: 2918

RSQLGDRLNVEVDAAPTVDLNQVLNETRS, SEQ ID NO: 2919

RCPLGDRLNVEVDAAPTVDLNQVLNETRS, SEQ ID NO: 2920

RSPLGDRLNVEVDAAPTVDLNQVLNETRS, SEQ ID NO: 2921

RCQLGDRLNVEVDTAPTVDLNQVLNETRS, SEQ ID NO: 2922

RSQLGDRLNVEVDTAPTVDLNQVLNETRS, SEQ ID NO: 2923

RCPLGDRLNVEVDTAPTVDLNQVLNETRS, SEQ ID NO: 2924

RSPLGDRLNVEVDTAPTVDLNQVLNETRS, SEQ ID NO: 2925

RCQLGDRLNVEVDAAPTVDLNRVLNETRS, SEQ ID NO: 2926

RSQLGDRLNVEVDAAPTVDLNRVLNETRS, SEQ ID NO: 2927

RCPLGDRLNVEVDAAPTVDLNRVLNETRS, SEQ ID NO: 2928

RSPLGDRLNVEVDAAPTVDLNRVLNETRS, SEQ ID NO: 2929

RCQLGDRLNVEVDTAPTVDLNRVLNETRS, SEQ ID NO: 2930

RSQLGDRLNVEVDTAPTVDLNRVLNETRS, SEQ ID NO: 2931

RCPLGDRLNVEVDTAPTVDLNRVLNETRS, SEQ ID NO: 2932

RSPLGDRLNVEVDTAPTVDLNRVLNETRS, SEQ ID NO: 2933

RCQLGDRLNVEVDAAPTVDLNQVLNETRN, SEQ ID NO: 2934

RSQLGDRLNVEVDAAPTVDLNQVLNETRN, SEQ ID NO: 2935

RCPLGDRLNVEVDAAPTVDLNQVLNETRN, SEQ ID NO: 2936

RSPLGDRLNVEVDAAPTVDLNQVLNETRN, SEQ ID NO: 2937

RCQLGDRLNVEVDTAPTVDLNQVLNETRN, SEQ ID NO: 2938

RSQLGDRLNVEVDTAPTVDLNQVLNETRN, SEQ ID NO: 2939

RCPLGDRLNVEVDTAPTVDLNQVLNETRN, SEQ ID NO: 2940

RSPLGDRLNVEVDTAPTVDLNQVLNETRN, SEQ ID NO: 2941

RCQLGDRLNVEVDAAPTVDLNRVLNETRN, SEQ ID NO: 2942

RSQLGDRLNVEVDAAPTVDLNRVLNETRN SEQ ID NO: 2943

RCPLGDRLNVEVDAAPTVDLNRVLNETRN, SEQ ID NO: 2944

RSPLGDRLNVEVDAAPTVDLNRVLNETRN, SEQ ID NO: 2945

RCQLGDRLNVEVDTAPTVDLNRVLNETRN, SEQ ID NO: 2946

RSQLGDRLNVEVDTAPTVDLNRVLNETRN, SEQ ID NO: 2947

RCPLGDRLNVEVDTAPTVDLNRVLNETRN, SEQ ID NO: 2948

RSPLGDRLNVEVDTAPTVDLNRVLNETRN, SEQ ID NO: 2949

CQLGDRLNVEVDAAPTVDLNQVLNETRSQ, SEQ ID NO: 2950

SQLGDRLNVEVDAAPTVDLNQVLNETRSQ, SEQ ID NO: 2951

CPLGDRLNVEVDAAPTVDLNQVLNETRSQ, SEQ ID NO: 2952

SPLGDRLNVEVDAAPTVDLNQVLNETRSQ, SEQ ID NO: 2953

CQLGDRLNVEVDTAPTVDLNQVLNETRSQ, SEQ ID NO: 2954

SQLGDRLNVEVDTAPTVDLNQVLNETRSQ, SEQ ID NO: 2955

CPLGDRLNVEVDTAPTVDLNQVLNETRSQ, SEQ ID NO: 2956

SPLGDRLNVEVDTAPTVDLNQVLNETRSQ, SEQ ID NO: 2957

CQLGDRLNVEVDAAPTVDLNRVLNETRSQ, SEQ ID NO: 2958

SQLGDRLNVEVDAAPTVDLNRVLNETRSQ, SEQ ID NO: 2959

CPLGDRLNVEVDAAPTVDLNRVLNETRSQ, SEQ ID NO: 2960

SPLGDRLNVEVDAAPTVDLNRVLNETRSQ, SEQ ID NO: 2961

CQLGDRLNVEVDTAPTVDLNRVLNETRSQ, SEQ ID NO: 2962

SQLGDRLNVEVDTAPTVDLNRVLNETRSQ, SEQ ID NO: 2963

CPLGDRLNVEVDTAPTVDLNRVLNETRSQ, SEQ ID NO: 2964

SPLGDRLNVEVDTAPTVDLNRVLNETRSQ, SEQ ID NO: 2965

CQLGDRLNVEVDAAPTVDLNQVLNETRNQ, SEQ ID NO: 2966

SQLGDRLNVEVDAAPTVDLNQVLNETRNQ, SEQ ID NO: 2967

CPLGDRLNVEVDAAPTVDLNQVLNETRNQ, SEQ ID NO: 2968

SPLGDRLNVEVDAAPTVDLNQVLNETRNQ, SEQ ID NO: 2969

CQLGDRLNVEVDTAPTVDLNQVLNETRNQ, SEQ ID NO: 2970

SQLGDRLNVEVDTAPTVDLNQVLNETRNQ, SEQ ID NO: 2971

CPLGDRLNVEVDTAPTVDLNQVLNETRNQ, SEQ ID NO: 2972

SPLGDRLNVEVDTAPTVDLNQVLNETRNQ, SEQ ID NO: 2973

CQLGDRLNVEVDAAPTVDLNRVLNETRNQ, SEQ ID NO: 2974

SQLGDRLNVEVDAAPTVDLNRVLNETRNQ, SEQ ID NO: 2975

CPLGDRLNVEVDAAPTVDLNRVLNETRNQ, SEQ ID NO: 2976

SPLGDRLNVEVDAAPTVDLNRVLNETRNQ, SEQ ID NO: 2977

CQLGDRLNVEVDTAPTVDLNRVLNETRNQ, SEQ ID NO: 2978

SQLGDRLNVEVDTAPTVDLNRVLNETRNQ, SEQ ID NO: 2979

CPLGDRLNVEVDTAPTVDLNRVLNETRNQ, SEQ ID NO: 2980

SPLGDRLNVEVDTAPTVDLNRVLNETRNQ, SEQ ID NO: 2981

QLGDRLNVEVDAAPTVDLNQVLNETRSQY, SEQ ID NO: 2982

PLGDRLNVEVDAAPTVDLNQVLNETRSQY, SEQ ID NO: 2983

QLGDRLNVEVDTAPTVDLNQVLNETRSQY, SEQ ID NO: 2984

PLGDRLNVEVDTAPTVDLNQVLNETRSQY, SEQ ID NO: 2985

QLGDRLNVEVDAAPTVDLNRVLNETRSQY, SEQ ID NO: 2986

PLGDRLNVEVDAAPTVDLNRVLNETRSQY, SEQ ID NO: 2987

QLGDRLNVEVDTAPTVDLNRVLNETRSQY, SEQ ID NO: 2988

PLGDRLNVEVDTAPTVDLNRVLNETRSQY, SEQ ID NO: 2989

QLGDRLNVEVDAAPTVDLNQVLNETRNQY, SEQ ID NO: 2990

PLGDRLNVEVDAAPTVDLNQVLNETRNQY, SEQ ID NO: 2991

QLGDRLNVEVDTAPTVDLNQVLNETRNQY, SEQ ID NO: 2992

PLGDRLNVEVDTAPTVDLNQVLNETRNQY, SEQ ID NO: 2993

QLGDRLNVEVDAAPTVDLNRVLNETRNQY, SEQ ID NO: 2994

PLGDRLNVEVDAAPTVDLNRVLNETRNQY, SEQ ID NO: 2995

QLGDRLNVEVDTAPTVDLNRVLNETRNQY, SEQ ID NO: 2996

PLGDRLNVEVDTAPTVDLNRVLNETRNQY, SEQ ID NO: 2997

LGDRLNVEVDAAPTVDLNQVLNETRSQYE, SEQ ID NO: 2998

LGDRLNVEVDTAPTVDLNQVLNETRSQYE, SEQ ID NO: 2999

LGDRLNVEVDAAPTVDLNRVLNETRSQYE, SEQ ID NO: 3000

LGDRLNVEVDTAPTVDLNRVLNETRSQYE, SEQ ID NO: 3001

LGDRLNVEVDAAPTVDLNQVLNETRNQYE, SEQ ID NO: 3002

LGDRLNVEVDTAPTVDLNQVLNETRNQYE, SEQ ID NO: 3003

LGDRLNVEVDAAPTVDLNRVLNETRNQYE, SEQ ID NO: 3004

LGDRLNVEVDTAPTVDLNRVLNETRNQYE, SEQ ID NO: 3005

GDRLNVEVDAAPTVDLNQVLNETRSQYEA, SEQ ID NO: 3006

GDRLNVEVDTAPTVDLNQVLNETRSQYEA, SEQ ID NO: 3007

GDRLNVEVDAAPTVDLNRVLNETRSQYEA, SEQ ID NO: 3008

GDRLNVEVDTAPTVDLNRVLNETRSQYEA, SEQ ID NO: 3009

GDRLNVEVDAAPTVDLNQVLNETRNQYEA, SEQ ID NO: 3010

GDRLNVEVDTAPTVDLNQVLNETRNQYEA, SEQ ID NO: 3011

GDRLNVEVDAAPTVDLNRVLNETRNQYEA, SEQ ID NO: 3012

GDRLNVEVDTAPTVDLNRVLNETRNQYEA, SEQ ID NO: 3013

DRLNVEVDAAPTVDLNQVLNETRSQYEAL, SEQ ID NO: 3014

DRLNVEVDTAPTVDLNQVLNETRSQYEAL, SEQ ID NO: 3015

DRLNVEVDAAPTVDLNRVLNETRSQYEAL, SEQ ID NO: 3016

DRLNVEVDTAPTVDLNRVLNETRSQYEAL, SEQ ID NO: 3017

DRLNVEVDAAPTVDLNQVLNETRNQYEAL, SEQ ID NO: 3018

DRLNVEVDTAPTVDLNQVLNETRNQYEAL, SEQ ID NO: 3019

DRLNVEVDAAPTVDLNRVLNETRNQYEAL, SEQ ID NO: 3020

DRLNVEVDTAPTVDLNRVLNETRNQYEAL, SEQ ID NO: 3021

EVNTLRCQLGDRLNVEVDAAPTVDLNQVLN, SEQ ID NO: 3022

EVNTLRSQLGDRLNVEVDAAPTVDLNQVLN, SEQ ID NO: 3023

EVNTLRCPLGDRLNVEVDAAPTVDLNQVLN, SEQ ID NO: 3024

EVNTLRSPLGDRLNVEVDAAPTVDLNQVLN, SEQ ID NO: 3025

EVNTLRCQLGDRLNVEVDTAPTVDLNQVLN, SEQ ID NO: 3026

EVNTLRSQLGDRLNVEVDTAPTVDLNQVLN, SEQ ID NO: 3027

EVNTLRCPLGDRLNVEVDTAPTVDLNQVLN, SEQ ID NO: 3028

EVNTLRSPLGDRLNVEVDTAPTVDLNQVLN, SEQ ID NO: 3029

EVNTLRCQLGDRLNVEVDAAPTVDLNRVLN, SEQ ID NO: 3030

EVNTLRCQLGDRLNVEVDAAPTVDLNRVLN, SEQ ID NO: 3031

EVNTLRCPLGDRLNVEVDAAPTVDLNRVLN, SEQ ID NO: 3032

EVNTLRSPLGDRLNVEVDAAPTVDLNRVLN, SEQ ID NO: 3033

EVNTLRCQLGDRLNVEVDTAPTVDLNRVLN, SEQ ID NO: 3034

EVNTLRSQLGDRLNVEVDTAPTVDLNRVLN, SEQ ID NO: 3035

EVNTLRCPLGDRLNVEVDTAPTVDLNRVLN, SEQ ID NO: 3036

EVNTLRSPLGDRLNVEVDTAPTVDLNRVLN, SEQ ID NO: 3037

VNTLRCQLGDRLNVEVDAAPTVDLNQVLNE, SEQ ID NO: 3038

VNTLRSQLGDRLNVEVDAAPTVDLNQVLNE, SEQ ID NO: 3039

VNTLRCPLGDRLNVEVDAAPTVDLNQVLNE, SEQ ID NO: 3040

VNTLRSPLGDRLNVEVDAAPTVDLNQVLNE, SEQ ID NO: 3041

VNTLRCQLGDRLNVEVDTAPTVDLNQVLNE, SEQ ID NO: 3042

VNTLRSQLGDRLNVEVDTAPTVDLNQVLNE, SEQ ID NO: 3043

VNTLRCPLGDRLNVEVDTAPTVDLNQVLNE, SEQ ID NO: 3044

VNTLRSPLGDRLNVEVDTAPTVDLNQVLNE, SEQ ID NO: 3045

VNTLRCQLGDRLNVEVDAAPTVDLNRVLNE, SEQ ID NO: 3046

VNTLRSQLGDRLNVEVDAAPTVDLNRVLNE, SEQ ID NO: 3047

VNTLRCPLGDRLNVEVDAAPTVDLNRVLNE, SEQ ID NO: 3048

VNTLRSPLGDRLNVEVDAAPTVDLNRVLNE, SEQ ID NO: 3049

VNTLRCQLGDRLNVEVDTAPTVDLNRVLNE, SEQ ID NO: 3050

VNTLRSQLGDRLNVEVDTAPTVDLNRVLNE, SEQ ID NO: 3051

VNTLRCPLGDRLNVEVDTAPTVDLNRVLNE, SEQ ID NO: 3052

VNTLRSPLGDRLNVEVDTAPTVDLNRVLNE, SEQ ID NO: 3053

NTLRCQLGDRLNVEVDAAPTVDLNQVLNET, SEQ ID NO: 3054

NTLRSQLGDRLNVEVDAAPTVDLNQVLNET, SEQ ID NO: 3055

NTLRCPLGDRLNVEVDAAPTVDLNQVLNET, SEQ ID NO: 3056

NTLRSPLGDRLNVEVDAAPTVDLNQVLNET, SEQ ID NO: 3057

NTLRCQLGDRLNVEVDTAPTVDLNQVLNET, SEQ ID NO: 3058

NTLRSQLGDRLNVEVDTAPTVDLNQVLNET, SEQ ID NO: 3059

NTLRCPLGDRLNVEVDTAPTVDLNQVLNET, SEQ ID NO: 3060

NTLRSPLGDRLNVEVDTAPTVDLNQVLNET, SEQ ID NO: 3061

NTLRCQLGDRLNVEVDAAPTVDLNRVLNET, SEQ ID NO: 3062

NTLRSQLGDRLNVEVDAAPTVDLNRVLNET, SEQ ID NO: 3063

NTLRCPLGDRLNVEVDAAPTVDLNRVLNET, SEQ ID NO: 3064

NTLRSPLGDRLNVEVDAAPTVDLNRVLNET, SEQ ID NO: 3065

NTLRCQLGDRLNVEVDTAPTVDLNRVLNET, SEQ ID NO: 3066

NTLRSQLGDRLNVEVDTAPTVDLNRVLNET, SEQ ID NO: 3067

NTLRCPLGDRLNVEVDTAPTVDLNRVLNET, SEQ ID NO: 3068

NTLRSPLGDRLNVEVDTAPTVDLNRVLNET, SEQ ID NO: 3069

TLRCQLGDRLNVEVDAAPTVDLNQVLNETR, SEQ ID NO: 3070

TLRSQLGDRLNVEVDAAPTVDLNQVLNETR, SEQ ID NO: 3071

TLRCPLGDRLNVEVDAAPTVDLNQVLNETR, SEQ ID NO: 3072

TLRSPLGDRLNVEVDAAPTVDLNQVLNETR, SEQ ID NO: 3073

TLRCQLGDRLNVEVDTAPTVDLNQVLNETR, SEQ ID NO: 3074

TLRSQLGDRLNVEVDTAPTVDLNQVLNETR, SEQ ID NO: 3075

TLRCPLGDRLNVEVDTAPTVDLNQVLNETR, SEQ ID NO: 3076

TLRSPLGDRLNVEVDTAPTVDLNQVLNETR, SEQ ID NO: 3077

TLRCQLGDRLNVEVDAAPTVDLNRVLNETR, SEQ ID NO: 3078

TLRSQLGDRLNVEVDAAPTVDLNRVLNETR, SEQ ID NO: 3079

TLRCPLGDRLNVEVDAAPTVDLNRVLNETR, SEQ ID NO: 3080

TLRSPLGDRLNVEVDAAPTVDLNRVLNETR, SEQ ID NO: 3081

TLRCQLGDRLNVEVDTAPTVDLNRVLNETR, SEQ ID NO: 3082

TLRSQLGDRLNVEVDTAPTVDLNRVLNETR, SEQ ID NO: 3083

TLRCPLGDRLNVEVDTAPTVDLNRVLNETR, SEQ ID NO: 3084

TLRSPLGDRLNVEVDTAPTVDLNRVLNETR, SEQ ID NO: 3085

LRCQLGDRLNVEVDAAPTVDLNQVLNETRS, SEQ ID NO: 3086

LRSQLGDRLNVEVDAAPTVDLNQVLNETRS, SEQ ID NO: 3087

LRCPLGDRLNVEVDAAPTVDLNQVLNETRS, SEQ ID NO: 3088

LRSPLGDRLNVEVDAAPTVDLNQVLNETRS, SEQ ID NO: 3089

LRCQLGDRLNVEVDTAPTVDLNQVLNETRS, SEQ ID NO: 3090

LRSQLGDRLNVEVDTAPTVDLNQVLNETRS, SEQ ID NO: 3091

LRCPLGDRLNVEVDTAPTVDLNQVLNETRS, SEQ ID NO: 3092

LRSPLGDRLNVEVDTAPTVDLNQVLNETRS, SEQ ID NO: 3093

LRCQLGDRLNVEVDAAPTVDLNRVLNETRS, SEQ ID NO: 3094

LRSQLGDRLNVEVDAAPTVDLNRVLNETRS, SEQ ID NO: 3095

LRCPLGDRLNVEVDAAPTVDLNRVLNETRS, SEQ ID NO: 3096

LRSPLGDRLNVEVDAAPTVDLNRVLNETRS, SEQ ID NO: 3097

LRCQLGDRLNVEVDTAPTVDLNRVLNETRS, SEQ ID NO: 3098

LRSQLGDRLNVEVDTAPTVDLNRVLNETRS, SEQ ID NO: 3099

LRCPLGDRLNVEVDTAPTVDLNRVLNETRS, SEQ ID NO: 3100

LRSPLGDRLNVEVDTAPTVDLNRVLNETRS, SEQ ID NO: 3101

LRCQLGDRLNVEVDAAPTVDLNQVLNETRN, SEQ ID NO: 3102

LRSQLGDRLNVEVDAAPTVDLNQVLNETRN, SEQ ID NO: 3103

LRCPLGDRLNVEVDAAPTVDLNQVLNETRN, SEQ ID NO: 3104

LRSPLGDRLNVEVDAAPTVDLNQVLNETRN, SEQ ID NO: 3105

LRCQLGDRLNVEVDTAPTVDLNQVLNETRN, SEQ ID NO: 3106

LRSQLGDRLNVEVDTAPTVDLNQVLNETRN, SEQ ID NO: 3107

LRCPLGDRLNVEVDTAPTVDLNQVLNETRN, SEQ ID NO: 3108

LRSPLGDRLNVEVDTAPTVDLNQVLNETRN, SEQ ID NO: 3109

LRCQLGDRLNVEVDAAPTVDLNRVLNETRN, SEQ ID NO: 3110

LRSQLGDRLNVEVDAAPTVDLNRVLNETRN, SEQ ID NO: 3111

LRCPLGDRLNVEVDAAPTVDLNRVLNETRN, SEQ ID NO: 3112

LRSPLGDRLNVEVDAAPTVDLNRVLNETRN, SEQ ID NO: 3113

LRCQLGDRLNVEVDTAPTVDLNRVLNETRN, SEQ ID NO: 3114

LRSQLGDRLNVEVDTAPTVDLNRVLNETRN, SEQ ID NO: 3115

LRCPLGDRLNVEVDTAPTVDLNRVLNETRN, SEQ ID NO: 3116

LRSPLGDRLNVEVDTAPTVDLNRVLNETRN, SEQ ID NO: 3117

RCQLGDRLNVEVDAAPTVDLNQVLNETRSQ, SEQ ID NO: 3118

RSQLGDRLNVEVDAAPTVDLNQVLNETRSQ, SEQ ID NO: 3119

RCPLGDRLNVEVDAAPTVDLNQVLNETRSQ, SEQ ID NO: 3120

RSPLGDRLNVEVDAAPTVDLNQVLNETRSQ, SEQ ID NO: 3121

RCQLGDRLNVEVDTAPTVDLNQVLNETRSQ, SEQ ID NO: 3122

RSQLGDRLNVEVDTAPTVDLNQVLNETRSQ, SEQ ID NO: 3123

RCPLGDRLNVEVDTAPTVDLNQVLNETRSQ, SEQ ID NO: 3124

RSPLGDRLNVEVDTAPTVDLNQVLNETRSQ, SEQ ID NO: 3125

RCQLGDRLNVEVDAAPTVDLNRVLNETRSQ, SEQ ID NO: 3126

RSQLGDRLNVEVDAAPTVDLNRVLNETRSQ, SEQ ID NO: 3127

RCPLGDRLNVEVDAAPTVDLNRVLNETRSQ, SEQ ID NO: 3128

RSPLGDRLNVEVDAAPTVDLNRVLNETRSQ, SEQ ID NO: 3129

RCQLGDRLNVEVDTAPTVDLNRVLNETRSQ, SEQ ID NO: 3130

RSQLGDRLNVEVDTAPTVDLNRVLNETRSQ, SEQ ID NO: 3131

RCPLGDRLNVEVDTAPTVDLNRVLNETRSQ, SEQ ID NO: 3132

RSPLGDRLNVEVDTAPTVDLNRVLNETRSQ, SEQ ID NO: 3133

RCQLGDRLNVEVDAAPTVDLNQVLNETRNQ, SEQ ID NO: 3134

RSQLGDRLNVEVDAAPTVDLNQVLNETRNQ, SEQ ID NO: 3135

RCPLGDRLNVEVDAAPTVDLNQVLNETRNQ, SEQ ID NO: 3136

RSPLGDRLNVEVDAAPTVDLNQVLNETRNQ, SEQ ID NO: 3137

RCQLGDRLNVEVDTAPTVDLNQVLNETRNQ, SEQ ID NO: 3138

RSQLGDRLNVEVDTAPTVDLNQVLNETRNQ, SEQ ID NO: 3139

RCPLGDRLNVEVDTAPTVDLNQVLNETRNQ, SEQ ID NO: 3140

RSPLGDRLNVEVDTAPTVDLNQVLNETRNQ, SEQ ID NO: 3141

RCQLGDRLNVEVDAAPTVDLNRVLNETRNQ, SEQ ID NO: 3142

RSQLGDRLNVEVDAAPTVDLNRVLNETRNQ, SEQ ID NO: 3143

RCPLGDRLNVEVDAAPTVDLNRVLNETRNQ, SEQ ID NO: 3144

RSPLGDRLNVEVDAAPTVDLNRVLNETRNQ, SEQ ID NO: 3145

RCQLGDRLNVEVDTAPTVDLNRVLNETRNQ, SEQ ID NO: 3146

RSQLGDRLNVEVDTAPTVDLNRVLNETRNQ, SEQ ID NO: 3147

RCPLGDRLNVEVDTAPTVDLNRVLNETRNQ, SEQ ID NO: 3148

RSPLGDRLNVEVDTAPTVDLNRVLNETRNQ, SEQ ID NO: 3149

CQLGDRLNVEVDAAPTVDLNQVLNETRSQY, SEQ ID NO: 3150

SQLGDRLNVEVDAAPTVDLNQVLNETRSQY, SEQ ID NO: 3151

CPLGDRLNVEVDAAPTVDLNQVLNETRSQY, SEQ ID NO: 3152

SPLGDRLNVEVDAAPTVDLNQVLNETRSQY, SEQ ID NO: 3153

CQLGDRLNVEVDTAPTVDLNQVLNETRSQY, SEQ ID NO: 3154

SQLGDRLNVEVDTAPTVDLNQVLNETRSQY, SEQ ID NO: 3155

CPLGDRLNVEVDTAPTVDLNQVLNETRSQY, SEQ ID NO: 3156

SPLGDRLNVEVDTAPTVDLNQVLNETRSQY, SEQ ID NO: 3157

CQLGDRLNVEVDAAPTVDLNRVLNETRSQY, SEQ ID NO: 3158

SQLGDRLNVEVDAAPTVDLNRVLNETRSQY, SEQ ID NO: 3159

CPLGDRLNVEVDAAPTVDLNRVLNETRSQY, SEQ ID NO: 3160

SPLGDRLNVEVDAAPTVDLNRVLNETRSQY, SEQ ID NO: 3161

CQLGDRLNVEVDTAPTVDLNRVLNETRSQY, SEQ ID NO: 3162

SQLGDRLNVEVDTAPTVDLNRVLNETRSQY, SEQ ID NO: 3163

CPLGDRLNVEVDTAPTVDLNRVLNETRSQY, SEQ ID NO: 3164

SPLGDRLNVEVDTAPTVDLNRVLNETRSQY, SEQ ID NO: 3165

CQLGDRLNVEVDAAPTVDLNQVLNETRNQY, SEQ ID NO: 3166

SQLGDRLNVEVDAAPTVDLNQVLNETRNQY, SEQ ID NO: 3167

CPLGDRLNVEVDAAPTVDLNQVLNETRNQY, SEQ ID NO: 3168

SPLGDRLNVEVDAAPTVDLNQVLNETRNQY, SEQ ID NO: 3169

CQLGDRLNVEVDTAPTVDLNQVLNETRNQY, SEQ ID NO: 3170

SQLGDRLNVEVDTAPTVDLNQVLNETRNQY, SEQ ID NO: 3171

CPLGDRLNVEVDTAPTVDLNQVLNETRNQY, SEQ ID NO: 3172

SPLGDRLNVEVDTAPTVDLNQVLNETRNQY, SEQ ID NO: 3173

CQLGDRLNVEVDAAPTVDLNRVLNETRNQY, SEQ ID NO: 3174

SQLGDRLNVEVDAAPTVDLNRVLNETRNQY, SEQ ID NO: 3175

CPLGDRLNVEVDAAPTVDLNRVLNETRNQY, SEQ ID NO: 3176

SPLGDRLNVEVDAAPTVDLNRVLNETRNQY, SEQ ID NO: 3177

CQLGDRLNVEVDTAPTVDLNRVLNETRNQY, SEQ ID NO: 3178

SQLGDRLNVEVDTAPTVDLNRVLNETRNQY, SEQ ID NO: 3179

CPLGDRLNVEVDTAPTVDLNRVLNETRNQY, SEQ ID NO: 3180

SPLGDRLNVEVDTAPTVDLNRVLNETRNQY, SEQ ID NO: 3181

QLGDRLNVEVDAAPTVDLNQVLNETRSQYE, SEQ ID NO: 3182

PLGDRLNVEVDAAPTVDLNQVLNETRSQYE, SEQ ID NO: 3183

QLGDRLNVEVDTAPTVDLNQVLNETRSQYE, SEQ ID NO: 3184

PLGDRLNVEVDTAPTVDLNQVLNETRSQYE, SEQ ID NO: 3185

QLGDRLNVEVDAAPTVDLNRVLNETRSQYE, SEQ ID NO: 3186

PLGDRLNVEVDAAPTVDLNRVLNETRSQYE, SEQ ID NO: 3187

QLGDRLNVEVDTAPTVDLNRVLNETRSQYE, SEQ ID NO: 3188

PLGDRLNVEVDTAPTVDLNRVLNETRSQYE, SEQ ID NO: 3189

QLGDRLNVEVDAAPTVDLNQVLNETRNQYE, SEQ ID NO: 3190

PLGDRLNVEVDAAPTVDLNQVLNETRNQYE, SEQ ID NO: 3191

QLGDRLNVEVDTAPTVDLNQVLNETRNQYE, SEQ ID NO: 3192

PLGDRLNVEVDTAPTVDLNQVLNETRNQYE, SEQ ID NO: 3193

QLGDRLNVEVDAAPTVDLNRVLNETRNQYE, SEQ ID NO: 3194

PLGDRLNVEVDAAPTVDLNRVLNETRNQYE, SEQ ID NO: 3195

QLGDRLNVEVDTAPTVDLNRVLNETRNQYE, SEQ ID NO: 3196

PLGDRLNVEVDTAPTVDLNRVLNETRNQYE, SEQ ID NO: 3197

LGDRLNVEVDAAPTVDLNQVLNETRSQYEA, SEQ ID NO: 3198

LGDRLNVEVDTAPTVDLNQVLNETRSQYEA, SEQ ID NO: 3199

LGDRLNVEVDAAPTVDLNRVLNETRSQYEA, SEQ ID NO: 3200

LGDRLNVEVDTAPTVDLNRVLNETRSQYEA, SEQ ID NO: 3201

LGDRLNVEVDAAPTVDLNQVLNETRNQYEA, SEQ ID NO: 3202

LGDRLNVEVDTAPTVDLNQVLNETRNQYEA, SEQ ID NO: 3203

LGDRLNVEVDAAPTVDLNRVLNETRNQYEA, SEQ ID NO: 3204

LGDRLNVEVDTAPTVDLNRVLNETRNQYEA, SEQ ID NO: 3205

GDRLNVEVDAAPTVDLNQVLNETRSQYEAL, SEQ ID NO: 3206

GDRLNVEVDTAPTVDLNQVLNETRSQYEAL, SEQ ID NO: 3207

GDRLNVEVDAAPTVDLNRVLNETRSQYEAL, SEQ ID NO: 3208

GDRLNVEVDTAPTVDLNRVLNETRSQYEAL, SEQ ID NO: 3209

GDRLNVEVDAAPTVDLNQVLNETRNQYEAL, SEQ ID NO: 3210

GDRLNVEVDTAPTVDLNQVLNETRNQYEAL, SEQ ID NO: 3211

GDRLNVEVDAAPTVDLNRVLNETRNQYEAL, SEQ ID NO: 3212

GDRLNVEVDTAPTVDLNRVLNETRNQYEAL, SEQ ID NO: 3213

EVNTLRCQLGDRLNVEVDAAPTVDLNQVLNE, SEQ ID NO: 3214

EVNTLRSQLGDRLNVEVDAAPTVDLNQVLNE, SEQ ID NO: 3215

EVNTLRCPLGDRLNVEVDAAPTVDLNQVLNE, SEQ ID NO: 3216

EVNTLRSPLGDRLNVEVDAAPTVDLNQVLNE, SEQ ID NO: 3217

EVNTLRCQLGDRLNVEVDTAPTVDLNQVLNE, SEQ ID NO: 3218

EVNTLRSQLGDRLNVEVDTAPTVDLNQVLNE, SEQ ID NO: 3219

EVNTLRCPLGDRLNVEVDTAPTVDLNQVLNE, SEQ ID NO: 3220

EVNTLRSPLGDRLNVEVDTAPTVDLNQVLNE, SEQ ID NO: 3221

EVNTLRCQLGDRLNVEVDAAPTVDLNRVLNE, SEQ ID NO: 3222

EVNTLRSQLGDRLNVEVDAAPTVDLNRVLNE, SEQ ID NO: 3223

EVNTLRCPLGDRLNVEVDAAPTVDLNRVLNE, SEQ ID NO: 3224

EVNTLRSPLGDRLNVEVDAAPTVDLNRVLNE, SEQ ID NO: 3225

SEQ ID NO: 3226
EVNTLRCQLGDRLNVEVDTAPTVDLNRVLNE,

SEQ ID NO: 3227
EVNTLRSQLGDRLNVEVDTAPTVDLNRVLNE,

SEQ ID NO: 3228
EVNTLRCPLGDRLNVEVDTAPTVDLNRVLNE,

SEQ ID NO: 3229
EVNTLRSPLGDRLNVEVDTAPTVDLNRVLNE,

SEQ ID NO: 3230
VNTLRCQLGDRLNVEVDAAPTVDLNQVLNET,

SEQ ID NO: 3231
VNTLRSQLGDRLNVEVDAAPTVDLNQVLNET,

SEQ ID NO: 3232
VNTLRCPLGDRLNVEVDAAPTVDLNQVLNET,

SEQ ID NO: 3233
VNTLRSPLGDRLNVEVDAAPTVDLNQVLNET,

SEQ ID NO: 3234
VNTLRCQLGDRLNVEVDTAPTVDLNQVLNET,

SEQ ID NO: 3235
VNTLRSQLGDRLNVEVDTAPTVDLNQVLNET,

SEQ ID NO: 3236
VNTLRCPLGDRLNVEVDTAPTVDLNQVLNET,

SEQ ID NO: 3237
VNTLRSPLGDRLNVEVDTAPTVDLNQVLNET,

SEQ ID NO: 3238
VNTLRCQLGDRLNVEVDAAPTVDLNRVLNET,

SEQ ID NO: 3239
VNTLRSQLGDRLNVEVDAAPTVDLNRVLNET,

SEQ ID NO: 3240
VNTLRCPLGDRLNVEVDAAPTVDLNRVLNET,

SEQ ID NO: 3241
VNTLRSPLGDRLNVEVDAAPTVDLNRVLNET,

SEQ ID NO: 3242
VNTLRCQLGDRLNVEVDTAPTVDLNRVLNET,

SEQ ID NO: 3243
VNTLRSQLGDRLNVEVDTAPTVDLNRVLNET,

SEQ ID NO: 3244
VNTLRCPLGDRLNVEVDTAPTVDLNRVLNET,

SEQ ID NO: 3245
VNTLRSPLGDRLNVEVDTAPTVDLNRVLNET,

SEQ ID NO: 3246
NTLRCQLGDRLNVEVDAAPTVDLNQVLNETR,

SEQ ID NO: 3247
NTLRSQLGDRLNVEVDAAPTVDLNQVLNETR,

SEQ ID NO: 3248
NTLRCPLGDRLNVEVDAAPTVDLNQVLNETR,

SEQ ID NO: 3249
NTLRSPLGDRLNVEVDAAPTVDLNQVLNETR,

SEQ ID NO: 3250
NTLRCQLGDRLNVEVDTAPTVDLNQVLNETR,

SEQ ID NO: 3251
NTLRSQLGDRLNVEVDTAPTVDLNQVLNETR,

SEQ ID NO: 3252
NTLRCPLGDRLNVEVDTAPTVDLNQVLNETR,

SEQ ID NO: 3253
NTLRSPLGDRLNVEVDTAPTVDLNQVLNETR,

SEQ ID NO: 3254
NTLRCQLGDRLNVEVDAAPTVDLNRVLNETR,

SEQ ID NO: 3255
NTLRSQLGDRLNVEVDAAPTVDLNRVLNETR,

SEQ ID NO: 3256
NTLRCPLGDRLNVEVDAAPTVDLNRVLNETR,

SEQ ID NO: 3257
NTLRSPLGDRLNVEVDAAPTVDLNRVLNETR,

SEQ ID NO: 3258
NTLRCQLGDRLNVEVDTAPTVDLNRVLNETR,

SEQ ID NO: 3259
NTLRSQLGDRLNVEVDTAPTVDLNRVLNETR,

SEQ ID NO: 3260
NTLRCPLGDRLNVEVDTAPTVDLNRVLNETR,

SEQ ID NO: 3261
NTLRSPLGDRLNVEVDTAPTVDLNRVLNETR,

SEQ ID NO: 3262
TLRCQLGDRLNVEVDAAPTVDLNQVLNETRS,

SEQ ID NO: 3263
TLRSQLGDRLNVEVDAAPTVDLNQVLNETRS,

SEQ ID NO: 3264
TLRCPLGDRLNVEVDAAPTVDLNQVLNETRS,

SEQ ID NO: 3265
TLRSPLGDRLNVEVDAAPTVDLNQVLNETRS,

SEQ ID NO: 3266
TLRCQLGDRLNVEVDTAPTVDLNQVLNETRS,

SEQ ID NO: 3267
TLRSQLGDRLNVEVDTAPTVDLNQVLNETRS,

SEQ ID NO: 3268
TLRCPLGDRLNVEVDTAPTVDLNQVLNETRS,

SEQ ID NO: 3269
TLRSPLGDRLNVEVDTAPTVDLNQVLNETRS,

SEQ ID NO: 3270
TLRCQLGDRLNVEVDAAPTVDLNRVLNETRS,

SEQ ID NO: 3271
TLRSQLGDRLNVEVDAAPTVDLNRVLNETRS,

SEQ ID NO: 3272
TLRCPLGDRLNVEVDAAPTVDLNRVLNETRS,

SEQ ID NO: 3273
TLRSPLGDRLNVEVDAAPTVDLNRVLNETRS,

SEQ ID NO: 3274
TLRCQLGDRLNVEVDTAPTVDLNRVLNETRS,

SEQ ID NO: 3275
TLRSQLGDRLNVEVDTAPTVDLNRVLNETRS,

SEQ ID NO: 3276
TLRCPLGDRLNVEVDTAPTVDLNRVLNETRS,

SEQ ID NO: 3277
TLRSPLGDRLNVEVDTAPTVDLNRVLNETRS,

SEQ ID NO: 3278
TLRCQLGDRLNVEVDAAPTVDLNQVLNETRN,

SEQ ID NO: 3279
TLRSQLGDRLNVEVDAAPTVDLNQVLNETRN,

TLRCPLGDRLNVEVDAAPTVDLNQVLNETRN, SEQ ID NO: 3280

TLRSPLGDRLNVEVDAAPTVDLNQVLNETRN, SEQ ID NO: 3281

TLRCQLGDRLNVEVDTAPTVDLNQVLNETRN, SEQ ID NO: 3282

TLRSQLGDRLNVEVDTAPTVDLNQVLNETRN, SEQ ID NO: 3283

TLRCPLGDRLNVEVDTAPTVDLNQVLNETRN, SEQ ID NO: 3284

TLRSPLGDRLNVEVDTAPTVDLNQVLNETRN, SEQ ID NO: 3285

TLRCQLGDRLNVEVDAAPTVDLNRVLNETRN, SEQ ID NO: 3286

TLRSQLGDRLNVEVDAAPTVDLNRVLNETRN, SEQ ID NO: 3287

TLRCPLGDRLNVEVDAAPTVDLNRVLNETRN, SEQ ID NO: 3288

TLRSPLGDRLNVEVDAAPTVDLNRVLNETRN, SEQ ID NO: 3289

TLRCQLGDRLNVEVDTAPTVDLNRVLNETRN, SEQ ID NO: 3290

TLRSQLGDRLNVEVDTAPTVDLNRVLNETRN, SEQ ID NO: 3291

TLRCPLGDRLNVEVDTAPTVDLNRVLNETRN, SEQ ID NO: 3292

TLRSPLGDRLNVEVDTAPTVDLNRVLNETRN, SEQ ID NO: 3293

LRCQLGDRLNVEVDAAPTVDLNQVLNETRSQ, SEQ ID NO: 3294

LRSQLGDRLNVEVDAAPTVDLNQVLNETRSQ, SEQ ID NO: 3295

LRCPLGDRLNVEVDAAPTVDLNQVLNETRSQ, SEQ ID NO: 3296

LRSPLGDRLNVEVDAAPTVDLNQVLNETRSQ, SEQ ID NO: 3297

LRCQLGDRLNVEVDTAPTVDLNQVLNETRSQ, SEQ ID NO: 3298

LRSQLGDRLNVEVDTAPTVDLNQVLNETRSQ, SEQ ID NO: 3299

LRCPLGDRLNVEVDTAPTVDLNQVLNETRSQ, SEQ ID NO: 3300

LRSPLGDRLNVEVDTAPTVDLNQVLNETRSQ, SEQ ID NO: 3301

LRCQLGDRLNVEVDAAPTVDLNRVLNETRSQ, SEQ ID NO: 3302

LRSQLGDRLNVEVDAAPTVDLNRVLNETRSQ, SEQ ID NO: 3303

LRCPLGDRLNVEVDAAPTVDLNRVLNETRSQ, SEQ ID NO: 3304

LRSPLGDRLNVEVDAAPTVDLNRVLNETRSQ, SEQ ID NO: 3305

LRCQLGDRLNVEVDTAPTVDLNRVLNETRSQ, SEQ ID NO: 3306

LRSQLGDRLNVEVDTAPTVDLNRVLNETRSQ, SEQ ID NO: 3307

LRCPLGDRLNVEVDTAPTVDLNRVLNETRSQ, SEQ ID NO: 3308

LRSPLGDRLNVEVDTAPTVDLNRVLNETRSQ, SEQ ID NO: 3309

LRCQLGDRLNVEVDAAPTVDLNQVLNETRNQ, SEQ ID NO: 3310

LRSQLGDRLNVEVDAAPTVDLNQVLNETRNQ, SEQ ID NO: 3311

LRCPLGDRLNVEVDAAPTVDLNQVLNETRNQ, SEQ ID NO: 3312

LRSPLGDRLNVEVDAAPTVDLNQVLNETRNQ, SEQ ID NO: 3313

LRCQLGDRLNVEVDTAPTVDLNQVLNETRNQ, SEQ ID NO: 3314

LRSQLGDRLNVEVDTAPTVDLNQVLNETRNQ, SEQ ID NO: 3315

LRCPLGDRLNVEVDTAPTVDLNQVLNETRNQ, SEQ ID NO: 3316

LRSPLGDRLNVEVDTAPTVDLNQVLNETRNQ, SEQ ID NO: 3317

LRCQLGDRLNVEVDAAPTVDLNRVLNETRNQ, SEQ ID NO: 3318

LRSQLGDRLNVEVDAAPTVDLNRVLNETRNQ, SEQ ID NO: 3319

LRCPLGDRLNVEVDAAPTVDLNRVLNETRNQ, SEQ ID NO: 3320

LRSPLGDRLNVEVDAAPTVDLNRVLNETRNQ, SEQ ID NO: 3321

LRCQLGDRLNVEVDTAPTVDLNRVLNETRNQ, SEQ ID NO: 3322

LRSQLGDRLNVEVDTAPTVDLNRVLNETRNQ, SEQ ID NO: 3323

LRCPLGDRLNVEVDTAPTVDLNRVLNETRNQ, SEQ ID NO: 3324

LRSPLGDRLNVEVDTAPTVDLNRVLNETRNQ, SEQ ID NO: 3325

RCQLGDRLNVEVDAAPTVDLNQVLNETRSQY, SEQ ID NO: 3326

RSQLGDRLNVEVDAAPTVDLNQVLNETRSQY, SEQ ID NO: 3327

RCPLGDRLNVEVDAAPTVDLNQVLNETRSQY, SEQ ID NO: 3328

RSPLGDRLNVEVDAAPTVDLNQVLNETRSQY, SEQ ID NO: 3329

RCQLGDRLNVEVDTAPTVDLNQVLNETRSQY, SEQ ID NO: 3330

RSQLGDRLNVEVDTAPTVDLNQVLNETRSQY, SEQ ID NO: 3331

RCPLGDRLNVEVDTAPTVDLNQVLNETRSQY, SEQ ID NO: 3332

RSPLGDRLNVEVDTAPTVDLNQVLNETRSQY, SEQ ID NO: 3333

RCQLGDRLNVEVDAAPTVDLNRVLNETRSQY, SEQ ID NO: 3334

RSQLGDRLNVEVDAAPTVDLNRVLNETRSQY, SEQ ID NO: 3335

RCPLGDRLNVEVDAAPTVDLNRVLNETRSQY, SEQ ID NO: 3336

RSPLGDRLNVEVDAAPTVDLNRVLNETRSQY, SEQ ID NO: 3337

RCQLGDRLNVEVDTAPTVDLNRVLNETRSQY, SEQ ID NO: 3338

RSQLGDRLNVEVDTAPTVDLNRVLNETRSQY, SEQ ID NO: 3339

RCPLGDRLNVEVDTAPTVDLNRVLNETRSQY, SEQ ID NO: 3340

RSPLGDRLNVEVDTAPTVDLNRVLNETRSQY, SEQ ID NO: 3341

RCQLGDRLNVEVDAAPTVDLNQVLNETRNQY, SEQ ID NO: 3342

RSQLGDRLNVEVDAAPTVDLNQVLNETRNQY, SEQ ID NO: 3343

RCPLGDRLNVEVDAAPTVDLNQVLNETRNQY, SEQ ID NO: 3344

RSPLGDRLNVEVDAAPTVDLNQVLNETRNQY, SEQ ID NO: 3345

RCQLGDRLNVEVDTAPTVDLNQVLNETRNQY, SEQ ID NO: 3346

RSQLGDRLNVEVDTAPTVDLNQVLNETRNQY, SEQ ID NO: 3347

RCPLGDRLNVEVDTAPTVDLNQVLNETRNQY, SEQ ID NO: 3348

RSPLGDRLNVEVDTAPTVDLNQVLNETRNQY, SEQ ID NO: 3349

RCQLGDRLNVEVDAAPTVDLNRVLNETRNQY, SEQ ID NO: 3350

RSQLGDRLNVEVDAAPTVDLNRVLNETRNQY, SEQ ID NO: 3351

RCPLGDRLNVEVDAAPTVDLNRVLNETRNQY, SEQ ID NO: 3352

RSPLGDRLNVEVDAAPTVDLNRVLNETRNQY, SEQ ID NO: 3353

RCQLGDRLNVEVDTAPTVDLNRVLNETRNQY, SEQ ID NO: 3354

RSQLGDRLNVEVDTAPTVDLNRVLNETRNQY, SEQ ID NO: 3355

RCPLGDRLNVEVDTAPTVDLNRVLNETRNQY, SEQ ID NO: 3356

RSPLGDRLNVEVDTAPTVDLNRVLNETRNQY, SEQ ID NO: 3357

CQLGDRLNVEVDAAPTVDLNQVLNETRSQYE, SEQ ID NO: 3358

SQLGDRLNVEVDAAPTVDLNQVLNETRSQYE, SEQ ID NO: 3359

CPLGDRLNVEVDAAPTVDLNQVLNETRSQYE, SEQ ID NO: 3360

SPLGDRLNVEVDAAPTVDLNQVLNETRSQYE, SEQ ID NO: 3361

CQLGDRLNVEVDTAPTVDLNQVLNETRSQYE, SEQ ID NO: 3362

SQLGDRLNVEVDTAPTVDLNQVLNETRSQYE, SEQ ID NO: 3363

CPLGDRLNVEVDTAPTVDLNQVLNETRSQYE, SEQ ID NO: 3364

SPLGDRLNVEVDTAPTVDLNQVLNETRSQYE, SEQ ID NO: 3365

CQLGDRLNVEVDAAPTVDLNRVLNETRSQYE, SEQ ID NO: 3366

SQLGDRLNVEVDAAPTVDLNRVLNETRSQYE, SEQ ID NO: 3367

CPLGDRLNVEVDAAPTVDLNRVLNETRSQYE, SEQ ID NO: 3368

SPLGDRLNVEVDAAPTVDLNRVLNETRSQYE, SEQ ID NO: 3369

CQLGDRLNVEVDTAPTVDLNRVLNETRSQYE, SEQ ID NO: 3370

SQLGDRLNVEVDTAPTVDLNRVLNETRSQYE, SEQ ID NO: 3371

CPLGDRLNVEVDTAPTVDLNRVLNETRSQYE, SEQ ID NO: 3372

SPLGDRLNVEVDTAPTVDLNRVLNETRSQYE, SEQ ID NO: 3373

CQLGDRLNVEVDAAPTVDLNQVLNETRNQYE, SEQ ID NO: 3374

SQLGDRLNVEVDAAPTVDLNQVLNETRNQYE, SEQ ID NO: 3375

CPLGDRLNVEVDAAPTVDLNQVLNETRNQYE, SEQ ID NO: 3376

SPLGDRLNVEVDAAPTVDLNQVLNETRNQYE, SEQ ID NO: 3377

CQLGDRLNVEVDTAPTVDLNQVLNETRNQYE, SEQ ID NO: 3378

SQLGDRLNVEVDTAPTVDLNQVLNETRNQYE, SEQ ID NO: 3379

CPLGDRLNVEVDTAPTVDLNQVLNETRNQYE, SEQ ID NO: 3380

SPLGDRLNVEVDTAPTVDLNQVLNETRNQYE, SEQ ID NO: 3381

CQLGDRLNVEVDAAPTVDLNRVLNETRNQYE, SEQ ID NO: 3382

SQLGDRLNVEVDAAPTVDLNRVLNETRNQYE, SEQ ID NO: 3383

CPLGDRLNVEVDAAPTVDLNRVLNETRNQYE, SEQ ID NO: 3384

SPLGDRLNVEVDAAPTVDLNRVLNETRNQYE, SEQ ID NO: 3385

CQLGDRLNVEVDTAPTVDLNRVLNETRNQYE, SEQ ID NO: 3386

SQLGDRLNVEVDTAPTVDLNRVLNETRNQYE, SEQ ID NO: 3387

CPLGDRLNVEVDTAPTVDLNRVLNETRNQYE, SEQ ID NO: 3388

SPLGDRLNVEVDTAPTVDLNRVLNETRNQYE, SEQ ID NO: 3389

QLGDRLNVEVDAAPTVDLNQVLNETRSQYEA, SEQ ID NO: 3390

PLGDRLNVEVDAAPTVDLNQVLNETRSQYEA, SEQ ID NO: 3391

QLGDRLNVEVDTAPTVDLNQVLNETRSQYEA, SEQ ID NO: 3392

PLGDRLNVEVDTAPTVDLNQVLNETRSQYEA, SEQ ID NO: 3393

QLGDRLNVEVDAAPTVDLNRVLNETRSQYEA, SEQ ID NO: 3394

PLGDRLNVEVDAAPTVDLNRVLNETRSQYEA, SEQ ID NO: 3395

QLGDRLNVEVDTAPTVDLNRVLNETRSQYEA, SEQ ID NO: 3396

PLGDRLNVEVDTAPTVDLNRVLNETRSQYEA, SEQ ID NO: 3397

QLGDRLNVEVDAAPTVDLNQVLNETRNQYEA, SEQ ID NO: 3398

PLGDRLNVEVDAAPTVDLNQVLNETRNQYEA, SEQ ID NO: 3399

QLGDRLNVEVDTAPTVDLNQVLNETRNQYEA, SEQ ID NO: 3400

PLGDRLNVEVDTAPTVDLNQVLNETRNQYEA, SEQ ID NO: 3401

QLGDRLNVEVDAAPTVDLNRVLNETRNQYEA, SEQ ID NO: 3402

PLGDRLNVEVDAAPTVDLNRVLNETRNQYEA, SEQ ID NO: 3403

QLGDRLNVEVDTAPTVDLNRVLNETRNQYEA, SEQ ID NO: 3404

PLGDRLNVEVDTAPTVDLNRVLNETRNQYEA, SEQ ID NO: 3405

LGDRLNVEVDAAPTVDLNQVLNETRSQYEAL, SEQ ID NO: 3406

LGDRLNVEVDTAPTVDLNQVLNETRSQYEAL, SEQ ID NO: 3407

LGDRLNVEVDAAPTVDLNRVLNETRSQYEAL, SEQ ID NO: 3408

LGDRLNVEVDTAPTVDLNRVLNETRSQYEAL, SEQ ID NO: 3409

LGDRLNVEVDAAPTVDLNQVLNETRNQYEAL, SEQ ID NO: 3410

LGDRLNVEVDTAPTVDLNQVLNETRNQYEAL, SEQ ID NO: 3411

ELGDRLNVEVDAAPTVDLNRVLNETRNQYEAL, SEQ ID NO: 3412

LGDRLNVEVDTAPTVDLNRVLNETRNQYEAL, SEQ ID NO: 3413

EVNTLRCQLGDRLNVEVDAAPTVDLNQVLNET, SEQ ID NO: 3414

EVNTLRSQLGDRLNVEVDAAPTVDLNQVLNET, SEQ ID NO: 3415

EVNTLRCPLGDRLNVEVDAAPTVDLNQVLNET, SEQ ID NO: 3416

EVNTLRSPLGDRLNVEVDAAPTVDLNQVLNET, SEQ ID NO: 3417

EVNTLRCQLGDRLNVEVDTAPTVDLNQVLNET, SEQ ID NO: 3418

EVNTLRSQLGDRLNVEVDTAPTVDLNQVLNET, SEQ ID NO: 3419

EVNTLRCPLGDRLNVEVDTAPTVDLNQVLNET, SEQ ID NO: 3420

EVNTLRSPLGDRLNVEVDTAPTVDLNQVLNET, SEQ ID NO: 3421

EVNTLRCQLGDRLNVEVDAAPTVDLNRVLNET, SEQ ID NO: 3422

EVNTLRSQLGDRLNVEVDAAPTVDLNRVLNET, SEQ ID NO: 3423

EVNTLRCPLGDRLNVEVDAAPTVDLNRVLNET, SEQ ID NO: 3424

EVNTLRSPLGDRLNVEVDAAPTVDLNRVLNET, SEQ ID NO: 3425

EVNTLRCQLGDRLNVEVDTAPTVDLNRVLNET, SEQ ID NO: 3426

EVNTLRSQLGDRLNVEVDTAPTVDLNRVLNET, SEQ ID NO: 3427

EVNTLRCPLGDRLNVEVDTAPTVDLNRVLNET, SEQ ID NO: 3428

EVNTLRSPLGDRLNVEVDTAPTVDLNRVLNET, SEQ ID NO: 3429

VNTLRCQLGDRLNVEVDAAPTVDLNQVLNETR, SEQ ID NO: 3430

VNTLRSQLGDRLNVEVDAAPTVDLNQVLNETR, SEQ ID NO: 3431

VNTLRCPLGDRLNVEVDAAPTVDLNQVLNETR, SEQ ID NO: 3432

VNTLRSPLGDRLNVEVDAAPTVDLNQVLNETR, SEQ ID NO: 3433

VNTLRCQLGDRLNVEVDTAPTVDLNQVLNETR, SEQ ID NO: 3434

VNTLRSQLGDRLNVEVDTAPTVDLNQVLNETR, SEQ ID NO: 3435

VNTLRCPLGDRLNVEVDTAPTVDLNQVLNETR, SEQ ID NO: 3436

VNTLRSPLGDRLNVEVDTAPTVDLNQVLNETR, SEQ ID NO: 3437

VNTLRCQLGDRLNVEVDAAPTVDLNRVLNETR, SEQ ID NO: 3438

VNTLRSQLGDRLNVEVDAAPTVDLNRVLNETR, SEQ ID NO: 3439

VNTLRCPLGDRLNVEVDAAPTVDLNRVLNETR, SEQ ID NO: 3440

VNTLRSPLGDRLNVEVDAAPTVDLNRVLNETR, SEQ ID NO: 3441

SEQ ID NO: 3442
VNTLRCQLGDRLNVEVDTAPTVDLNRVLNETR,

SEQ ID NO: 3443
VNTLRSQLGDRLNVEVDTAPTVDLNRVLNETR,

SEQ ID NO: 3444
VNTLRCPLGDRLNVEVDTAPTVDLNRVLNETR,

SEQ ID NO: 3445
VNTLRSPLGDRLNVEVDTAPTVDLNRVLNETR,

SEQ ID NO: 3446
NTLRCQLGDRLNVEVDAAPTVDLNQVLNETRS,

SEQ ID NO: 3447
NTLRSQLGDRLNVEVDAAPTVDLNQVLNETRS,

SEQ ID NO: 3448
NTLRCPLGDRLNVEVDAAPTVDLNQVLNETRS,

SEQ ID NO: 3449
NTLRSPLGDRLNVEVDAAPTVDLNQVLNETRS,

SEQ ID NO: 3450
NTLRCQLGDRLNVEVDTAPTVDLNQVLNETRS,

SEQ ID NO: 3451
NTLRSQLGDRLNVEVDTAPTVDLNQVLNETRS,

SEQ ID NO: 3452
NTLRCPLGDRLNVEVDTAPTVDLNQVLNETRS,

SEQ ID NO: 3453
NTLRSPLGDRLNVEVDTAPTVDLNQVLNETRS,

SEQ ID NO: 3454
NTLRCQLGDRLNVEVDAAPTVDLNRVLNETRS,

SEQ ID NO: 3455
NTLRSQLGDRLNVEVDAAPTVDLNRVLNETRS,

SEQ ID NO: 3456
NTLRCPLGDRLNVEVDAAPTVDLNRVLNETRS,

SEQ ID NO: 3457
NTLRSPLGDRLNVEVDAAPTVDLNRVLNETRS,

SEQ ID NO: 3458
NTLRCQLGDRLNVEVDTAPTVDLNRVLNETRS,

SEQ ID NO: 3459
NTLRSQLGDRLNVEVDTAPTVDLNRVLNETRS,

SEQ ID NO: 3460
NTLRCPLGDRLNVEVDTAPTVDLNRVLNETRS,

SEQ ID NO: 3461
NTLRSPLGDRLNVEVDTAPTVDLNRVLNETRS,

SEQ ID NO: 3462
NTLRCQLGDRLNVEVDAAPTVDLNQVLNETRN,

SEQ ID NO: 3463
NTLRSQLGDRLNVEVDAAPTVDLNQVLNETRN,

SEQ ID NO: 3464
NTLRCPLGDRLNVEVDAAPTVDLNQVLNETRN,

SEQ ID NO: 3465
NTLRSPLGDRLNVEVDAAPTVDLNQVLNETRN,

SEQ ID NO: 3466
NTLRCQLGDRLNVEVDTAPTVDLNQVLNETRN,

SEQ ID NO: 3467
NTLRSQLGDRLNVEVDTAPTVDLNQVLNETRN,

SEQ ID NO: 3468
NTLRCPLGDRLNVEVDTAPTVDLNQVLNETRN,

SEQ ID NO: 3469
NTLRSPLGDRLNVEVDTAPTVDLNQVLNETRN,

SEQ ID NO: 3470
NTLRCQLGDRLNVEVDAAPTVDLNRVLNETRN,

SEQ ID NO: 3471
NTLRSQLGDRLNVEVDAAPTVDLNRVLNETRN,

SEQ ID NO: 3472
NTLRCPLGDRLNVEVDAAPTVDLNRVLNETRN,

SEQ ID NO: 3473
NTLRSPLGDRLNVEVDAAPTVDLNRVLNETRN,

SEQ ID NO: 3474
NTLRCQLGDRLNVEVDTAPTVDLNRVLNETRN,

SEQ ID NO: 3475
NTLRSQLGDRLNVEVDTAPTVDLNRVLNETRN,

SEQ ID NO: 3476
NTLRCPLGDRLNVEVDTAPTVDLNRVLNETRN,

SEQ ID NO: 3477
NTLRSPLGDRLNVEVDTAPTVDLNRVLNETRN,

SEQ ID NO: 3478
TLRCQLGDRLNVEVDAAPTVDLNQVLNETRSQ,

SEQ ID NO: 3479
TLRSQLGDRLNVEVDAAPTVDLNQVLNETRSQ,

SEQ ID NO: 3480
TLRCPLGDRLNVEVDAAPTVDLNQVLNETRSQ,

SEQ ID NO: 3481
TLRSPLGDRLNVEVDAAPTVDLNQVLNETRSQ,

SEQ ID NO: 3482
TLRCQLGDRLNVEVDTAPTVDLNQVLNETRSQ,

SEQ ID NO: 3483
TLRSQLGDRLNVEVDTAPTVDLNQVLNETRSQ,

SEQ ID NO: 3484
TLRCPLGDRLNVEVDTAPTVDLNQVLNETRSQ,

SEQ ID NO: 3485
TLRSPLGDRLNVEVDTAPTVDLNQVLNETRSQ,

SEQ ID NO: 3486
TLRCQLGDRLNVEVDAAPTVDLNRVLNETRSQ,

SEQ ID NO: 3487
TLRSQLGDRLNVEVDAAPTVDLNRVLNETRSQ,

SEQ ID NO: 3488
TLRCPLGDRLNVEVDAAPTVDLNRVLNETRSQ,

SEQ ID NO: 3489
TLRSPLGDRLNVEVDAAPTVDLNRVLNETRSQ,

SEQ ID NO: 3490
TLRCQLGDRLNVEVDTAPTVDLNRVLNETRSQ,

SEQ ID NO: 3491
TLRSQLGDRLNVEVDTAPTVDLNRVLNETRSQ,

SEQ ID NO: 3492
TLRCPLGDRLNVEVDTAPTVDLNRVLNETRSQ,

SEQ ID NO: 3493
TLRSPLGDRLNVEVDTAPTVDLNRVLNETRSQ,

SEQ ID NO: 3494
TLRCQLGDRLNVEVDAAPTVDLNQVLNETRNQ,

SEQ ID NO: 3495
TLRSQLGDRLNVEVDAAPTVDLNQVLNETRNQ,

TLRCPLGDRLNVEVDAAPTVDLNQVLNETRNQ, SEQ ID NO: 3496

TLRSPLGDRLNVEVDAAPTVDLNQVLNETRNQ, SEQ ID NO: 3497

TLRCQLGDRLNVEVDTAPTVDLNQVLNETRNQ, SEQ ID NO: 3498

TLRSQLGDRLNVEVDTAPTVDLNQVLNETRNQ, SEQ ID NO: 3499

TLRCPLGDRLNVEVDTAPTVDLNQVLNETRNQ, SEQ ID NO: 3500

TLRSPLGDRLNVEVDTAPTVDLNQVLNETRNQ, SEQ ID NO: 3501

TLRCQLGDRLNVEVDAAPTVDLNRVLNETRNQ, SEQ ID NO: 3502

TLRSQLGDRLNVEVDAAPTVDLNRVLNETRNQ, SEQ ID NO: 3503

TLRCPLGDRLNVEVDAAPTVDLNRVLNETRNQ, SEQ ID NO: 3504

TLRSPLGDRLNVEVDAAPTVDLNRVLNETRNQ, SEQ ID NO: 3505

TLRCQLGDRLNVEVDTAPTVDLNRVLNETRNQ, SEQ ID NO: 3506

TLRSQLGDRLNVEVDTAPTVDLNRVLNETRNQ, SEQ ID NO: 3507

TLRCPLGDRLNVEVDTAPTVDLNRVLNETRNQ, SEQ ID NO: 3508

TLRSPLGDRLNVEVDTAPTVDLNRVLNETRNQ, SEQ ID NO: 3509

LRCQLGDRLNVEVDAAPTVDLNQVLNETRSQY, SEQ ID NO: 3510

LRSQLGDRLNVEVDAAPTVDLNQVLNETRSQY, SEQ ID NO: 3511

LRCPLGDRLNVEVDAAPTVDLNQVLNETRSQY, SEQ ID NO: 3512

LRSPLGDRLNVEVDAAPTVDLNQVLNETRSQY, SEQ ID NO: 3513

LRCQLGDRLNVEVDTAPTVDLNQVLNETRSQY, SEQ ID NO: 3514

LRSQLGDRLNVEVDTAPTVDLNQVLNETRSQY, SEQ ID NO: 3515

LRCPLGDRLNVEVDTAPTVDLNQVLNETRSQY, SEQ ID NO: 3516

LRSPLGDRLNVEVDTAPTVDLNQVLNETRSQY, SEQ ID NO: 3517

LRCQLGDRLNVEVDAAPTVDLNRVLNETRSQY, SEQ ID NO: 3518

LRSQLGDRLNVEVDAAPTVDLNRVLNETRSQY, SEQ ID NO: 3519

LRCPLGDRLNVEVDAAPTVDLNRVLNETRSQY, SEQ ID NO: 3520

LRSPLGDRLNVEVDAAPTVDLNRVLNETRSQY, SEQ ID NO: 3521

LRCQLGDRLNVEVDTAPTVDLNRVLNETRSQY, SEQ ID NO: 3522

LRSQLGDRLNVEVDTAPTVDLNRVLNETRSQY, SEQ ID NO: 3523

LRCPLGDRLNVEVDTAPTVDLNRVLNETRSQY, SEQ ID NO: 3524

LRSPLGDRLNVEVDTAPTVDLNRVLNETRSQY, SEQ ID NO: 3525

LRCQLGDRLNVEVDAAPTVDLNQVLNETRNQY, SEQ ID NO: 3526

LRSQLGDRLNVEVDAAPTVDLNQVLNETRNQY, SEQ ID NO: 3527

LRCPLGDRLNVEVDAAPTVDLNQVLNETRNQY, SEQ ID NO: 3528

LRSPLGDRLNVEVDAAPTVDLNQVLNETRNQY, SEQ ID NO: 3529

LRCQLGDRLNVEVDTAPTVDLNQVLNETRNQY, SEQ ID NO: 3530

LRSQLGDRLNVEVDTAPTVDLNQVLNETRNQY, SEQ ID NO: 3531

LRCPLGDRLNVEVDTAPTVDLNQVLNETRNQY, SEQ ID NO: 3532

LRSPLGDRLNVEVDTAPTVDLNQVLNETRNQY, SEQ ID NO: 3533

LRCQLGDRLNVEVDAAPTVDLNRVLNETRNQY, SEQ ID NO: 3534

LRSQLGDRLNVEVDAAPTVDLNRVLNETRNQY, SEQ ID NO: 3535

LRCPLGDRLNVEVDAAPTVDLNRVLNETRNQY, SEQ ID NO: 3536

LRSPLGDRLNVEVDAAPTVDLNRVLNETRNQY, SEQ ID NO: 3537

LRCQLGDRLNVEVDTAPTVDLNRVLNETRNQY, SEQ ID NO: 3538

LRSQLGDRLNVEVDTAPTVDLNRVLNETRNQY, SEQ ID NO: 3539

LRCPLGDRLNVEVDTAPTVDLNRVLNETRNQY, SEQ ID NO: 3540

LRSPLGDRLNVEVDTAPTVDLNRVLNETRNQY, SEQ ID NO: 3541

RCQLGDRLNVEVDAAPTVDLNQVLNETRSQYE, SEQ ID NO: 3542

RSQLGDRLNVEVDAAPTVDLNQVLNETRSQYE, SEQ ID NO: 3543

RCPLGDRLNVEVDAAPTVDLNQVLNETRSQYE, SEQ ID NO: 3544

RSPLGDRLNVEVDAAPTVDLNQVLNETRSQYE, SEQ ID NO: 3545

RCQLGDRLNVEVDTAPTVDLNQVLNETRSQYE, SEQ ID NO: 3546

RSQLGDRLNVEVDTAPTVDLNQVLNETRSQYE, SEQ ID NO: 3547

RCPLGDRLNVEVDTAPTVDLNQVLNETRSQYE, SEQ ID NO: 3548

RSPLGDRLNVEVDTAPTVDLNQVLNETRSQYE, SEQ ID NO: 3549

RCQLGDRLNVEVDAAPTVDLNRVLNETRSQYE, SEQ ID NO: 3550

RSQLGDRLNVEVDAAPTVDLNRVLNETRSQYE, SEQ ID NO: 3551

RCPLGDRLNVEVDAAPTVDLNRVLNETRSQYE, SEQ ID NO: 3552

RSPLGDRLNVEVDAAPTVDLNRVLNETRSQYE, SEQ ID NO: 3553

RCQLGDRLNVEVDTAPTVDLNRVLNETRSQYE, SEQ ID NO: 3554

RSQLGDRLNVEVDTAPTVDLNRVLNETRSQYE, SEQ ID NO: 3555

RCPLGDRLNVEVDTAPTVDLNRVLNETRSQYE, SEQ ID NO: 3556

RSPLGDRLNVEVDTAPTVDLNRVLNETRSQYE, SEQ ID NO: 3557

RCQLGDRLNVEVDAAPTVDLNQVLNETRNQYE, SEQ ID NO: 3558

RSQLGDRLNVEVDAAPTVDLNQVLNETRNQYE, SEQ ID NO: 3559

RCPLGDRLNVEVDAAPTVDLNQVLNETRNQYE, SEQ ID NO: 3560

RSPLGDRLNVEVDAAPTVDLNQVLNETRNQYE, SEQ ID NO: 3561

RCQLGDRLNVEVDTAPTVDLNQVLNETRNQYE, SEQ ID NO: 3562

RSQLGDRLNVEVDTAPTVDLNQVLNETRNQYE, SEQ ID NO: 3563

RCPLGDRLNVEVDTAPTVDLNQVLNETRNQYE, SEQ ID NO: 3564

RSPLGDRLNVEVDTAPTVDLNQVLNETRNQYE, SEQ ID NO: 3565

RCQLGDRLNVEVDAAPTVDLNRVLNETRNQYE, SEQ ID NO: 3566

RSQLGDRLNVEVDAAPTVDLNRVLNETRNQYE, SEQ ID NO: 3567

RCPLGDRLNVEVDAAPTVDLNRVLNETRNQYE, SEQ ID NO: 3568

RSPLGDRLNVEVDAAPTVDLNRVLNETRNQYE, SEQ ID NO: 3569

RCQLGDRLNVEVDTAPTVDLNRVLNETRNQYE, SEQ ID NO: 3570

RSQLGDRLNVEVDTAPTVDLNRVLNETRNQYE, SEQ ID NO: 3571

RCPLGDRLNVEVDTAPTVDLNRVLNETRNQYE, SEQ ID NO: 3572

RSPLGDRLNVEVDTAPTVDLNRVLNETRNQYE, SEQ ID NO: 3573

CQLGDRLNVEVDAAPTVDLNQVLNETRSQYEA, SEQ ID NO: 3574

SQLGDRLNVEVDAAPTVDLNQVLNETRSQYEA, SEQ ID NO: 3575

CPLGDRLNVEVDAAPTVDLNQVLNETRSQYEA, SEQ ID NO: 3576

SPLGDRLNVEVDAAPTVDLNQVLNETRSQYEA, SEQ ID NO: 3577

CQLGDRLNVEVDTAPTVDLNQVLNETRSQYEA, SEQ ID NO: 3578

SQLGDRLNVEVDTAPTVDLNQVLNETRSQYEA, SEQ ID NO: 3579

CPLGDRLNVEVDTAPTVDLNQVLNETRSQYEA, SEQ ID NO: 3580

SPLGDRLNVEVDTAPTVDLNQVLNETRSQYEA, SEQ ID NO: 3581

CQLGDRLNVEVDAAPTVDLNRVLNETRSQYEA, SEQ ID NO: 3582

SQLGDRLNVEVDAAPTVDLNRVLNETRSQYEA, SEQ ID NO: 3583

CPLGDRLNVEVDAAPTVDLNRVLNETRSQYEA, SEQ ID NO: 3584

SPLGDRLNVEVDAAPTVDLNRVLNETRSQYEA, SEQ ID NO: 3585

CQLGDRLNVEVDTAPTVDLNRVLNETRSQYEA, SEQ ID NO: 3586

SQLGDRLNVEVDTAPTVDLNRVLNETRSQYEA, SEQ ID NO: 3587

CPLGDRLNVEVDTAPTVDLNRVLNETRSQYEA, SEQ ID NO: 3588

SPLGDRLNVEVDTAPTVDLNRVLNETRSQYEA, SEQ ID NO: 3589

CQLGDRLNVEVDAAPTVDLNQVLNETRNQYEA, SEQ ID NO: 3590

SQLGDRLNVEVDAAPTVDLNQVLNETRNQYEA, SEQ ID NO: 3591

CPLGDRLNVEVDAAPTVDLNQVLNETRNQYEA, SEQ ID NO: 3592

SPLGDRLNVEVDAAPTVDLNQVLNETRNQYEA, SEQ ID NO: 3593

CQLGDRLNVEVDTAPTVDLNQVLNETRNQYEA, SEQ ID NO: 3594

SQLGDRLNVEVDTAPTVDLNQVLNETRNQYEA, SEQ ID NO: 3595

CPLGDRLNVEVDTAPTVDLNQVLNETRNQYEA, SEQ ID NO: 3596

SPLGDRLNVEVDTAPTVDLNQVLNETRNQYEA, SEQ ID NO: 3597

CQLGDRLNVEVDAAPTVDLNRVLNETRNQYEA, SEQ ID NO: 3598

SQLGDRLNVEVDAAPTVDLNRVLNETRNQYEA, SEQ ID NO: 3599

CPLGDRLNVEVDAAPTVDLNRVLNETRNQYEA, SEQ ID NO: 3600

SPLGDRLNVEVDAAPTVDLNRVLNETRNQYEA, SEQ ID NO: 3601

CQLGDRLNVEVDTAPTVDLNRVLNETRNQYEA, SEQ ID NO: 3602

SQLGDRLNVEVDTAPTVDLNRVLNETRNQYEA, SEQ ID NO: 3603

```
                                              SEQ ID NO: 3604
CPLGDRLNVEVDTAPTVDLNRVLNETRNQYEA,

SEQ ID NO: 3605
SPLGDRLNVEVDTAPTVDLNRVLNETRNQYEA,

SEQ ID NO: 3606
QLGDRLNVEVDAAPTVDLNQVLNETRSQYEAL,

SEQ ID NO: 3607
PLGDRLNVEVDAAPTVDLNQVLNETRSQYEAL,

SEQ ID NO: 3608
QLGDRLNVEVDTAPTVDLNQVLNETRSQYEAL,

SEQ ID NO: 3609
PLGDRLNVEVDTAPTVDLNQVLNETRSQYEAL,

SEQ ID NO: 3610
QLGDRLNVEVDAAPTVDLNRVLNETRSQYEAL,

SEQ ID NO: 3611
PLGDRLNVEVDAAPTVDLNRVLNETRSQYEAL,

SEQ ID NO: 3612
QLGDRLNVEVDTAPTVDLNRVLNETRSQYEAL,

SEQ ID NO: 3613
PLGDRLNVEVDTAPTVDLNRVLNETRSQYEAL,

SEQ ID NO: 3614
QLGDRLNVEVDAAPTVDLNQVLNETRNQYEAL,

SEQ ID NO: 3615
PLGDRLNVEVDAAPTVDLNQVLNETRNQYEAL,

SEQ ID NO: 3616
QLGDRLNVEVDTAPTVDLNQVLNETRNQYEAL,

SEQ ID NO: 3617
PLGDRLNVEVDTAPTVDLNQVLNETRNQYEAL,

SEQ ID NO: 3618
QLGDRLNVEVDAAPTVDLNRVLNETRNQYEAL,

SEQ ID NO: 3619
PLGDRLNVEVDAAPTVDLNRVLNETRNQYEAL,

SEQ ID NO: 3620
QLGDRLNVEVDTAPTVDLNRVLNETRNQYEAL,

SEQ ID NO: 3621
PLGDRLNVEVDTAPTVDLNRVLNETRNQYEAL,

SEQ ID NO: 3622
EVNTLRCQLGDRLNVEVDAAPTVDLNQVLNETR,

SEQ ID NO: 3623
EVNTLRSQLGDRLNVEVDAAPTVDLNQVLNETR,

SEQ ID NO: 3624
EVNTLRCPLGDRLNVEVDAAPTVDLNQVLNETR,

SEQ ID NO: 3625
EVNTLRSPLGDRLNVEVDAAPTVDLNQVLNETR,

SEQ ID NO: 3626
EVNTLRCQLGDRLNVEVDTAPTVDLNQVLNETR,

SEQ ID NO: 3627
EVNTLRSQLGDRLNVEVDTAPTVDLNQVLNETR,

SEQ ID NO: 3628
EVNTLRCPLGDRLNVEVDTAPTVDLNQVLNETR,

SEQ ID NO: 3629
EVNTLRSPLGDRLNVEVDTAPTVDLNQVLNETR,

SEQ ID NO: 3630
EVNTLRCQLGDRLNVEVDAAPTVDLNRVLNETR,

SEQ ID NO: 3631
EVNTLRSQLGDRLNVEVDAAPTVDLNRVLNETR,

SEQ ID NO: 3632
EVNTLRCPLGDRLNVEVDAAPTVDLNRVLNETR,

SEQ ID NO: 3633
EVNTLRSPLGDRLNVEVDAAPTVDLNRVLNETR,

SEQ ID NO: 3634
EVNTLRCQLGDRLNVEVDTAPTVDLNRVLNETR,

SEQ ID NO: 3635
EVNTLRSQLGDRLNVEVDTAPTVDLNRVLNETR,

SEQ ID NO: 3636
EVNTLRCPLGDRLNVEVDTAPTVDLNRVLNETR,

SEQ ID NO: 3637
EVNTLRSPLGDRLNVEVDTAPTVDLNRVLNETR,

SEQ ID NO: 3638
VNTLRCQLGDRLNVEVDAAPTVDLNQVLNETRS,

SEQ ID NO: 3639
VNTLRSQLGDRLNVEVDAAPTVDLNQVLNETRS,

SEQ ID NO: 3640
VNTLRCPLGDRLNVEVDAAPTVDLNQVLNETRS,

SEQ ID NO: 3641
VNTLRSPLGDRLNVEVDAAPTVDLNQVLNETRS,

SEQ ID NO: 3642
VNTLRCQLGDRLNVEVDTAPTVDLNQVLNETRS,

SEQ ID NO: 3643
VNTLRSQLGDRLNVEVDTAPTVDLNQVLNETRS,

SEQ ID NO: 3644
VNTLRCPLGDRLNVEVDTAPTVDLNQVLNETRS,

SEQ ID NO: 3645
VNTLRSPLGDRLNVEVDTAPTVDLNQVLNETRS,

SEQ ID NO: 3646
VNTLRCQLGDRLNVEVDAAPTVDLNRVLNETRS,

SEQ ID NO: 3647
VNTLRSQLGDRLNVEVDAAPTVDLNRVLNETRS,

SEQ ID NO: 3648
VNTLRCPLGDRLNVEVDAAPTVDLNRVLNETRS,

SEQ ID NO: 3649
VNTLRSPLGDRLNVEVDAAPTVDLNRVLNETRS,

SEQ ID NO: 3650
VNTLRCQLGDRLNVEVDTAPTVDLNRVLNETRS,

SEQ ID NO: 3651
VNTLRSQLGDRLNVEVDTAPTVDLNRVLNETRS,

SEQ ID NO: 3652
VNTLRCPLGDRLNVEVDTAPTVDLNRVLNETRS,

SEQ ID NO: 3653
VNTLRSPLGDRLNVEVDTAPTVDLNRVLNETRS,

SEQ ID NO: 3654
VNTLRCQLGDRLNVEVDAAPTVDLNQVLNETRN,

SEQ ID NO: 3655
VNTLRSQLGDRLNVEVDAAPTVDLNQVLNETRN,

SEQ ID NO: 3656
VNTLRCPLGDRLNVEVDAAPTVDLNQVLNETRN,

SEQ ID NO: 3657
VNTLRSPLGDRLNVEVDAAPTVDLNQVLNETRN,
```

VNTLRCQLGDRLNVEVDTAPTVDLNQVLNETRN, SEQ ID NO: 3658

VNTLRSQLGDRLNVEVDTAPTVDLNQVLNETRN, SEQ ID NO: 3659

VNTLRCPLGDRLNVEVDTAPTVDLNQVLNETRN, SEQ ID NO: 3660

VNTLRSPLGDRLNVEVDTAPTVDLNQVLNETRN, SEQ ID NO: 3661

VNTLRCQLGDRLNVEVDAAPTVDLNRVLNETRN, SEQ ID NO: 3662

VNTLRSQLGDRLNVEVDAAPTVDLNRVLNETRN, SEQ ID NO: 3663

VNTLRCPLGDRLNVEVDAAPTVDLNRVLNETRN, SEQ ID NO: 3664

VNTLRSPLGDRLNVEVDAAPTVDLNRVLNETRN, SEQ ID NO: 3665

VNTLRCQLGDRLNVEVDTAPTVDLNRVLNETRN, SEQ ID NO: 3666

VNTLRSQLGDRLNVEVDTAPTVDLNRVLNETRN, SEQ ID NO: 3667

VNTLRCPLGDRLNVEVDTAPTVDLNRVLNETRN, SEQ ID NO: 3668

VNTLRSPLGDRLNVEVDTAPTVDLNRVLNETRN, SEQ ID NO: 3669

NTLRCQLGDRLNVEVDAAPTVDLNQVLNETRSQ, SEQ ID NO: 3670

NTLRSQLGDRLNVEVDAAPTVDLNQVLNETRSQ, SEQ ID NO: 3671

NTLRCPLGDRLNVEVDAAPTVDLNQVLNETRSQ, SEQ ID NO: 3672

NTLRSPLGDRLNVEVDAAPTVDLNQVLNETRSQ, SEQ ID NO: 3673

NTLRCQLGDRLNVEVDTAPTVDLNQVLNETRSQ, SEQ ID NO: 3674

NTLRSQLGDRLNVEVDTAPTVDLNQVLNETRSQ, SEQ ID NO: 3675

NTLRCPLGDRLNVEVDTAPTVDLNQVLNETRSQ, SEQ ID NO: 3676

NTLRSPLGDRLNVEVDTAPTVDLNQVLNETRSQ, SEQ ID NO: 3677

NTLRCQLGDRLNVEVDAAPTVDLNRVLNETRSQ, SEQ ID NO: 3678

NTLRSQLGDRLNVEVDAAPTVDLNRVLNETRSQ, SEQ ID NO: 3679

NTLRCPLGDRLNVEVDAAPTVDLNRVLNETRSQ, SEQ ID NO: 3680

NTLRSPLGDRLNVEVDAAPTVDLNRVLNETRSQ, SEQ ID NO: 3681

NTLRCQLGDRLNVEVDTAPTVDLNRVLNETRSQ, SEQ ID NO: 3682

NTLRSQLGDRLNVEVDTAPTVDLNRVLNETRSQ, SEQ ID NO: 3683

NTLRCPLGDRLNVEVDTAPTVDLNRVLNETRSQ, SEQ ID NO: 3684

NTLRSPLGDRLNVEVDTAPTVDLNRVLNETRSQ, SEQ ID NO: 3685

NTLRCQLGDRLNVEVDAAPTVDLNQVLNETRNQ, SEQ ID NO: 3686

NTLRSQLGDRLNVEVDAAPTVDLNQVLNETRNQ, SEQ ID NO: 3687

NTLRCPLGDRLNVEVDAAPTVDLNQVLNETRNQ, SEQ ID NO: 3688

NTLRSPLGDRLNVEVDAAPTVDLNQVLNETRNQ, SEQ ID NO: 3689

NTLRCQLGDRLNVEVDTAPTVDLNQVLNETRNQ, SEQ ID NO: 3690

NTLRSQLGDRLNVEVDTAPTVDLNQVLNETRNQ, SEQ ID NO: 3691

NTLRCPLGDRLNVEVDTAPTVDLNQVLNETRNQ, SEQ ID NO: 3692

NTLRSPLGDRLNVEVDTAPTVDLNQVLNETRNQ, SEQ ID NO: 3693

NTLRCQLGDRLNVEVDAAPTVDLNRVLNETRNQ, SEQ ID NO: 3694

NTLRSQLGDRLNVEVDAAPTVDLNRVLNETRNQ, SEQ ID NO: 3695

NTLRCPLGDRLNVEVDAAPTVDLNRVLNETRNQ, SEQ ID NO: 3696

NTLRSPLGDRLNVEVDAAPTVDLNRVLNETRNQ, SEQ ID NO: 3697

NTLRCQLGDRLNVEVDTAPTVDLNRVLNETRNQ, SEQ ID NO: 3698

NTLRSQLGDRLNVEVDTAPTVDLNRVLNETRNQ, SEQ ID NO: 3699

NTLRCPLGDRLNVEVDTAPTVDLNRVLNETRNQ, SEQ ID NO: 3700

NTLRSPLGDRLNVEVDTAPTVDLNRVLNETRNQ, SEQ ID NO: 3701

TLRCQLGDRLNVEVDAAPTVDLNQVLNETRSQY, SEQ ID NO: 3702

TLRSQLGDRLNVEVDAAPTVDLNQVLNETRSQY, SEQ ID NO: 3703

TLRCPLGDRLNVEVDAAPTVDLNQVLNETRSQY, SEQ ID NO: 3704

TLRSPLGDRLNVEVDAAPTVDLNQVLNETRSQY, SEQ ID NO: 3705

TLRCQLGDRLNVEVDTAPTVDLNQVLNETRSQY, SEQ ID NO: 3706

TLRSQLGDRLNVEVDTAPTVDLNQVLNETRSQY, SEQ ID NO: 3707

TLRCPLGDRLNVEVDTAPTVDLNQVLNETRSQY, SEQ ID NO: 3708

TLRSPLGDRLNVEVDTAPTVDLNQVLNETRSQY, SEQ ID NO: 3709

TLRCQLGDRLNVEVDAAPTVDLNRVLNETRSQY, SEQ ID NO: 3710

TLRSQLGDRLNVEVDAAPTVDLNRVLNETRSQY, SEQ ID NO: 3711

```
                                       SEQ ID NO: 3712
TLRCPLGDRLNVEVDAAPTVDLNRVLNETRSQY,

SEQ ID NO: 3713
TLRSPLGDRLNVEVDAAPTVDLNRVLNETRSQY,

SEQ ID NO: 3714
TLRCQLGDRLNVEVDTAPTVDLNRVLNETRSQY,

SEQ ID NO: 3715
TLRSQLGDRLNVEVDTAPTVDLNRVLNETRSQY,

SEQ ID NO: 3716
TLRCPLGDRLNVEVDTAPTVDLNRVLNETRSQY,

SEQ ID NO: 3717
TLRSPLGDRLNVEVDTAPTVDLNRVLNETRSQY,

SEQ ID NO: 3718
TLRCQLGDRLNVEVDAAPTVDLNQVLNETRNQY,

SEQ ID NO: 3719
TLRSQLGDRLNVEVDAAPTVDLNQVLNETRNQY,

SEQ ID NO: 3720
TLRCPLGDRLNVEVDAAPTVDLNQVLNETRNQY,

SEQ ID NO: 3721
TLRSPLGDRLNVEVDAAPTVDLNQVLNETRNQY,

SEQ ID NO: 3722
TLRCQLGDRLNVEVDTAPTVDLNQVLNETRNQY,

SEQ ID NO: 3723
TLRSQLGDRLNVEVDTAPTVDLNQVLNETRNQY,

SEQ ID NO: 3724
TLRCPLGDRLNVEVDTAPTVDLNQVLNETRNQY,

SEQ ID NO: 3725
TLRSPLGDRLNVEVDTAPTVDLNQVLNETRNQY,

SEQ ID NO: 3726
TLRCQLGDRLNVEVDAAPTVDLNRVLNETRNQY,

SEQ ID NO: 3727
TLRSQLGDRLNVEVDAAPTVDLNRVLNETRNQY,

SEQ ID NO: 3728
TLRCPLGDRLNVEVDAAPTVDLNRVLNETRNQY,

SEQ ID NO: 3729
TLRSPLGDRLNVEVDAAPTVDLNRVLNETRNQY,

SEQ ID NO: 3730
TLRCQLGDRLNVEVDTAPTVDLNRVLNETRNQY,

SEQ ID NO: 3731
TLRSQLGDRLNVEVDTAPTVDLNRVLNETRNQY,

SEQ ID NO: 3732
TLRCPLGDRLNVEVDTAPTVDLNRVLNETRNQY,

SEQ ID NO: 3733
TLRSPLGDRLNVEVDTAPTVDLNRVLNETRNQY,

SEQ ID NO: 3734
LRCQLGDRLNVEVDAAPTVDLNQVLNETRSQYE,

SEQ ID NO: 3735
LRSQLGDRLNVEVDAAPTVDLNQVLNETRSQYE,

SEQ ID NO: 3736
LRCPLGDRLNVEVDAAPTVDLNQVLNETRSQYE,

SEQ ID NO: 3737
LRSPLGDRLNVEVDAAPTVDLNQVLNETRSQYE,

SEQ ID NO: 3738
LRCQLGDRLNVEVDTAPTVDLNQVLNETRSQYE,

SEQ ID NO: 3739
LRSQLGDRLNVEVDTAPTVDLNQVLNETRSQYE,

SEQ ID NO: 3740
LRCPLGDRLNVEVDTAPTVDLNQVLNETRSQYE,

SEQ ID NO: 3741
LRSPLGDRLNVEVDTAPTVDLNQVLNETRSQYE,

SEQ ID NO: 3742
LRCQLGDRLNVEVDAAPTVDLNRVLNETRSQYE,

SEQ ID NO: 3743
LRSQLGDRLNVEVDAAPTVDLNRVLNETRSQYE,

SEQ ID NO: 3744
LRCPLGDRLNVEVDAAPTVDLNRVLNETRSQYE,

SEQ ID NO: 3745
LRSPLGDRLNVEVDAAPTVDLNRVLNETRSQYE,

SEQ ID NO: 3746
LRCQLGDRLNVEVDTAPTVDLNRVLNETRSQYE,

SEQ ID NO: 3747
LRSQLGDRLNVEVDTAPTVDLNRVLNETRSQYE,

SEQ ID NO: 3748
LRCPLGDRLNVEVDTAPTVDLNRVLNETRSQYE,

SEQ ID NO: 3749
LRSPLGDRLNVEVDTAPTVDLNRVLNETRSQYE,

SEQ ID NO: 3750
LRCQLGDRLNVEVDAAPTVDLNQVLNETRNQYE,

SEQ ID NO: 3751
LRSQLGDRLNVEVDAAPTVDLNQVLNETRNQYE,

SEQ ID NO: 3752
LRCPLGDRLNVEVDAAPTVDLNQVLNETRNQYE,

SEQ ID NO: 3753
LRSPLGDRLNVEVDAAPTVDLNQVLNETRNQYE,

SEQ ID NO: 3754
LRCQLGDRLNVEVDTAPTVDLNQVLNETRNQYE,

SEQ ID NO: 3755
LRSQLGDRLNVEVDTAPTVDLNQVLNETRNQYE,

SEQ ID NO: 3756
LRCPLGDRLNVEVDTAPTVDLNQVLNETRNQYE,

SEQ ID NO: 3757
LRSPLGDRLNVEVDTAPTVDLNQVLNETRNQYE,

SEQ ID NO: 3758
LRCQLGDRLNVEVDAAPTVDLNRVLNETRNQYE,

SEQ ID NO: 3759
LRSQLGDRLNVEVDAAPTVDLNRVLNETRNQYE,

SEQ ID NO: 3760
LRCPLGDRLNVEVDAAPTVDLNRVLNETRNQYE,

SEQ ID NO: 3761
LRSPLGDRLNVEVDAAPTVDLNRVLNETRNQYE,

SEQ ID NO: 3762
LRCQLGDRLNVEVDTAPTVDLNRVLNETRNQYE,

SEQ ID NO: 3763
LRSQLGDRLNVEVDTAPTVDLNRVLNETRNQYE,

SEQ ID NO: 3764
LRCPLGDRLNVEVDTAPTVDLNRVLNETRNQYE,

SEQ ID NO: 3765
LRSPLGDRLNVEVDTAPTVDLNRVLNETRNQYE,
```

RCQLGDRLNVEVDAAPTVDLNQVLNETRSQYEA, SEQ ID NO: 3766

RSQLGDRLNVEVDAAPTVDLNQVLNETRSQYEA, SEQ ID NO: 3767

RCPLGDRLNVEVDAAPTVDLNQVLNETRSQYEA, SEQ ID NO: 3768

RSPLGDRLNVEVDAAPTVDLNQVLNETRSQYEA, SEQ ID NO: 3769

RCQLGDRLNVEVDTAPTVDLNQVLNETRSQYEA, SEQ ID NO: 3770

RSQLGDRLNVEVDTAPTVDLNQVLNETRSQYEA, SEQ ID NO: 3771

RCPLGDRLNVEVDTAPTVDLNQVLNETRSQYEA, SEQ ID NO: 3772

RSPLGDRLNVEVDTAPTVDLNQVLNETRSQYEA, SEQ ID NO: 3773

RCQLGDRLNVEVDAAPTVDLNRVLNETRSQYEA, SEQ ID NO: 3774

RSQLGDRLNVEVDAAPTVDLNRVLNETRSQYEA, SEQ ID NO: 3775

RCPLGDRLNVEVDAAPTVDLNRVLNETRSQYEA, SEQ ID NO: 3776

RSPLGDRLNVEVDAAPTVDLNRVLNETRSQYEA, SEQ ID NO: 3777

RCQLGDRLNVEVDTAPTVDLNRVLNETRSQYEA, SEQ ID NO: 3778

RSQLGDRLNVEVDTAPTVDLNRVLNETRSQYEA, SEQ ID NO: 3779

RCPLGDRLNVEVDTAPTVDLNRVLNETRSQYEA, SEQ ID NO: 3780

RSPLGDRLNVEVDTAPTVDLNRVLNETRSQYEA, SEQ ID NO: 3781

RCQLGDRLNVEVDAAPTVDLNQVLNETRNQYEA, SEQ ID NO: 3782

RSQLGDRLNVEVDAAPTVDLNQVLNETRNQYEA, SEQ ID NO: 3783

RCPLGDRLNVEVDAAPTVDLNQVLNETRNQYEA, SEQ ID NO: 3784

RSPLGDRLNVEVDAAPTVDLNQVLNETRNQYEA, SEQ ID NO: 3785

RCQLGDRLNVEVDTAPTVDLNQVLNETRNQYEA, SEQ ID NO: 3786

RSQLGDRLNVEVDTAPTVDLNQVLNETRNQYEA, SEQ ID NO: 3787

RCPLGDRLNVEVDTAPTVDLNQVLNETRNQYEA, SEQ ID NO: 3788

RSPLGDRLNVEVDTAPTVDLNQVLNETRNQYEA, SEQ ID NO: 3789

RCQLGDRLNVEVDAAPTVDLNRVLNETRNQYEA, SEQ ID NO: 3790

RSQLGDRLNVEVDAAPTVDLNRVLNETRNQYEA, SEQ ID NO: 3791

RCPLGDRLNVEVDAAPTVDLNRVLNETRNQYEA, SEQ ID NO: 3792

RSPLGDRLNVEVDAAPTVDLNRVLNETRNQYEA, SEQ ID NO: 3793

RCQLGDRLNVEVDTAPTVDLNRVLNETRNQYEA, SEQ ID NO: 3794

RSQLGDRLNVEVDTAPTVDLNRVLNETRNQYEA, SEQ ID NO: 3795

RCPLGDRLNVEVDTAPTVDLNRVLNETRNQYEA, SEQ ID NO: 3796

RSPLGDRLNVEVDTAPTVDLNRVLNETRNQYEA, SEQ ID NO: 3797

CQLGDRLNVEVDAAPTVDLNQVLNETRSQYEAL, SEQ ID NO: 3798

SQLGDRLNVEVDAAPTVDLNQVLNETRSQYEAL, SEQ ID NO: 3799

CPLGDRLNVEVDAAPTVDLNQVLNETRSQYEAL, SEQ ID NO: 3800

SPLGDRLNVEVDAAPTVDLNQVLNETRSQYEAL, SEQ ID NO: 3801

CQLGDRLNVEVDTAPTVDLNQVLNETRSQYEAL, SEQ ID NO: 3802

SQLGDRLNVEVDTAPTVDLNQVLNETRSQYEAL, SEQ ID NO: 3803

CPLGDRLNVEVDTAPTVDLNQVLNETRSQYEAL, SEQ ID NO: 3804

SPLGDRLNVEVDTAPTVDLNQVLNETRSQYEAL, SEQ ID NO: 3805

CQLGDRLNVEVDAAPTVDLNRVLNETRSQYEAL, SEQ ID NO: 3806

SQLGDRLNVEVDAAPTVDLNRVLNETRSQYEAL, SEQ ID NO: 3807

CPLGDRLNVEVDAAPTVDLNRVLNETRSQYEAL, SEQ ID NO: 3808

SPLGDRLNVEVDAAPTVDLNRVLNETRSQYEAL, SEQ ID NO: 3809

CQLGDRLNVEVDTAPTVDLNRVLNETRSQYEAL, SEQ ID NO: 3810

SQLGDRLNVEVDTAPTVDLNRVLNETRSQYEAL, SEQ ID NO: 3811

CPLGDRLNVEVDTAPTVDLNRVLNETRSQYEAL, SEQ ID NO: 3812

SPLGDRLNVEVDTAPTVDLNRVLNETRSQYEAL, SEQ ID NO: 3813

CQLGDRLNVEVDAAPTVDLNQVLNETRNQYEAL, SEQ ID NO: 3814

SQLGDRLNVEVDAAPTVDLNQVLNETRNQYEAL, SEQ ID NO: 3815

CPLGDRLNVEVDAAPTVDLNQVLNETRNQYEAL, SEQ ID NO: 3816

SPLGDRLNVEVDAAPTVDLNQVLNETRNQYEAL, SEQ ID NO: 3817

CQLGDRLNVEVDTAPTVDLNQVLNETRNQYEAL, SEQ ID NO: 3818

SQLGDRLNVEVDTAPTVDLNQVLNETRNQYEAL, SEQ ID NO: 3819

```
                                              SEQ ID NO: 3820
CPLGDRLNVEVDTAPTVDLNQVLNETRNQYEAL,

SEQ ID NO: 3821
SPLGDRLNVEVDTAPTVDLNQVLNETRNQYEAL,

SEQ ID NO: 3822
CQLGDRLNVEVDAAPTVDLNRVLNETRNQYEAL,

SEQ ID NO: 3823
SQLGDRLNVEVDAAPTVDLNRVLNETRNQYEAL,

SEQ ID NO: 3824
CPLGDRLNVEVDAAPTVDLNRVLNETRNQYEAL,

SEQ ID NO: 3825
SPLGDRLNVEVDAAPTVDLNRVLNETRNQYEAL,

SEQ ID NO: 3826
CQLGDRLNVEVDTAPTVDLNRVLNETRNQYEAL,

SEQ ID NO: 3827
SQLGDRLNVEVDTAPTVDLNRVLNETRNQYEAL,

SEQ ID NO: 3828
CPLGDRLNVEVDTAPTVDLNRVLNETRNQYEAL,

SEQ ID NO: 3829
SPLGDRLNVEVDTAPTVDLNRVLNETRNQYEAL,

SEQ ID NO: 3830
EVNTLRCQLGDRLNVEVDAAPTVDLNQVLNETRS,

SEQ ID NO: 3831
EVNTLRSQLGDRLNVEVDAAPTVDLNQVLNETRS,

SEQ ID NO: 3832
EVNTLRCPLGDRLNVEVDAAPTVDLNQVLNETRS,

SEQ ID NO: 3833
EVNTLRSPLGDRLNVEVDAAPTVDLNQVLNETRS,

SEQ ID NO: 3834
EVNTLRCQLGDRLNVEVDTAPTVDLNQVLNETRS,

SEQ ID NO: 3835
EVNTLRSQLGDRLNVEVDTAPTVDLNQVLNETRS,

SEQ ID NO: 3836
EVNTLRCPLGDRLNVEVDTAPTVDLNQVLNETRS,

SEQ ID NO: 3837
EVNTLRSPLGDRLNVEVDTAPTVDLNQVLNETRS,

SEQ ID NO: 3838
EVNTLRCQLGDRLNVEVDAAPTVDLNRVLNETRS,

SEQ ID NO: 3839
EVNTLRSQLGDRLNVEVDAAPTVDLNRVLNETRS,

SEQ ID NO: 3840
EVNTLRCPLGDRLNVEVDAAPTVDLNRVLNETRS,

SEQ ID NO: 3841
EVNTLRSPLGDRLNVEVDAAPTVDLNRVLNETRS,

SEQ ID NO: 3842
EVNTLRCQLGDRLNVEVDTAPTVDLNRVLNETRS,

SEQ ID NO: 3843
EVNTLRSQLGDRLNVEVDTAPTVDLNRVLNETRS,

SEQ ID NO: 3844
EVNTLRCPLGDRLNVEVDTAPTVDLNRVLNETRS,

SEQ ID NO: 3845
EVNTLRSPLGDRLNVEVDTAPTVDLNRVLNETRS,

SEQ ID NO: 3846
EVNTLRCQLGDRLNVEVDAAPTVDLNQVLNETRN,

SEQ ID NO: 3847
EVNTLRSQLGDRLNVEVDAAPTVDLNQVLNETRN,

SEQ ID NO: 3848
EVNTLRCPLGDRLNVEVDAAPTVDLNQVLNETRN,

SEQ ID NO: 3849
EVNTLRSPLGDRLNVEVDAAPTVDLNQVLNETRN,

SEQ ID NO: 3850
EVNTLRCQLGDRLNVEVDTAPTVDLNQVLNETRN,

SEQ ID NO: 3851
EVNTLRSQLGDRLNVEVDTAPTVDLNQVLNETRN,

SEQ ID NO: 3852
EVNTLRCPLGDRLNVEVDTAPTVDLNQVLNETRN,

SEQ ID NO: 3853
EVNTLRSPLGDRLNVEVDTAPTVDLNQVLNETRN,

SEQ ID NO: 3854
EVNTLRCQLGDRLNVEVDAAPTVDLNRVLNETRN,

SEQ ID NO: 3855
EVNTLRSQLGDRLNVEVDAAPTVDLNRVLNETRN,

SEQ ID NO: 3856
EVNTLRCPLGDRLNVEVDAAPTVDLNRVLNETRN,

SEQ ID NO: 3857
EVNTLRSPLGDRLNVEVDAAPTVDLNRVLNETRN,

SEQ ID NO: 3858
EVNTLRCQLGDRLNVEVDTAPTVDLNRVLNETRN,

SEQ ID NO: 3859
EVNTLRSQLGDRLNVEVDTAPTVDLNRVLNETRN,

SEQ ID NO: 3860
EVNTLRCPLGDRLNVEVDTAPTVDLNRVLNETRN,

SEQ ID NO: 3861
EVNTLRSPLGDRLNVEVDTAPTVDLNRVLNETRN,

SEQ ID NO: 3862
VNTLRCQLGDRLNVEVDAAPTVDLNQVLNETRSQ,

SEQ ID NO: 3863
VNTLRSQLGDRLNVEVDAAPTVDLNQVLNETRSQ,

SEQ ID NO: 3864
VNTLRCPLGDRLNVEVDAAPTVDLNQVLNETRSQ,

SEQ ID NO: 3865
VNTLRSPLGDRLNVEVDAAPTVDLNQVLNETRSQ,

SEQ ID NO: 3866
VNTLRCQLGDRLNVEVDTAPTVDLNQVLNETRSQ,

SEQ ID NO: 3867
VNTLRSQLGDRLNVEVDTAPTVDLNQVLNETRSQ,

SEQ ID NO: 3868
VNTLRCPLGDRLNVEVDTAPTVDLNQVLNETRSQ,

SEQ ID NO: 3869
VNTLRSPLGDRLNVEVDTAPTVDLNQVLNETRSQ,

SEQ ID NO: 3870
VNTLRCQLGDRLNVEVDAAPTVDLNRVLNETRSQ,

SEQ ID NO: 3871
VNTLRSQLGDRLNVEVDAAPTVDLNRVLNETRSQ,

SEQ ID NO: 3872
VNTLRCPLGDRLNVEVDAAPTVDLNRVLNETRSQ,

SEQ ID NO: 3873
VNTLRSPLGDRLNVEVDAAPTVDLNRVLNETRSQ,
```

VNTLRCQLGDRLNVEVDTAPTVDLNRVLNETRSQ, SEQ ID NO: 3874

VNTLRSQLGDRLNVEVDTAPTVDLNRVLNETRSQ, SEQ ID NO: 3875

VNTLRCPLGDRLNVEVDTAPTVDLNRVLNETRSQ, SEQ ID NO: 3876

VNTLRSPLGDRLNVEVDTAPTVDLNRVLNETRSQ, SEQ ID NO: 3877

VNTLRCQLGDRLNVEVDAAPTVDLNQVLNETRNQ, SEQ ID NO: 3878

VNTLRSQLGDRLNVEVDAAPTVDLNQVLNETRNQ, SEQ ID NO: 3879

VNTLRCPLGDRLNVEVDAAPTVDLNQVLNETRNQ, SEQ ID NO: 3880

VNTLRSPLGDRLNVEVDAAPTVDLNQVLNETRNQ, SEQ ID NO: 3881

VNTLRCQLGDRLNVEVDTAPTVDLNQVLNETRNQ, SEQ ID NO: 3882

VNTLRSQLGDRLNVEVDTAPTVDLNQVLNETRNQ, SEQ ID NO: 3883

VNTLRCPLGDRLNVEVDTAPTVDLNQVLNETRNQ, SEQ ID NO: 3884

VNTLRSPLGDRLNVEVDTAPTVDLNQVLNETRNQ, SEQ ID NO: 3885

VNTLRCQLGDRLNVEVDAAPTVDLNRVLNETRNQ, SEQ ID NO: 3886

VNTLRSQLGDRLNVEVDAAPTVDLNRVLNETRNQ, SEQ ID NO: 3887

VNTLRCPLGDRLNVEVDAAPTVDLNRVLNETRNQ, SEQ ID NO: 3888

VNTLRSPLGDRLNVEVDAAPTVDLNRVLNETRNQ, SEQ ID NO: 3889

VNTLRCQLGDRLNVEVDTAPTVDLNRVLNETRNQ, SEQ ID NO: 3890

VNTLRSQLGDRLNVEVDTAPTVDLNRVLNETRNQ, SEQ ID NO: 3891

VNTLRCPLGDRLNVEVDTAPTVDLNRVLNETRNQ, SEQ ID NO: 3892

VNTLRSPLGDRLNVEVDTAPTVDLNRVLNETRNQ, SEQ ID NO: 3893

NTLRCQLGDRLNVEVDAAPTVDLNQVLNETRSQY, SEQ ID NO: 3894

NTLRSQLGDRLNVEVDAAPTVDLNQVLNETRSQY, SEQ ID NO: 3895

NTLRCPLGDRLNVEVDAAPTVDLNQVLNETRSQY, SEQ ID NO: 3896

NTLRSPLGDRLNVEVDAAPTVDLNQVLNETRSQY, SEQ ID NO: 3897

NTLRCQLGDRLNVEVDTAPTVDLNQVLNETRSQY, SEQ ID NO: 3898

NTLRSQLGDRLNVEVDTAPTVDLNQVLNETRSQY, SEQ ID NO: 3899

NTLRCPLGDRLNVEVDTAPTVDLNQVLNETRSQY, SEQ ID NO: 3900

NTLRSPLGDRLNVEVDTAPTVDLNQVLNETRSQY, SEQ ID NO: 3901

NTLRCQLGDRLNVEVDAAPTVDLNRVLNETRSQY, SEQ ID NO: 3902

NTLRSQLGDRLNVEVDAAPTVDLNRVLNETRSQY, SEQ ID NO: 3903

NTLRCPLGDRLNVEVDAAPTVDLNRVLNETRSQY, SEQ ID NO: 3904

NTLRSPLGDRLNVEVDAAPTVDLNRVLNETRSQY, SEQ ID NO: 3905

NTLRCQLGDRLNVEVDTAPTVDLNRVLNETRSQY, SEQ ID NO: 3906

NTLRSQLGDRLNVEVDTAPTVDLNRVLNETRSQY, SEQ ID NO: 3907

NTLRCPLGDRLNVEVDTAPTVDLNRVLNETRSQY, SEQ ID NO: 3908

NTLRSPLGDRLNVEVDTAPTVDLNRVLNETRSQY, SEQ ID NO: 3909

NTLRCQLGDRLNVEVDAAPTVDLNQVLNETRNQY, SEQ ID NO: 3910

NTLRSQLGDRLNVEVDAAPTVDLNQVLNETRNQY, SEQ ID NO: 3911

NTLRCPLGDRLNVEVDAAPTVDLNQVLNETRNQY, SEQ ID NO: 3912

NTLRSPLGDRLNVEVDAAPTVDLNQVLNETRNQY, SEQ ID NO: 3913

NTLRCQLGDRLNVEVDTAPTVDLNQVLNETRNQY, SEQ ID NO: 3914

NTLRSQLGDRLNVEVDTAPTVDLNQVLNETRNQY, SEQ ID NO: 3915

NTLRCPLGDRLNVEVDTAPTVDLNQVLNETRNQY, SEQ ID NO: 3916

NTLRSPLGDRLNVEVDTAPTVDLNQVLNETRNQY, SEQ ID NO: 3917

NTLRCQLGDRLNVEVDAAPTVDLNRVLNETRNQY, SEQ ID NO: 3918

NTLRSQLGDRLNVEVDAAPTVDLNRVLNETRNQY, SEQ ID NO: 3919

NTLRCPLGDRLNVEVDAAPTVDLNRVLNETRNQY, SEQ ID NO: 3920

NTLRSPLGDRLNVEVDAAPTVDLNRVLNETRNQY, SEQ ID NO: 3921

NTLRCQLGDRLNVEVDTAPTVDLNRVLNETRNQY, SEQ ID NO: 3922

NTLRSQLGDRLNVEVDTAPTVDLNRVLNETRNQY, SEQ ID NO: 3923

NTLRCPLGDRLNVEVDTAPTVDLNRVLNETRNQY, SEQ ID NO: 3924

NTLRSPLGDRLNVEVDTAPTVDLNRVLNETRNQY, SEQ ID NO: 3925

TLRCQLGDRLNVEVDAAPTVDLNQVLNETRSQYE, SEQ ID NO: 3926

TLRSQLGDRLNVEVDAAPTVDLNQVLNETRSQYE, SEQ ID NO: 3927

SEQ ID NO: 3928
TLRCPLGDRLNVEVDAAPTVDLNQVLNETRSQYE,

SEQ ID NO: 3929
TLRSPLGDRLNVEVDAAPTVDLNQVLNETRSQYE,

SEQ ID NO: 3930
TLRCQLGDRLNVEVDTAPTVDLNQVLNETRSQYE,

SEQ ID NO: 3931
TLRSQLGDRLNVEVDTAPTVDLNQVLNETRSQYE,

SEQ ID NO: 3932
TLRCPLGDRLNVEVDTAPTVDLNQVLNETRSQYE,

SEQ ID NO: 3933
TLRSPLGDRLNVEVDTAPTVDLNQVLNETRSQYE,

SEQ ID NO: 3934
TLRCQLGDRLNVEVDAAPTVDLNRVLNETRSQYE,

SEQ ID NO: 3935
TLRSQLGDRLNVEVDAAPTVDLNRVLNETRSQYE,

SEQ ID NO: 3936
TLRCPLGDRLNVEVDAAPTVDLNRVLNETRSQYE,

SEQ ID NO: 3937
TLRSPLGDRLNVEVDAAPTVDLNRVLNETRSQYE,

SEQ ID NO: 3938
TLRCQLGDRLNVEVDTAPTVDLNRVLNETRSQYE,

SEQ ID NO: 3939
TLRSQLGDRLNVEVDTAPTVDLNRVLNETRSQYE,

SEQ ID NO: 3940
TLRCPLGDRLNVEVDTAPTVDLNRVLNETRSQYE,

SEQ ID NO: 3941
TLRSPLGDRLNVEVDTAPTVDLNRVLNETRSQYE,

SEQ ID NO: 3942
TLRCQLGDRLNVEVDAAPTVDLNQVLNETRNQYE,

SEQ ID NO: 3943
TLRSQLGDRLNVEVDAAPTVDLNQVLNETRNQYE,

SEQ ID NO: 3944
TLRCPLGDRLNVEVDAAPTVDLNQVLNETRNQYE,

SEQ ID NO: 3945
TLRSPLGDRLNVEVDAAPTVDLNQVLNETRNQYE,

SEQ ID NO: 3946
TLRCQLGDRLNVEVDTAPTVDLNQVLNETRNQYE,

SEQ ID NO: 3947
TLRSQLGDRLNVEVDTAPTVDLNQVLNETRNQYE,

SEQ ID NO: 3948
TLRCPLGDRLNVEVDTAPTVDLNQVLNETRNQYE,

SEQ ID NO: 3949
TLRSPLGDRLNVEVDTAPTVDLNQVLNETRNQYE,

SEQ ID NO: 3950
TLRCQLGDRLNVEVDAAPTVDLNRVLNETRNQYE,

SEQ ID NO: 3951
TLRSQLGDRLNVEVDAAPTVDLNRVLNETRNQYE,

SEQ ID NO: 3952
TLRCPLGDRLNVEVDAAPTVDLNRVLNETRNQYE,

SEQ ID NO: 3953
TLRSPLGDRLNVEVDAAPTVDLNRVLNETRNQYE,

SEQ ID NO: 3954
TLRCQLGDRLNVEVDTAPTVDLNRVLNETRNQYE,

SEQ ID NO: 3955
TLRSQLGDRLNVEVDTAPTVDLNRVLNETRNQYE,

SEQ ID NO: 3956
TLRCPLGDRLNVEVDTAPTVDLNRVLNETRNQYE,

SEQ ID NO: 3957
TLRSPLGDRLNVEVDTAPTVDLNRVLNETRNQYE,

SEQ ID NO: 3958
LRCQLGDRLNVEVDAAPTVDLNQVLNETRSQYEA,

SEQ ID NO: 3959
LRSQLGDRLNVEVDAAPTVDLNQVLNETRSQYEA,

SEQ ID NO: 3960
LRCPLGDRLNVEVDAAPTVDLNQVLNETRSQYEA,

SEQ ID NO: 3961
LRSPLGDRLNVEVDAAPTVDLNQVLNETRSQYEA,

SEQ ID NO: 3962
LRCQLGDRLNVEVDTAPTVDLNQVLNETRSQYEA,

SEQ ID NO: 3963
LRSQLGDRLNVEVDTAPTVDLNQVLNETRSQYEA,

SEQ ID NO: 3964
LRCPLGDRLNVEVDTAPTVDLNQVLNETRSQYEA,

SEQ ID NO: 3965
LRSPLGDRLNVEVDTAPTVDLNQVLNETRSQYEA,

SEQ ID NO: 3966
LRCQLGDRLNVEVDAAPTVDLNRVLNETRSQYEA,

SEQ ID NO: 3967
LRSQLGDRLNVEVDAAPTVDLNRVLNETRSQYEA,

SEQ ID NO: 3968
LRCPLGDRLNVEVDAAPTVDLNRVLNETRSQYEA,

SEQ ID NO: 3969
LRSPLGDRLNVEVDAAPTVDLNRVLNETRSQYEA,

SEQ ID NO: 3970
LRCQLGDRLNVEVDTAPTVDLNRVLNETRSQYEA,

SEQ ID NO: 3971
LRSQLGDRLNVEVDTAPTVDLNRVLNETRSQYEA,

SEQ ID NO: 3972
LRCPLGDRLNVEVDTAPTVDLNRVLNETRSQYEA,

SEQ ID NO: 3973
LRSPLGDRLNVEVDTAPTVDLNRVLNETRSQYEA,

SEQ ID NO: 3974
LRCQLGDRLNVEVDAAPTVDLNQVLNETRNQYEA,

SEQ ID NO: 3975
LRSQLGDRLNVEVDAAPTVDLNQVLNETRNQYEA,

SEQ ID NO: 3976
LRCPLGDRLNVEVDAAPTVDLNQVLNETRNQYEA,

SEQ ID NO: 3977
LRSPLGDRLNVEVDAAPTVDLNQVLNETRNQYEA,

SEQ ID NO: 3978
LRCQLGDRLNVEVDTAPTVDLNQVLNETRNQYEA,

SEQ ID NO: 3979
LRSQLGDRLNVEVDTAPTVDLNQVLNETRNQYEA,

SEQ ID NO: 3980
LRCPLGDRLNVEVDTAPTVDLNQVLNETRNQYEA,

SEQ ID NO: 3981
LRSPLGDRLNVEVDTAPTVDLNQVLNETRNQYEA,

SEQ ID NO: 3982
LRCQLGDRLNVEVDAAPTVDLNRVLNETRNQYEA,

SEQ ID NO: 3983
LRSQLGDRLNVEVDAAPTVDLNRVLNETRNQYEA,

SEQ ID NO: 3984
LRCPLGDRLNVEVDAAPTVDLNRVLNETRNQYEA,

SEQ ID NO: 3985
LRSPLGDRLNVEVDAAPTVDLNRVLNETRNQYEA,

SEQ ID NO: 3986
LRCQLGDRLNVEVDTAPTVDLNRVLNETRNQYEA,

SEQ ID NO: 3987
LRSQLGDRLNVEVDTAPTVDLNRVLNETRNQYEA,

SEQ ID NO: 3988
LRCPLGDRLNVEVDTAPTVDLNRVLNETRNQYEA,

SEQ ID NO: 3989
LRSPLGDRLNVEVDTAPTVDLNRVLNETRNQYEA,

SEQ ID NO: 3990
RCQLGDRLNVEVDAAPTVDLNQVLNETRSQYEAL,

SEQ ID NO: 3991
RSQLGDRLNVEVDAAPTVDLNQVLNETRSQYEAL,

SEQ ID NO: 3992
RCPLGDRLNVEVDAAPTVDLNQVLNETRSQYEAL,

SEQ ID NO: 3993
RSPLGDRLNVEVDAAPTVDLNQVLNETRSQYEAL,

SEQ ID NO: 3994
RCQLGDRLNVEVDTAPTVDLNQVLNETRSQYEAL,

SEQ ID NO: 3995
RSQLGDRLNVEVDTAPTVDLNQVLNETRSQYEAL,

SEQ ID NO: 3996
RCPLGDRLNVEVDTAPTVDLNQVLNETRSQYEAL,

SEQ ID NO: 3997
RSPLGDRLNVEVDTAPTVDLNQVLNETRSQYEAL,

SEQ ID NO: 3998
RCQLGDRLNVEVDAAPTVDLNRVLNETRSQYEAL,

SEQ ID NO: 3999
RSQLGDRLNVEVDAAPTVDLNRVLNETRSQYEAL,

SEQ ID NO: 4000
RCPLGDRLNVEVDAAPTVDLNRVLNETRSQYEAL,

SEQ ID NO: 4001
RSPLGDRLNVEVDAAPTVDLNRVLNETRSQYEAL,

SEQ ID NO: 4002
RCQLGDRLNVEVDTAPTVDLNRVLNETRSQYEAL,

SEQ ID NO: 4003
RSQLGDRLNVEVDTAPTVDLNRVLNETRSQYEAL,

SEQ ID NO: 4004
RCPLGDRLNVEVDTAPTVDLNRVLNETRSQYEAL,

SEQ ID NO: 4005
RSPLGDRLNVEVDTAPTVDLNRVLNETRSQYEAL,

SEQ ID NO: 4006
RCQLGDRLNVEVDAAPTVDLNQVLNETRNQYEAL,

SEQ ID NO: 4007
RSQLGDRLNVEVDAAPTVDLNQVLNETRNQYEAL,

SEQ ID NO: 4008
RCPLGDRLNVEVDAAPTVDLNQVLNETRNQYEAL,

SEQ ID NO: 4009
RSPLGDRLNVEVDAAPTVDLNQVLNETRNQYEAL,

SEQ ID NO: 4010
RCQLGDRLNVEVDTAPTVDLNQVLNETRNQYEAL,

SEQ ID NO: 4011
RSQLGDRLNVEVDTAPTVDLNQVLNETRNQYEAL,

SEQ ID NO: 4012
RCPLGDRLNVEVDTAPTVDLNQVLNETRNQYEAL,

SEQ ID NO: 4013
RSPLGDRLNVEVDTAPTVDLNQVLNETRNQYEAL,

SEQ ID NO: 4014
RCQLGDRLNVEVDAAPTVDLNRVLNETRNQYEAL,

SEQ ID NO: 4015
RSQLGDRLNVEVDAAPTVDLNRVLNETRNQYEAL,

SEQ ID NO: 4016
RCPLGDRLNVEVDAAPTVDLNRVLNETRNQYEAL,

SEQ ID NO: 4017
RSPLGDRLNVEVDAAPTVDLNRVLNETRNQYEAL,

SEQ ID NO: 4018
RCQLGDRLNVEVDTAPTVDLNRVLNETRNQYEAL,

SEQ ID NO: 4019
RSQLGDRLNVEVDTAPTVDLNRVLNETRNQYEAL,

SEQ ID NO: 4020
RCPLGDRLNVEVDTAPTVDLNRVLNETRNQYEAL,

SEQ ID NO: 4021
RSPLGDRLNVEVDTAPTVDLNRVLNETRNQYEAL,

SEQ ID NO: 4022
EVNTLRCQLGDRLNVEVDAAPTVDLNQVLNETRSQ,

SEQ ID NO: 4023
EVNTLRSQLGDRLNVEVDAAPTVDLNQVLNETRSQ,

SEQ ID NO: 4024
EVNTLRCPLGDRLNVEVDAAPTVDLNQVLNETRSQ,

SEQ ID NO: 4025
EVNTLRSPLGDRLNVEVDAAPTVDLNQVLNETRSQ,

SEQ ID NO: 4026
EVNTLRCQLGDRLNVEVDTAPTVDLNQVLNETRSQ,

SEQ ID NO: 4027
EVNTLRSQLGDRLNVEVDTAPTVDLNQVLNETRSQ,

SEQ ID NO: 4028
EVNTLRCPLGDRLNVEVDTAPTVDLNQVLNETRSQ,

SEQ ID NO: 4029
EVNTLRSPLGDRLNVEVDTAPTVDLNQVLNETRSQ,

SEQ ID NO: 4030
EVNTLRCQLGDRLNVEVDAAPTVDLNRVLNETRSQ,

SEQ ID NO: 4031
EVNTLRSQLGDRLNVEVDAAPTVDLNRVLNETRSQ,

SEQ ID NO: 4032
EVNTLRCPLGDRLNVEVDAAPTVDLNRVLNETRSQ,

SEQ ID NO: 4033
EVNTLRSPLGDRLNVEVDAAPTVDLNRVLNETRSQ,

SEQ ID NO: 4034
EVNTLRCQLGDRLNVEVDTAPTVDLNRVLNETRSQ,

SEQ ID NO: 4035
EVNTLRSQLGDRLNVEVDTAPTVDLNRVLNETRSQ,

SEQ ID NO: 4036
EVNTLRCPLGDRLNVEVDTAPTVDLNRVLNETRSQ,

SEQ ID NO: 4037
EVNTLRSPLGDRLNVEVDTAPTVDLNRVLNETRSQ,

SEQ ID NO: 4038
EVNTLRCQLGDRLNVEVDAAPTVDLNQVLNETRNQ,

SEQ ID NO: 4039
EVNTLRSQLGDRLNVEVDAAPTVDLNQVLNETRNQ,

SEQ ID NO: 4040
EVNTLRCPLGDRLNVEVDAAPTVDLNQVLNETRNQ,

SEQ ID NO: 4041
EVNTLRSPLGDRLNVEVDAAPTVDLNQVLNETRNQ,

SEQ ID NO: 4042
EVNTLRCQLGDRLNVEVDTAPTVDLNQVLNETRNQ,

SEQ ID NO: 4043
EVNTLRSQLGDRLNVEVDTAPTVDLNQVLNETRNQ,

SEQ ID NO: 4044
EVNTLRCPLGDRLNVEVDTAPTVDLNQVLNETRNQ,

SEQ ID NO: 4045
EVNTLRSPLGDRLNVEVDTAPTVDLNQVLNETRNQ,

SEQ ID NO: 4046
EVNTLRCQLGDRLNVEVDAAPTVDLNRVLNETRNQ,

SEQ ID NO: 4047
EVNTLRSQLGDRLNVEVDAAPTVDLNRVLNETRNQ,

SEQ ID NO: 4048
EVNTLRCPLGDRLNVEVDAAPTVDLNRVLNETRNQ,

SEQ ID NO: 4049
EVNTLRSPLGDRLNVEVDAAPTVDLNRVLNETRNQ,

SEQ ID NO: 4050
EVNTLRCQLGDRLNVEVDTAPTVDLNRVLNETRNQ,

SEQ ID NO: 4051
EVNTLRSQLGDRLNVEVDTAPTVDLNRVLNETRNQ,

SEQ ID NO: 4052
EVNTLRCPLGDRLNVEVDTAPTVDLNRVLNETRNQ,

SEQ ID NO: 4053
EVNTLRSPLGDRLNVEVDTAPTVDLNRVLNETRNQ,

SEQ ID NO: 4054
VNTLRCQLGDRLNVEVDAAPTVDLNQVLNETRSQY,

SEQ ID NO: 4055
VNTLRSQLGDRLNVEVDAAPTVDLNQVLNETRSQY,

SEQ ID NO: 4056
VNTLRCPLGDRLNVEVDAAPTVDLNQVLNETRSQY,

SEQ ID NO: 4057
VNTLRSPLGDRLNVEVDAAPTVDLNQVLNETRSQY,

SEQ ID NO: 4058
VNTLRCQLGDRLNVEVDTAPTVDLNQVLNETRSQY,

SEQ ID NO: 4059
VNTLRSQLGDRLNVEVDTAPTVDLNQVLNETRSQY,

SEQ ID NO: 4060
VNTLRCPLGDRLNVEVDTAPTVDLNQVLNETRSQY,

SEQ ID NO: 4061
VNTLRSPLGDRLNVEVDTAPTVDLNQVLNETRSQY,

SEQ ID NO: 4062
VNTLRCQLGDRLNVEVDAAPTVDLNRVLNETRSQY,

SEQ ID NO: 4063
VNTLRSQLGDRLNVEVDAAPTVDLNRVLNETRSQY,

SEQ ID NO: 4064
VNTLRCPLGDRLNVEVDAAPTVDLNRVLNETRSQY,

SEQ ID NO: 4065
VNTLRSPLGDRLNVEVDAAPTVDLNRVLNETRSQY,

SEQ ID NO: 4066
VNTLRCQLGDRLNVEVDTAPTVDLNRVLNETRSQY,

SEQ ID NO: 4067
VNTLRSQLGDRLNVEVDTAPTVDLNRVLNETRSQY,

SEQ ID NO: 4068
VNTLRCPLGDRLNVEVDTAPTVDLNRVLNETRSQY,

SEQ ID NO: 4069
VNTLRSPLGDRLNVEVDTAPTVDLNRVLNETRSQY,

SEQ ID NO: 4070
VNTLRCQLGDRLNVEVDAAPTVDLNQVLNETRNQY,

SEQ ID NO: 4071
VNTLRSQLGDRLNVEVDAAPTVDLNQVLNETRNQY,

SEQ ID NO: 4072
VNTLRCPLGDRLNVEVDAAPTVDLNQVLNETRNQY,

SEQ ID NO: 4073
VNTLRSPLGDRLNVEVDAAPTVDLNQVLNETRNQY,

SEQ ID NO: 4074
VNTLRCQLGDRLNVEVDTAPTVDLNQVLNETRNQY,

SEQ ID NO: 4075
VNTLRSQLGDRLNVEVDTAPTVDLNQVLNETRNQY,

SEQ ID NO: 4076
VNTLRCPLGDRLNVEVDTAPTVDLNQVLNETRNQY,

SEQ ID NO: 4077
VNTLRSPLGDRLNVEVDTAPTVDLNQVLNETRNQY,

SEQ ID NO: 4078
VNTLRCQLGDRLNVEVDAAPTVDLNRVLNETRNQY,

SEQ ID NO: 4079
VNTLRSQLGDRLNVEVDAAPTVDLNRVLNETRNQY,

SEQ ID NO: 4080
VNTLRCPLGDRLNVEVDAAPTVDLNRVLNETRNQY,

SEQ ID NO: 4081
VNTLRSPLGDRLNVEVDAAPTVDLNRVLNETRNQY,

SEQ ID NO: 4082
VNTLRCQLGDRLNVEVDTAPTVDLNRVLNETRNQY,

SEQ ID NO: 4083
VNTLRSQLGDRLNVEVDTAPTVDLNRVLNETRNQY,

SEQ ID NO: 4084
VNTLRCPLGDRLNVEVDTAPTVDLNRVLNETRNQY,

SEQ ID NO: 4085
VNTLRSPLGDRLNVEVDTAPTVDLNRVLNETRNQY,

SEQ ID NO: 4086
NTLRCQLGDRLNVEVDAAPTVDLNQVLNETRSQYE,

SEQ ID NO: 4087
NTLRSQLGDRLNVEVDAAPTVDLNQVLNETRSQYE,

SEQ ID NO: 4088
NTLRCPLGDRLNVEVDAAPTVDLNQVLNETRSQYE,

SEQ ID NO: 4089
NTLRSPLGDRLNVEVDAAPTVDLNQVLNETRSQYE,

```
                                                SEQ ID NO: 4090
NTLRCQLGDRLNVEVDTAPTVDLNQVLNETRSQYE,

SEQ ID NO: 4091
NTLRSQLGDRLNVEVDTAPTVDLNQVLNETRSQYE,

SEQ ID NO: 4092
NTLRCPLGDRLNVEVDTAPTVDLNQVLNETRSQYE,

SEQ ID NO: 4093
NTLRSPLGDRLNVEVDTAPTVDLNQVLNETRSQYE,

SEQ ID NO: 4094
NTLRCQLGDRLNVEVDAAPTVDLNRVLNETRSQYE,

SEQ ID NO: 4095
NTLRSQLGDRLNVEVDAAPTVDLNRVLNETRSQYE,

SEQ ID NO: 4096
NTLRCPLGDRLNVEVDAAPTVDLNRVLNETRSQYE,

SEQ ID NO: 4097
NTLRSPLGDRLNVEVDAAPTVDLNRVLNETRSQYE,

SEQ ID NO: 4098
NTLRCQLGDRLNVEVDTAPTVDLNRVLNETRSQYE,

SEQ ID NO: 4099
NTLRSQLGDRLNVEVDTAPTVDLNRVLNETRSQYE,

SEQ ID NO: 4100
NTLRCPLGDRLNVEVDTAPTVDLNRVLNETRSQYE,

SEQ ID NO: 4101
NTLRSPLGDRLNVEVDTAPTVDLNRVLNETRSQYE,

SEQ ID NO: 4102
NTLRCQLGDRLNVEVDAAPTVDLNQVLNETRNQYE,

SEQ ID NO: 4103
NTLRSQLGDRLNVEVDAAPTVDLNQVLNETRNQYE,

SEQ ID NO: 4104
NTLRCPLGDRLNVEVDAAPTVDLNQVLNETRNQYE,

SEQ ID NO: 4105
NTLRSPLGDRLNVEVDAAPTVDLNQVLNETRNQYE,

SEQ ID NO: 4106
NTLRCQLGDRLNVEVDTAPTVDLNQVLNETRNQYE,

SEQ ID NO: 4107
NTLRSQLGDRLNVEVDTAPTVDLNQVLNETRNQYE,

SEQ ID NO: 4108
NTLRCPLGDRLNVEVDTAPTVDLNQVLNETRNQYE,

SEQ ID NO: 4109
NTLRSPLGDRLNVEVDTAPTVDLNQVLNETRNQYE,

SEQ ID NO: 4110
NTLRCQLGDRLNVEVDAAPTVDLNRVLNETRNQYE,

SEQ ID NO: 4111
NTLRSQLGDRLNVEVDAAPTVDLNRVLNETRNQYE,

SEQ ID NO: 4112
NTLRCPLGDRLNVEVDAAPTVDLNRVLNETRNQYE,

SEQ ID NO: 4113
NTLRSPLGDRLNVEVDAAPTVDLNRVLNETRNQYE,

SEQ ID NO: 4114
NTLRCQLGDRLNVEVDTAPTVDLNRVLNETRNQYE,

SEQ ID NO: 4115
NTLRSQLGDRLNVEVDTAPTVDLNRVLNETRNQYE,

SEQ ID NO: 4116
NTLRCPLGDRLNVEVDTAPTVDLNRVLNETRNQYE,

SEQ ID NO: 4117
NTLRSPLGDRLNVEVDTAPTVDLNRVLNETRNQYE,

SEQ ID NO: 4118
TLRCQLGDRLNVEVDAAPTVDLNQVLNETRSQYEA,

SEQ ID NO: 4119
TLRSQLGDRLNVEVDAAPTVDLNQVLNETRSQYEA,

SEQ ID NO: 4120
TLRCPLGDRLNVEVDAAPTVDLNQVLNETRSQYEA,

SEQ ID NO: 4121
TLRSPLGDRLNVEVDAAPTVDLNQVLNETRSQYEA,

SEQ ID NO: 4122
TLRCQLGDRLNVEVDTAPTVDLNQVLNETRSQYEA,

SEQ ID NO: 4123
TLRSQLGDRLNVEVDTAPTVDLNQVLNETRSQYEA,

SEQ ID NO: 4124
TLRCPLGDRLNVEVDTAPTVDLNQVLNETRSQYEA,

SEQ ID NO: 4125
TLRSPLGDRLNVEVDTAPTVDLNQVLNETRSQYEA,

SEQ ID NO: 4126
TLRCQLGDRLNVEVDAAPTVDLNRVLNETRSQYEA,

SEQ ID NO: 4127
TLRSQLGDRLNVEVDAAPTVDLNRVLNETRSQYEA,

SEQ ID NO: 4128
TLRCPLGDRLNVEVDAAPTVDLNRVLNETRSQYEA,

SEQ ID NO: 4129
TLRSPLGDRLNVEVDAAPTVDLNRVLNETRSQYEA,

SEQ ID NO: 4130
TLRCQLGDRLNVEVDTAPTVDLNRVLNETRSQYEA,

SEQ ID NO: 4131
TLRSQLGDRLNVEVDTAPTVDLNRVLNETRSQYEA,

SEQ ID NO: 4132
TLRCPLGDRLNVEVDTAPTVDLNRVLNETRSQYEA,

SEQ ID NO: 4133
TLRSPLGDRLNVEVDTAPTVDLNRVLNETRSQYEA,

SEQ ID NO: 4134
TLRCQLGDRLNVEVDAAPTVDLNQVLNETRNQYEA,

SEQ ID NO: 4135
TLRSQLGDRLNVEVDAAPTVDLNQVLNETRNQYEA,

SEQ ID NO: 4136
TLRCPLGDRLNVEVDAAPTVDLNQVLNETRNQYEA,

SEQ ID NO: 4137
TLRSPLGDRLNVEVDAAPTVDLNQVLNETRNQYEA,

SEQ ID NO: 4138
TLRCQLGDRLNVEVDTAPTVDLNQVLNETRNQYEA,

SEQ ID NO: 4139
TLRSQLGDRLNVEVDTAPTVDLNQVLNETRNQYEA,

SEQ ID NO: 4140
TLRCPLGDRLNVEVDTAPTVDLNQVLNETRNQYEA,

SEQ ID NO: 4141
TLRSPLGDRLNVEVDTAPTVDLNQVLNETRNQYEA,

SEQ ID NO: 4142
TLRCQLGDRLNVEVDAAPTVDLNRVLNETRNQYEA,

SEQ ID NO: 4143
TLRSQLGDRLNVEVDAAPTVDLNRVLNETRNQYEA,
```

```
                                    SEQ ID NO: 4144
TLRCPLGDRLNVEVDAAPTVDLNRVLNETRNQYEA,

SEQ ID NO: 4145
TLRSPLGDRLNVEVDAAPTVDLNRVLNETRNQYEA,

SEQ ID NO: 4146
TLRCQLGDRLNVEVDTAPTVDLNRVLNETRNQYEA,

SEQ ID NO: 4147
TLRSQLGDRLNVEVDTAPTVDLNRVLNETRNQYEA,

SEQ ID NO: 4148
TLRCPLGDRLNVEVDTAPTVDLNRVLNETRNQYEA,

SEQ ID NO: 4149
TLRSPLGDRLNVEVDTAPTVDLNRVLNETRNQYEA,

SEQ ID NO: 4150
LRCQLGDRLNVEVDAAPTVDLNQVLNETRSQYEAL,

SEQ ID NO: 4151
LRSQLGDRLNVEVDAAPTVDLNQVLNETRSQYEAL,

SEQ ID NO: 4152
LRCPLGDRLNVEVDAAPTVDLNQVLNETRSQYEAL,

SEQ ID NO: 4153
LRSPLGDRLNVEVDAAPTVDLNQVLNETRSQYEAL,

SEQ ID NO: 4154
LRCQLGDRLNVEVDTAPTVDLNQVLNETRSQYEAL,

SEQ ID NO: 4155
LRSQLGDRLNVEVDTAPTVDLNQVLNETRSQYEAL,

SEQ ID NO: 4156
LRCPLGDRLNVEVDTAPTVDLNQVLNETRSQYEAL,

SEQ ID NO: 4157
LRSPLGDRLNVEVDTAPTVDLNQVLNETRSQYEAL,

SEQ ID NO: 4158
LRCQLGDRLNVEVDAAPTVDLNRVLNETRSQYEAL,

SEQ ID NO: 4159
LRSQLGDRLNVEVDAAPTVDLNRVLNETRSQYEAL,

SEQ ID NO: 4160
LRCPLGDRLNVEVDAAPTVDLNRVLNETRSQYEAL,

SEQ ID NO: 4161
LRSPLGDRLNVEVDAAPTVDLNRVLNETRSQYEAL,

SEQ ID NO: 4162
LRCQLGDRLNVEVDTAPTVDLNRVLNETRSQYEAL,

SEQ ID NO: 4163
LRSQLGDRLNVEVDTAPTVDLNRVLNETRSQYEAL,

SEQ ID NO: 4164
LRCPLGDRLNVEVDTAPTVDLNRVLNETRSQYEAL,

SEQ ID NO: 4165
LRSPLGDRLNVEVDTAPTVDLNRVLNETRSQYEAL,

SEQ ID NO: 4166
LRCQLGDRLNVEVDAAPTVDLNQVLNETRNQYEAL,

SEQ ID NO: 4167
LRSQLGDRLNVEVDAAPTVDLNQVLNETRNQYEAL,

SEQ ID NO: 4168
LRCPLGDRLNVEVDAAPTVDLNQVLNETRNQYEAL,

SEQ ID NO: 4169
LRSPLGDRLNVEVDAAPTVDLNQVLNETRNQYEAL,

SEQ ID NO: 4170
LRCQLGDRLNVEVDTAPTVDLNQVLNETRNQYEAL,

SEQ ID NO: 4171
LRSQLGDRLNVEVDTAPTVDLNQVLNETRNQYEAL,

SEQ ID NO: 4172
LRCPLGDRLNVEVDTAPTVDLNQVLNETRNQYEAL,

SEQ ID NO: 4173
LRSPLGDRLNVEVDTAPTVDLNQVLNETRNQYEAL,

SEQ ID NO: 4174
LRCQLGDRLNVEVDAAPTVDLNRVLNETRNQYEAL,

SEQ ID NO: 4175
LRSQLGDRLNVEVDAAPTVDLNRVLNETRNQYEAL,

SEQ ID NO: 4176
LRCPLGDRLNVEVDAAPTVDLNRVLNETRNQYEAL,

SEQ ID NO: 4177
LRSPLGDRLNVEVDAAPTVDLNRVLNETRNQYEAL,

SEQ ID NO: 4178
LRCQLGDRLNVEVDTAPTVDLNRVLNETRNQYEAL,

SEQ ID NO: 4179
LRSQLGDRLNVEVDTAPTVDLNRVLNETRNQYEAL,

SEQ ID NO: 4180
LRCPLGDRLNVEVDTAPTVDLNRVLNETRNQYEAL,

SEQ ID NO: 4181
LRSPLGDRLNVEVDTAPTVDLNRVLNETRNQYEAL,

SEQ ID NO: 4182
EVNTLRCQLGDRLNVEVDAAPTVDLNQVLNETRSQY,

SEQ ID NO: 4183
EVNTLRSQLGDRLNVEVDAAPTVDLNQVLNETRSQY,

SEQ ID NO: 4184
EVNTLRCPLGDRLNVEVDAAPTVDLNQVLNETRSQY,

SEQ ID NO: 4185
EVNTLRSPLGDRLNVEVDAAPTVDLNQVLNETRSQY,

SEQ ID NO: 4186
EVNTLRCQLGDRLNVEVDTAPTVDLNQVLNETRSQY,

SEQ ID NO: 4187
EVNTLRSQLGDRLNVEVDTAPTVDLNQVLNETRSQY,

SEQ ID NO: 4188
EVNTLRCPLGDRLNVEVDTAPTVDLNQVLNETRSQY,

SEQ ID NO: 4189
EVNTLRSPLGDRLNVEVDTAPTVDLNQVLNETRSQY,

SEQ ID NO: 4190
EVNTLRCQLGDRLNVEVDAAPTVDLNRVLNETRSQY,

SEQ ID NO: 4191
EVNTLRSQLGDRLNVEVDAAPTVDLNRVLNETRSQY,

SEQ ID NO: 4192
EVNTLRCPLGDRLNVEVDAAPTVDLNRVLNETRSQY,

SEQ ID NO: 4193
EVNTLRSPLGDRLNVEVDAAPTVDLNRVLNETRSQY,

SEQ ID NO: 4194
EVNTLRCQLGDRLNVEVDTAPTVDLNRVLNETRSQY,

SEQ ID NO: 4195
EVNTLRSQLGDRLNVEVDTAPTVDLNRVLNETRSQY,

SEQ ID NO: 4196
EVNTLRCPLGDRLNVEVDTAPTVDLNRVLNETRSQY,

SEQ ID NO: 4197
EVNTLRSPLGDRLNVEVDTAPTVDLNRVLNETRSQY,
```

SEQ ID NO: 4198
EVNTLRCQLGDRLNVEVDAAPTVDLNQVLNETRNQY,

SEQ ID NO: 4199
EVNTLRSQLGDRLNVEVDAAPTVDLNQVLNETRNQY,

SEQ ID NO: 4200
EVNTLRCPLGDRLNVEVDAAPTVDLNQVLNETRNQY,

SEQ ID NO: 4201
EVNTLRSPLGDRLNVEVDAAPTVDLNQVLNETRNQY,

SEQ ID NO: 4202
EVNTLRCQLGDRLNVEVDTAPTVDLNQVLNETRNQY,

SEQ ID NO: 4203
EVNTLRSQLGDRLNVEVDTAPTVDLNQVLNETRNQY,

SEQ ID NO: 4204
EVNTLRCPLGDRLNVEVDTAPTVDLNQVLNETRNQY,

SEQ ID NO: 4205
EVNTLRSPLGDRLNVEVDTAPTVDLNQVLNETRNQY,

SEQ ID NO: 4206
EVNTLRCQLGDRLNVEVDAAPTVDLNRVLNETRNQY,

SEQ ID NO: 4207
EVNTLRSQLGDRLNVEVDAAPTVDLNRVLNETRNQY,

SEQ ID NO: 4208
EVNTLRCPLGDRLNVEVDAAPTVDLNRVLNETRNQY,

SEQ ID NO: 4209
EVNTLRSPLGDRLNVEVDAAPTVDLNRVLNETRNQY,

SEQ ID NO: 4210
EVNTLRCQLGDRLNVEVDTAPTVDLNRVLNETRNQY,

SEQ ID NO: 4211
EVNTLRSQLGDRLNVEVDTAPTVDLNRVLNETRNQY,

SEQ ID NO: 4212
EVNTLRCPLGDRLNVEVDTAPTVDLNRVLNETRNQY,

SEQ ID NO: 4213
EVNTLRSPLGDRLNVEVDTAPTVDLNRVLNETRNQY,

SEQ ID NO: 4214
VNTLRCQLGDRLNVEVDAAPTVDLNQVLNETRSQYE,

SEQ ID NO: 4215
VNTLRSQLGDRLNVEVDAAPTVDLNQVLNETRSQYE,

SEQ ID NO: 4216
VNTLRCPLGDRLNVEVDAAPTVDLNQVLNETRSQYE,

SEQ ID NO: 4217
VNTLRSPLGDRLNVEVDAAPTVDLNQVLNETRSQYE,

SEQ ID NO: 4218
VNTLRCQLGDRLNVEVDTAPTVDLNQVLNETRSQYE,

SEQ ID NO: 4219
VNTLRSQLGDRLNVEVDTAPTVDLNQVLNETRSQYE,

SEQ ID NO: 4220
VNTLRCPLGDRLNVEVDTAPTVDLNQVLNETRSQYE,

SEQ ID NO: 4221
VNTLRSPLGDRLNVEVDTAPTVDLNQVLNETRSQYE,

SEQ ID NO: 4222
VNTLRCQLGDRLNVEVDAAPTVDLNRVLNETRSQYE,

SEQ ID NO: 4223
VNTLRSQLGDRLNVEVDAAPTVDLNRVLNETRSQYE,

SEQ ID NO: 4224
VNTLRCPLGDRLNVEVDAAPTVDLNRVLNETRSQYE,

SEQ ID NO: 4225
VNTLRSPLGDRLNVEVDAAPTVDLNRVLNETRSQYE,

SEQ ID NO: 4226
VNTLRCQLGDRLNVEVDTAPTVDLNRVLNETRSQYE,

SEQ ID NO: 4227
VNTLRSQLGDRLNVEVDTAPTVDLNRVLNETRSQYE,

SEQ ID NO: 4228
VNTLRCPLGDRLNVEVDTAPTVDLNRVLNETRSQYE,

SEQ ID NO: 4229
VNTLRSPLGDRLNVEVDTAPTVDLNRVLNETRSQYE,

SEQ ID NO: 4230
VNTLRCQLGDRLNVEVDAAPTVDLNQVLNETRNQYE,

SEQ ID NO: 4231
VNTLRSQLGDRLNVEVDAAPTVDLNQVLNETRNQYE,

SEQ ID NO: 4232
VNTLRCPLGDRLNVEVDAAPTVDLNQVLNETRNQYE,

SEQ ID NO: 4233
VNTLRSPLGDRLNVEVDAAPTVDLNQVLNETRNQYE,

SEQ ID NO: 4234
VNTLRCQLGDRLNVEVDTAPTVDLNQVLNETRNQYE,

SEQ ID NO: 4235
VNTLRSQLGDRLNVEVDTAPTVDLNQVLNETRNQYE,

SEQ ID NO: 4236
VNTLRCPLGDRLNVEVDTAPTVDLNQVLNETRNQYE,

SEQ ID NO: 4237
VNTLRSPLGDRLNVEVDTAPTVDLNQVLNETRNQYE,

SEQ ID NO: 4238
VNTLRCQLGDRLNVEVDAAPTVDLNRVLNETRNQYE,

SEQ ID NO: 4239
VNTLRSQLGDRLNVEVDAAPTVDLNRVLNETRNQYE,

SEQ ID NO: 4240
VNTLRCPLGDRLNVEVDAAPTVDLNRVLNETRNQYE,

SEQ ID NO: 4241
VNTLRSPLGDRLNVEVDAAPTVDLNRVLNETRNQYE,

SEQ ID NO: 4242
VNTLRCQLGDRLNVEVDTAPTVDLNRVLNETRNQYE,

SEQ ID NO: 4243
VNTLRSQLGDRLNVEVDTAPTVDLNRVLNETRNQYE,

SEQ ID NO: 4244
VNTLRCPLGDRLNVEVDTAPTVDLNRVLNETRNQYE,

SEQ ID NO: 4245
VNTLRSPLGDRLNVEVDTAPTVDLNRVLNETRNQYE,

SEQ ID NO: 4246
NTLRCQLGDRLNVEVDAAPTVDLNQVLNETRSQYEA,

SEQ ID NO: 4247
NTLRSQLGDRLNVEVDAAPTVDLNQVLNETRSQYEA,

SEQ ID NO: 4248
NTLRCPLGDRLNVEVDAAPTVDLNQVLNETRSQYEA,

SEQ ID NO: 4249
NTLRSPLGDRLNVEVDAAPTVDLNQVLNETRSQYEA,

SEQ ID NO: 4250
NTLRCQLGDRLNVEVDTAPTVDLNQVLNETRSQYEA,

SEQ ID NO: 4251
NTLRSQLGDRLNVEVDTAPTVDLNQVLNETRSQYEA,

SEQ ID NO: 4252
NTLRCPLGDRLNVEVDTAPTVDLNQVLNETRSQYEA,

SEQ ID NO: 4253
NTLRSPLGDRLNVEVDTAPTVDLNQVLNETRSQYEA,

SEQ ID NO: 4254
NTLRCQLGDRLNVEVDAAPTVDLNRVLNETRSQYEA,

SEQ ID NO: 4255
NTLRSQLGDRLNVEVDAAPTVDLNRVLNETRSQYEA,

SEQ ID NO: 4256
NTLRCPLGDRLNVEVDAAPTVDLNRVLNETRSQYEA,

SEQ ID NO: 4257
NTLRSPLGDRLNVEVDAAPTVDLNRVLNETRSQYEA,

SEQ ID NO: 4258
NTLRCQLGDRLNVEVDTAPTVDLNRVLNETRSQYEA,

SEQ ID NO: 4259
NTLRSQLGDRLNVEVDTAPTVDLNRVLNETRSQYEA,

SEQ ID NO: 4260
NTLRCPLGDRLNVEVDTAPTVDLNRVLNETRSQYEA,

SEQ ID NO: 4261
NTLRSPLGDRLNVEVDTAPTVDLNRVLNETRSQYEA,

SEQ ID NO: 4262
NTLRCQLGDRLNVEVDAAPTVDLNQVLNETRNQYEA,

SEQ ID NO: 4263
NTLRSQLGDRLNVEVDAAPTVDLNQVLNETRNQYEA,

SEQ ID NO: 4264
NTLRCPLGDRLNVEVDAAPTVDLNQVLNETRNQYEA,

SEQ ID NO: 4265
NTLRSPLGDRLNVEVDAAPTVDLNQVLNETRNQYEA,

SEQ ID NO: 4266
NTLRCQLGDRLNVEVDTAPTVDLNQVLNETRNQYEA,

SEQ ID NO: 4267
NTLRSQLGDRLNVEVDTAPTVDLNQVLNETRNQYEA,

SEQ ID NO: 4268
NTLRCPLGDRLNVEVDTAPTVDLNQVLNETRNQYEA,

SEQ ID NO: 4269
NTLRSPLGDRLNVEVDTAPTVDLNQVLNETRNQYEA,

SEQ ID NO: 4270
NTLRCQLGDRLNVEVDAAPTVDLNRVLNETRNQYEA,

SEQ ID NO: 4271
NTLRSQLGDRLNVEVDAAPTVDLNRVLNETRNQYEA,

SEQ ID NO: 4272
NTLRCPLGDRLNVEVDAAPTVDLNRVLNETRNQYEA,

SEQ ID NO: 4273
NTLRSPLGDRLNVEVDAAPTVDLNRVLNETRNQYEA,

SEQ ID NO: 4274
NTLRCQLGDRLNVEVDTAPTVDLNRVLNETRNQYEA,

SEQ ID NO: 4275
NTLRSQLGDRLNVEVDTAPTVDLNRVLNETRNQYEA,

SEQ ID NO: 4276
NTLRCPLGDRLNVEVDTAPTVDLNRVLNETRNQYEA,

SEQ ID NO: 4277
NTLRSPLGDRLNVEVDTAPTVDLNRVLNETRNQYEA,

SEQ ID NO: 4278
TLRCQLGDRLNVEVDAAPTVDLNQVLNETRSQYEAL,

SEQ ID NO: 4279
TLRSQLGDRLNVEVDAAPTVDLNQVLNETRSQYEAL,

SEQ ID NO: 4280
TLRCPLGDRLNVEVDAAPTVDLNQVLNETRSQYEAL,

SEQ ID NO: 4281
TLRSPLGDRLNVEVDAAPTVDLNQVLNETRSQYEAL,

SEQ ID NO: 4282
TLRCQLGDRLNVEVDTAPTVDLNQVLNETRSQYEAL,

SEQ ID NO: 4283
TLRSQLGDRLNVEVDTAPTVDLNQVLNETRSQYEAL,

SEQ ID NO: 4284
TLRCPLGDRLNVEVDTAPTVDLNQVLNETRSQYEAL,

SEQ ID NO: 4285
TLRSPLGDRLNVEVDTAPTVDLNQVLNETRSQYEAL,

SEQ ID NO: 4286
TLRCQLGDRLNVEVDAAPTVDLNRVLNETRSQYEAL,

SEQ ID NO: 4287
TLRSQLGDRLNVEVDAAPTVDLNRVLNETRSQYEAL,

SEQ ID NO: 4288
TLRCPLGDRLNVEVDAAPTVDLNRVLNETRSQYEAL,

SEQ ID NO: 4289
TLRSPLGDRLNVEVDAAPTVDLNRVLNETRSQYEAL,

SEQ ID NO: 4290
TLRCQLGDRLNVEVDTAPTVDLNRVLNETRSQYEAL,

SEQ ID NO: 4291
TLRSQLGDRLNVEVDTAPTVDLNRVLNETRSQYEAL,

SEQ ID NO: 4292
TLRCPLGDRLNVEVDTAPTVDLNRVLNETRSQYEAL,

SEQ ID NO: 4293
TLRSPLGDRLNVEVDTAPTVDLNRVLNETRSQYEAL,

SEQ ID NO: 4294
TLRCQLGDRLNVEVDAAPTVDLNQVLNETRNQYEAL,

SEQ ID NO: 4295
TLRSQLGDRLNVEVDAAPTVDLNQVLNETRNQYEAL,

SEQ ID NO: 4296
TLRCPLGDRLNVEVDAAPTVDLNQVLNETRNQYEAL,

SEQ ID NO: 4297
TLRSPLGDRLNVEVDAAPTVDLNQVLNETRNQYEAL,

SEQ ID NO: 4298
TLRCQLGDRLNVEVDTAPTVDLNQVLNETRNQYEAL,

SEQ ID NO: 4299
TLRSQLGDRLNVEVDTAPTVDLNQVLNETRNQYEAL,

SEQ ID NO: 4300
TLRCPLGDRLNVEVDTAPTVDLNQVLNETRNQYEAL,

SEQ ID NO: 4301
TLRSPLGDRLNVEVDTAPTVDLNQVLNETRNQYEAL,

SEQ ID NO: 4302
TLRCQLGDRLNVEVDAAPTVDLNRVLNETRNQYEAL,

SEQ ID NO: 4303
TLRSQLGDRLNVEVDAAPTVDLNRVLNETRNQYEAL,

SEQ ID NO: 4304
TLRCPLGDRLNVEVDAAPTVDLNRVLNETRNQYEAL,

SEQ ID NO: 4305
TLRSPLGDRLNVEVDAAPTVDLNRVLNETRNQYEAL,

SEQ ID NO: 4306
TLRCQLGDRLNVEVDTAPTVDLNRVLNETRNQYEAL,

SEQ ID NO: 4307
TLRSQLGDRLNVEVDTAPTVDLNRVLNETRNQYEAL,

SEQ ID NO: 4308
TLRCPLGDRLNVEVDTAPTVDLNRVLNETRNQYEAL,

SEQ ID NO: 4309
TLRSPLGDRLNVEVDTAPTVDLNRVLNETRNQYEAL,

SEQ ID NO: 4310
EVNTLRCQLGDRLNVEVDAAPTVDLNQVLNETRSQYE,

SEQ ID NO: 4311
EVNTLRSQLGDRLNVEVDAAPTVDLNQVLNETRSQYE,

SEQ ID NO: 4312
EVNTLRCPLGDRLNVEVDAAPTVDLNQVLNETRSQYE,

SEQ ID NO: 4313
EVNTLRSPLGDRLNVEVDAAPTVDLNQVLNETRSQYE,

SEQ ID NO: 4314
EVNTLRCQLGDRLNVEVDTAPTVDLNQVLNETRSQYE,

SEQ ID NO: 4315
EVNTLRSQLGDRLNVEVDTAPTVDLNQVLNETRSQYE,

SEQ ID NO: 4316
EVNTLRCPLGDRLNVEVDTAPTVDLNQVLNETRSQYE,

SEQ ID NO: 4317
EVNTLRSPLGDRLNVEVDTAPTVDLNQVLNETRSQYE,

SEQ ID NO: 4318
EVNTLRCQLGDRLNVEVDAAPTVDLNRVLNETRSQYE,

SEQ ID NO: 4319
EVNTLRSQLGDRLNVEVDAAPTVDLNRVLNETRSQYE,

SEQ ID NO: 4320
EVNTLRCPLGDRLNVEVDAAPTVDLNRVLNETRSQYE,

SEQ ID NO: 4321
EVNTLRSPLGDRLNVEVDAAPTVDLNRVLNETRSQYE,

SEQ ID NO: 4322
EVNTLRCQLGDRLNVEVDTAPTVDLNRVLNETRSQYE,

SEQ ID NO: 4323
EVNTLRSQLGDRLNVEVDTAPTVDLNRVLNETRSQYE,

SEQ ID NO: 4324
EVNTLRCPLGDRLNVEVDTAPTVDLNRVLNETRSQYE,

SEQ ID NO: 4325
EVNTLRSPLGDRLNVEVDTAPTVDLNRVLNETRSQYE,

SEQ ID NO: 4326
EVNTLRCQLGDRLNVEVDAAPTVDLNQVLNETRNQYE,

SEQ ID NO: 4327
EVNTLRSQLGDRLNVEVDAAPTVDLNQVLNETRNQYE,

SEQ ID NO: 4328
EVNTLRCPLGDRLNVEVDAAPTVDLNQVLNETRNQYE,

SEQ ID NO: 4329
EVNTLRSPLGDRLNVEVDAAPTVDLNQVLNETRNQYE,

SEQ ID NO: 4330
EVNTLRCQLGDRLNVEVDTAPTVDLNQVLNETRNQYE,

SEQ ID NO: 4331
EVNTLRSQLGDRLNVEVDTAPTVDLNQVLNETRNQYE,

SEQ ID NO: 4332
EVNTLRCPLGDRLNVEVDTAPTVDLNQVLNETRNQYE,

SEQ ID NO: 4333
EVNTLRSPLGDRLNVEVDTAPTVDLNQVLNETRNQYE,

SEQ ID NO: 4334
EVNTLRCQLGDRLNVEVDAAPTVDLNRVLNETRNQYE,

SEQ ID NO: 4335
EVNTLRSQLGDRLNVEVDAAPTVDLNRVLNETRNQYE,

SEQ ID NO: 4336
EVNTLRCPLGDRLNVEVDAAPTVDLNRVLNETRNQYE,

SEQ ID NO: 4337
EVNTLRSPLGDRLNVEVDAAPTVDLNRVLNETRNQYE,

SEQ ID NO: 4338
EVNTLRCQLGDRLNVEVDTAPTVDLNRVLNETRNQYE,

SEQ ID NO: 4339
EVNTLRSQLGDRLNVEVDTAPTVDLNRVLNETRNQYE,

SEQ ID NO: 4340
EVNTLRCPLGDRLNVEVDTAPTVDLNRVLNETRNQYE,

SEQ ID NO: 4341
EVNTLRSPLGDRLNVEVDTAPTVDLNRVLNETRNQYE,

SEQ ID NO: 4342
VNTLRCQLGDRLNVEVDAAPTVDLNQVLNETRSQYEA,

SEQ ID NO: 4343
VNTLRSQLGDRLNVEVDAAPTVDLNQVLNETRSQYEA,

SEQ ID NO: 4344
VNTLRCPLGDRLNVEVDAAPTVDLNQVLNETRSQYEA,

SEQ ID NO: 4345
VNTLRSPLGDRLNVEVDAAPTVDLNQVLNETRSQYEA,

SEQ ID NO: 4346
VNTLRCQLGDRLNVEVDTAPTVDLNQVLNETRSQYEA,

SEQ ID NO: 4347
VNTLRSQLGDRLNVEVDTAPTVDLNQVLNETRSQYEA,

SEQ ID NO: 4348
VNTLRCPLGDRLNVEVDTAPTVDLNQVLNETRSQYEA,

SEQ ID NO: 4349
VNTLRSPLGDRLNVEVDTAPTVDLNQVLNETRSQYEA,

SEQ ID NO: 4350
VNTLRCQLGDRLNVEVDAAPTVDLNRVLNETRSQYEA,

SEQ ID NO: 4351
VNTLRSQLGDRLNVEVDAAPTVDLNRVLNETRSQYEA,

SEQ ID NO: 4352
VNTLRCPLGDRLNVEVDAAPTVDLNRVLNETRSQYEA,

SEQ ID NO: 4353
VNTLRSPLGDRLNVEVDAAPTVDLNRVLNETRSQYEA,

SEQ ID NO: 4354
VNTLRCQLGDRLNVEVDTAPTVDLNRVLNETRSQYEA,

SEQ ID NO: 4355
VNTLRSQLGDRLNVEVDTAPTVDLNRVLNETRSQYEA,

SEQ ID NO: 4356
VNTLRCPLGDRLNVEVDTAPTVDLNRVLNETRSQYEA,

SEQ ID NO: 64357
VNTLRSPLGDRLNVEVDTAPTVDLNRVLNETRSQYEA,

SEQ ID NO: 4358
VNTLRCQLGDRLNVEVDAAPTVDLNQVLNETRNQYEA,

SEQ ID NO: 4359
VNTLRSQLGDRLNVEVDAAPTVDLNQVLNETRNQYEA,

SEQ ID NO: 4360
VNTLRCPLGDRLNVEVDAAPTVDLNQVLNETRNQYEA,

SEQ ID NO: 4361
VNTLRSPLGDRLNVEVDAAPTVDLNQVLNETRNQYEA,

SEQ ID NO: 4362
VNTLRCQLGDRLNVEVDTAPTVDLNQVLNETRNQYEA,

SEQ ID NO: 4363
VNTLRSQLGDRLNVEVDTAPTVDLNQVLNETRNQYEA,

SEQ ID NO: 4364
VNTLRCPLGDRLNVEVDTAPTVDLNQVLNETRNQYEA,

SEQ ID NO: 4365
VNTLRSPLGDRLNVEVDTAPTVDLNQVLNETRNQYEA,

SEQ ID NO: 4366
VNTLRCQLGDRLNVEVDAAPTVDLNRVLNETRNQYEA,

SEQ ID NO: 4367
VNTLRSQLGDRLNVEVDAAPTVDLNRVLNETRNQYEA,

SEQ ID NO: 4368
VNTLRCPLGDRLNVEVDAAPTVDLNRVLNETRNQYEA,

SEQ ID NO: 4369
VNTLRSPLGDRLNVEVDAAPTVDLNRVLNETRNQYEA,

SEQ ID NO: 4370
VNTLRCQLGDRLNVEVDTAPTVDLNRVLNETRNQYEA,

SEQ ID NO: 4371
VNTLRSQLGDRLNVEVDTAPTVDLNRVLNETRNQYEA,

SEQ ID NO: 4372
VNTLRCPLGDRLNVEVDTAPTVDLNRVLNETRNQYEA,

SEQ ID NO: 4373
VNTLRSPLGDRLNVEVDTAPTVDLNRVLNETRNQYEA,

SEQ ID NO: 4374
NTLRCQLGDRLNVEVDAAPTVDLNQVLNETRSQYEAL,

SEQ ID NO: 4375
NTLRSQLGDRLNVEVDAAPTVDLNQVLNETRSQYEAL,

SEQ ID NO: 4376
NTLRCPLGDRLNVEVDAAPTVDLNQVLNETRSQYEAL,

SEQ ID NO: 4377
NTLRSPLGDRLNVEVDAAPTVDLNQVLNETRSQYEAL,

SEQ ID NO: 4378
NTLRCQLGDRLNVEVDTAPTVDLNQVLNETRSQYEAL,

SEQ ID NO: 4379
NTLRSQLGDRLNVEVDTAPTVDLNQVLNETRSQYEAL,

SEQ ID NO: 4380
NTLRCPLGDRLNVEVDTAPTVDLNQVLNETRSQYEAL,

SEQ ID NO: 4381
NTLRSPLGDRLNVEVDTAPTVDLNQVLNETRSQYEAL,

SEQ ID NO: 4382
NTLRCQLGDRLNVEVDAAPTVDLNRVLNETRSQYEAL,

SEQ ID NO: 4383
NTLRSQLGDRLNVEVDAAPTVDLNRVLNETRSQYEAL,

SEQ ID NO: 4384
NTLRCPLGDRLNVEVDAAPTVDLNRVLNETRSQYEAL,

SEQ ID NO: 4385
NTLRSPLGDRLNVEVDAAPTVDLNRVLNETRSQYEAL,

SEQ ID NO: 4386
NTLRCQLGDRLNVEVDTAPTVDLNRVLNETRSQYEAL,

SEQ ID NO: 4387
NTLRSQLGDRLNVEVDTAPTVDLNRVLNETRSQYEAL,

SEQ ID NO: 4388
NTLRCPLGDRLNVEVDTAPTVDLNRVLNETRSQYEAL,

SEQ ID NO: 4389
NTLRSPLGDRLNVEVDTAPTVDLNRVLNETRSQYEAL,

SEQ ID NO: 4390
NTLRCQLGDRLNVEVDAAPTVDLNQVLNETRNQYEAL,

SEQ ID NO: 4391
NTLRSQLGDRLNVEVDAAPTVDLNQVLNETRNQYEAL,

SEQ ID NO: 4392
NTLRCPLGDRLNVEVDAAPTVDLNQVLNETRNQYEAL,

SEQ ID NO: 4393
NTLRSPLGDRLNVEVDAAPTVDLNQVLNETRNQYEAL,

SEQ ID NO: 4394
NTLRCQLGDRLNVEVDTAPTVDLNQVLNETRNQYEAL,

SEQ ID NO: 4395
NTLRSQLGDRLNVEVDTAPTVDLNQVLNETRNQYEAL,

SEQ ID NO: 4396
NTLRCPLGDRLNVEVDTAPTVDLNQVLNETRNQYEAL,

SEQ ID NO: 4397
NTLRSPLGDRLNVEVDTAPTVDLNQVLNETRNQYEAL,

SEQ ID NO: 4398
NTLRCQLGDRLNVEVDAAPTVDLNRVLNETRNQYEAL,

SEQ ID NO: 4399
NTLRSQLGDRLNVEVDAAPTVDLNRVLNETRNQYEAL,

SEQ ID NO: 4400
NTLRCPLGDRLNVEVDAAPTVDLNRVLNETRNQYEAL,

SEQ ID NO: 4401
NTLRSPLGDRLNVEVDAAPTVDLNRVLNETRNQYEAL,

SEQ ID NO: 4402
NTLRCQLGDRLNVEVDTAPTVDLNRVLNETRNQYEAL,

SEQ ID NO: 4403
NTLRSQLGDRLNVEVDTAPTVDLNRVLNETRNQYEAL,

SEQ ID NO: 4404
NTLRCPLGDRLNVEVDTAPTVDLNRVLNETRNQYEAL,

SEQ ID NO: 4405
NTLRSPLGDRLNVEVDTAPTVDLNRVLNETRNQYEAL,

SEQ ID NO: 4406
EVNTLRCQLGDRLNVEVDAAPTVDLNQVLNETRSQYEA,

SEQ ID NO: 4407
EVNTLRSQLGDRLNVEVDAAPTVDLNQVLNETRSQYEA,

SEQ ID NO: 4408
EVNTLRCPLGDRLNVEVDAAPTVDLNQVLNETRSQYEA,

SEQ ID NO: 4409
EVNTLRSPLGDRLNVEVDAAPTVDLNQVLNETRSQYEA,

SEQ ID NO: 4410
EVNTLRCQLGDRLNVEVDTAPTVDLNQVLNETRSQYEA,

SEQ ID NO: 4411
EVNTLRSQLGDRLNVEVDTAPTVDLNQVLNETRSQYEA,

SEQ ID NO: 4412
EVNTLRCPLGDRLNVEVDTAPTVDLNQVLNETRSQYEA,

SEQ ID NO: 4413
EVNTLRSPLGDRLNVEVDTAPTVDLNQVLNETRSQYEA,

SEQ ID NO: 4414
EVNTLRCQLGDRLNVEVDAAPTVDLNRVLNETRSQYEA,

SEQ ID NO: 4415
EVNTLRSQLGDRLNVEVDAAPTVDLNRVLNETRSQYEA,

SEQ ID NO: 4416
EVNTLRCPLGDRLNVEVDAAPTVDLNRVLNETRSQYEA,

SEQ ID NO: 4417
EVNTLRSPLGDRLNVEVDAAPTVDLNRVLNETRSQYEA,

SEQ ID NO: 4418
EVNTLRCQLGDRLNVEVDTAPTVDLNRVLNETRSQYEA,

SEQ ID NO: 4419
EVNTLRSQLGDRLNVEVDTAPTVDLNRVLNETRSQYEA,

SEQ ID NO: 4420
EVNTLRCPLGDRLNVEVDTAPTVDLNRVLNETRSQYEA,

SEQ ID NO: 4421
EVNTLRSPLGDRLNVEVDTAPTVDLNRVLNETRSQYEA,

SEQ ID NO: 4422
EVNTLRCQLGDRLNVEVDAAPTVDLNQVLNETRNQYEA,

SEQ ID NO: 4423
EVNTLRSQLGDRLNVEVDAAPTVDLNQVLNETRNQYEA,

SEQ ID NO: 4424
EVNTLRCPLGDRLNVEVDAAPTVDLNQVLNETRNQYEA,

SEQ ID NO: 4425
EVNTLRSPLGDRLNVEVDAAPTVDLNQVLNETRNQYEA,

SEQ ID NO: 4426
EVNTLRCQLGDRLNVEVDTAPTVDLNQVLNETRNQYEA,

SEQ ID NO: 4427
EVNTLRSQLGDRLNVEVDTAPTVDLNQVLNETRNQYEA,

SEQ ID NO: 4428
EVNTLRCPLGDRLNVEVDTAPTVDLNQVLNETRNQYEA,

SEQ ID NO: 4429
EVNTLRSPLGDRLNVEVDTAPTVDLNQVLNETRNQYEA,

SEQ ID NO: 4430
EVNTLRCQLGDRLNVEVDAAPTVDLNRVLNETRNQYEA,

SEQ ID NO: 4431
EVNTLRSQLGDRLNVEVDAAPTVDLNRVLNETRNQYEA,

SEQ ID NO: 4432
EVNTLRCPLGDRLNVEVDAAPTVDLNRVLNETRNQYEA,

SEQ ID NO: 4433
EVNTLRSPLGDRLNVEVDAAPTVDLNRVLNETRNQYEA,

SEQ ID NO: 4434
EVNTLRCQLGDRLNVEVDTAPTVDLNRVLNETRNQYEA,

SEQ ID NO: 4435
EVNTLRSQLGDRLNVEVDTAPTVDLNRVLNETRNQYEA,

SEQ ID NO: 4436
EVNTLRCPLGDRLNVEVDTAPTVDLNRVLNETRNQYEA,

SEQ ID NO: 4437
EVNTLRSPLGDRLNVEVDTAPTVDLNRVLNETRNQYEA,

SEQ ID NO: 4438
VNTLRCQLGDRLNVEVDAAPTVDLNQVLNETRSQYEAL,

SEQ ID NO: 4439
VNTLRSQLGDRLNVEVDAAPTVDLNQVLNETRSQYEAL,

SEQ ID NO: 4440
VNTLRCPLGDRLNVEVDAAPTVDLNQVLNETRSQYEAL,

SEQ ID NO: 4441
VNTLRSPLGDRLNVEVDAAPTVDLNQVLNETRSQYEAL,

SEQ ID NO: 4442
VNTLRCQLGDRLNVEVDTAPTVDLNQVLNETRSQYEAL,

SEQ ID NO: 4443
VNTLRSQLGDRLNVEVDTAPTVDLNQVLNETRSQYEAL,

SEQ ID NO: 4444
VNTLRCPLGDRLNVEVDTAPTVDLNQVLNETRSQYEAL,

SEQ ID NO: 4445
VNTLRSPLGDRLNVEVDTAPTVDLNQVLNETRSQYEAL,

SEQ ID NO: 4446
VNTLRCQLGDRLNVEVDAAPTVDLNRVLNETRSQYEAL,

SEQ ID NO: 4447
VNTLRSQLGDRLNVEVDAAPTVDLNRVLNETRSQYEAL,

SEQ ID NO: 4448
VNTLRCPLGDRLNVEVDAAPTVDLNRVLNETRSQYEAL,

SEQ ID NO: 4449
VNTLRSPLGDRLNVEVDAAPTVDLNRVLNETRSQYEAL,

SEQ ID NO: 4450
VNTLRCQLGDRLNVEVDTAPTVDLNRVLNETRSQYEAL,

SEQ ID NO: 4451
VNTLRSQLGDRLNVEVDTAPTVDLNRVLNETRSQYEAL,

SEQ ID NO: 4452
VNTLRCPLGDRLNVEVDTAPTVDLNRVLNETRSQYEAL,

SEQ ID NO: 4453
VNTLRSPLGDRLNVEVDTAPTVDLNRVLNETRSQYEAL,

SEQ ID NO: 4454
VNTLRCQLGDRLNVEVDAAPTVDLNQVLNETRNQYEAL,

SEQ ID NO: 4455
VNTLRSQLGDRLNVEVDAAPTVDLNQVLNETRNQYEAL,

SEQ ID NO: 4456
VNTLRCPLGDRLNVEVDAAPTVDLNQVLNETRNQYEAL,

SEQ ID NO: 4457
VNTLRSPLGDRLNVEVDAAPTVDLNQVLNETRNQYEAL,

SEQ ID NO: 4458
VNTLRCQLGDRLNVEVDTAPTVDLNQVLNETRNQYEAL,

SEQ ID NO: 4459
VNTLRSQLGDRLNVEVDTAPTVDLNQVLNETRNQYEAL,

SEQ ID NO: 4460
VNTLRCPLGDRLNVEVDTAPTVDLNQVLNETRNQYEAL,

SEQ ID NO: 4461
VNTLRSPLGDRLNVEVDTAPTVDLNQVLNETRNQYEAL,

SEQ ID NO: 4462
VNTLRCQLGDRLNVEVDAAPTVDLNRVLNETRNQYEAL,

SEQ ID NO: 4463
VNTLRSQLGDRLNVEVDAAPTVDLNRVLNETRNQYEAL,

SEQ ID NO: 4464
VNTLRCPLGDRLNVEVDAAPTVDLNRVLNETRNQYEAL,

SEQ ID NO: 4465
VNTLRSPLGDRLNVEVDAAPTVDLNRVLNETRNQYEAL,

SEQ ID NO: 4466
VNTLRCQLGDRLNVEVDTAPTVDLNRVLNETRNQYEAL,

SEQ ID NO: 4467
VNTLRSQLGDRLNVEVDTAPTVDLNRVLNETRNQYEAL,

-continued

SEQ ID NO: 4468
VNTLRCPLGDRLNVEVDTAPTVDLNRVLNETRNQYEAL,

SEQ ID NO: 4469
VNTLRSPLGDRLNVEVDTAPTVDLNRVLNETRNQYEAL,

As is well known in the art, the use of the designation (C/S) means the amino acid at that position may be either C or S, (Q/P) means the amino acid at that position may be either Q or P, (A/T) means the amino acid at that position may be either A or T, (Q/R) means the amino acid at that position may be either Q or R and (S/N) means the amino acid at that position may be either S or N. It is also understood that the terms C-terminus or carboxy terminus are used interchangeably and are used herein as they are normally used in the art. An amino acid is composed of a carbon atom known as the a-carbon to which is attached a a-carboxylic acid, an a-amine and a side chain. In the peptide bond polymerization, the a-amino group from one amino acid binds to the a-carboxylic acid group of an adjacent amino acid in the peptide polymer. The polymer thus includes a free a-carboxylic acid on one end (the C-terminus) and a free a-amine group on the opposite end (the N-terminus or amino terminus). Any of the peptides disclosed herein may be modified to increase the stability and activity of the compositions as is well known in the art. Such modifications would include, but is not limited to bonding of acetyl or amide groups to the appropriate ends of the peptides.

It is also understood that one of skill in the art would understand that the peptides are disclosed using the one letter amino acid abbreviations as follows:
A=Ala=alanine
R=Arg=arginine
N=Asp=asparagine
D=Asp=aspartic acid
C=Cys=cysteine
E=Glu=glutamic acid
Q=Gln=glutamine
G=Gly=glycine
H=His=histidine
I=Ile=isoleucine
L=Leu=leucine
K=Lys=lysine
M=Met=methionine
F=Phe=phenylalanine
P=Pro=proline
S=Ser=serine
T=Thr=threonine
W=Trp=tryptophan
Y=Tyr=tyrosine
V=Val=valine The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

Selected peptides derived from the keratin consensus sequence were chemically synthesized and used to demonstrate the bioactivity of the peptides. Normal human adult dermal fibroblasts were cultured in fibroblast growth medium (Clonetics™/BioWhittaker, San Diego, Calif., USA). Passage 5 cells were seeded into wells of 96 well plates at 5×10³ cells/well. Test peptide solutions were prepared at approximately 1.5 mg/ml in sterile water. Small volumes of 0.1N NH4OH were added dropwise to peptide the peptide solutions to completely solubilize the peptides as recommended by the manufacturer (New England Peptide, Inc., Fitchburg, Miss., USA). The volume of NH4OH added to the solution was recorded and used to adjust beginning concentration. Solutions were serially diluted in fibroblast culture medium from 100-0.001 µg/ml, then added to the cells and cultured for 5 days. At day 3, test and control media were removed from each well by vacuum and replaced with fresh test or control solutions. Samples were evaluated in 4 replicate wells. Note in each plate, wells were selected at random to be used as baseline controls to account for any variation in cell seeding between plates. After 5 days, cell proliferation was assessed spectrophotometrically using the Cell Titer96® Cell Proliferation Assay (Promega Corp., Madison, Wis., USA). Absorbance values were normalized to baseline controls and expressed as percent increased (positive values) or decreased (negative values) proliferation.

| Mitogenic Effects of 19 Peptides on Human Fibroblasts in Culture for 5 Days | | | | | | | | |
|---|---|---|---|---|---|---|---|---|
| Peptides for Cell Culture Studies | | | concentration (ug/mL) | | | | | |
| Peptide | Acidity | MW | 100 | 10 | 1 | 0.1 | 0.01 | 0.001 |
| H2N-VEVDAA-OH | acidic 2x | 602 | −9.5% | −1.3% | −4.7% | −9.0% | 2.3% | 11.0% |
| H2N-SPLGD-OH | acidic 1x | 487 | −4.3% | −1.2% | 1.5% | −4.2% | 1.7% | 11.8% |
| H2N-LGDRL-OH | acid/base | 572 | −3.8% | −3.1% | −4.8% | 0.6% | 0.0% | 10.3% |
| H2N-DLNRVL-OH | acid/base | 728 | −1.2% | −3.5% | −2.8% | −0.4% | 11.5% | 14.4% |
| H2N-DLNQ-OH | acidic 1x | 488 | −3.6% | −0.7% | −0.8% | 2.6% | 8.9% | 15.9% |
| H2N-VDTAPTV-OH | acidic 1x | 701 | −5.5% | 5.5% | 0.7% | 1.2% | 7.9% | 10.4% |

-continued

| Mitogenic Effects of 19 Peptides on Human Fibroblasts in Culture for 5 Days | | | | | | | | |
|---|---|---|---|---|---|---|---|---|
| Peptides for Cell Culture Studies | | | concentration (ug/mL) | | | | | |
| Peptide | Acidity | MW | 100 | 10 | 1 | 0.1 | 0.01 | 0.001 |
| H2N-AAPTV-OH | neutral | 457 | −5.9% | −5.9% | 2.8% | 0.3% | −0.2% | 11.0% |
| H2N-AAPTVD-OH | acidic 1x | 572 | 1.6% | −2.0% | 1.7% | −1.1% | 7.9% | 11.6% |
| H2N-DAAPTV-OH | acidic 1x | 572 | −2.7% | −6.1% | 3.5% | 7.5% | 9.5% | −3.0% |
| H2N-TAPTV-OH | neutral | 487 | 0.7% | −2.7% | 8.2% | 9.4% | −1.2% | 5.2% |
| H2N-DTAPTV-OH | acidic 1x | 602 | 7.6% | 2.2% | 2.9% | 6.7% | 2.5% | 3.2% |
| H2N-TAPTVD-OH | acidic 1x | 602 | 6.9% | 4.0% | 2.1% | −0.5% | −0.9% | 0.3% |
| H2N-APTVDLN-OH | acidic 1x | 728 | 6.7% | 8.1% | −6.0% | 2.8% | 3.9% | 1.2% |
| H2N-VDTAPT-OH | acidic 1x | 602 | 4.4% | −0.1% | 2.5% | 6.8% | 4.2% | 9.0% |
| H2N-EVDAAPT-OH | acidic 2x | 701 | 4.1% | 16.5% | 7.1% | 5.4% | 8.9% | 6.5% |
| H2N-VDAAPT-OH | acidic 1x | 572 | 13.3% | 6.2% | 4.5% | −3.6% | 2.9% | 1.6% |
| H2N-RLNVEV-OH | acid/base | 728 | 10.6% | 6.4% | 1.9% | −4.3% | −6.0% | −2.6% |
| H2N-LNVEV-OH | acidic 1x | 572 | 13.9% | 15.9% | −11.4% | −10.8% | 0.9% | −1.0% |
| H2N-TLRSP-OH | basic 1x | 572 | 18.8% | 14.7% | 6.6% | 7.7% | 1.9% | 4.7% |
| Fibroblast GF | | | | | | 70.3% | | |

It is understood that the test concentrations may be further optimized to determine the optimal concentration of each peptide formulation for either activation or inhibition of cell proliferation. However, the data contained in this example demonstrate the activity of the peptide compositions in the fibroblast assay. The test data further demonstrates like activity for peptides that contain thematic amino acid sequences LGD, DLN, APTV, SEQ ID NO:67, or LNVEV, SEQ ID NO:118.

Numerous advantages of the invention covered by this document have been set forth in the foregoing description. It will be understood, however, that this disclosure is, in many respects, only illustrative. Changes may be made in details, particularly in matters of reagents, concentrations, and step order, and still fall within the spirit and scope of the invention.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US08324346B2). An electronic copy of the "Sequence Listing" will also be available from the USPTO upon request and payment of the fee set forth in 37 CFR 1.19(b)(3).

The invention claimed is:

1. An isolated bioactive peptide consisting of amino acid sequence LNVEV, SEQ ID NO:118.

2. A composition in the form of a powder, lotion, hydrogel, oil, emulsion, paste, polish or cream, wherein the composition comprises the bioactive peptide of claim 1 in combination with a carrier.

3. A wound dressing comprising the bioactive peptide of claim 1.

4. The wound dressing of claim 3, wherein the wound dressing is a sheet comprising a keratin-derived product.

5. The wound dressing of claim 3, further defined as an adhesive bandage.

6. A tissue engineering scaffold comprising the bioactive peptide of claim 1.

7. The tissue engineering scaffold of claim 6, wherein the tissue engineering scaffold comprises an insoluble material, at least a part of which is obtained from a keratin product.

8. A composition in the form of a hydrogel, wherein the bioactive peptide of claim 1 is contained in or associated with the hydrogel.

9. The composition of claim 8, wherein the hydrogel comprises a keratin-derived hydrogel.

10. A composition for topical application to the skin of a human or animal subject, said composition comprising the bioactive peptide of claim 1, contained in a lotion, gel, paste, cream, or aqueous solution.

11. The composition of claim 10, for topical application to damaged epithelial tissue.

12. The composition of claim 11, wherein the epithelial tissue is skin, nasal, oral, gastro-intestinal, anal, vaginal, ear, eye, lung, or urogenital epithelial tissue.

13. The composition of claim 11, wherein the damaged epithelial tissue comprises a wound, a rash, diaper rash, a burn, a sunburn, a cut, an abrasion, a puncture, a sore, a bedsore, an ulcer, or wrinkled skin.

14. The composition of claim 10, wherein the peptide concentration is from about 100 µg/ml to about $1 \times 10^{-6}$ µg/ml.

15. A composition for cosmetic application to skin comprising the bioactive peptide of claim 1 combined with a carrier.

16. The composition of claim 15, wherein the composition is a moisturizer, a deodorant, an anti-aging/skin repair preparation, a cleanser, a toner, an eye care composition, a lip care composition, a fingernail care composition, a toenail care composition, a scalp care composition, a sun care composition, a hand care composition, or a body care composition.

17. The composition of claim 15, wherein the composition is an after-care product for a skin insult.

18. The composition of claim 17, wherein the skin insult is a chemical peel, sunburn, depilatory irritation, razor-shaving nick, an abrasion, or scalp irritation from hair treatment.

19. The composition of claim 15, wherein the composition is a water-based makeup.

20. The composition of claim 15, wherein the composition is a hair care product.

21. The composition of claim 20, wherein the product is a shampoo or hair conditioner.

22. A wound dressing comprising the bioactive peptide of claim 1 contained in, or adhered to a sheet, film or fabric dressing.

23. The wound dressing of claim 22, wherein the dressing comprises a keratin derivative.

24. The wound dressing of claim 22, wherein said wound dressing is an adhesive bandage.

25. The wound dressing of claim 22, wherein the dressing comprises wool or cotton fabric.

26. The wound dressing of claim 22, wherein the dressing is a woven keratin sheet.

27. The wound dressing of claim 22, wherein the dressing is a non-woven sheet or film comprising a water insoluble keratin.

28. A cell growth scaffold comprising a keratin-derived sheet material, porous material or hydrogel, and further comprising the bioactive peptide of claim 1 contained in, or non-covalently adhered thereto.

29. The cell growth scaffold of claim 28, further defined as a spinal implant, a bone growth scaffold, a scaffold for growth of epithelial tissue, a bandage, a non-woven sheet or a woven sheet.

30. The cell growth scaffold of claim 29, wherein the non-woven or woven sheets comprise wool pads, woven keratin, keratin bonded to polymer sheets, or cross-linked keratin.

31. The cell growth scaffold of claim 28, further comprising an envelope containing the peptides.

32. The cell growth scaffold of claim 28, comprising peptides bonded or adhered to the surface of a metal, silicone or polymer implant.

33. The bioactive peptide of claim 1, and in which the N-terminal a-amine group is acetylated.

34. The bioactive peptide of claim 1, and in which the C-terminal a-carboxy group is a carboxamide.

35. A method of increasing cellular proliferation comprising contacting skin or bone, tissue cells with a bioactive peptide consisting of amino acid sequence LNVEV, SEQ ID NO:118.

36. The method of claim 35, wherein the cells are fibroblasts, keratinocytes, or osteoblasts.

* * * * *